(12) United States Patent
Gao et al.

(10) Patent No.: US 9,914,724 B2
(45) Date of Patent: Mar. 13, 2018

(54) C-ARYL GLYCOSID DERIVATIVES, PHARMACEUTICAL COMPOSITION, PREPARATION PROCESS AND USES THEREOF

(71) Applicant: SHANGHAI DE NOVO PHARMATECH CO. LTD., Shanghai (CN)

(72) Inventors: Daxin Gao, Shanghai (CN); Heping Yang, Shanghai (CN); Pei Wang, Shanghai (CN)

(73) Assignee: SHANGHAI DE NOVO PHARMATECH CO., LTD., Shanghai (CN)

( * ) Notice: Subject to any disclaimer, the term of this patent is extended or adjusted under 35 U.S.C. 154(b) by 0 days.

(21) Appl. No.: 15/304,493

(22) PCT Filed: Apr. 1, 2015

(86) PCT No.: PCT/CN2015/075651
§ 371 (c)(1),
(2) Date: Dec. 28, 2016

(87) PCT Pub. No.: WO2015/158206
PCT Pub. Date: Oct. 22, 2015

(65) Prior Publication Data
US 2017/0037038 A1 Feb. 9, 2017

(30) Foreign Application Priority Data

Apr. 14, 2014 (CN) .......................... 2014 1 0148116
Aug. 11, 2014 (CN) .......................... 2014 1 0392098

(51) Int. Cl.
C07H 7/04 (2006.01)
C07D 407/12 (2006.01)
A61K 31/351 (2006.01)
A61K 45/06 (2006.01)

(52) U.S. Cl.
CPC .......... *C07D 407/12* (2013.01); *A61K 31/351* (2013.01); *A61K 45/06* (2013.01); *C07H 7/04* (2013.01); *Y02P 20/55* (2015.11)

(58) Field of Classification Search
None
See application file for complete search history.

(56) References Cited

U.S. PATENT DOCUMENTS

2003/0114390 A1 6/2003 Washburn et al.
2005/0209166 A1 9/2005 Eckhardt et al.

FOREIGN PATENT DOCUMENTS

CN 1802366 A 7/2006
CN 103270033 A 8/2013
CN 105001213 A 8/2014
CN 104059042 A 9/2014
CN 105017236 A 4/2015
WO 01/27128 A1 4/2001
WO 02/083066 A2 10/2002
WO 03/099836 A1 12/2003
(Continued)

OTHER PUBLICATIONS

Wolff, Manfred E. "Burger's Medicinal Chemistry, 5ed, Part I", John Wiley & Sons, 1995, pp. 975-977.*
(Continued)

*Primary Examiner* — Traviss C McIntosh, III
(74) *Attorney, Agent, or Firm* — Masuvalley & Partners

(57) ABSTRACT

This invention relates to a kind of C- aryl glycoside derivatives, its pharmaceutical compositions, preparation methods, and uses thereof. The preparation method comprises: method 1: in a solvent, deprotecting the acetyl protecting groups of compound 1-f in the presence of a base; method 2: 1) compound 2-g reacts with

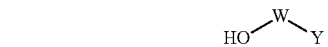

via Mitsunobu reaction; 2) deprotecting the acetyl protecting groups of compound 2-f obtained from step 1; method 3: 1) compound 2-g reacts with

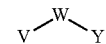

via nucleophilic substitution reaction; 2) deprotecting the acetyl protecting groups of compound 3-f obtained from step 1. The pharmaceutical composition comprises a kind of C-aryl glycoside derivatives; it's pharmaceutically acceptable salts and/or prodrugs thereof and excipient thereof. This invention relates to a kind of C- aryl glycoside derivatives, it's pharmaceutically acceptable salts or compositions thereof for preparing a SGLT inhibitor. The C- aryl glycoside derivatives of this invention provides a new direction for SGLT inhibitors.

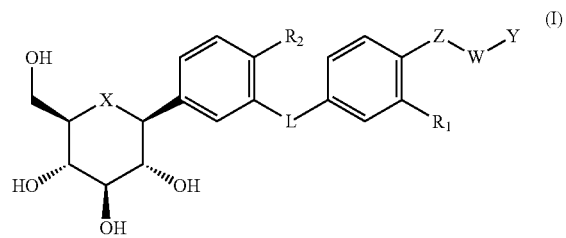

17 Claims, No Drawings

(56) References Cited

FOREIGN PATENT DOCUMENTS

| WO | 04/063209 A2 | 7/2004 |
| WO | 2005/012326 A1 | 2/2005 |
| WO | 2011/048148 A2 | 4/2011 |
| WO | 2012/025857 A1 | 3/2012 |
| WO | 2012/109996 A1 | 8/2012 |
| WO | 2013/000275 A1 | 1/2013 |

OTHER PUBLICATIONS

Banker, G.S. et al, "Modern Pharmaceutics, 3ed.", Marcel Dekker, New York, 1996, p. 596.*

Zhao Jing, Dai De-zai, "Development of Drugs for Treatment of Diabetic Complication", Progress in Pharmaceutical Sciences ,2003,27:88-91, with translation.

Handlon, A.L., "Sodium glucose co-transporter 2 (SGLT2) inhibitors as potential antidiabetic agents" , Expert Opin. Ther. Patents (2005) 15(11):1531-1540.

Ernest M. Wright, "Renal Na+-glucose cotransporters", Am JPhysiol Renal Physiol, 2001, 280:10-18.

Edward C. Chao and Robert R. Henry, "SGLT2 inhibition—a novel strategy for diabetes treatment", Nature Reviews Drug Discovery, 2010, vol. 9. No. 7. 551-559.

Wei Meng, et al., "Discovery of Dapagliflozin: A Potent, Selective Renal Sodium-Dependent Glucose Cotransporter 2 (SGLT2) Inhibitor for the Treatment of Type 2 Diabetes", J. Med. Chem. 2008, 51, 1145-1149.

Chinese Patent Application No. 201410148116.X(not published) with translation.

Written Opinion of ISA/CN, International Search Report dated Jul. 9, 2015 in International Application No. PCT/CN2015/075651, total 6 pages with translation.

ISA/CN, International Search Report dated Jul. 9, 2015 in International Application No. PCT/CN2015/075651, total 8 pages with translation.

\* cited by examiner

C-ARYL GLYCOSID DERIVATIVES, PHARMACEUTICAL COMPOSITION, PREPARATION PROCESS AND USES THEREOF

RELATED APPLICATIONS

This application is a national phase application under 35 U.S.C. § 371 of International Patent Application No. PCT/CN2015/075651, filed on Apr. 1, 2015, which claims priority under 35 U.S.C. § 119 to Chinese Patent Application No. 201410148116.X, filed on Apr. 14, 2014, and Chinese Patent Application No. 201410392098.X, filed on Aug. 11, 2014, the contents of which are hereby expressly incorporated by reference in their entirety for all purposes.

FIELD OF THE INVENTION

Disclosed is a kind of C- aryl glycoside derivatives, its stereoisomers, prodrugs, pharmaceutical accepted salts, pharmaceutical compositions, preparation methods and uses thereof.

BACKGROUND OF THE INVENTION

Diabetes is a metabolic disorder characterized by high blood sugar and its global incidence is increasing. About 90% of diabetes is type II diabetes due to excessive hepatic glucose caused by peripheral insulin resistance and high blood sugar (Pharmaceutical Development, 2003, 27: 88-91). Currently, the most commonly used drugs for type II diabetes including sulfonylurea, biguanides, α-carbon glucosidase inhibitor and insulin have good blood glucose control and lowing effect. However, they have many drug-related side effects, such as weight gain, reduced insulin secretion, hypoglycemia, and gastrointestinal adverse reactions. Therefore, there is unmet medical need to develop safer and more efficacious oral anti-diabetic drugs.

The sodium-glucose co-transporters (SGLTs) plays an important role in maintaining stable blood glucose level. SGLT-1 is mainly expressed in small intestine, kidney, heart and brain. In contrast, SGLT2's major physiological function is absorption of glucose in the small intestine. SGLT-2 is specifically distributed in the kidney proximal convoluted tubule 51 segment, and is responsible for the reabsorption of 90% glucose. The remaining 10% is carried out by SGLT-1 in the proximal convoluted tubule S3 segment. Therefore, the re-absorption of glucose can be specifically reduced by inhibiting SGLT-2's activity in the kidney resulting in excretion of excessive glucose in the urine without body weight increase or hypoglycemia. Therefore, SGLT2 inhibitor represents highly promising anti-diabetic drug (Handlon, A. L., Expert Opin. Ther. Patents 2005, 15(11):1531-1540; Am J Physiol Renal Physiol 2001, 280: 10-18).

Multiple SGLT2 inhibitors have been disclosed as published in Handlon, A. L., Expert Opin. Ther. Patents 2005, 15(11):1531-1540; Nature Reviews Drug Discovery, 2010, Vol. 9, No. 7, 551-559; WO01/27128, WO02/083066, WO03/099836, US2003/0114390, WO 04/063209, WO2005/012326, US2005/0209166. The FDA approved SGLT2 inhibitors include Jansen's Canagliflozin (approved on Mar. 29, 2013), AstraZeneca and BMS's Dapagliflozin (approved on Jan. 8, 2014), Boehringer Ingelheim's Empagliflozin (approved by CHMP on Mar. 21, 2014).

DETAILED DESCRIPTION OF THE INVENTION

The technical problem to be solved by the present invention is to provide a kind of C- aryl glycoside derivatives, and its stereoisomers, prodrugs, pharmaceutical accept salts thereof with an excellent inhibitory effect on SGLT, and the pharmaceutical compositions containing the same, the preparation methods and uses thereof.

The present invention relates to a C- aryl glycoside derivative of formula (I), its stereoisomers, stable isotope derivatives, prodrugs thereof, or a pharmaceutically acceptable salt thereof;

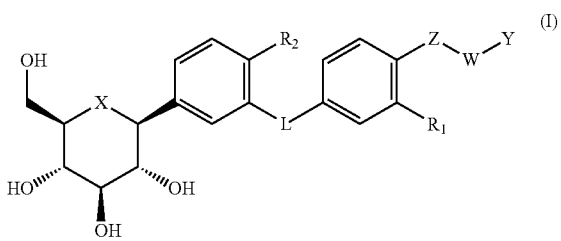

Wherein, X is O or S; L is $CH_2$, $CD_2$, C=O or $CF_2$; Z is $CH_2$, S, O or a single bond; W is a single bond or $(CH_2)_n$, n=1, 2 or 3;

Y is a bicyclic group; wherein the bicyclic group is preferably $C_{5-8}$ cycloalkyl fused $C_6$ aryl, $C_{5-8}$ cycloalkyl fused $C_{3-5}$ heteroaryl, $C_{3-7}$ heterocycloalkyl fused $C_6$ aryl, $C_{3-7}$ heterocycloalkyl fused $C_{3-5}$ heteroaryl, $C_6$ aryl fused $C_6$ aryl, $C_{3-5}$ heteroaryl fused $C_6$ aryl, or $C_{3-5}$ heteroaryl fused $C_{3-5}$ heteroaryl; wherein said bicyclic group can be substituted by 1 or more substituent(s) at any position independently selected from: H, alkyl, CN, halogen, $CF_3$, OH, amino, $C_{2-6}$ alkenyl, $C_{2-6}$ alkynyl, alkoxy, haloalkyoxy, cycloalkyl, cycloalkyloxy, cycloalkylalkyl, cycloalkylalkoxy, heterocycloalkyl, heterocycloalkyloxy, heterocycloalkylalkyl, heterocycloalkylalkoxy, alkylamino, carbonyl, COOH, $COOR_7$, $COR_7$, $CONR_7R_{7a}$, $-NHCOR_7$, $-NHSO_2R_7$, aryl, heteroaryl, alkylsulfonyl, arylsulfonyl, or heteroarylsulfonyl; the substituent of bicyclic group can be further substituted by one or more substituent(s) selected from: alkyl, halogen, $CF_3$, OH, CN, amino, alkoxy, or haloalkoxy;

$R_1$ is H, halogen, CN, alkyl, alkoxy, haloalkoxy, $OCD_3$, $OC_2D_5$, or $CF_3$;

$R_2$ is H, alkyl, halogen, $CF_3$, CN, OH, amino, alkoxy, haloalkoxy, $OCD_3$, $OC_2D_5$, $C_{2-6}$ alkenyl, $C_{2-6}$ alkynyl, cycloalkyl, heterocycloalkyl, alkylamino, carbonyl, COOH, $COOR_7$, $COR_7$, $CONR_7R_{7a}$, $-NHCOR_7$, $-NHSO_2R_7$, aryl, heteroaryl, alkylsulfonyl, arylsulfonyl, or heteroarylsulfonyl;

$R_7$ and $R_{7a}$ are independently selected from alkyl, cycloalkyl, or heterocycloalkyl; or $R_7$ and $R_{7a}$ together with the nitrogen atom to which they are attached, form a 3- to 7-membered heterocycloalkyl ring;

When $R_2$ is halogen, it is preferably Cl.

The 3- to 7-membered heterocycloalkyl ring formed by $R_7$ and $R_{7a}$ together with the nitrogen atom to which they are attached, may further contain 1 to 3 heteroatoms or groups in the ring: N, O, S, SO, or $SO_2$.

The 3- to 7-membered heterocycloalkyl ring formed by $R_7$ and $R_{7a}$ together with the nitrogen atom to which they are attached, can be further substituted by alkyl and/or methylsulfonyl.

In the present invention, in Y, wherein $C_{3-7}$ heterocycloalkyl fused $C_6$ aryl is preferably $C_{4-6}$ heterocycloalkyl fused $C_6$ aryl; $C_{3-5}$ heteroaryl fused $C_6$ aryl is preferably $C_{3-4}$ heteroaryl fused $C_6$ aryl.

In the present invention, Y is more preferably (but not limited to) any one of the following Y1 to Y24:
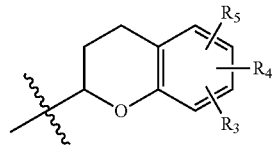 Y1
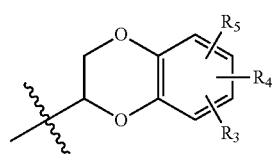 Y2
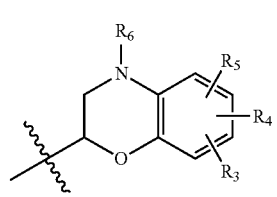 Y3
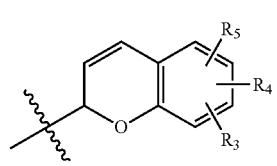 Y4
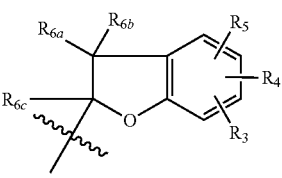 Y5
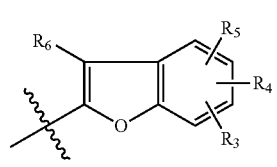 Y6
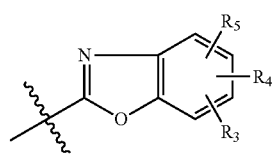 Y7
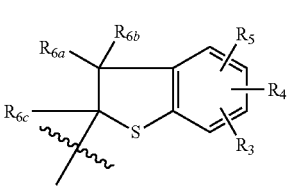 Y8
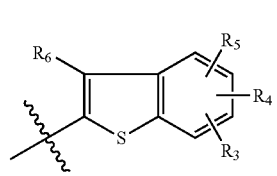 Y9
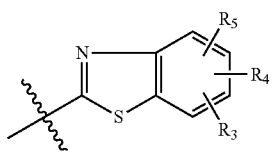 Y10
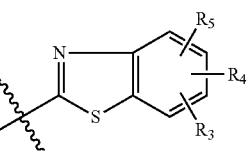 Y11
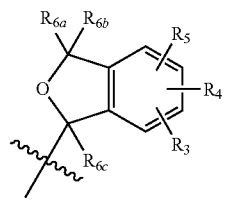 Y12
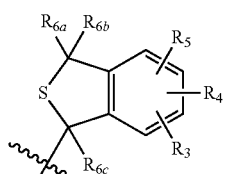 Y13
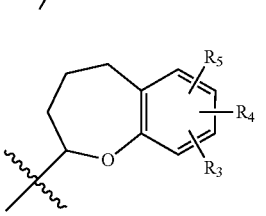 Y14
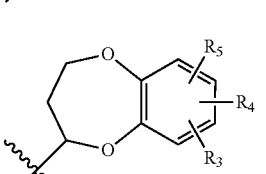 Y15
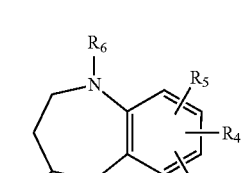 Y16
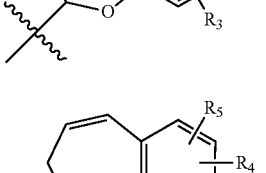 Y17

-continued

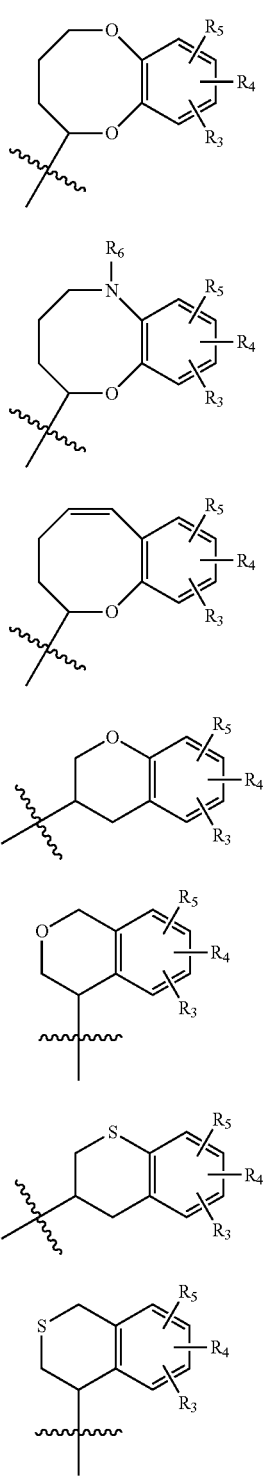

Wherein, $R_3$, $R_4$, $R_5$, $R_6$, $R_{6a}$, $R_{6b}$ and $R_{6c}$ are independently H, alkyl, CN, halogen, $CF_3$, OH, amino, $C_{2-6}$ alkenyl, $C_{2-6}$ alkynyl, alkoxy, haloalkoxy, cycloalkyl, cycloalkyloxy, cycloalkylalkyl, cycloalkylalkoxy, heterocycloalkyl, heterocycloalkyloxy, heterocycloalkylalkyl, heterocycloalkylalkoxy, alkylamino, carbonyl, COOH, $COOR_7$, $COR_7$, $CONR_7R_{7a}$, —$NHCOR_7$, —$NHSO_2R_7$, aryl, heteroaryl, alkylsulfonyl, arylsulfonyl, or heteroarylsulfonyl;

$R_3$, $R_4$, $R_5$, $R_6$, $R_{6a}$, $R_{6b}$ and $R_{6c}$ can be further substituted by any one of the following substituents: alkyl, halogen, $CF_3$, OH, CN, amino, alkoxy, or haloalkoxy;

Wherein, $R_6$ and $R_{6a}$ together with the atom to which they are attached, form a 3- to 8-membered cycloalkyl ring or 3- to 8-membered heterocycloalkyl ring; wherein the 3- to 8-membered heterocycloalkyl ring preferably contains 1 to 3 heteroatoms or groups in the ring: N, O, S, SO, or $SO_2$; wherein the 3- to 8-membered cycloalkyl ring or 3- to 8-membered heterocycloalkyl ring can be substituted by alkyl and/or halogen.

In the present invention, Y is preferably

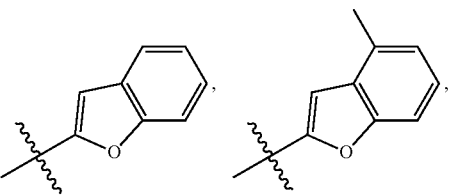

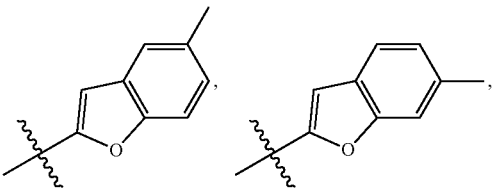

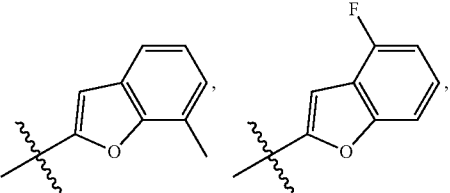

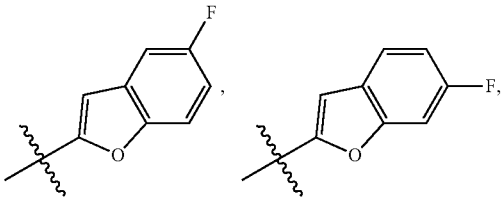

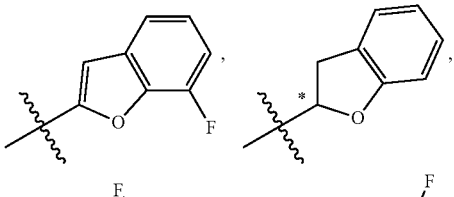

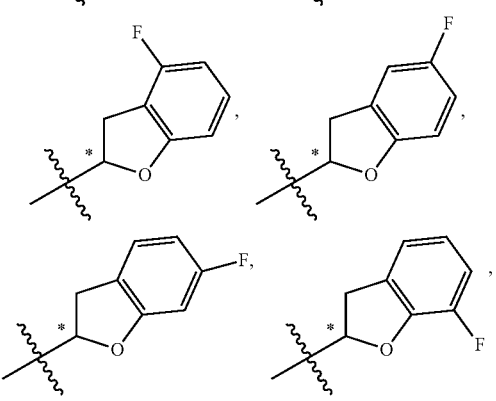

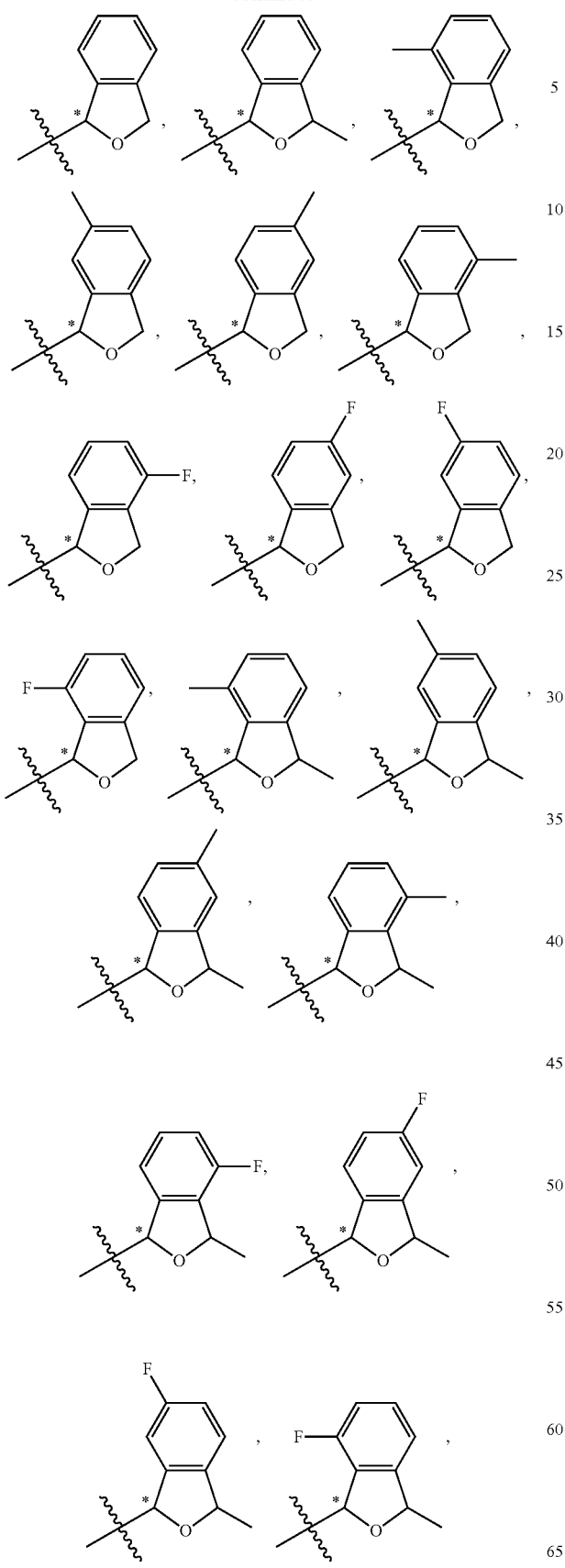
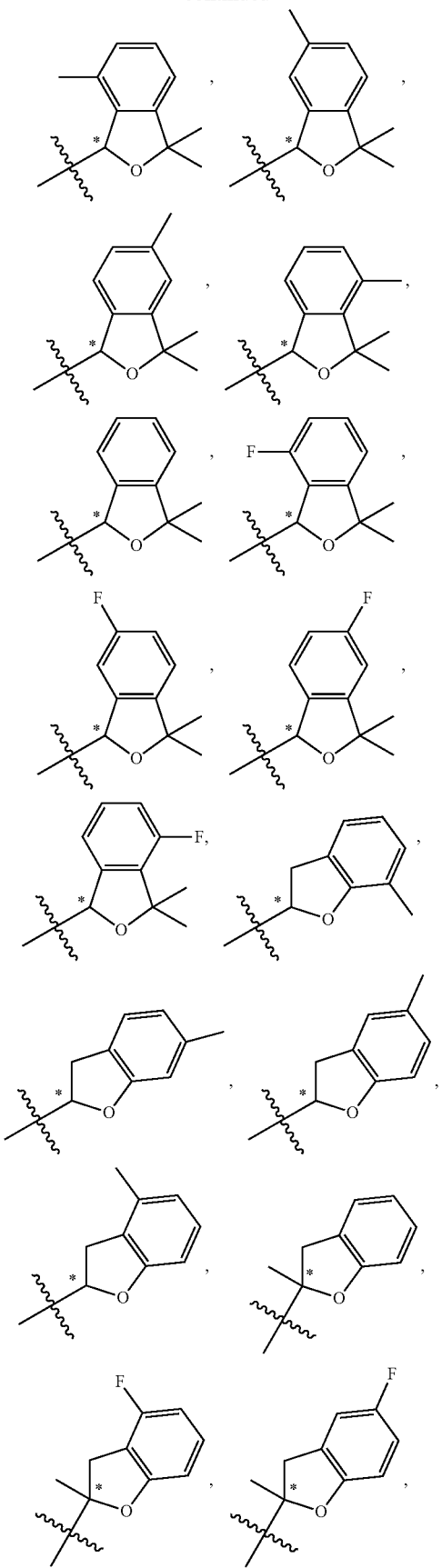

-continued
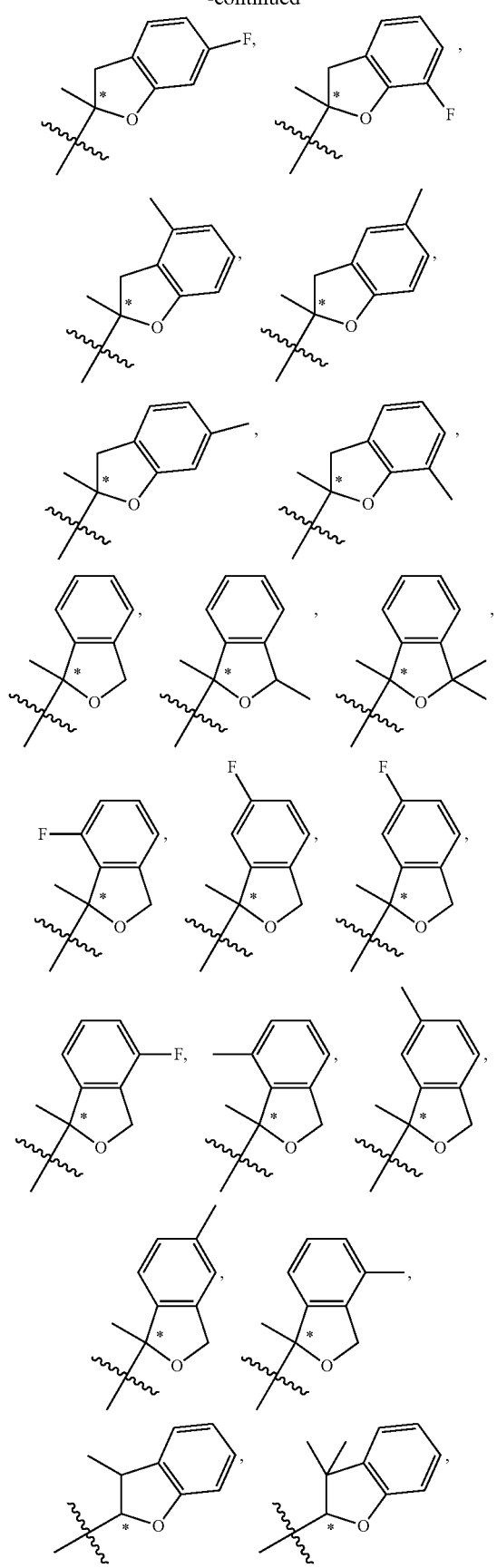
-continued
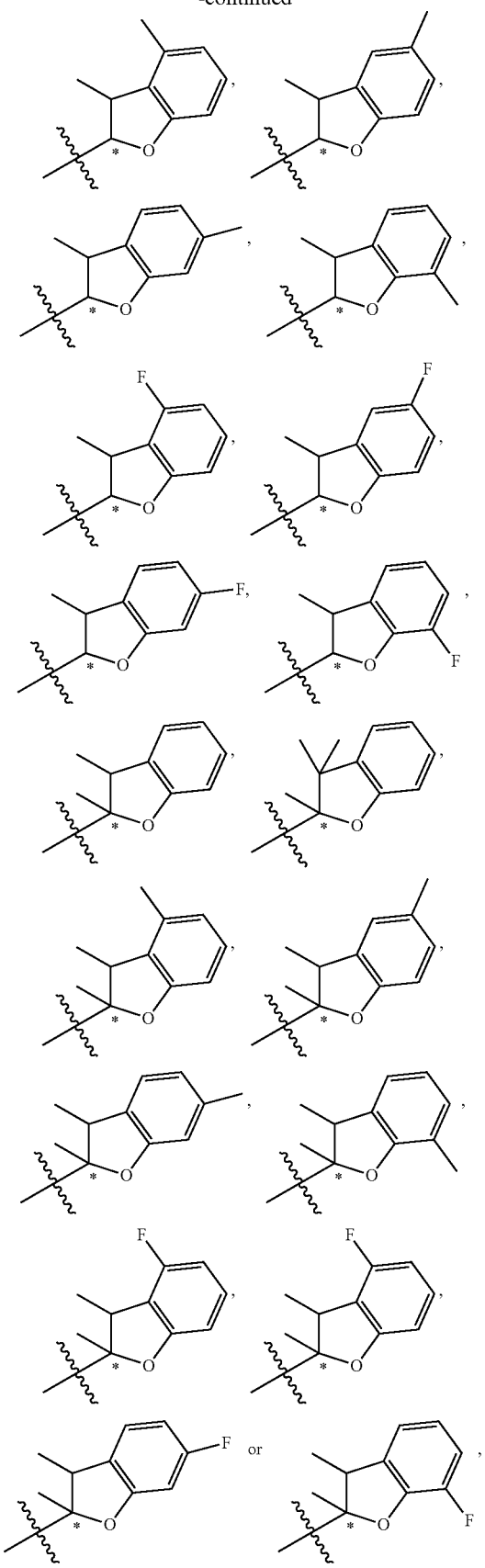

more preferably

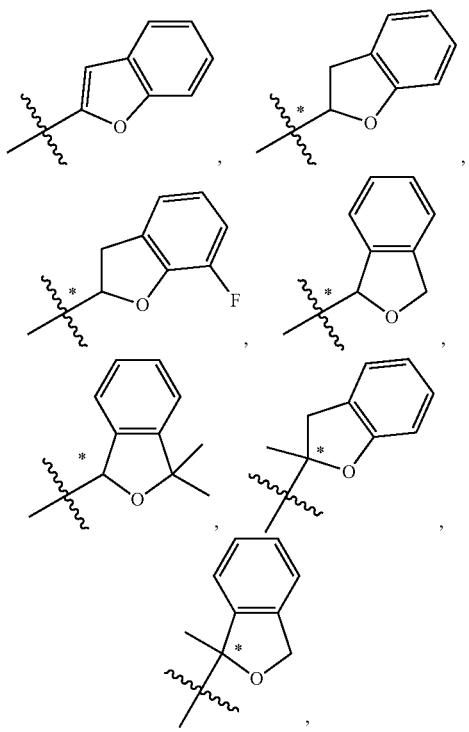

* denotes chiral carbon, including raceme, the absolute configuration of S or R.

One subset of C- aryl glycoside derivatives of formula (I), preferably the below formulae IA, IB or IC:

(IA)

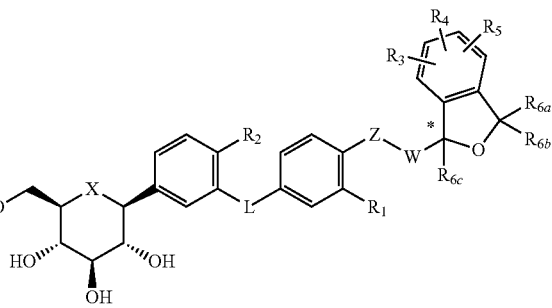

In IA, X is O; L is CH$_2$; Z is O; W is (CH$_2$)$_n$; n is 1 or 2; R$_1$, R$_2$, R$_3$, R$_4$, R$_5$, R$_6$ are the same as described previously;

(IB)

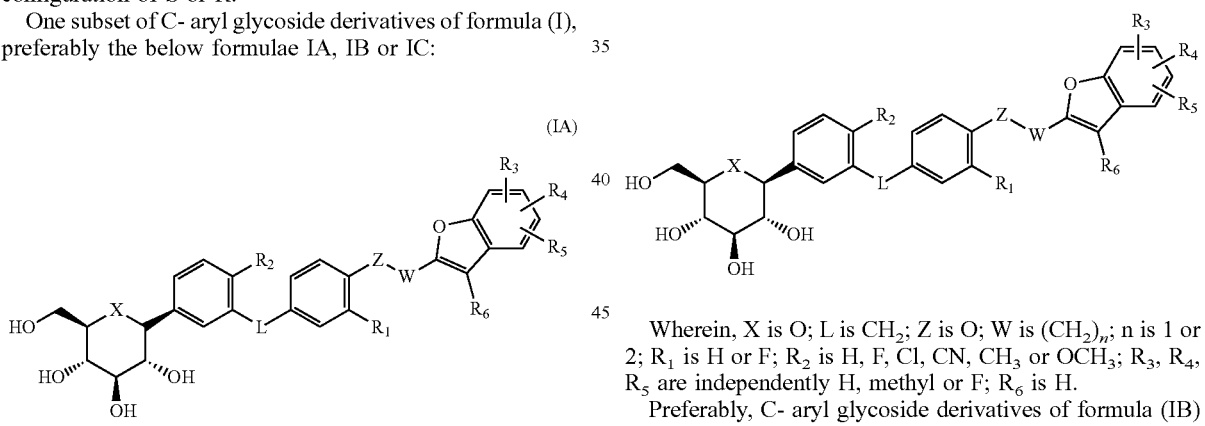

In IB, X is O; L is CH$_2$; Z is O; W is (CH$_2$)$_n$; n is 1 or 2; R$_1$, R$_2$, R$_3$, R$_4$, R$_5$, R$_{6a}$, R$_{6b}$, R$_{6c}$, are the same as described previously; * denotes chiral carbon, including raceme, the absolute configuration of S or R.

(IC)

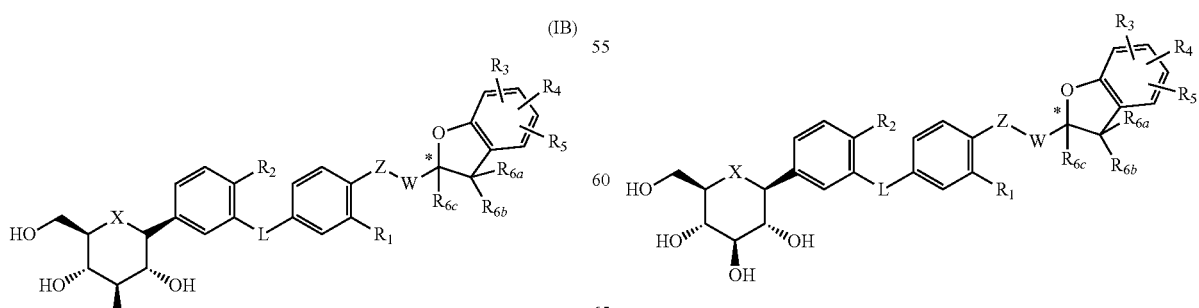

In IC, X is O; L is CH$_2$; Z is O; W is (CH$_2$)$_n$; n is 1 or 2; R$_1$, R$_2$, R$_3$, R$_4$, R$_5$, R$_{6a}$, R$_{6b}$, R$_{6c}$, are the same as described previously; * denotes chiral carbon, including raceme, the absolute configuration of S or R.

Wherein, the absolute configurations of S, R of the carbon atoms labeled with * and their raceme are all included in formulae IB and IC.

Preferably, C- aryl glycoside derivatives of formula (IA) is:

(IA)

Wherein, X is O; L is CH$_2$; Z is O; W is (CH$_2$)$_n$; n is 1 or 2; R$_1$ is H or F; R$_2$ is H, F, Cl, CN, CH$_3$ or OCH$_3$; R$_3$, R$_4$, R$_5$ are independently H, methyl or F; R$_6$ is H.

Preferably, C- aryl glycoside derivatives of formula (IB) is:

(IB)

Wherein, X is O; L is CH$_2$; Z is O; W is (CH$_2$)$_n$; n is 1 or 2; R$_1$ is H or F; R$_2$ is H, F, Cl, CN, CH$_3$ or OCH$_3$; R$_3$, R$_4$, $R_5$ are independently H, methyl or F; $R_{6a}$, $R_{6b}$, and $R_{6c}$ are independently H or $CH_3$; * denotes chiral carbon, including raceme, the absolute configuration of S or R.

Preferably, C-aryl glycoside derivatives of formula (IC) is:

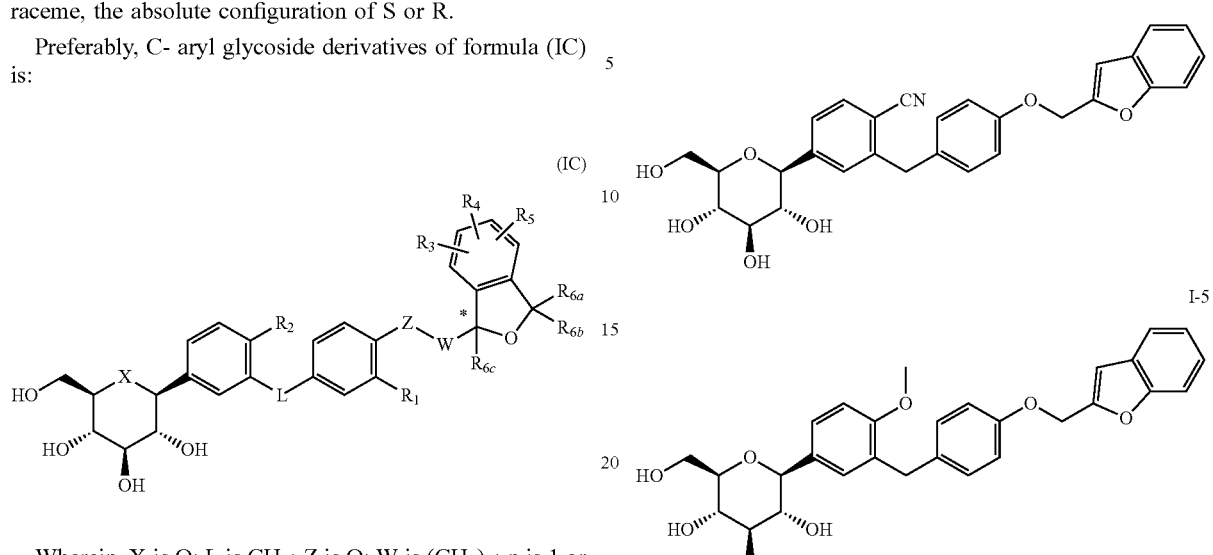

(IC)

Wherein, X is O; L is $CH_2$; Z is O; W is $(CH_2)_n$; n is 1 or 2; $R_1$ is H or F; $R_2$ is H, F, Cl, CN, $CH_3$ or $OCH_3$; $R_3$, $R_4$, $R_5$ are independently H, methyl or F; $R_{6a}$, $R_{6b}$, and $R_{6c}$ are independently H or $CH_3$; * denotes chiral carbon, including raceme, the absolute configuration of S or R.

The C-aryl glycoside derivatives of formula (I) are selected from the following compounds of I-1 to I-148:

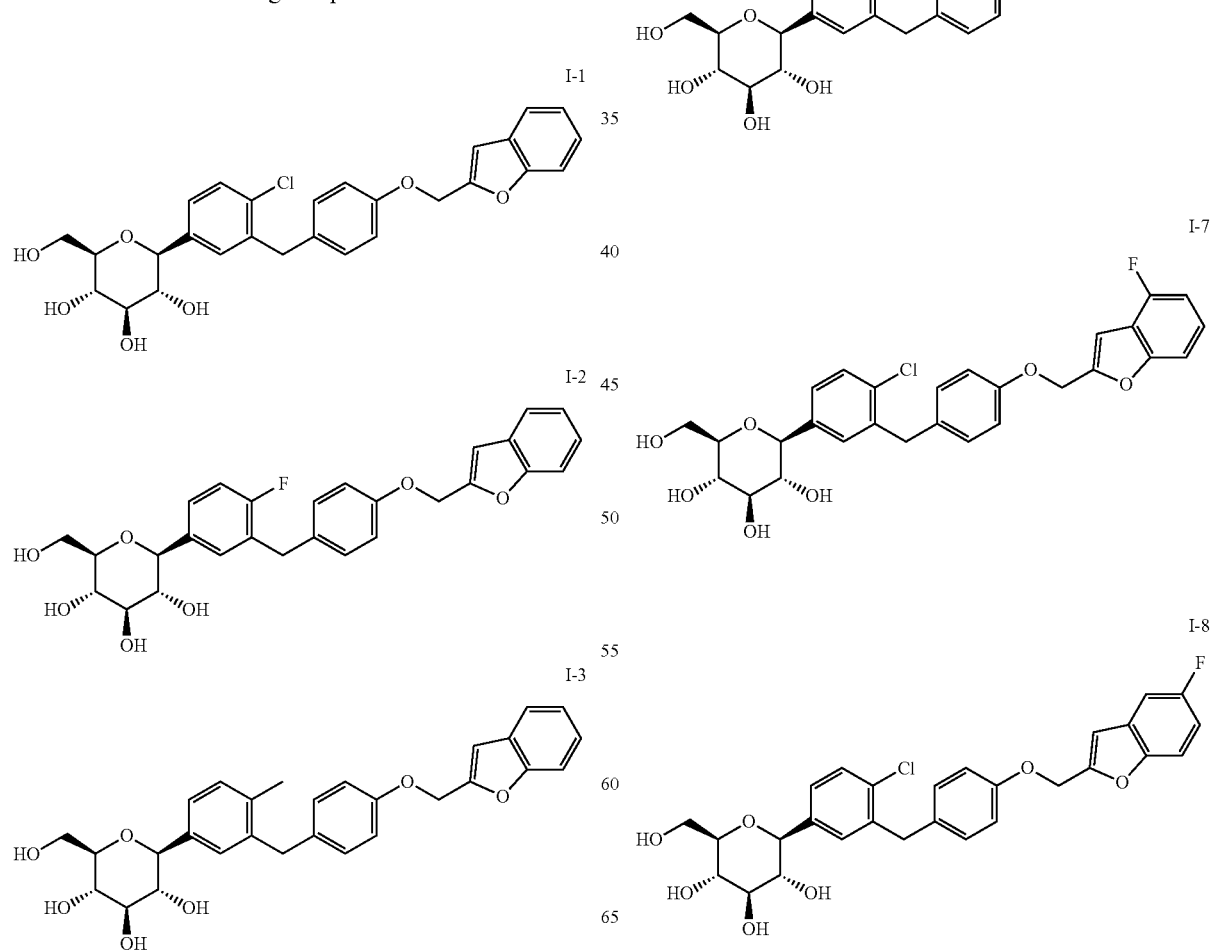

-continued
I-9
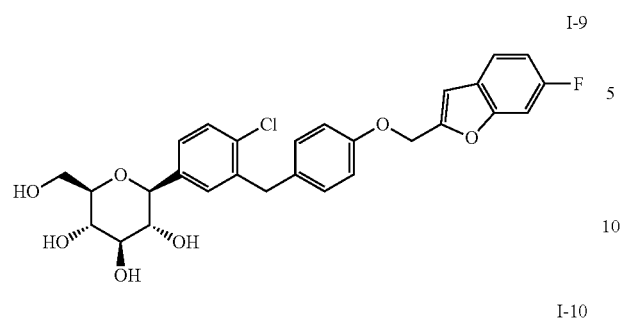
I-10
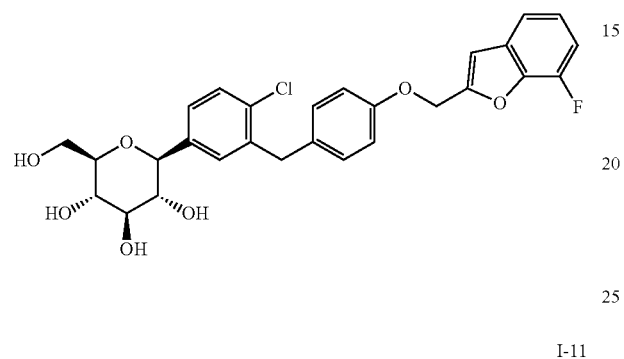
I-11
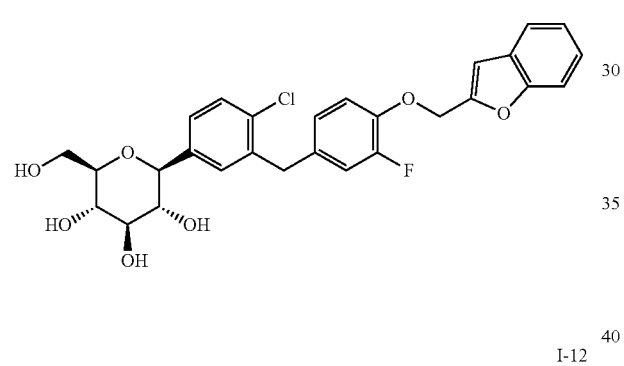
I-12
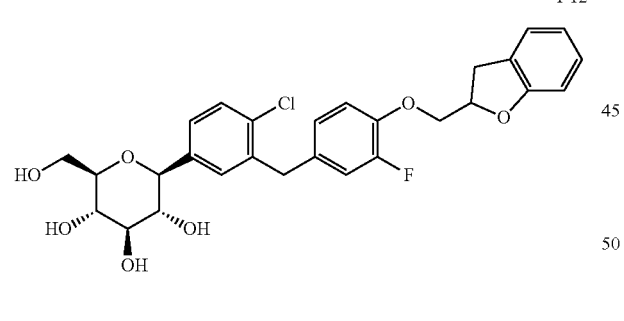
I-13
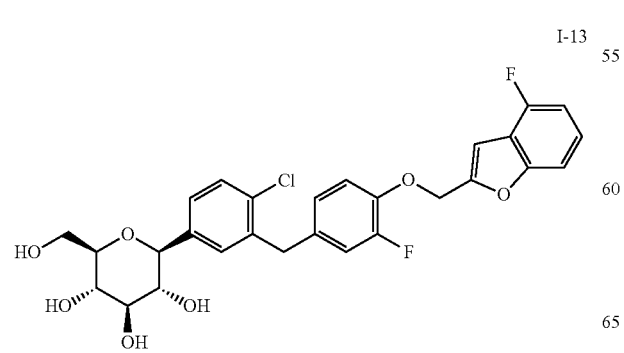
-continued
I-14
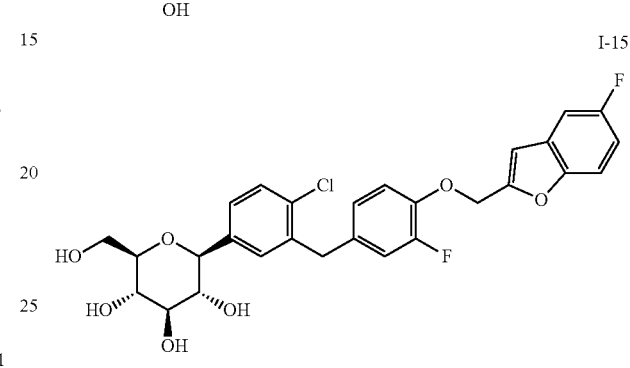
I-15
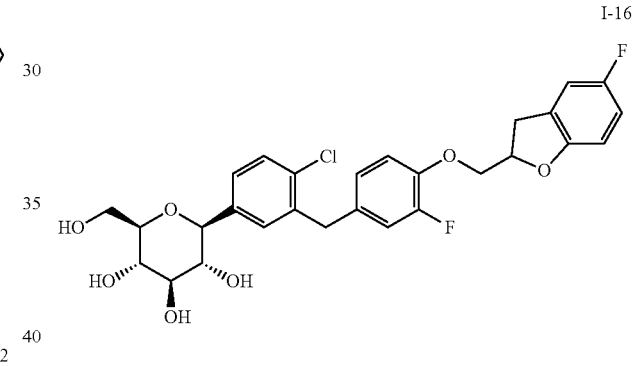
I-16
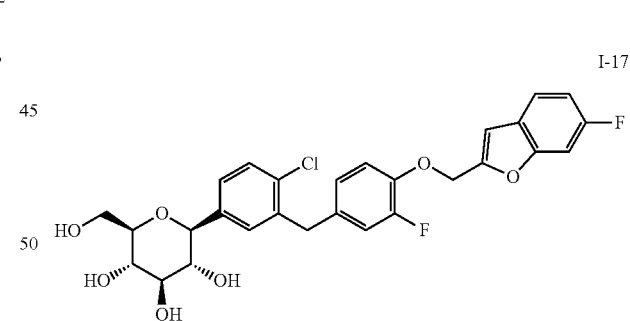
I-17
I-18
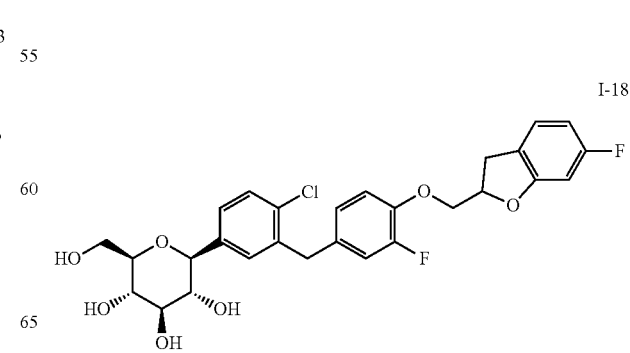

-continued
I-19
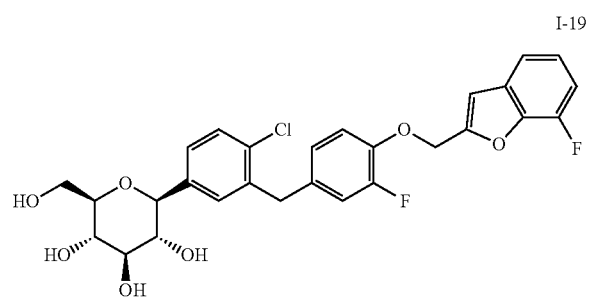
I-20
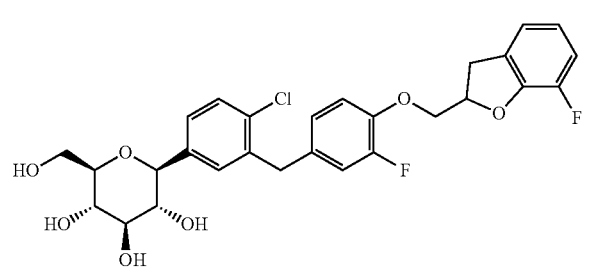
I-21
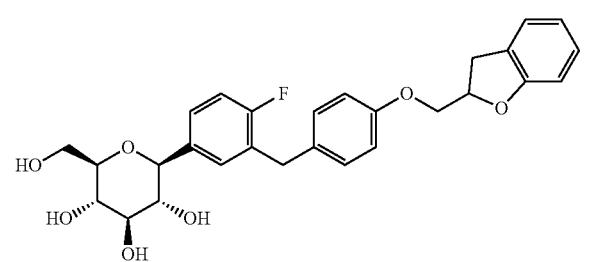
I-22
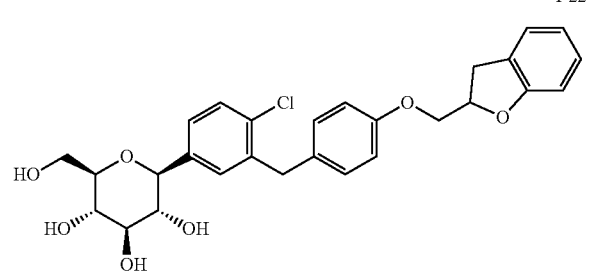
I-23
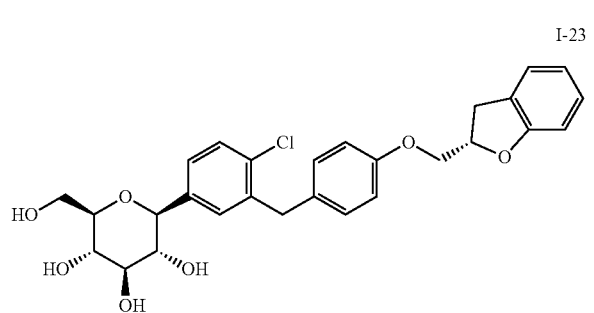
-continued
I-24
I-25
I-26
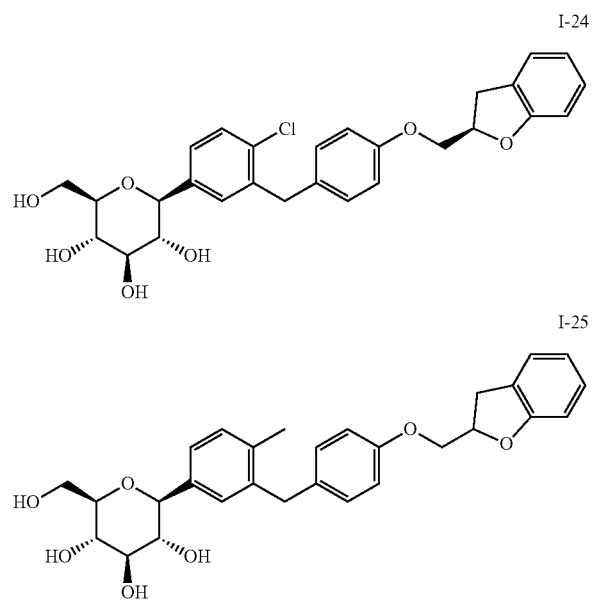
I-27
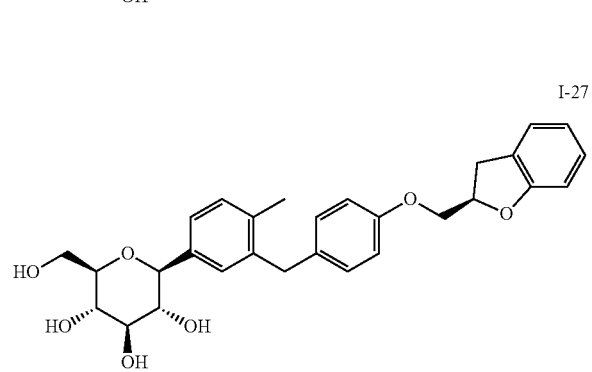
I-28
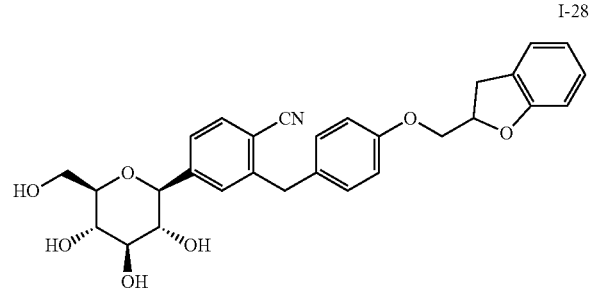

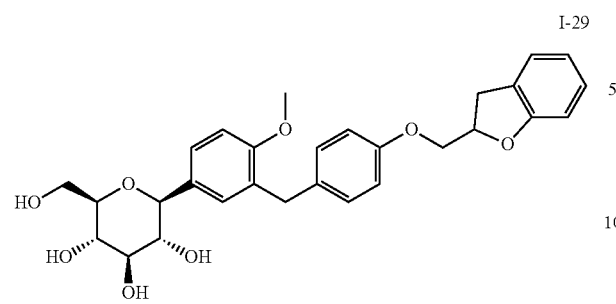
I-29
I-34
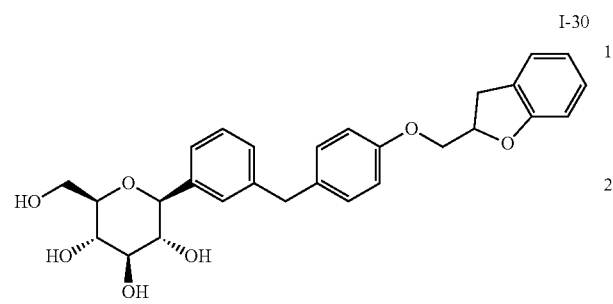
I-30
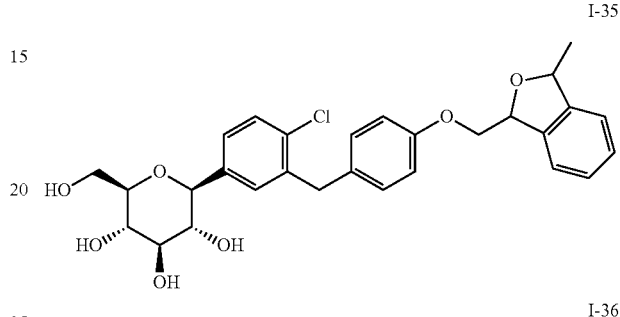
I-35
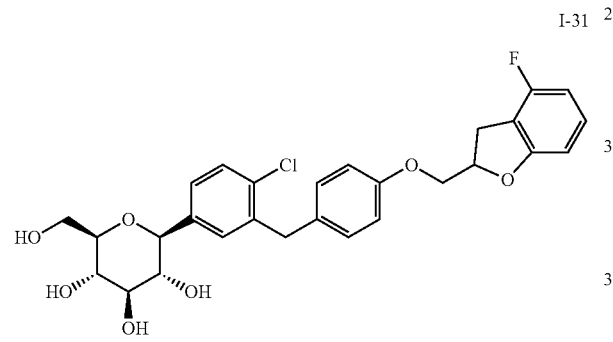
I-31
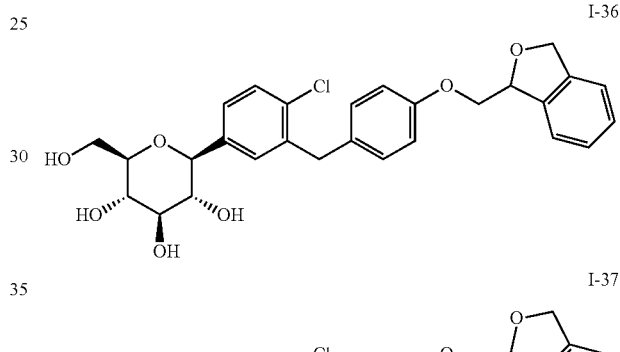
I-36
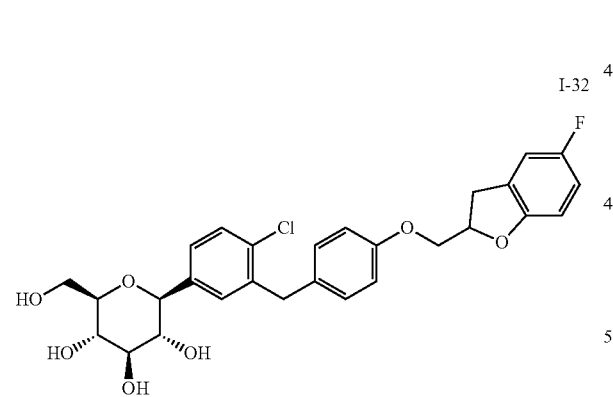
I-32
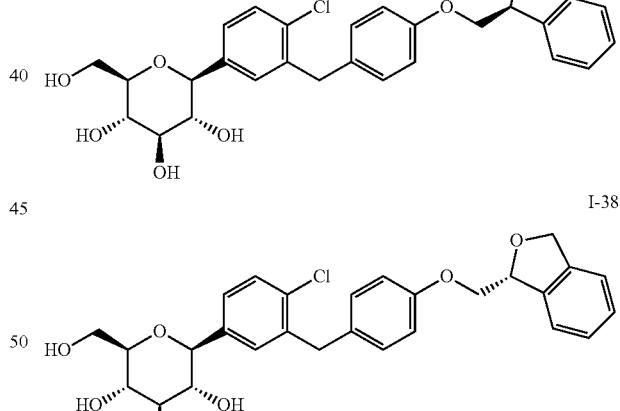
I-37
I-38
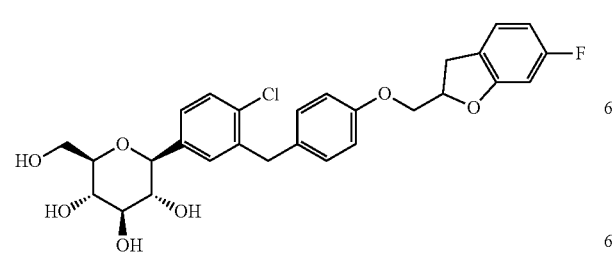
I-33
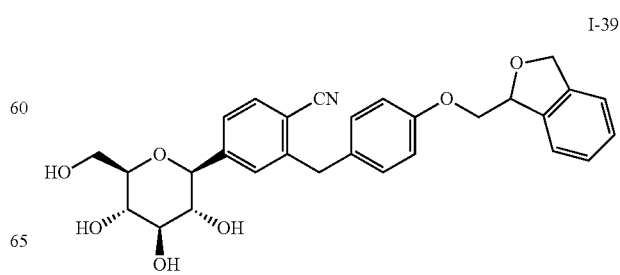
I-39

I-40
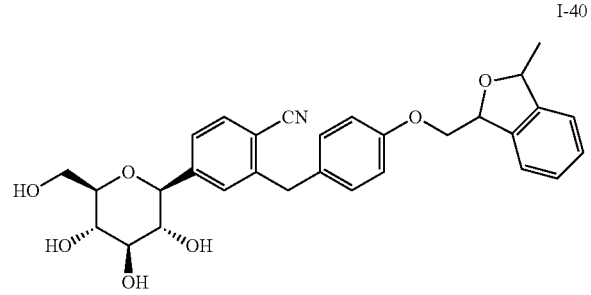
I-41
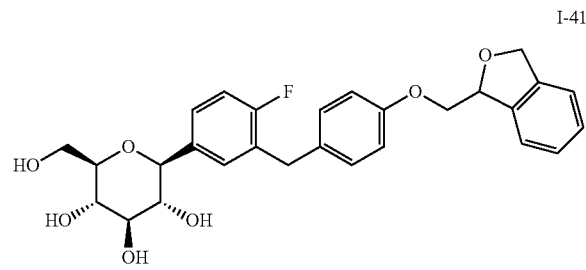
I-42
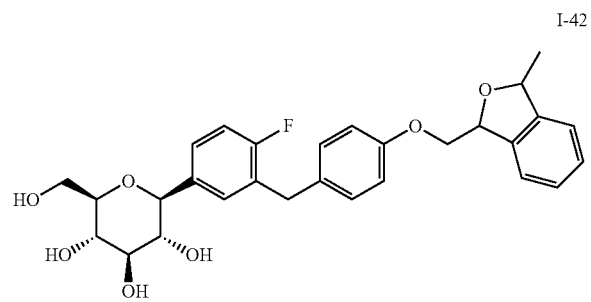
I-43
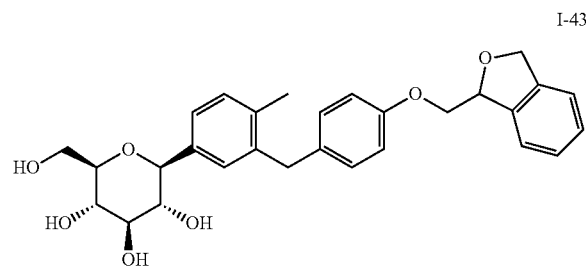
I-44
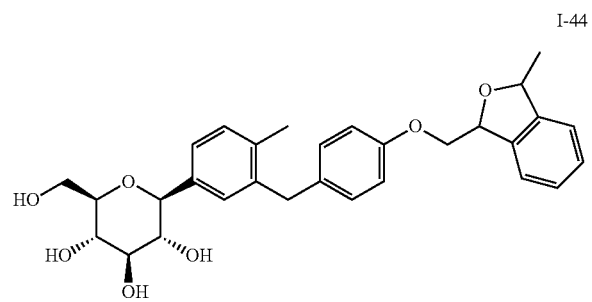
I-45
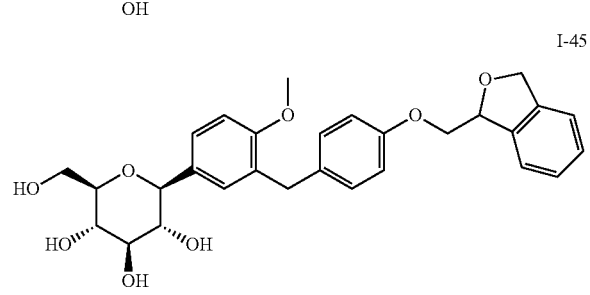
I-46
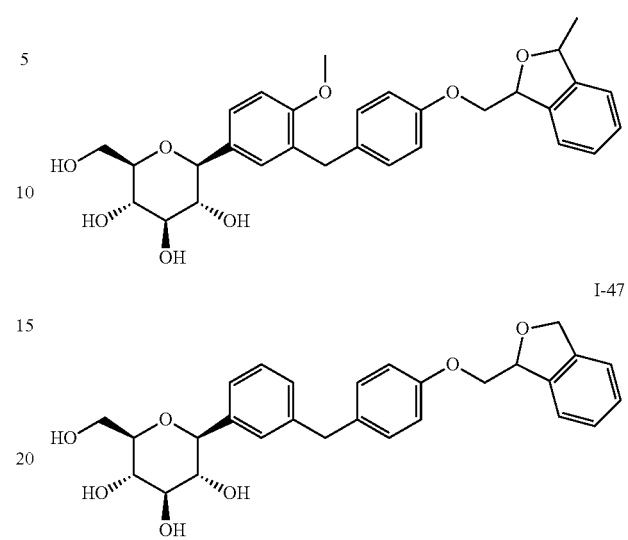
I-47
I-48
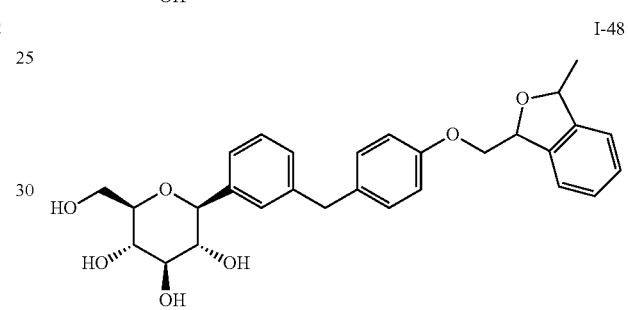
I-49
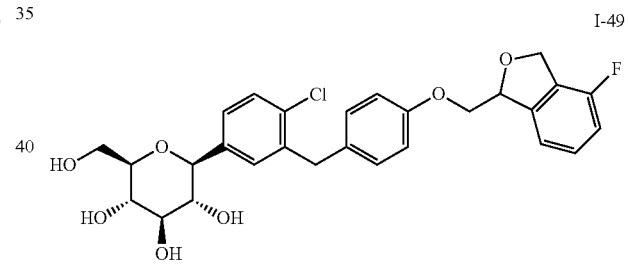
I-50
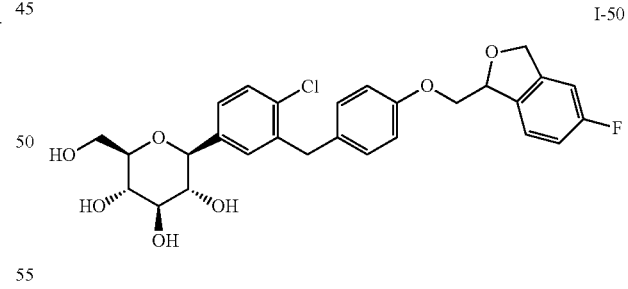
I-51
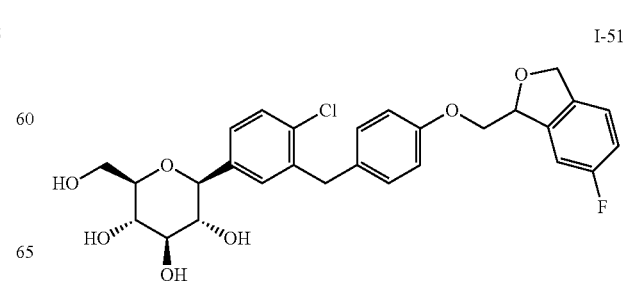

I-52 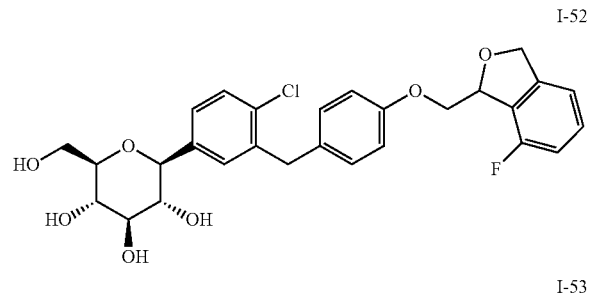
I-53 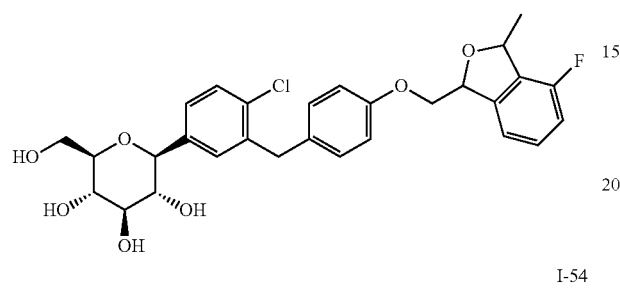
I-54 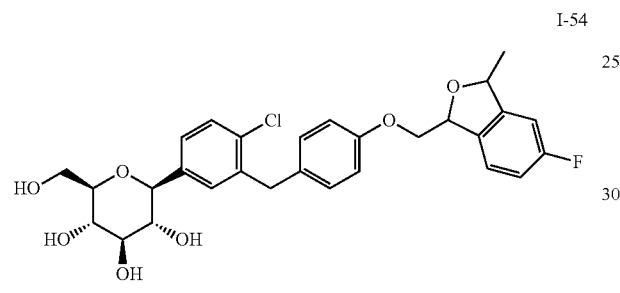
I-55 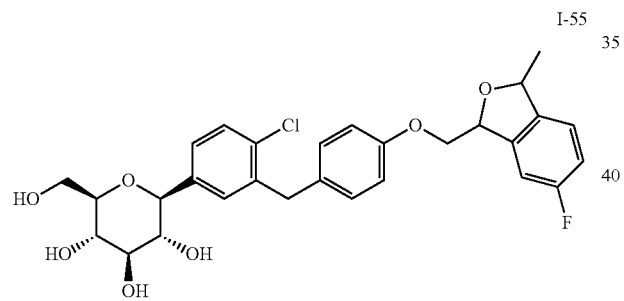
I-56 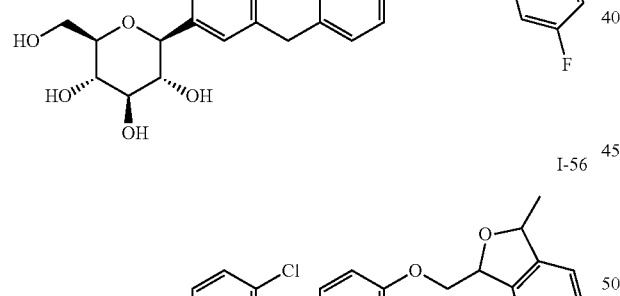
I-57 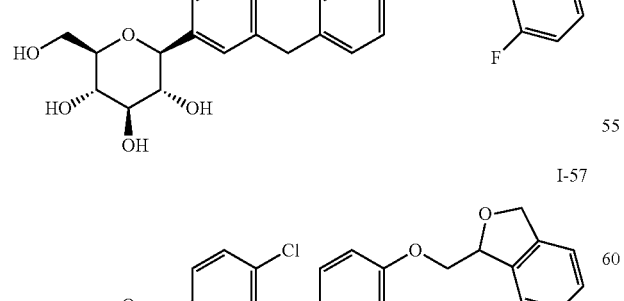
I-58 
I-59 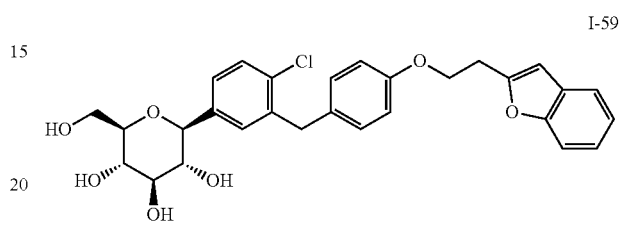
I-60 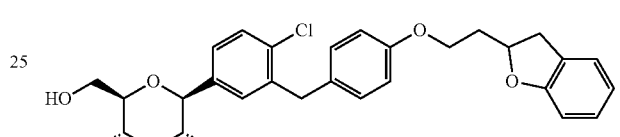
I-61 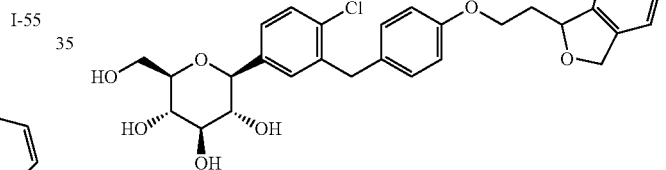
I-62 
I-63 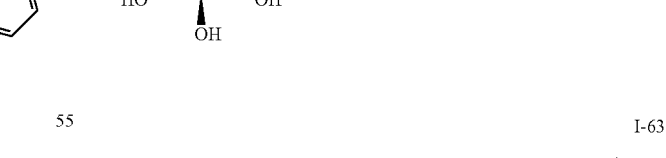

I-64
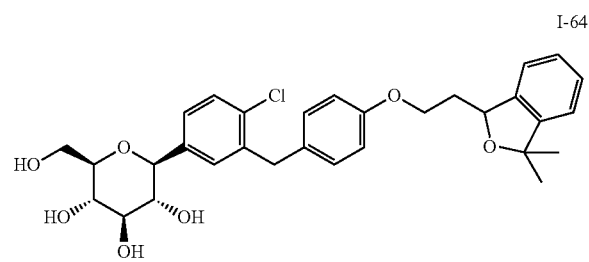
I-65
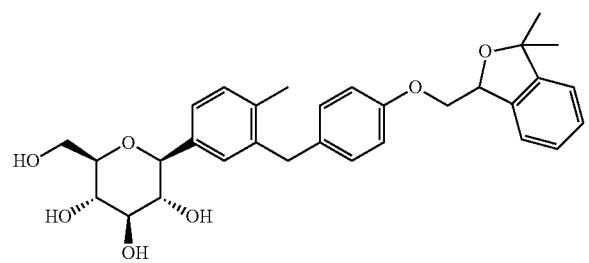
I-66
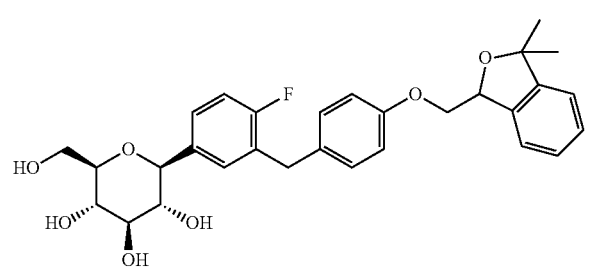
I-67
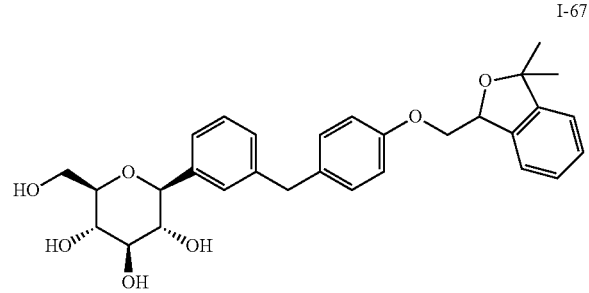
I-68
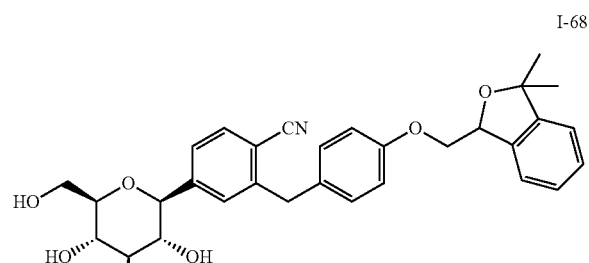
I-69
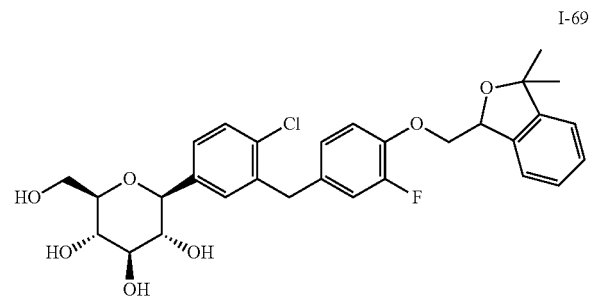
I-70
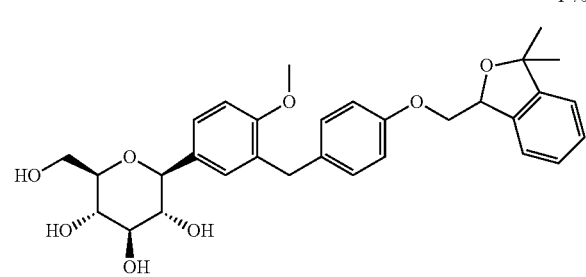
I-71
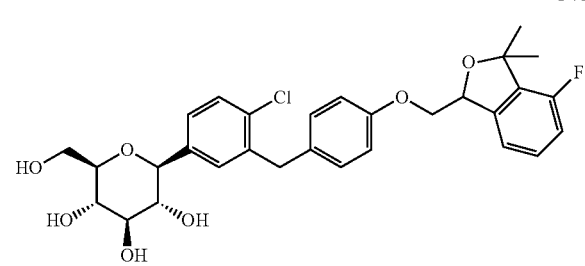
I-72
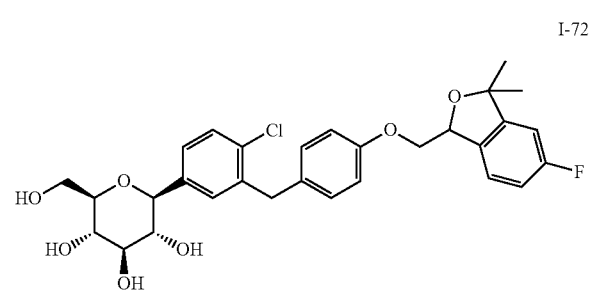
I-73
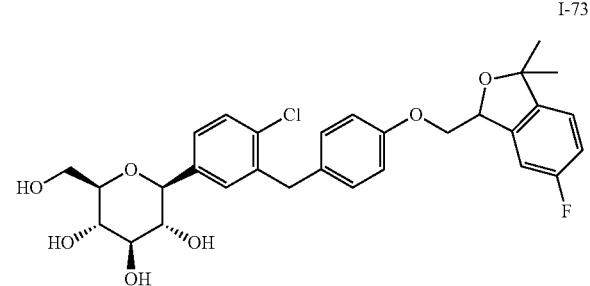

I-74
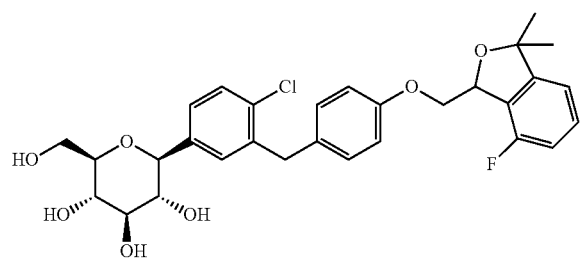
I-75
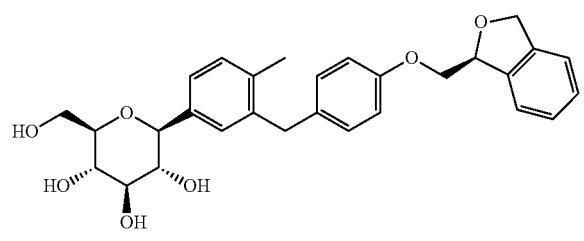
I-76
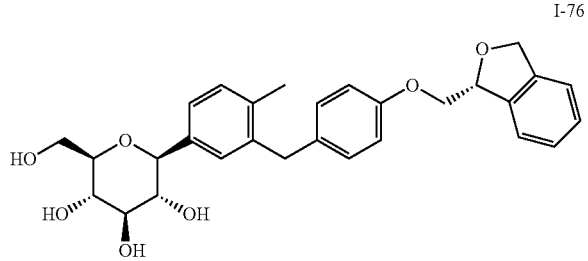
I-77
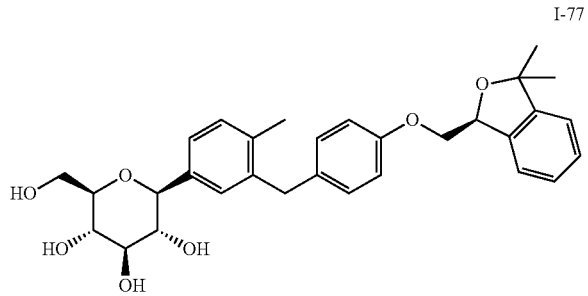
I-78
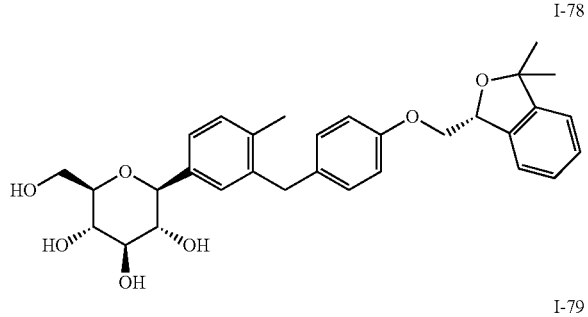
I-79
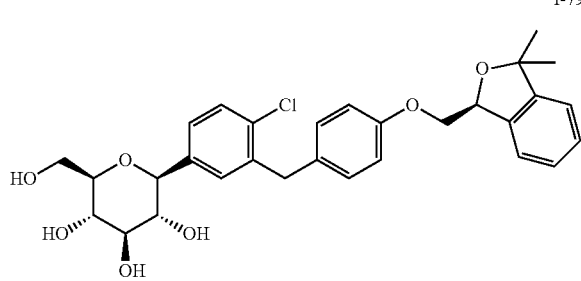
I-80
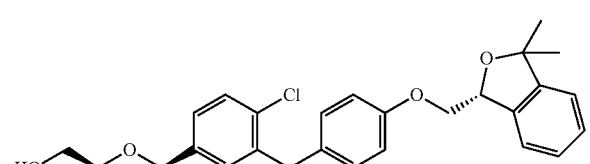
I-81
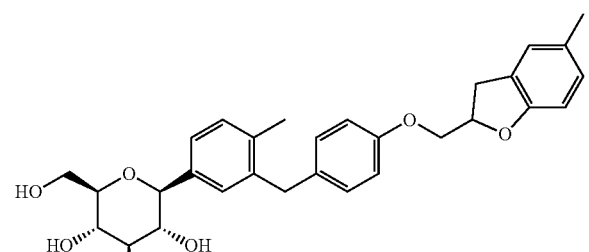
I-82
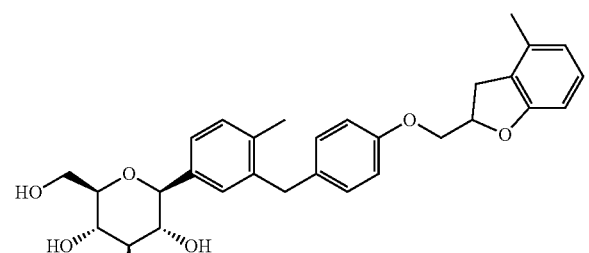
I-83
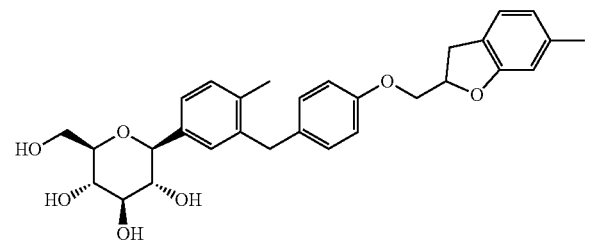
I-84
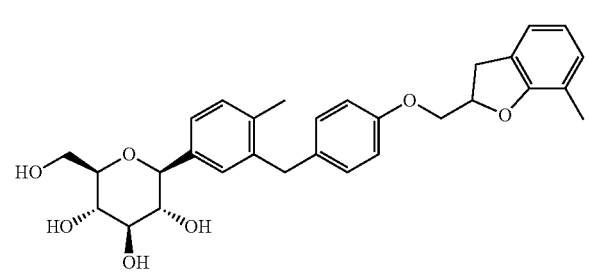

I-85
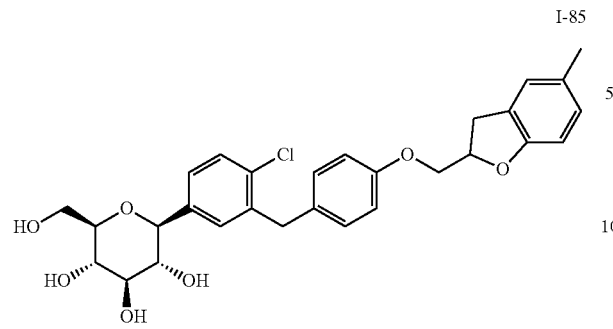
I-86
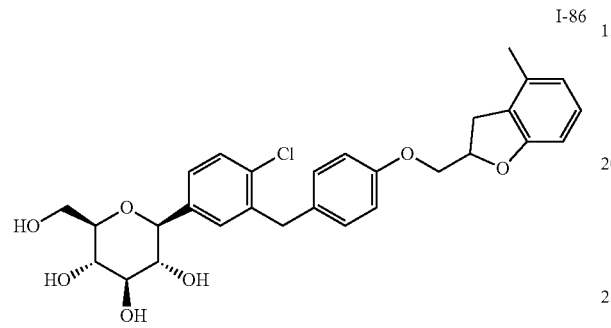
I-87
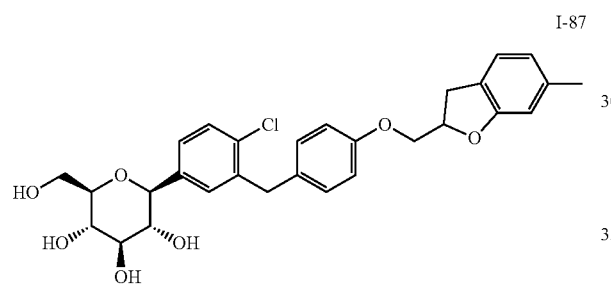
I-88
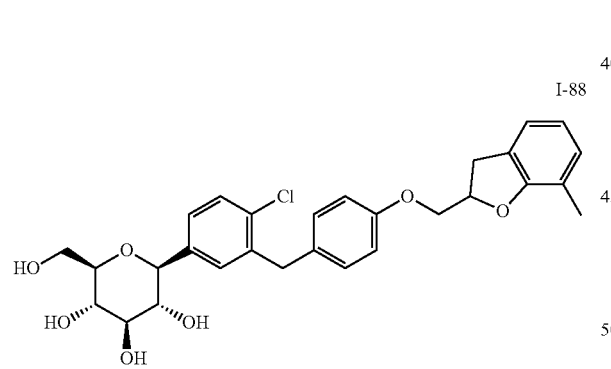
I-89
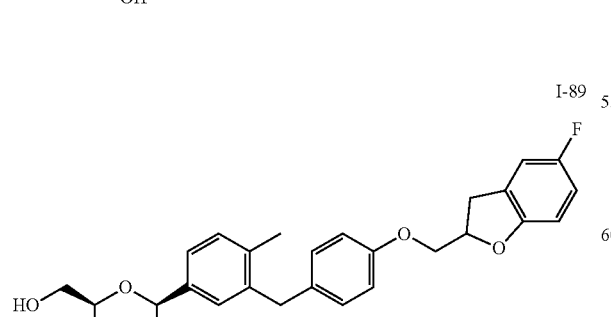
I-90
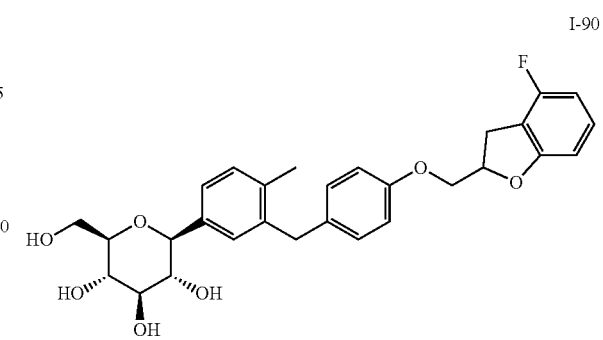
I-91
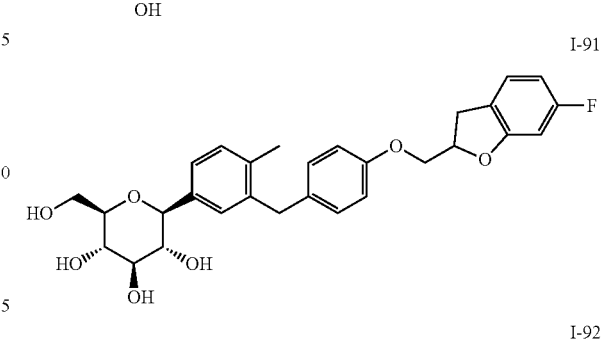
I-92
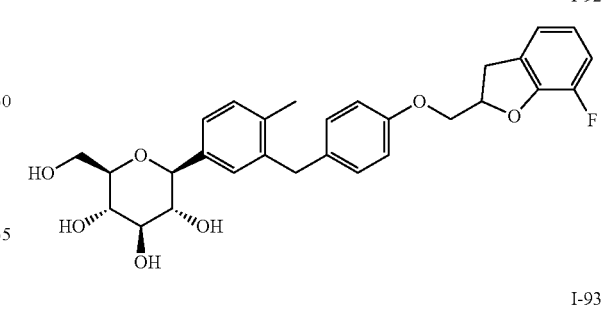
I-93
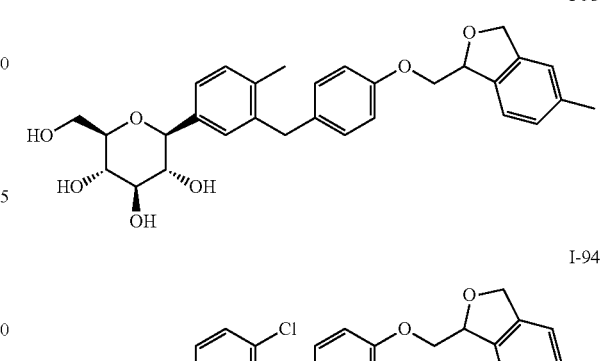
I-94
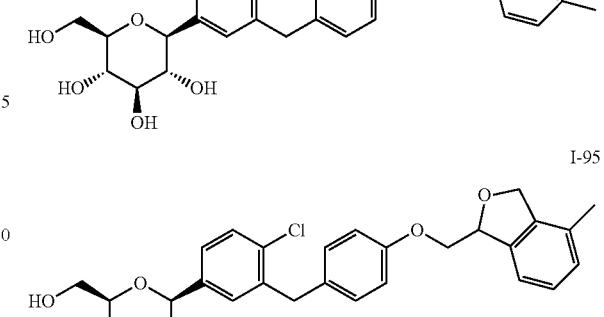
I-95

I-96
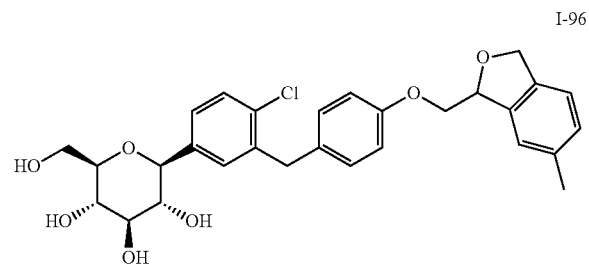
I-97
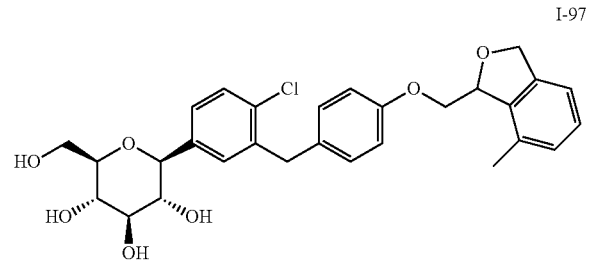
I-98
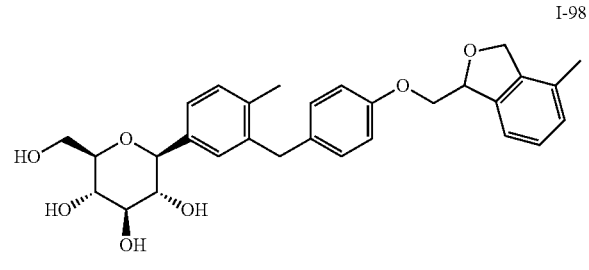
I-99
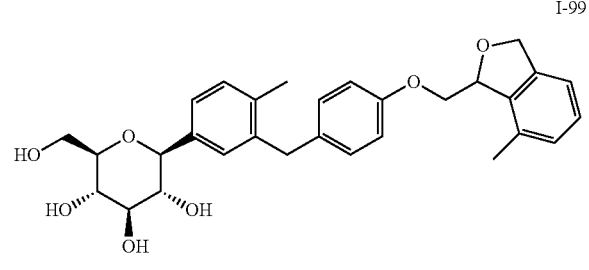
I-100
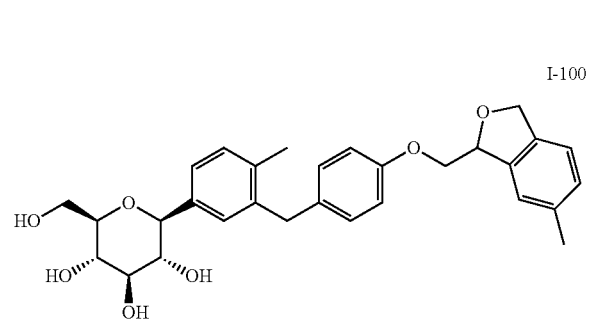
I-101
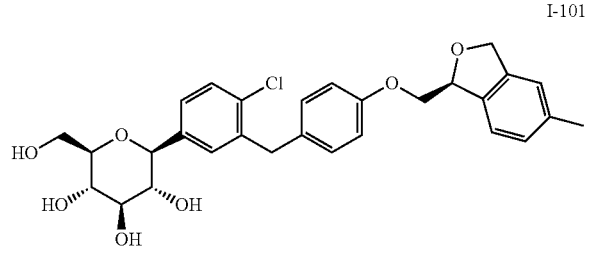
I-102
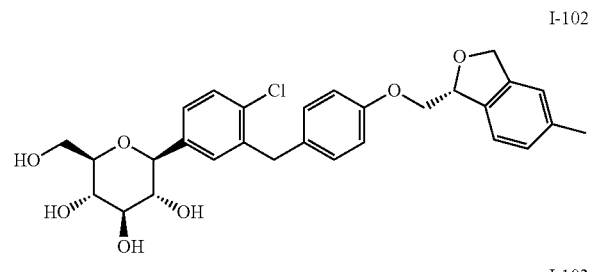
I-103
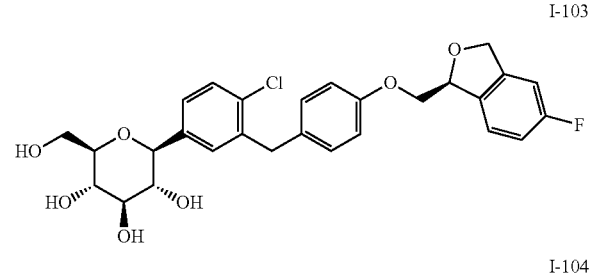
I-104
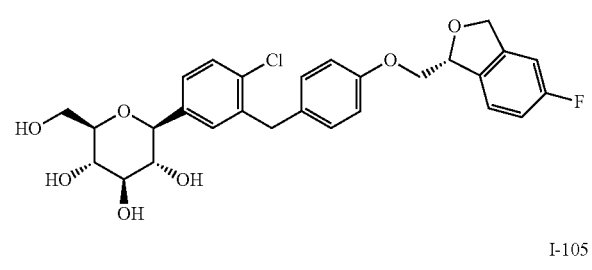
I-105
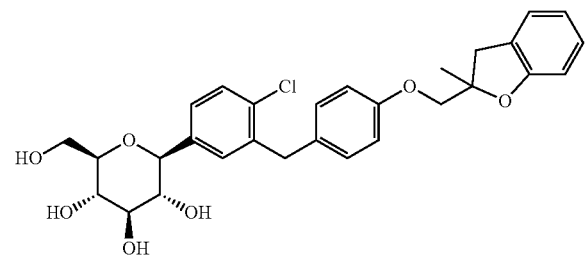
I-106
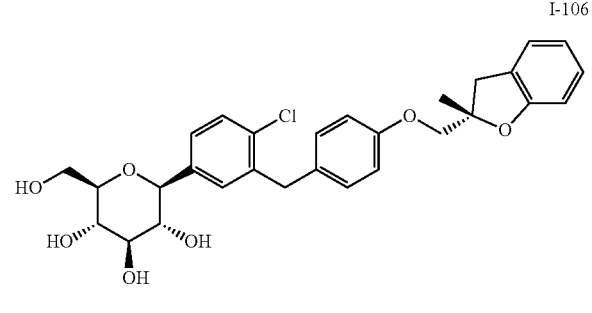
I-107
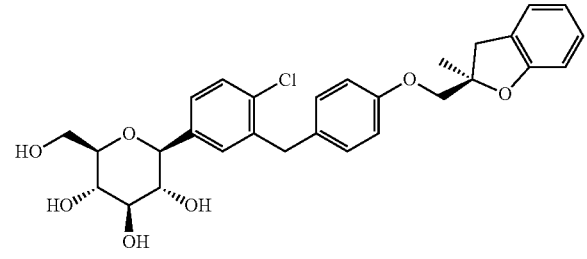

I-108
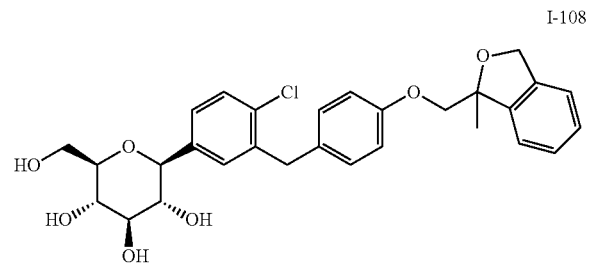
I-109
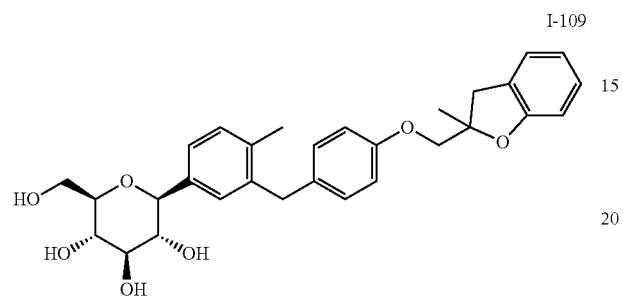
I-110
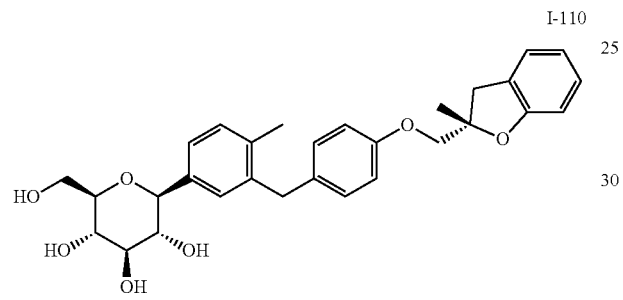
I-111
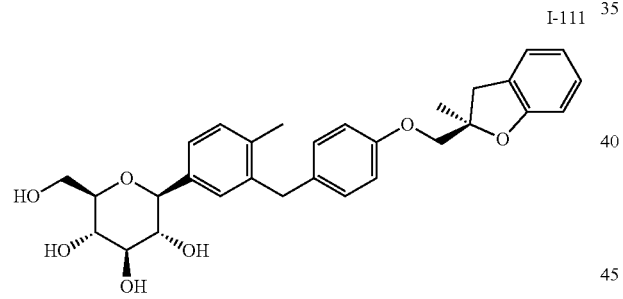
I-112
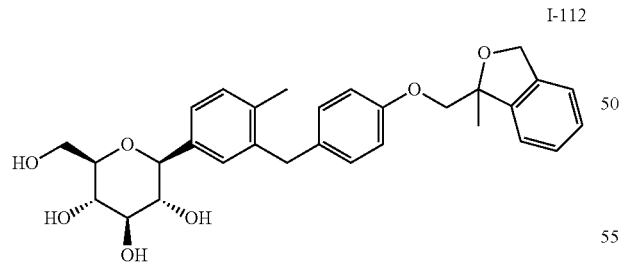
I-113
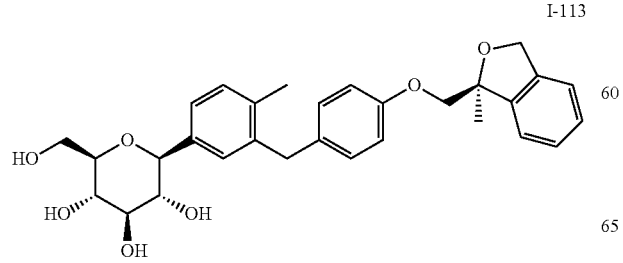
I-114
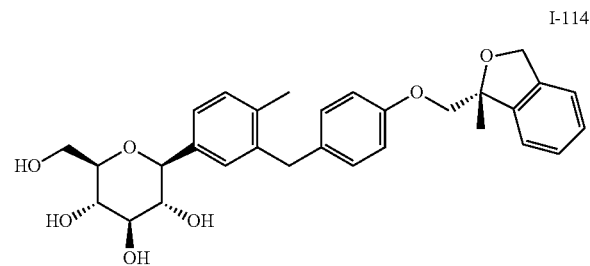
I-115
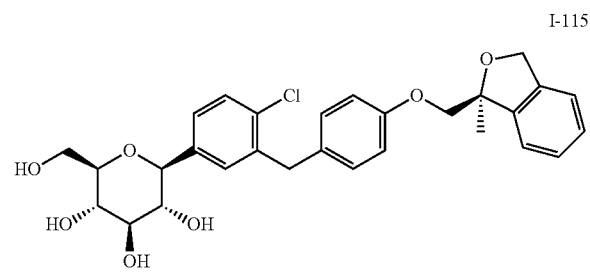
I-116
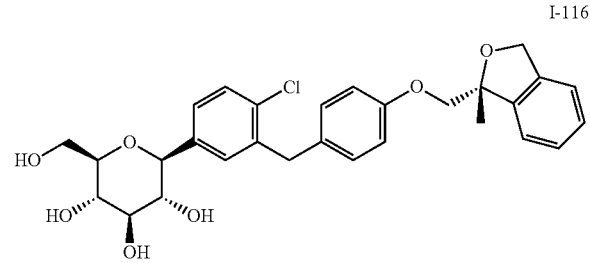
I-117
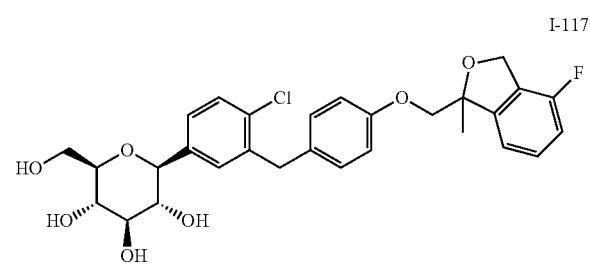
I-118
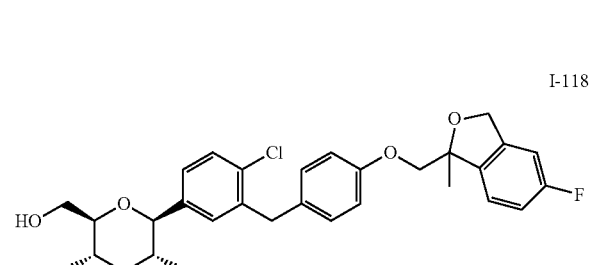
I-119
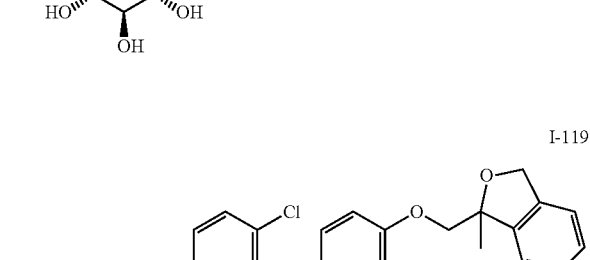
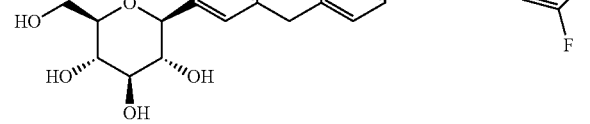

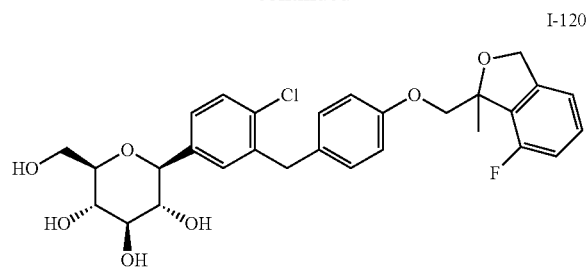
I-120
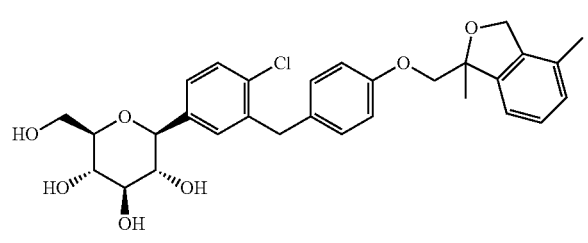
I-121
I-122
I-123
I-124
I-125
I-126
I-127
I-128
I-129
I-130
I-131

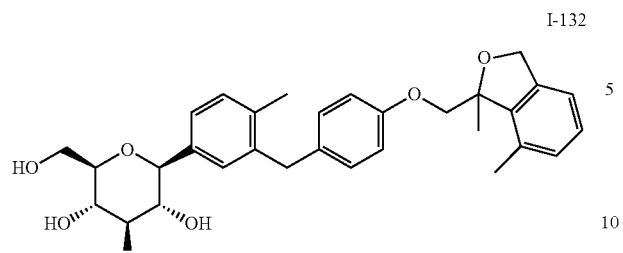
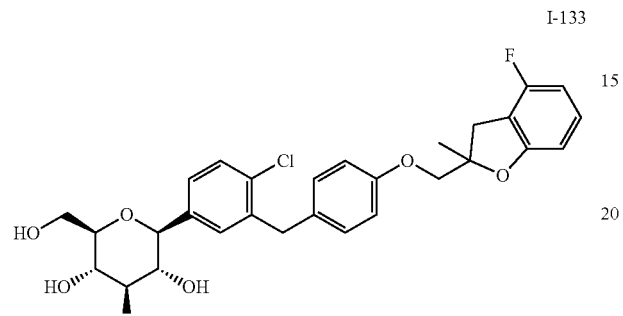

I-142

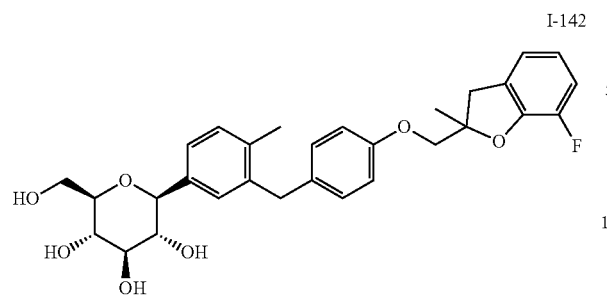

I-143

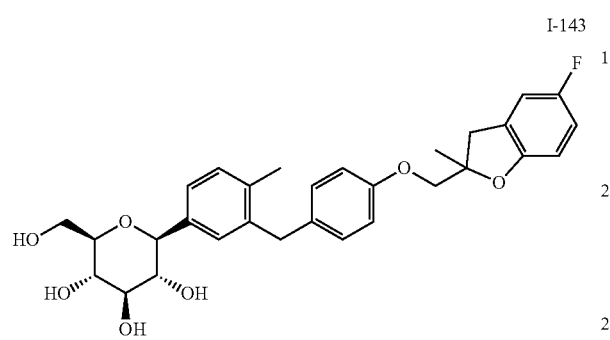

I-144

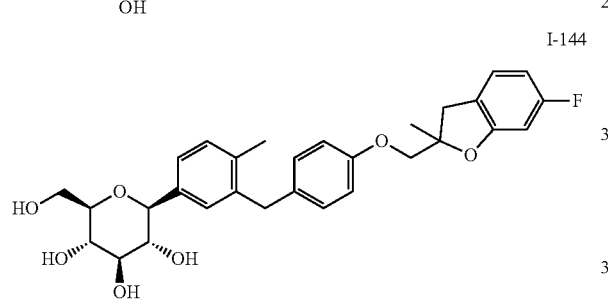

I-145

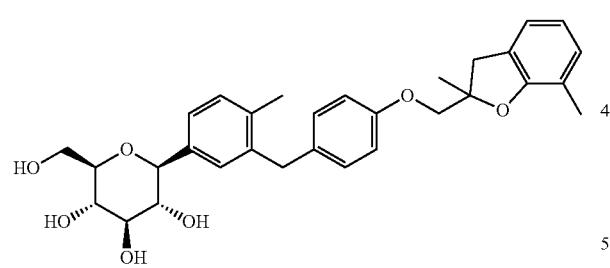

I-146

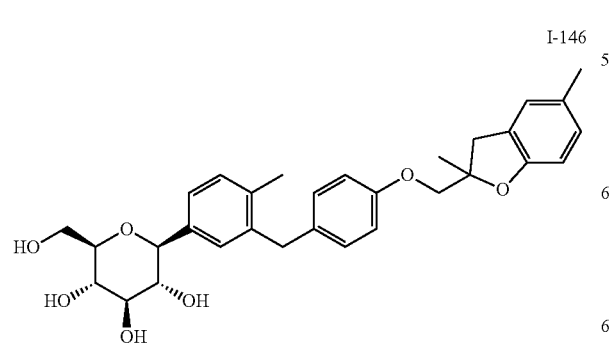

I-147

I-148

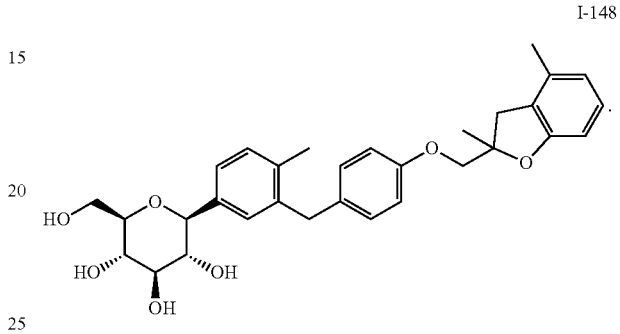

The present invention further relates to a process for preparing the C-aryl glycoside derivatives of formula (I), which is any one of the following methods:

Method 1: the method includes: in a solvent, deprotecting the acetyl protecting groups of compound 1-f in the presence of a base.

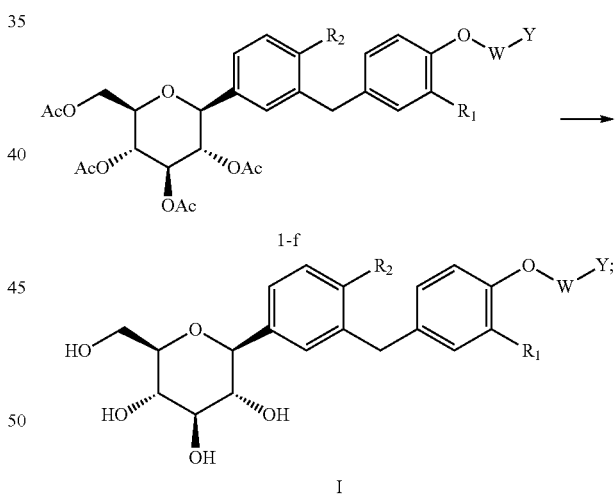

Method 2: the method includes: 1) in a solvent, compound 2-g reacts with

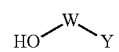

via Mitsunobu reaction in the presence of a condensation reagent; 2) in a solvent, deprotecting the acetyl protecting groups of compound 2-f obtained from step 1 in the presence of a base;

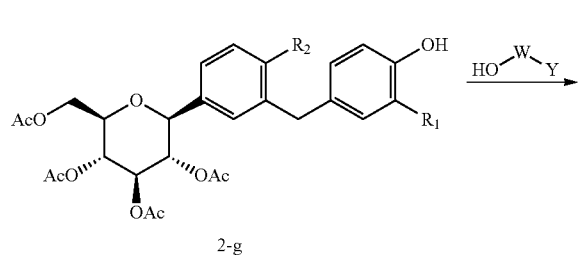

2-g

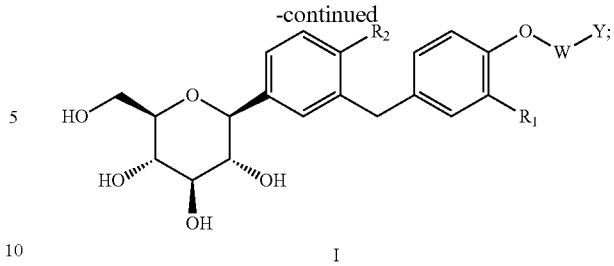

I

Wherein, V is Cl, Br, or I; other groups and symbols are the same as described previously.

wherein, in method 1, the conditions and procedures of the deacetylation reaction are commonly used in the art, in the present invention, the following condition is preferred: the solvent is preferably methanol, or a mixed solvent of methanol, THF and H₂O, when using a mixed solvent, the volume ratio of methanol, THF to H₂O is preferably 4:1:0.5-0.5:1:0.5, the amount of solvent is preferably 5-15 mL/mmol relative to the mole of compound 1-f; the base is preferably alkali alcoholate or alkali hydroxide, more preferably sodium methanolate or lithium hydroxide; the mole ratio of a base to compound 1-f is preferably 0.1:1-2:1; the reaction temperature is preferably in the range from 0 to 30° C.; the reaction can be detected by TLC, typically to the disappearance of the compound 1-f as the end of the reaction, preferably 0.5-12 h; after the reaction is finished, the product can be further purified through the post-treatment, preferably includes: the reaction system is adjusted pH to 6-8 with acetic acid, and then evaporated under vacuum, the residue is purified by column chromatography on silica gel or prep-TLC. The purification conditions and procedures of column chromatography or prep-TLC are commonly used in the art. In the present invention, preferably, the deacetylation reaction uses sodium methylate and methanol system, or sodium hydroxide, methanol, THF and water system. Wherein the volume ratio of methanol, THF to H₂O is preferably 4:1:0.5-0.5:1:0.5.

In method 1, the preparation method of compound 1-f is commonly used method well known in the art, preferably includes: in a solvent, a hydroxyl acetylation reaction is carried out with compound 1-e, and then recrystallization.

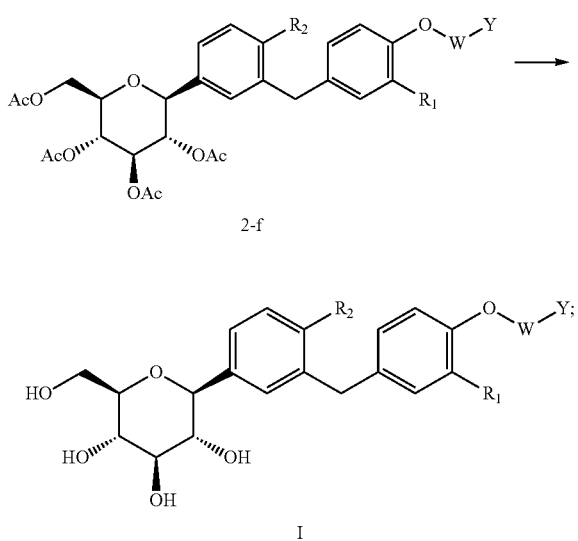

I

Method 3: the method includes: 1) in a solvent, compounds 3-g reacts with

via nucleophilic substitution reaction in the presence of a base; 2) in a solvent, deprotecting the acetyl protecting groups of compound 3-f obtained from step 1 in the presence of a base;

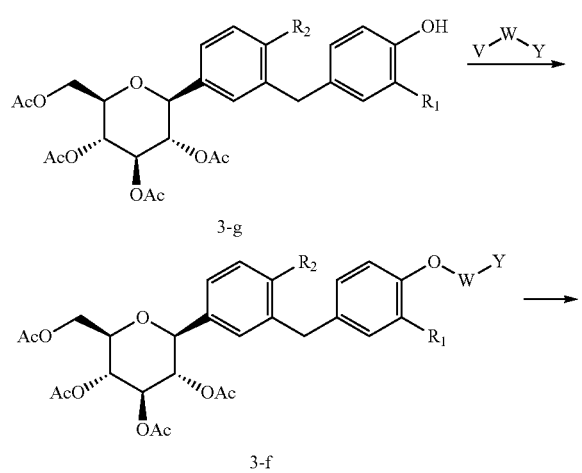

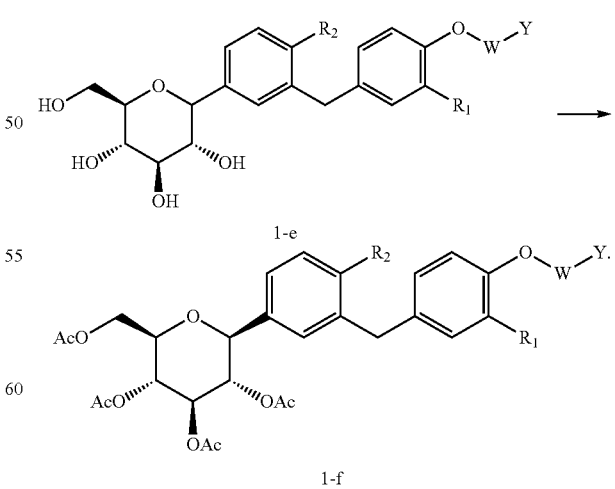

The acetylation reaction are commonly used acetylation reaction well known in the art, the reaction procedures and conditions can according to the reference: *J. Med. Chem.* 2008, 51, 1145-1149, the present invention is preferably the following conditions: the solvent is preferably DCM, the amount of solvent is preferably 5-20 mL/mmol relative to the mol of compound 1-e; wherein in the acetylation reaction, the acetylation reagent is preferably acetic anhydride; the mole ratio of acetylation reagent to compound 1-e is preferably 5:1-20:1. The procedure of the recrystallization is preferred: the solvent is preferably aqueous ethanol with a volume fraction not less than 50% and less than 100%, or absolute ethanol. The amount of ethanol for recrystallization is preferably 3-10 mL/mmol relative to the mole of compound 1-e. The recrystallization temperature is preferably in the range from 50 to 100° C.

In method 1, the preparation method of compound 1-e is commonly used method well known in the art, preferably includes: in a solvent, a reduction reaction is carried out with compound 1-d, boron trifluoride etherate and triethylsilane.

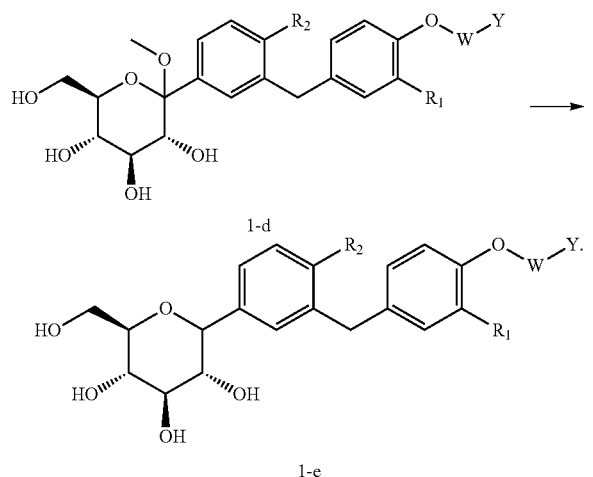

Wherein, the solvent is commonly used in the art, preferably a mixed solvent of DCM and acetonitrile, the volume ratio of DCM to acetonitrile is preferably 1:1-1:2. The amount of the solvent is generally not affect the progress of the reaction, the amount of solvent is preferably 5-15 mL/mmol relative to the mole of compound 1-d. Wherein, in boron trifluoride etherate and triethylsilane system, the mole ratio of triethylsilane to boron trifluoride etherate is preferably 1:1-1.5:1, the mole ratio of triethylsilane to compound 1-d is preferably 1.5:1-3:1. The reduction temperature is preferably in a range from −20 to 10° C. The reaction can be detected by HPLC or TLC, typically to the disappearance of the compound 1-d as the end of the reaction, preferably 2-5 h. After the reaction is finished, the product can be further purified through the post-treatment, preferably includes: the reaction system is quenched by addition of saturated NaHCO$_3$ aqueous solution, and then extracted with organic solvent, the organic layer is dried, the solvent is evaporated under vacuum to afford compound 1-e. Compound 1-e obtained from above treatment is usually not purified and directly used for the next step.

In method 1, the preparation method of compound 1-d is commonly used method well known in the art, which can according to the reference: *J. Med. Chem.* 2008, 51, 1145-1149, in the present invention is preferably the following conditions: In a solvent, at −78 to −60° C., treating compound 1-c with alkali lithium reagent for 0.5-1 h, and then treating with 2,3,4,6-tetrakis-O-(trimethylsilyl)-D-glucono-lactone (according to the reference: *J. Med. Chem.* 2008, 51, 1145-1149) for 0.5-2 h (preferably 1 h), and then at 10-30° C., treating with methanesulfonic acid methanol solution.

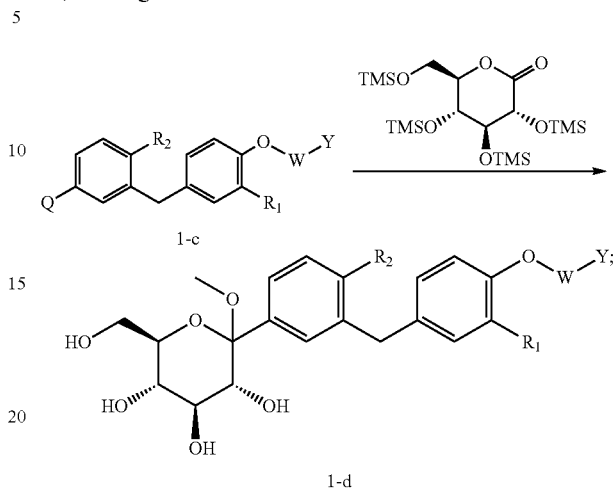

Wherein, Q is Br or I.

The solvent is commonly used in the art, preferably a mixed solvent of THF and toluene, the volume ratio of THF to toluene is preferably 1:1-1:4. The organic lithium regent is preferably tert-butyllithium or n-butyllithium; when R$_2$ is CN, The organic lithium regent is preferably tert-butyllithium. The mole ratio of organic lithium regent to compound 1-c is preferably 0.9:1-2:1, the mole ratio of 2,3,4,6-tetrakis-O-(trimethylsilyl)-D-gluconolactone to compound 1-c is preferably 1:1-1.5:1. Wherein, the molarity of the methanesulfonic acid solution in methanol is 0.5-1.2 mol/L. The mole ratio of methanesulfonic acid to compound 1-c is preferably 1.2:1-3:1. The reaction can be detected by HPLC or TLC, typically to the disappearance of the compound 1-c as the end of the reaction.

In method 1, the preparation method of compound 1-c is preferably includes the following steps: in a solvent, a reduction reaction is carried out with compound 1-b, boron trifluoride etherate and triethylsilane.

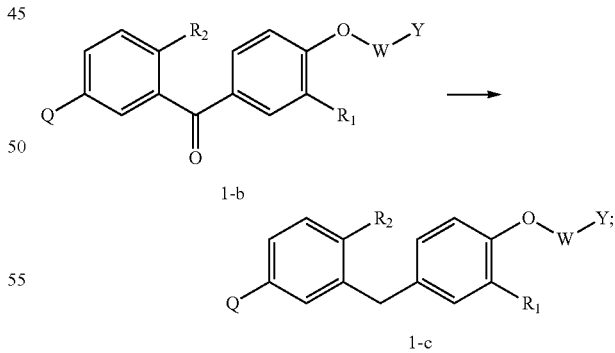

Wherein, Q is Br or I.

The solvent is commonly used in the art, preferably a mixed solvent of 1,2-dichloroethane and acetonitrile, the volume ratio of 1,2-dichloroethane to acetonitrile is preferably 1:2-2:1. The amount of the solvent is generally not affect the progress of the reaction, the amount of solvent is preferably 5-15 mL/mmol relative to the mole of compound 1-b. Wherein in boron trifluoride etherate and triethylsilane system, the mole ratio of triethylsilane to boron trifluoride etherate is preferably 1.2:1-3:1, the mole ratio of triethylsilane to compound 1-b is preferably 1.5:1-4:1. The reduction temperature is preferably in the range from 0 to 30° C. The reaction can be detected by HPLC or TLC, typically to the disappearance of the compound 1-b as the end of the reaction. After the reaction is finished, the product can be further purified through the post-treatment, preferably includes: the reaction system is quenched by addition of saturated NaHCO$_3$ aqueous solution, and then extracted with organic solvent, the organic layer is dried, the solvent is evaporated under vacuum to afford compound 1-c. Compound 1-c can be purified by column chromatography on silica gel or by recrystallization.

In method 1, in the preparation method of compound 1-c, when R$_2$ is CN, the preparation method for compound 1-c is preferably includes the following steps: in a solvent, a reduction reaction is carried out with compound 1-b and sodium hydroxide/methanol system, and then the reaction was carried out with triethylsilane and boron trifluoride etherate system to afford compound 1-c. The sodium hydroxide and methanol system are commonly used in the art. The mole ratio of sodium hydroxide to compound 1-b is preferably 1:1-3:1. The amount of the solvent is generally not affect the progress of the reaction, the amount of solvent is preferably 5-20 mL/mmol relative to the mole of compound 1-b.

In method 1, the preparation method of compound 1-b is preferably included the following steps: in a solvent, a nucleophilic substitution reaction is carried out with compound 1-a and $$HO\diagdown W \diagdown Y.$$

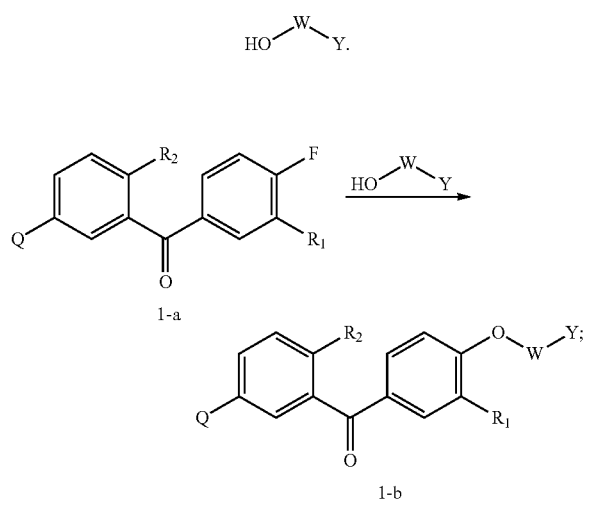

Wherein, Q is Br or I.

The solvent is commonly used in the art, preferably N,N-dimethylformamide. The amount of the solvent is generally not affect the progress of the reaction, the amount of solvent is preferably 2-20 mL/mmol relative to the mole of compound 1-a. the base can be alkali alcoholate, preferably potassium tert-butanolate. The mole ratio of a base to Compound 1-a is preferably in the range from 0.9 to 2.5. The mole ratio of to compound 1-a is preferably 1.0:1-2.0:1. the reaction temperature is preferably in the range from 20 to 50° C.; the reaction can be detected by HPLC or TLC, typically to the disappearance of the compound 1-a as the end of the reaction, preferably 1-18 h; after the reaction is finished, the product can be further purified through the post-treatment, preferably includes: the reaction system is diluted with solvent, the organic layer is washed with water and brine, dried, the solvent is evaporated under vacuum to afford compound 1-b. the crude product is purified by column chromatography on silica gel or recrystallization. The purification method by column chromatography on silica gel or recrystallization is commonly used method well known in the art. The procedure of the recrystallization is preferred: the solvent is preferably aqueous ethanol with a volume fraction not less than 50% and less than 100%, or absolute ethanol. The amount of ethanol for recrystallization is preferably 2-50 mL/mmol.

In method 2, in step 1, compound 2-g can be prepared by the conventional method in the art, for example: WO2011/048148A2. The solvent is commonly used in the art, preferably THF. The amount of the solvent is generally not affect the progress of the reaction, the amount of solvent is preferably 2-20 mL/mmol relative to the mole of compound 2-g. The condensation system is commonly used in the art, preferably triphenylphosphine and diethyl azodicarboxylate, or triphenylphosphine and diisopropyl azodicarboxylate. The mole ratio of triphenylphosphine to DEAD is preferably 1:1-1.5:1. The mole ratio of triphenylphosphine to DIAD is preferably 1:1-1.5:1. The mole ratio of $$HO\diagdown W \diagdown Y$$

to compound 2-g is preferably 1:1-3:1. the Mitsunobu reaction temperature is preferably in the range from 0 to 30° C.; the reaction can be detected by HPLC or TLC, typically to the disappearance of the compound 2-g as the end of the reaction, preferably 2-15 h; after the reaction is finished, the product can be further purified through the post-treatment, preferably includes: the reaction system is diluted with a solvent, the organic layer is washed with NH$_4$Cl aqueous solution and brine, dried, the solvent is evaporated under vacuum to afford compound 2-g. The crude product is purified by column chromatography on silica gel. The purification method by column chromatography on silica gel is commonly used method well known in the art.

In method 2, in step 2, the conditions and procedures of deacetylation reaction are commonly used in the art. In the present invention the preferably deacetylation reaction condition and procedure are the same as method 1.

In method 3, in step 1, compound 3-g can be prepared by the conventional method in the art, for example: WO2011/048148A2. The solvent is commonly used in the art, preferably N,N-dimethylformamide or dimethyl sulfoxide. The amount of the solvent is generally not affect the progress of the reaction, the amount of solvent is preferably 5-20 mL/mmol relative to the mole of compound 3-g. The base is preferably Cs$_2$CO$_3$ or K$_2$CO$_3$. The mole ratio of a base to compound 3-g is preferably in the range from 1 to 2.5. The mole ratio of

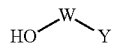

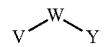

to compound 3-g is preferably in the range from 1 to 2.5. the nucleophilic substitution reaction temperature is preferably in the range from 40 to 65° C.; the reaction can be detected by HPLC or TLC, typically to the disappearance of the compound 3-g as the end of the reaction, preferably 2-15 h; after the reaction is finished, the product can be further purified through the post-treatment, preferably includes: the reaction system is diluted with ethyl acetate, the organic layer is washed with $NH_4Cl$ aqueous solution and brine, dried, the solvent is evaporated under vacuum to afford compound 3-g. The crude product is purified by column chromatography on silica gel. The purification method by column chromatography on silica gel is commonly used method well known in the art.

In method 3, in step 2, the conditions and procedures of deacetylation reaction are commonly used in the art. In the present invention the preferably deacetylation reaction condition and procedure are the same as method 1.

In the present invention, all compounds can be prepared via method 1 described previously.

The present invention also relates to any one of the following compounds:

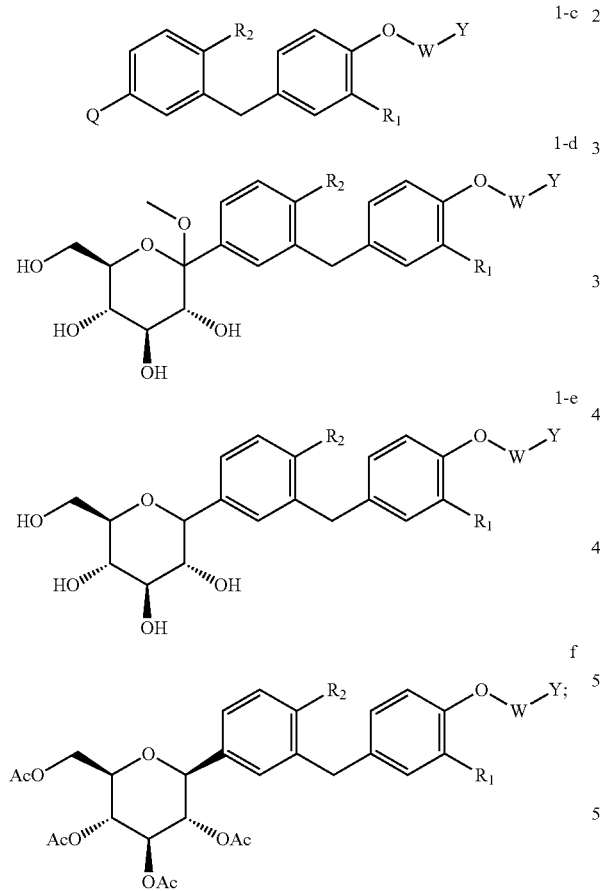

Wherein, all the groups are the same as described previously; compound f could be compound 1-f, compound 2-f, or compound 3-f.

Unless otherwise stated, the following terms in this invention have the following definitions:

The term "alkyl" as used herein, refers to a saturated aliphatic hydrocarbon group including 1 to 20 carbon atoms straight chain and branched chain groups. Preferably an alkyl group is having 1 to 10 carbon atoms, more preferably having 1 to 8 carbon atoms. For example: methyl, ethyl, n-propyl, iso-propyl, n-butyl, sec-butyl, iso-butyl, tert-butyl, n-pentyl, n-hexyl, n-heptyl, n-octyl, n-nonyl, and n-decyl, 4,4-dimethylpentyl, 2,2,4-trimethylpentyl, undecanyl, docecanyl, and their isomers, etc.

The term "cycloalkyl" as used herein, refers to a saturated or partially unsaturated (contain 1 or 2 double bond) monocyclic, bicyclic or tricyclic cycloalkyl ring group containing 3 to 20 carbon atoms. Preferably 3 to 10-mono-cycloalkyl, more preferably 5 to 8-mono-cycloalkyl. For example: cyclopropyl, cyclobutyl, cyclopentyl, cyclohexyl, cycloheptyl, cyclooctyl, cyclodecanyl, cyclodocecanyl, cyclohexenyl, bornyl, decahydronaphthyl, bicyclo [2.2.1] heptenyl, etc. The term "$C_{5-8}$ cycloalkyl" refers to a cycloalkyl ring group containing 5 to 8 carbon atoms.

The term "heterocycloalkyl" as used herein, refers to a saturated or partially unsaturated (containing 1 or 2 double bonds) non-aromatic ring system consisting of carbon atoms and heteroatom(s) independently selected from O, N, and S. wherein said ring system can be mono-cyclic, bi-cyclic or tir-cyclic ring system. Preferably 3 to 10-heterocycloalkyl, more preferably 5 to 8-heterocycloalkyl, most preferably 5 to 8-mono-heterocycloalkyl. In the present invention, the heterocycloalkyl preferably contains 1, or 2 heteroatoms, and the N, C or S can independently be oxidized in the cyclic ring system. The N atom can further be substituted to form tertiary amine or ammonium salts. For example: aziridinyl, tetrahydrofuran-2-yl, morpholin-4-yl, thiomorpholin-4-yl, thiomorpholin-4-yl-S-oxide, piperidin-1-yl, N-alkyl-piperidin-4-yl, pyrrolidin-1-yl, N-alkyl-pyrrolidin-2-yl, pyrazin-1-yl, and 4-alkyl-pyrazin-1-yl,

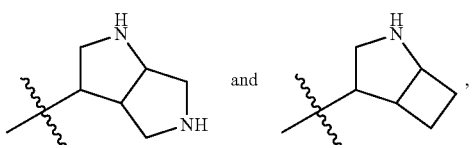 [SMILES: *C1CNC2CNCC12 ; *C1CNC2CCC12]

etc.

The term "$C_{3-7}$ heterocycloalkyl" refers to a mono-heterocycloalkyl ring group containing 3 to 7 carbon atoms, wherein the number of heteroatom is 1 or 2. The term "$C_{4-6}$ heterocycloalkyl" refers to a mono-heterocycloalkyl ring group containing 4 to 6 carbon atoms, wherein the number of heteroatom is 1 or 2.

The term "cycloalkylalkyl" as used herein, refers to a cycloalkyl, as defined herein, appended to the parent molecular moiety through an alkyl group, as defined herein. Wherein, "cycloalkylalkyl" includes the definitions of the above alkyl and cycloalkyl.

The term "heterocycloalkylalkyl" as used herein, refers to a heterocyloalkyl, as defined herein, appended to the parent molecular moiety through an alkyl group, as defined herein. Wherein, "heterocycloalkylalkyl" includes the definitions of the above alkyl and heterocycloalkyl.

The term "alkoxy" as used herein, refers to a cyclic or non-cyclic alkyl group having a number of carbon atoms, as defined herein, appended to the parent molecular moiety through an oxygen atom, which includes alkyloxy, cycloalkyloxy, and heterocycloalkyloxy. Wherein, "alkoxy" includes the definitions of the above alkyl, heterocycloalkyl, and cycloalkyl.

The term "cycloalkylalkoxy" as used herein, refers to an alkyl hydrogen atom of the alkoxy group, as defined herein, is substituted by a cycloalkyl. Wherein, "cycloalkylalkoxy" includes the definitions of the above cycloalkyl and alkoxy.

The term "heterocycloalkylalkoxy" as used herein, refers to an alkyl hydrogen atom of the alkoxy group, as defined herein, is substituted by a heterocycloalkyl. Wherein, "heterocycloalkylalkoxy" includes the definitions of the above heterocycloalkyl and alkoxy.

The term "alkenyl" as used herein, refers to a straight, branched chain or cyclic non-aromatic hydrocarbon ring containing from 1 to 3 carbon-carbon double bonds, preferable one carbon-carbon double bond. The term "$C_{2-6}$ alkenyl" refers to an alkenyl group containing 2 to 6 carbon atoms, includes: vinyl, 2-propenyl, 2-butenyl, 2-methylbutenyl and cyclohexenyl. Wherein said alkenyl can be further substituted.

The term "alkynyl" as used herein, refers to a straight, branched chain or cyclic non-aromatic hydrocarbon ring containing from 1 to 3 carbon-carbon triple bonds, preferable one carbon-carbon triple bond. The term "$C_{2-6}$ alkynyl" refers to an alkynyl group containing 2-6 carbon atoms, includes: ethynyl, 2-propynyl, 2-butynyl, and 3-methylbutynyl.

The term "aryl" as used herein, refers to any stable 6 to 10 membered mono or bicyclic aromatic group, for example, phenyl, naphthyl, tetrahydronaphthyl, 2,3-dihydro-1H-indenyl, or biphenyl, etc. The term "$C_6$ aryl" refers to a 6 membered aryl, for example phenyl.

The term "heteroaryl", as used herein, refers to an aromatic ring group containing at least one heteroatom independently selected from N, O, and S. Wherein said heteroaryl can be a 5- to 7-membered monocyclic heteroaryl or a 7- to 12-membered bicyclic heteroaryl. Preferably 5- to 6-membered heteroaryl. In the present invention, the number of heteroatoms prefers to be 1, or 2, includes: indazolyl, isoindazolyl, indolyl, isoindolyl, benzofuranyl, benzothienyl, benzo[d][1,3]dioxolyl, benzothiazolyl, benzoxazolyl, quinolinyl, isoquinolinyl and quinazolinyl, etc. The term "$C_{3-5}$ heteroaryl" refers to a mono-heteroaryl containing 3- to 5-carbon atoms, the number of heteroatoms is 1, or 2. The term "$C_{3-4}$ heteroaryl" refers to a mono-heteroaryl containing 3- to 4-carbon atoms, the number of heteroatoms is 1, or 2.

The term "bicyclic group", as used herein, refers to two monocyclic rings across a bond between two adjacent atoms to form a fused ring group; wherein said monocyclic ring includes aryl, heteroaryl, cycloalkyl and heterocycloalkyl ring. In the present invention, two rings of a bicyclic group include at least one aromatic ring. "$C_{5-8}$ cycloalkyl fused $C_6$ aryl" includes, but is not limited to, bicyclo[4.2.0]octa-1,3,5-triene, 2,3-dihydro-1H-indene, 1,2,3,4-tetrahydronaphthalene, 6,7,8,9-tetrahydro-5H-benzo[7]annulene, 6,9-dihydro-5H-benzo[7] annulene, or 5,6,7,8,9,10-hexahydrobenzo[8]annulene; "$C_{5-8}$ cycloalkyl fused $C_{3-5}$ heteroaryl" includes, but is not limited to, 2,3-cyclopentenopyridine, 5,6-dihydro-4H-cyclopenta[b]thiophene, or 5,6-dihydro-4H-cyclopenta[b]furan; "$C_{4-6}$ heterocycloalkyl fused $C_6$ aryl" includes, but is not limited to, 2,3-dihydrobenzofuran

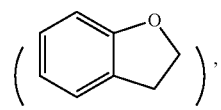

1,3-dihydroisobenzofuran

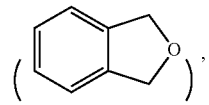

indoline, 2,3-dihydrobenzo[b]thiophene, 2H-chromene, 1,2,3,4-tetrahydroquinoline, 2,3-dihydrobenzo[b][1,4]dioxine, 3,4-dihydro-2H-benzo[b][1,4]oxazine,

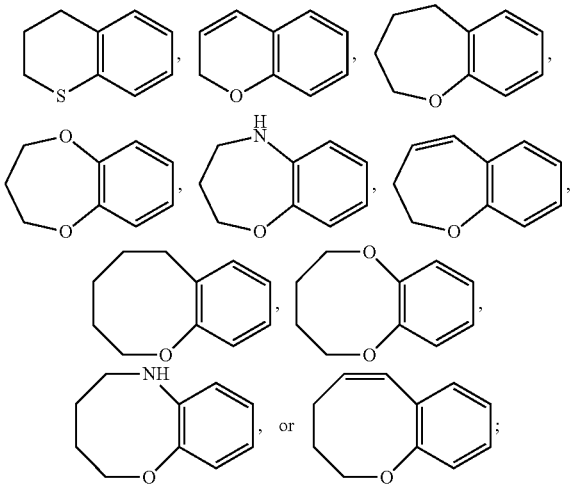

"$C_{3-7}$ heterocycloalkyl fused $C_{3-5}$ heteroaryl" includes, but is not limited to, naphthyridine,

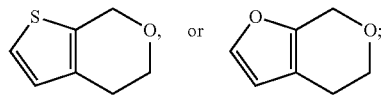 [SMILES: c1cc2c(s1)COCC2 ; c1cc2c(o1)COCC2]

"$C_6$ aryl fused $C_6$ aryl" includes, but is not limited to, naphthalene; "$C_{3-4}$ heteroaryl fused $C_6$ aryl" includes, but is not limited to, benzofuran, benzo[b]thiophene, indole, benzothiazole, benzoxazole, indazole, benzopyridazine, benzimidazole, quinoline, isoquinoline; "$C_{3-5}$ heteroaryl fused $C_{3-5}$ heteroaryl" includes, but is not limited to, purine or pteridine;

When bicyclic group contains a non-aromatic ring, it is preferably attached to the side group W of formula I through any ring atom contained within the non-aromatic ring. The non-aromatic ring is preferably selected from a cycloalkyl or heterocycloalkyl ring. When bicyclic group contains two aromatic rings, it is preferably attached to the side group W of formula I through any ring atom contained within the bicyclic ring group, wherein said aromatic ring can be selected from aryl or heteroaryl ring. Wherein, "bicyclic group" includes the definitions of the above aryl, heterocycloalkyl, cycloalkyl and heteroaryl.

The term "halo" or "halogen" as used herein refers to Cl, Br, I or F.

The term "haloalkyl" as used herein, refers to an alkyl group as defined herein, is substituted by at least one halogen, as defined herein. Wherein, "haloalkyl" includes the definitions of the above halogen and alkyl.

The term "haloalkoxy" as used herein, means an alkoxy group as defined herein, is substituted by at least one halogen, as defined herein. Wherein, "haloalkoxy" includes the definitions of the above halogen and alkoxy.

The term "amino" as used herein, refers to —NH$_2$. The term "alkylamino" as used herein, refers to at least one hydrogen of an amino group is substituted by alkyl. Wherein, "alkylamino" includes the definitions of the above alkyl, heterocycloalkyl and cycloalkyl.

The term "sulfonyl" as used herein, refers to —SO$_2$—.

The term "alkylsulfonyl" as used herein, refers to an alkyl group appends to the parent molecular moiety through —SO$_2$—. Wherein, "alkylsulfonyl" includes the definitions of the above alkyl and sulfonyl.

The term "arylsulfonyl" as used herein, refers to an aryl group appends to the parent molecular moiety through —SO$_2$—. Wherein, "arylsulfonyl" includes the definitions of the above aryl and sulfonyl.

The term "heteroarylsulfonyl" as used herein, refers to a heteroaryl group appends to the parent molecular moiety through —SO$_2$—. Wherein, "heteroarylsulfonyl" includes the definitions of the above heteroaryl and sulfonyl.

The present invention also relates to a pharmaceutical composition comprising a C- aryl glycoside derivative of formula (I), its isotope-labeled derivatives, a pharmaceutically acceptable salt and/or prodrug thereof, and a pharmaceutically acceptable excipient.

The term "stereoisomer" includes enantiomer and diastereomer.

The described isotope-labeled derivatives include: the hydrogen atom (1 to 5) of a compound of formula (I) is substituted by 1 to 5 deuterium atoms, respectively; the carbon atom (1 to 3) of a compound of formula (I) is substituted is substituted by 1 to 3 C$_{14}$ atoms; or the oxygen atom of a compound of formula (I) is substituted by 1 to 3 O$_{18}$ atoms.

The pharmaceutical composition described herein further comprises other drugs or pharmaceutical agents for treatment of diabetes.

The term "prodrug" as used herein, refers to compound which can be transformed to the original active compound after in vivo metabolism. Wherein said prodrug is includes, but is not limited to the ester or hydrate of C- aryl glycoside derivatives of formula I.

The described pharmaceutically acceptable excipient is a pharmaceutically acceptable carrier, diluent, and/or vehicle.

The present invention also relates to the use of a C- aryl glycoside derivative of formula (I), a pharmaceutically acceptable salt or use of the pharmaceutical composition disclosed herein in preparation of SGLT inhibitors.

The present invention also relates to the use of a C- aryl glycoside derivative of formula (I), a pharmaceutically acceptable salt thereof or use of the pharmaceutical composition disclosed herein in the preparation of a drug in treating SGLT mediated relevant diseases.

The described SGLT mediated relevant diseases include diabetes (type II and type I), diabetic complications, obesity, hypertension, and any diabetes related metabolic disorders.

The present invention also relates to the use of a C- aryl glycoside derivative of formula (I), a pharmaceutically acceptable salt thereof or use of the pharmaceutical composition disclosed herein combined with additional pharmaceutical agents.

The described additional pharmaceutical agents preferably include one or more agents for the treatment of diabetes, diabetic complications, hyperlipidemia, obesity and hypertension.

In the present invention, preferably synthetic procedure is shown as below:

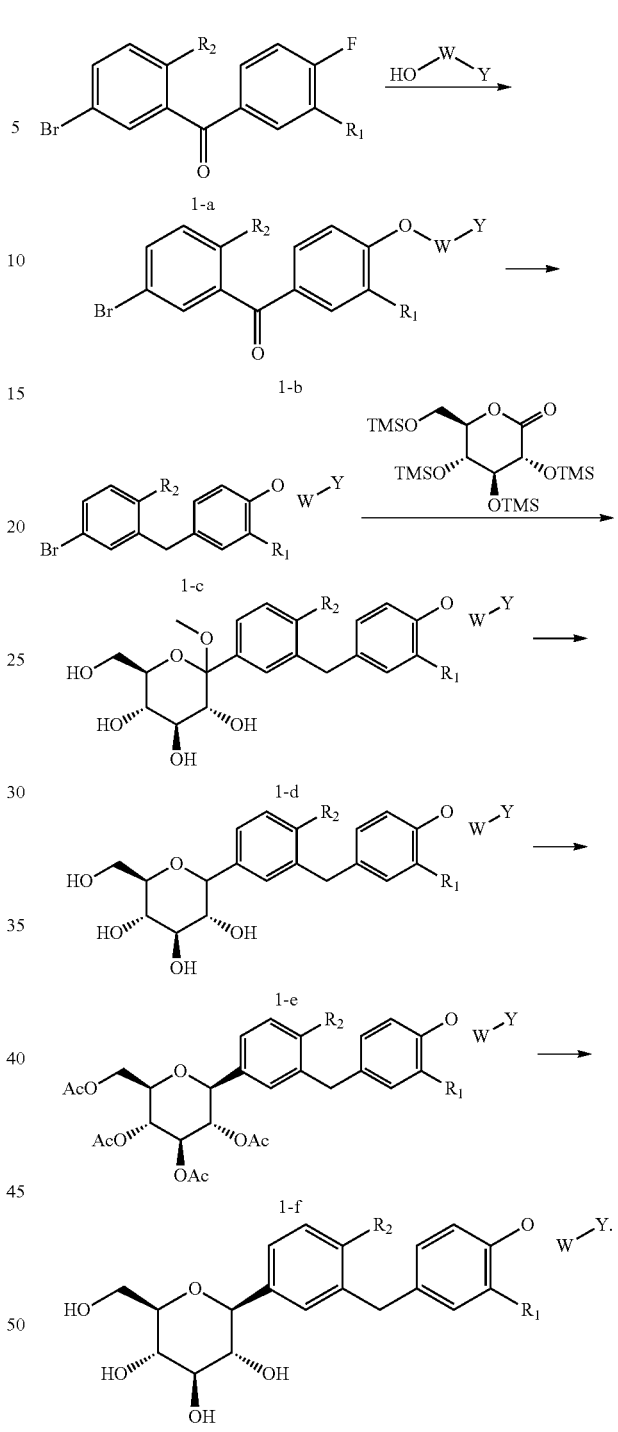

The term "room temperature" as used herein, refers to 10-30° C.

Under the basis of no violation of common sense in the art, the above described preferably conditions, can be combined together, to achieve the preferably examples in this invention.

In the present invention, all of the reagents and materials are commercially available.

The advantages of this invention include: the aryl glycoside derivatives have potent inhibitory activity against SGLT-2, and can effectively treat SGLT related diseases, and represent new anti-diabetic drug.

EXAMPLES

The following examples serve to illustrate this invention, but the examples should not be considered as limiting the scope of the invention. Some of the experimental methods of the following examples that are not indicated the specific conditions, can in according with the commonly used reaction conditions and procedures, or in accordance with the product specifications.

All the structures of the compounds in the present invention were confirmed by $^1$H NMR and/or MS.

NMR chemical shifts (δ) were recorded in ppm ($10^{-6}$). NMR Spectra: Bruker AVANCE-400 spectrometer in proper solvent: $CDCl_3$, $CD_3OD$, $DMSO-d_6$, δ in ppm rel. to $Me_4Si$ as internal standard.

The analytical low-resolution mass spectra (MS) were recorded on Aglient 1200HPLC/6120 using a XBridge C18, 4.6×50 mm, 3.5 μm using a gradient elution method. The gradient elution method 1 is: 80-5% solvent $A_1$ and 20-95% solvent $B_1$ (1.8 mins), then 95% solvent $B_1$ and 5% solvent $A_1$ (more than 3 mins). "v/v %" as used herein, means a percentage of the volume of a solvent in the volume of the total solvent. Solvent $A_1$: 0.01% trifluoroacetic acid (TFA) aqueous solution; Solvent $B_1$: 0.01% TFA acetonitrile solution. The gradient elution method 2 is: 80-5% solvent $A_2$ and 20-95% solvent $B_2$ (1.5 mins), then 95% solvent $B_2$ and 5% solvent $A_2$ (more than 2 mins). "v/v %" as used herein, means a percentage of the volume of a solvent in the volume of the total solvent. Solvent $A_2$: 10 mM ammonium bicarbonate aqueous solution; Solvent $B_2$: acetonitrile.

The chiral analysis of compounds in the present invention could be analyzed by supercritical fluid chromatography SFC Method Station (Thar, Waters), analysis method is A, $B_1$, $B_2$ or C; or chiral high performance liquid chromatography Chiral HPLC (Agilent 1200), analysis method is D; detection wavelength is 214 nm or 254 nm.

Chiral analysis method A: OJ-H 4.6×250 mm, 5 um (DAICEL), mobile phase: $CO_2$/methanol (0.1% diethylamine, % means volume percentage)=60/40; flow rate: 3 mL/min, column temperature: 40° C.;

Chiral analysis method $B_1$: OZ-H 4.6×250 mm, 5 um (DAICEL), mobile phase: $CO_2$/methanol (0.1% diethylamine, % means volume percentage)=55/45; flow rate: 3 mL/min, column temperature: 40° C.;

Chiral analysis method $B_2$: OZ-H 4.6×250 mm, 5 um (DAICEL), mobile phase: $CO_2$/methanol (0.2% ammonia in methanol, % means volume percentage)=55/45; flow rate: 3 mL/min, column temperature: 40° C.;

Chiral analysis method C: OJ-H 4.6×250 mm, 5 um (DAICEL), mobile phase: $CO_2$/methanol (0.1% diethylamine, % means volume percentage)=55/45; flow rate: 3 mL/min, column temperature: 40° C.;

Chiral analysis method D: IC 4.6×250 mm, 5 um (DAICEL), mobile phase: hexane (0.1% diethylamine, % means volume percentage)/methanol (0.1% diethylamine, % means volume percentage)=80/20; flow rate: 1 mL/min, column temperature: 40° C.;

The compounds in the present invention could be separated by chiral high performance liquid chromatography (Chiral HPLC), or supercritical fluid chromatography (SFC), chiral separation method is A, B, C, D or E.

Chiral HPLC was performed on HPLC-Gilso GX-281 Method Station. Wherein Chiral resolution Method A: chiral column: CHIRALPAK OZ-H 30*250 mm 5um (Daicel), mobile phase: hexane (0.1% diethylamine, % means volume percentage)/ethanol (0.1% diethylamine, % means volume percentage)=30/70, flow rate: 30 g/min, column temperature: 25° C., sample concentration: 12.5 mg/mL, injection volume: 4 mL; Chiral resolution Method B: chiral column: OZ-H 30*250 mm 5 um (Daicel), mobile phase: methanol (0.5% diethylamine, % means volume percentage), flow rate: 50 mL/min, column temperature: 35° C., sample concentration: 18 mg/mL, injection volume: 1 mL; Chiral resolution Method C: chiral column: CHIRALPAK IC 20*250 mm 5um (Daicel), mobile phase: hexane/ethanol=80/20, flow rate: 50 mL/min, column temperature: 40° C., sample concentration: 6-12 mg/mL, injection volume: 2.0 mL;

SFC was performed on SFC-80 (Thar, Waters). Wherein Chiral resolution Method D: chiral column: OJ-H 20*250 mm 5um (Daicel), mobile phase: $CO_2$/methanol (0.5% ammonia aqueous solution, % means volume percentage)=45/55, flow rate: 80 g/min, column temperature: 35° C.; Chiral resolution Method E: chiral column: CHIRALPAK OZ-H 20*250 mm 5 um (Daicel), mobile phase: $CO_2$/methanol (0.2% ammonia in methanol, % means volume percentage)=50/50, flow rate: 80 g/min, column temperature: 35° C.

Optical rotations of the compounds in the present invention were measured on RUDOLPH Automatic Polarimeter, light source: Na-D, length of the sample pool: 1 cm.

TLC was Yantai Huanghai HSGF254 or Qingdao GF254 silica gel plate. Column chromatography generally used Yantai Huanghai 200-300 mesh silica gel as carrier.

Example 1: Synthesis of 2, 3, 4, 6-tetrakis-O-(trimethylsilyl)-D-gluconolactone

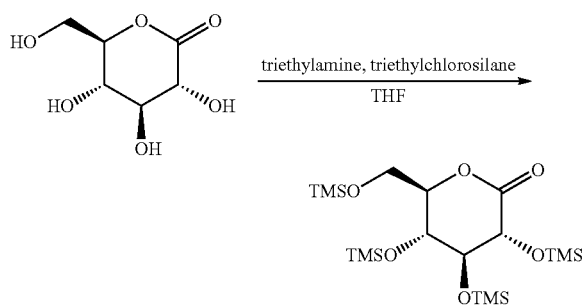

To an ice-cooling solution of delta-Gluconolactone (100.0 g, 0.56 mol) in tetrahydrofuran (THF) (700 mL) was added triethylamine (511 g, 5.05 mol), and then added triethylchlorosilane (427 g, 3.93 mol) dropwise for about 1 h. The resulted mixture was stirred under ice-bath for 2 h, and then warmed up to room temperature and stirred for overnight. The mixture was diluted with ethyl acetate (2 L), and washed successively with saturated $NaH_2PO_4$ aqueous solution (1 L×2), $H_2O$ (1 L) and brine (1 L×2). The organic layer was dried over $MgSO_4$, filtered and concentrated to afford colorless oil. And then the residue was added toluene (100 mL×2), and evaporated under vacuum to constant weight to afford 2,3,4,6-tetrakis-O-(trimethylsilyl)-D-gluconolactone (254 g, yield: 97%) as colorless liquid.

$^1$H NMR (400 MHz, $CDCl_3$): δ 4.17-4.20 (m, 1H), 4.01 (d, J=8.0 Hz, 1H), 3.92 (t, J=7.2 Hz, 1H), 3.75-3.85 (m, 3H), 0.21 (s, 9H), 0.19 (s, 9H), 0.18 (S, 9H), 0.14 (s, 9H).

Example 2: Synthesis of 5-bromo-2-cyanobenzoic acid

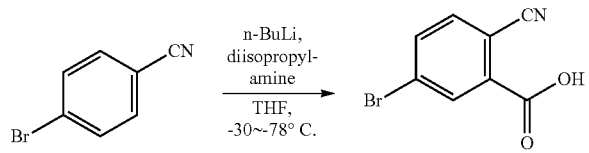 [SMILES: N#Cc1ccc(Br)cc1 ; N#Cc1ccc(Br)cc1C(=O)O]

To a solution of diisopropylamine (6.67 g, 65.9 mmol) in THF (50 mL) was added n-butyllithium (n-BuLi) (26.3 mL, 65.9 mmol, 2.5 M solution in hexane) at −30° C. under nitrogen. The resulted mixture was stirred at −30° C. for 30 min, and then cooled down to −70° C. The mixture was added 4-bromobenzonitrile (10 g, 54.9 mmol) and stirred at −70° C. for 30 min, after this, the mixture was added dry ice. The reaction was warmed up to room temperature and stirred for overnight. The reaction was diluted with $H_2O$ (50 mL) and ethyl acetate (100 mL), separated the organic layer, the aqueous layer was extracted with ethyl acetate (100 mL×2). The combined organic layer was washed with brine, dried over sodium sulfate, filtered and concentrated under vacuum to afford 5-bromo-2-cyanobenzoic acid (7.25 g, yield: 58%) as a white solid.

m/z: [M−H]⁻ 225.9

Example 3: Synthesis of 5-bromo-2-methoxybenzoic acid

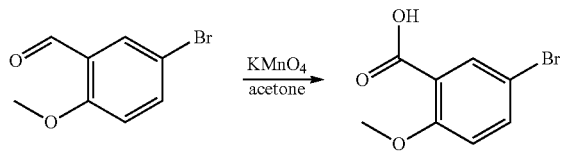

To a solution of 5-bromo-2-methoxybenzaldehyde (20 g, 93.0 mmol) in acetone (100 mL) was added potassium permanganate ($KMnO_4$) (14.7 g, 93.0 mmol) in small portions at 5° C. during 2 h. The resulted mixture was stirred at room temperature for overnight, and then the mixture was filtered. The filtrate was adjusted pH=1 by using hydrochloric acid (5 M), the yellow solid was filtered and dried under vacuum to afford 5-bromo-2-methoxybenzoic acid (10.5 g, yield: 49%).

m/z: [M−H]⁻ 228.9

Example 4: Synthesis of (5-bromo-2-methoxyphenyl)(4-fluorophenyl)methanone

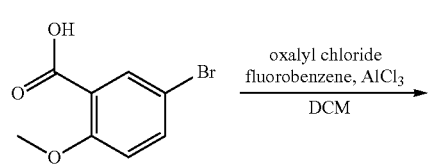

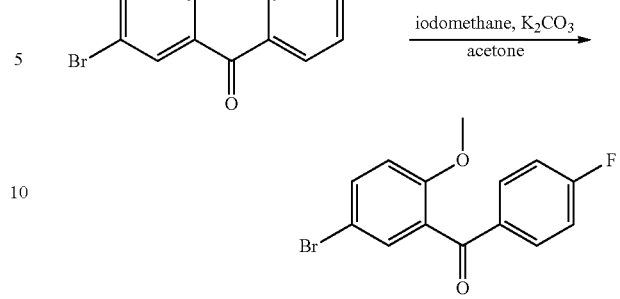

Step 1: (5-bromo-2-hydroxyphenyl)(4-fluorophenyl)methanone

To a solution of 5-bromo-2-methoxybenzoic acid (obtained from example 3) in dichloromethane (20 mL) was added oxalyl chloride (1.24 g, 9.74 mmol) dropwise. The resulted mixture was stirred at room temperature for 2 h. Excess oxalyl chloride was evaporated. The residue was dissolved in fluorobenzene (6.24 g, 64.9 mmol), and then the mixture was added $AlCl_3$ (0.95 g, 7.14 mmol) and stirred at 75° C. for 2 h. The resulted mixture was poured into ice water (30 g), and extracted with ethyl acetate (30 mL×3). The combined organic layer was dried over sodium sulfate and concentrated under vacuum to afford (5-bromo-2-hydroxyphenyl)(4-fluorophenyl)methanone (1.57 g, yield: 82%).

Step 2: (5-bromo-2-methoxyphenyl)(4-fluorophenyl)methanone

To a solution of (5-bromo-2-hydroxyphenyl)(4-fluorophenyl)methanone (obtained from step 1) (920 mg, 3.12 mmol) in acetone (10 mL) was added $K_2CO_3$ (861 mg, 6.24 mmol) and iodomethane (663 mg, 4.68 mmol). The resulted mixture was stirred at 10° C. for 1 h. And then filtered, the filtrate was evaporated under vacuum to afford (5-bromo-2-methoxyphenyl) (4-fluorophenyl)methanone (930 mg, yield: 97%).

$^1$H NMR (400 MHz, $CDCl_3$): δ 7.82-7.86 (m, 2H), 7.58 (dd, J=8.8, 2.8 Hz, 1H), 7.46 (d, J=2.8 Hz, 1H), 7.13 (t, J=8.8 Hz, 2H), 6.90 (d, J=8.8 Hz, 1H), 3.74 (s, 3H).

Example 5: Synthesis of (5-bromo-2-chlorophenyl)(4-fluorophenyl)methanone

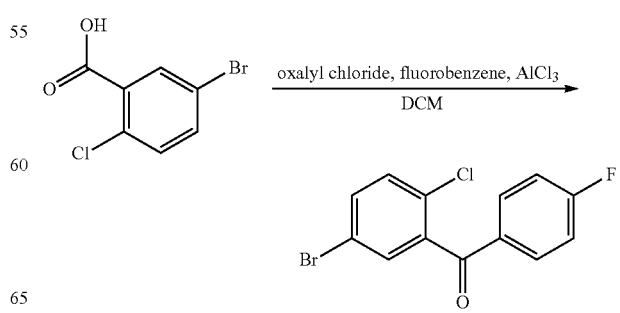

To a solution of 5-bromo-2-chlorobenzoic acid (100 g, 0.42 mol) in dichloromethane (500 mL) was added oxalyl chloride (107 mL, 1.27 mol) and N, N-dimethylformamide (DMF) dropwise (2 mL). The resulted mixture was stirred at room temperature for 2 h. Excess oxalyl chloride was evaporated. The residue was dissolved in fluorobenzene (500 mL), and then the mixture was added AlCl$_3$ (62 g, 0.46 mol) and stirred at 75° C. for overnight. The mixture was poured into ice water (2 L), and added hydrochloric acid (400 mL), and the aqueous layer was extracted with ethyl acetate (500 mL×3). The combined organic layer was washed with 5% NaOH aqueous solution, hydrochloric acid (2 M) and brine, dried over sodium sulfate and concentrated under vacuum to afford (5-bromo-2-chlorophenyl)(4-fluorophenyl)methanone (104 g, yield: 78%).

$^1$H NMR (400 MHz, CDCl$_3$): δ 7.84-7.87 (m, 2H), 7.58 (dd, J=8.8, 2.4 Hz, 1H), 7.52 (d, J=2.4 Hz, 1H), 7.36 (d, J=8.8 Hz, 1H), 7.18 (t, J=8.4 Hz, 2H).

Compounds of Examples 6-8 were Prepared According to the Synthetic Method of Example 5

Example 6: (3-bromophenyl)(4-fluorophenyl)methanone

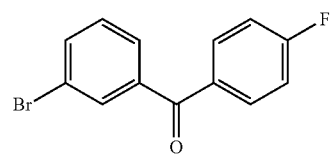 [SMILES: O=C(c1ccc(F)cc1)c1cccc(Br)c1]

m/z: [M+H]$^+$278.9

Example 7: 4-bromo-2-(4-fluorobenzoyl)benzonitrile

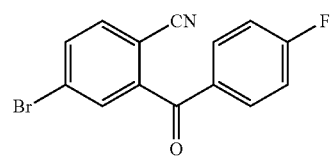 [SMILES: N#Cc1ccc(Br)cc1C(=O)c1ccc(F)cc1]

$^1$H NMR (400 MHz, CDCl$_3$): δ 7.82-7.85 (m, 3H), 7.66 (dd, J=8.0, 1.6 Hz, 1H), 7.63 (d, J=1.6 Hz, 1H), 7.20 (t, J=8.4 Hz, 2H).

Example 8: (5-bromo-2-methylphenyl)(4-fluorophenyl)methanone

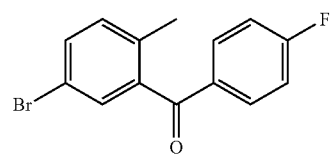 [SMILES: Cc1ccc(Br)cc1C(=O)c1ccc(F)cc1]

m/z: [M+H]$^+$292.9

Example 9: Synthesis of benzofuran-2-ylmethanol

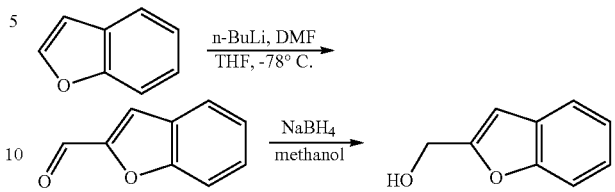

Step 1: benzofuran-2-carbaldehyde

To a solution of benzofuran (10 g, 84.7 mmol) in dry THF was added n-BuLi (2.5 M solution in hexane, 33.9 mL, 84.7 mmol) dropwise at −78° C. under nitrogen, the mixture was stirred at −78° C. for 0.5 h, and then added DMF (19.6 mL, 254 mmol). The resulted mixture was kept at −78° C. and stirred for 1 h. The reaction was quenched by addition of saturated NH$_4$Cl aqueous solution (20 mL), and then added ethyl acetate (300 mL) and H$_2$O (100 mL), the aqueous layer was extracted with ethyl acetate (50 mL). The combined organic layer was washed with water and brine, dried over sodium sulfate and concentrated under vacuum, the residue was purified by column chromatography on silica gel (ethyl acetate:petroleum ether=10:1) to afford benzofuran-2-carbaldehyde (7.5 g, yield: 61%) as yellow oil.

$^1$H NMR (400 MHz, CDCl$_3$): δ 9.90 (s, 1H), 7.78 (d, J=8.8 Hz, 1H), 7.63 (d, J=8.2 Hz, 1H), 7.59 (s, 1H), 7.53-7.57 (m, 1H), 7.35-7.39 (m, 1H).

Step 2: benzofuran-2-ylmethanol

To an ice-cooling solution of benzofuran-2-carbaldehyde (4.0 g, 27.4 mmol) in methanol (40 mL) was added NaBH$_4$ (1.55 g) in small portions. The resulted mixture was stirred for 1 h, and then the reaction was diluted with ethyl acetate (100 mL), the organic layer was washed with H$_2$O (50 mL×3) and brine, dried over sodium sulfate, filtered and concentrated under vacuum to afford benzofuran-2-ylmethanol (4.0 g, yield: 98%) as yellow oil.

$^1$H NMR (400 MHz, CDCl$_3$): δ 7.57-7.59 (m, 1H), 7.48-7.50 (m, 1H), 7.23-7.33 (m, 2H), 6.66 (s, 1H), 4.78 (s, 2H), 2.03 (brs, 1H).

Example 10: Synthesis of (3,3-dimethyl-1,3-dihydroisobenzofuran-1-yl)methanol

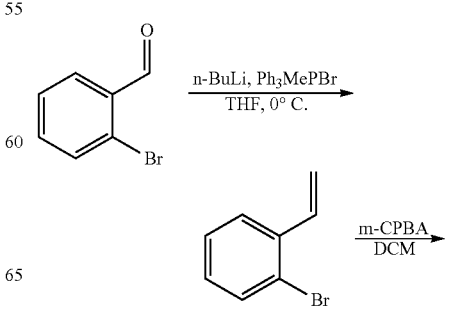

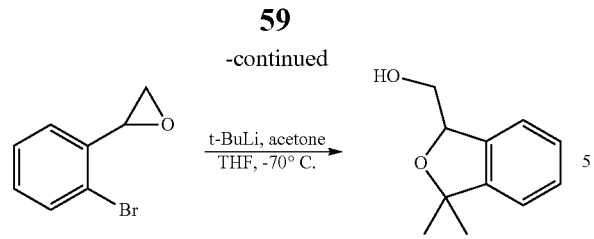

Step 1: 1-Bromo-2-Vinylbenzene

To an ice-cooling mixture of methyltriphenylphosphonium bromide (16.2 g, 45 mmol) in THF (50 mL) was added n-BuLi (2.5 M solution in hexane, 18 mL, 45 mmol) dropwise. The reaction mixture was stirred at 0° C. for 1 h until the solid was dissolved, and then added 2-bromobenzaldehyde (8.0 g, 43 mmol). The reaction mixture was stirred at 0° C. for 1 h. The mixture was poured into water (20 mL), and extracted with ethyl acetate. The combined organic layer was dried over sodium sulfate and concentrated under vacuum. The residue was purified by column chromatography on silica gel (petroleum ether:ethyl acetate=10:1) to afford 1-bromo-2-vinylbenzene (5.2 g, yield: 65%) as yellow oil.

Step 2: 2-(2-bromophenyl)oxirane

To an ice-cooling mixture of 1-bromo-2-vinylbenzene (obtained from step 1) (3.0 g, 13.1 mmol) in DCM (20 mL) was added 3-chloroperoxybenzoic acid (m-CPBA) (2.0 g, 10.9 mmol) in small portions. The reaction mixture was stirred at 0° C. for 2 h, and then the mixture was quenched by addition of saturated NaHCO$_3$ aqueous solution (30 mL). The aqueous layer was extracted with ethyl acetate (50 mL×3). The combined organic layer was dried over sodium sulfate and concentrated under vacuum. The residue was purified by prep-TLC (petroleum ether:ethyl acetate=10:1) to afford 2-(2-bromophenyl)oxirane (1.2 g, yield: 54%) as yellow oil.

Step 3: (3,3-dimethyl-1,3-dihydroisobenzofuran-1-yl)methanol

To a solution of 2-(2-bromophenyl)oxirane (obtained from step 2) (930 mg, 4.67 mmol) in THF (10 mL) was added tert-butyllithium (t-BuLi) (1.3 M solution in pentane, 7.1 mL, 9.34 mmol) dropwise at −70° C. The reaction mixture was stirred for 10 min, and then added acetone (542 mg, 9.34 mmol). The reaction mixture was slowly warmed up to 15° C. and stirred for 1 h. The mixture was poured into water (20 mL), and the aqueous layer was extracted with ethyl acetate. The combined organic layer was dried over sodium sulfate and concentrated under vacuum. The residue was purified by prep-TLC (petroleum ether:ethyl acetate=1:1) to afford (3,3-dimethyl-1,3-dihydroisobenzofuran-1-yl)methanol (670 mg, yield: 80%) as light yellow oil.

$^1$H NMR (400 MHz, CDCl$_3$): δ 7.31-7.34 (m, 2H), 7.15-7.21 (m, 2H), 5.31-5.34 (m, 1H), 3.95-4.00 (m, 1H), 3.77-3.83 (m, 1H), 1.60 (s, 3H), 1.52 (s, 3H).

Example 11: Synthesis of (1,3-dihydroisobenzofuran-1-yl)methanol

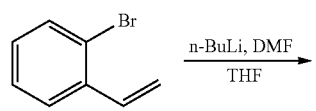

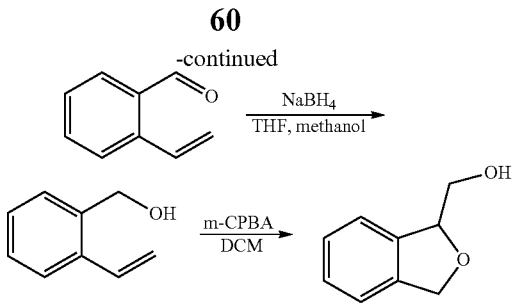

Step 1: 2-vinylbenzaldehyde

To a solution of 1-bromo-2-vinylbenzene (obtained from Example 10 step 1) (3 g, 16.4 mmol) in THF (20 mL) was added n-BuLi (2.5 M solution in hexane, 7.2 mL, 18.0 mmol) dropwise at −78° C. The reaction mixture was stirred at −70° C. for 1 h, and then added DMF (1.8 g, 24.6 mmol). The reaction mixture was slowly warmed up to room temperature and stirred for 30 min. The mixture was poured into water (20 mL), and the aqueous layer was extracted with ethyl acetate (20 mL×2). The combined organic layer was dried over sodium sulfate and concentrated under vacuum to afford 2-vinylbenzaldehyde (2.0 g, yield: 91%).

Step 2: (2-vinylphenyl)methanol

To a solution of 2-vinylbenzaldehyde (obtained from step 1) (2.0 g, 15.3 mmol) in a mixed solvent of methanol (14 mL) and THF (14 mL) was added NaBH$_4$ (1.15 g, 30.3 mmol) in small portions at 0° C. The resulted mixture was stirred at room temperature for 2 h, and then the reaction was diluted with ethyl acetate (50 mL), the organic layer was washed with saturated NH$_4$Cl aqueous solution and brine, dried over sodium sulfate, filtered and concentrated under vacuum to afford (2-vinylphenyl)methanol (2.0 g, yield: 100%).

Step 3: (1,3-dihydroisobenzofuran-1-yl)methanol

To a mixture of (2-vinylphenyl)methanol (obtained from step 2) (1.0 g, 7.45 mmol) in DCM (10 mL) was added m-CPBA (1.82 g, 8.94 mmol) in small portions at 0° C. The reaction mixture was stirred at room temperature for overnight, and then the mixture was diluted with DCM (30 mL) and washed with saturated NaHCO$_3$ aqueous solution and brine. The organic layer was dried over sodium sulfate and concentrated under vacuum. The residue was purified by prep-TLC (petroleum ether:ethyl acetate=4:1) to afford (1,3-dihydroisobenzofuran-1-yl) methanol (260 mg, yield: 23%) as yellow oil.

m/z: [M+H]$^+$151.1

Example 12: Synthesis of (1-methyl-1,3-dihydroisobenzofuran-1-yl)methanol

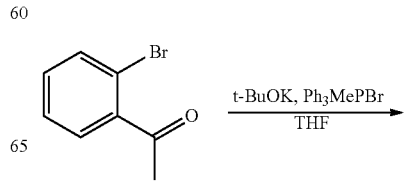

-continued

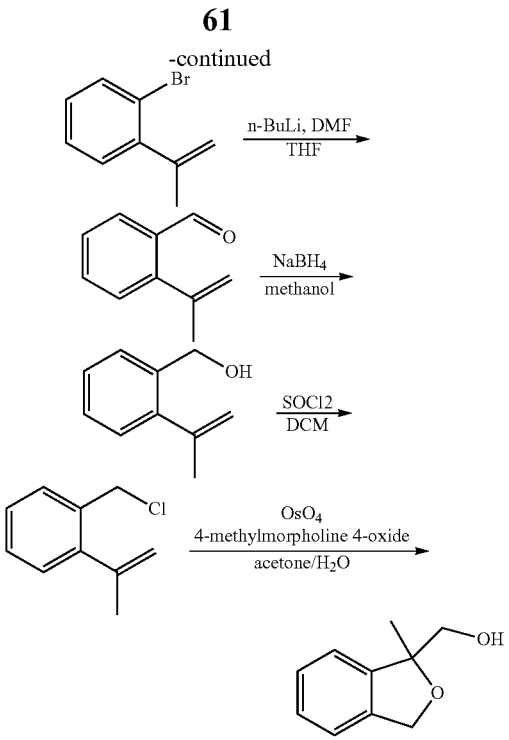

Step 1: 1-bromo-2-(prop-1-en-2-yl)benzene

Potassium tert-butanolate (t-BuOK) (21.1 g, 0.188 mol) was suspended in THF (250 mL) under nitrogen. The suspension was cooled down in ice-bath to keep the inner temperature below 10° C., and then added methyltriphenylphosphonium bromide (67.3 g, 0.188 mol) in small portions. The resulted mixture was kept below 10° C. and stirred for 2 h. After this, the mixture was cooled down to 0° C. and added 1-(2-bromophenyl)ethanone (25 g, 0.126 mol), the inner temperature was kept below 5° C. during this period. The resulted mixture was stirred for 16 h, and then added $H_2O$ (250 mL), and then extracted with ethyl acetate (200 mL×3). The combined organic layer was washed with brine, dried over sodium sulfate, filtered and concentrated under vacuum to afford 1-bromo-2-(prop-1-en-2-yl)benzene (18.1 g, yield: 71%) as light yellow oil.

$^1$H NMR (400 MHz, $CDCl_3$): δ 7.58 (dd, J=7.6, 1.2 Hz, 1H), 7.27-7.31 (m, 1H), 7.21-7.23 (m, 1H), 7.12-7.16 (m, 1H), 5.26 (m, 1H), 4.97 (m, 1H), 2.13 (s, 3H).

Step 2: 2-(prop-1-en-2-yl)benzaldehyde

To a solution of 1-bromo-2-(prop-1-en-2-yl)benzene (obtained from step 1) (16 g, 81 mmol) in THF (160 mL) was added n-BuLi (2.5 M solution in hexane, 35.7 mL, 89.0 mmol) dropwise at −65° C., the inner temperature was kept below −60° C. during this period. The reaction mixture was stirred at −65° C. for 30 min, and then added DMF (8.9 g, 122 mmol). The reaction mixture was slowly warmed up to room temperature and stirred for 2 h. The reaction was quenched by addition of saturated $NH_4Cl$ aqueous solution, and the aqueous layer was extracted with ethyl acetate (200 mL×2). The combined organic layer was washed with brine, dried over sodium sulfate and concentrated to afford 2-(prop-1-en-2-yl)benzaldehyde (11.8 g, yield: 99%) as yellow oil.

Step 3: (2-(prop-1-en-2-yl)phenyl)methanol

To a solution of 2-(prop-1-en-2-yl)benzaldehyde (obtained from step 2) (11.8 g, 80 mmol) in methanol (95 mL) was added $NaBH_4$ (3.67 g, 97 mmol) in small portions at 0-5° C. The resulted mixture was stirred at the same temperature for 2 h, and then the reaction was quenched by addition of hydrochloric acid (2 M), and the mixture was extracted with ethyl acetate (100 mL×3). The combined organic phase was washed with brine (100 mL), dried over sodium sulfate, filtered and concentrated. The residue was purified by column chromatography on silica gel (petroleum ether:ethyl acetate=15:1) to afford (2-(prop-1-en-2-yl)phenyl) methanol (8.8 g, yield: 74%) as light yellow oil.

$^1$H NMR ($CDCl_3$, 400 Hz): δ 7.47-7.49 (m, 1H), 7.28-7.33 (m, 2H), 7.19-7.21 (m, 1H), 5.27 (m, 1H), 4.93 (m, 1H), 4.72 (s, 2H), 2.10 (s, 3H).

Step 4: 1-(chloromethyl)-2-(prop-1-en-2-yl)benzene

To a solution of (2-(prop-1-en-2-yl)phenyl)methanol (obtained from step 3) (7.0 g, 47.2 mmol) in DCM (70 mL) was added thionyl chloride (6.2 g, 52.3 mmol) dropwise at 0-5° C. The resulted mixture was stirred at the same temperature for 1 h and then diluted with saturated $NaHCO_3$ aqueous solution (20 mL), the aqueous layer was extracted with DCM (50 mL×3). The combined organic layer was washed with brine (100 mL), dried over sodium sulfate, filtered and concentrated to afford 1-(chloromethyl)-2-(prop-1-en-2-yl) benzene (7.5 g, yield: 95%) as light yellow oil.

Step 5: (1-methyl-1,3-dihydroisobenzofuran-1-yl)methanol

To a solution of 1-(chloromethyl)-2-(prop-1-en-2-yl)benzene (obtained from step 4) (7.5 g, 45 mmol) in a mixed solvent of acetone (75 mL) and $H_2O$ (18.5 mL) was successively added 4-methylmorpholine 4-oxide (15.8 g, 135 mmol) and $OsO_4$ (0.04 g, 0.02 mmol) at 0-5° C. The resulted mixture was stirred at room temperature for 16 h and then the reaction was quenched by addition of saturated $Na_2SO_3$ aqueous solution and stirred for further 30 min, the aqueous layer was extracted with ethyl acetate (100 mL×3). The combined organic layer was washed with brine (100 mL), dried over sodium sulfate, filtered and concentrated. The residue was purified by column chromatography on silica gel (petroleum ether:ethyl acetate=5:1) to afford (1-methyl-1,3-dihydroisobenzofuran-1-yl)methanol (3.7 g, yield: 50%) as colorless oil.

$^1$H NMR ($CDCl_3$, 400 Hz): δ 7.28-7.31 (m, 2H), 7.22-7.24 (m, 1H), 7.15-7.17 (m, 1H), 5.14 (s, 2H), 3.68-3.74 (m, 2H), 2.49 (brs, 1H), 1.50 (s, 3H).

Example 13: (S)-(1,3-dihydroisobenzofuran-1-yl)methanol

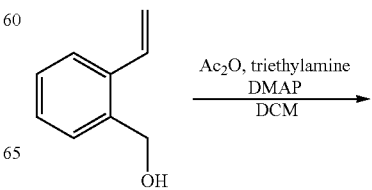

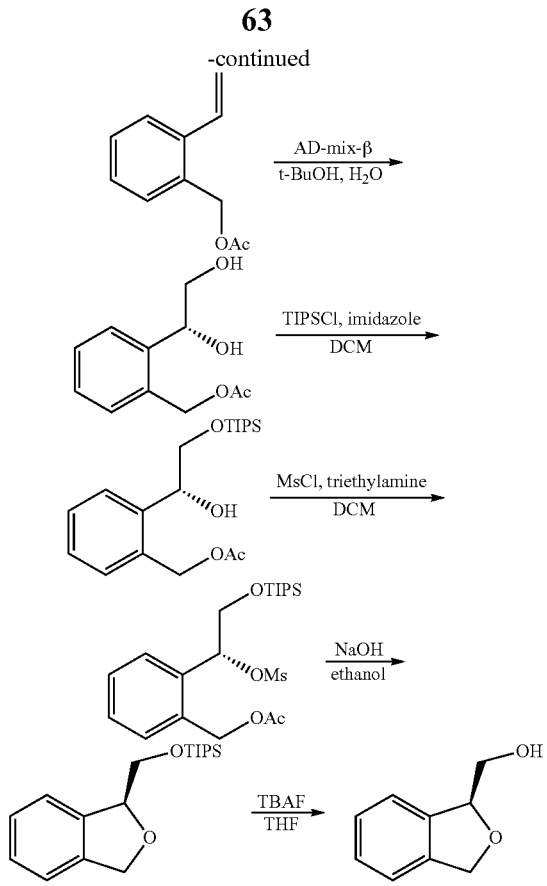

Step 1: 2-vinylbenzyl acetate

To a solution of (2-vinylphenyl)methanol (3.0 g, 22.4 mmol) and triethylamine (4.5 g, 44.7 mmol) in DCM (20 mL) was added acetic anhydride (Ac$_2$O) (4.6 g, 44.7 mmol) and catalytic amount of 4-dimethylaminopyridine (DMAP) (50 mg). The resulted mixture was stirred at room temperature for overnight, and then diluted with DCM (30 mL). The organic layer was washed with H$_2$O and brine successively, dried over sodium sulfate, filtered and concentrated. The residue was purified by column chromatography on silica gel to afford 2-vinylbenzyl acetate (3.9 g, yield: 96%) as light yellow oil.

Step 2: (R)-2-(1,2-dihydroxyethyl)benzyl acetate

A mixture of AD-mix-β (4.5 g) in tert-butanol (10 mL) and H$_2$O (10 mL) was cooled down to 0° C., 2-vinylbenzyl acetate (500 mg, 3.5 mmol) was added and the mixture was stirred at 0° C. for overnight, then the mixture was quenched by addition of Na$_2$SO$_3$, the aqueous layer was extracted with ethyl acetate (30 mL×3). The combined organic layer was washed with brine (100 mL), dried over sodium sulfate, filtered and concentrated. The residue was purified by column chromatography on silica gel to afford (R)-2-(1,2-dihydroxyethyl)benzyl acetate (432 mg, yield: 58%) as light yellow oil.

$^1$H NMR (400 MHz, CDCl$_3$): δ 7.50-7.58 (m, 1H), 7.32-7.42 (m, 3H), 5.18 (dd, J=12.0 Hz, 2H), 5.08 (m, 1H), 3.66-3.78 (m, 2H), 3.01 (s, 1H), 2.54 (s, 1H), 2.14 (s, 3H).

Step 3: (R)-2-(1-hydroxy-2-((triisopropylsilyl)oxy) ethyl)benzyl acetate

A solution of (R)-2-(1,2-dihydroxyethyl)benzyl acetate (200 mg, 0.95 mmol) and imidazole (77 mg, 1.14 mmol) in DCM (2 mL) was cooled down to 0° C., triisopropylsilyl chloride (TIPSCl) (201 mg, 1.05 mmol) was added dropwise and the mixture was warmed up to room temperature and stirred for overnight, then the mixture was concentrated. The residue was purified by column chromatography on silica gel (petroleum ether:ethyl acetate=4:1) to afford (R)-2-(1-hydroxy-2-((triisopropylsilyl)oxy)ethyl)benzyl acetate (128 mg) as light yellow oil.

$^1$H NMR (400 MHz, CDCl$_3$): δ 7.61-7.63 (m, 1H), 7.32-7.43 (m, 3H), 5.17 (dd, J=12.0 Hz, 2H), 5.08 (m, 1H), 3.88-3.92 (m, 1H), 3.65-3.69 (m, 1H), 3.20 (s, 1H), 1.14 (s, 12H), 1.12 (s, 6H).

Step 4: (R)-2-(1-(methylsulfonyloxy)-2-((triisopropylsilyl)oxy)ethyl)benzyl acetate To a solution of (R)-2-(1-hydroxy-2-((triisopropylsilyl)oxy)ethyl)benzyl acetate (60 mg, 0.16 mmol) in DCM (2 mL) was added triethylamine (50 mg, 0.49 mmol), and then added methanesulfonyl chloride (SOCl$_2$) (37 mg, 0.32 mmol, in 0.5 mL DCM) dropwise. The resulted mixture was stirred at room temperature for 2 h. After the mixture was diluted with DCM, the organic layer was washed with hydrochloric acid (2 M) and brine, dried over sodium sulfate, filtered and concentrated. The residue was used directly for next step without further purification.

Step 5: (S)-((1,3-dihydroisobenzofuran-1-yl) methoxy)triisopropylsilane

To a solution of compound obtained from step 4 (73 mg, 0.16 mmol) in dry ethanol (1 mL) was added NaOH (13 mg, 0.32 mmol, in 0.5 mL ethanol). The resulted mixture was stirred at room temperature for 1 h, and then concentrated to dryness. The residue was purified by prep-TLC to afford (S)-((1,3-dihydroisobenzofuran-1-yl)methoxy)triisopropylsilane (33 mg, yield: 66% for two steps) as colorless oil.

$^1$H NMR (400 MHz, CDCl$_3$): δ 7.22-7.36 (m, 4H), 5.29 (t, J=5.2 Hz, 1H), 5.10-5.20 (m, 2H), 3.98 (dd, J=5.2, 10.0 Hz, 1H), 3.90 (dd, J=5.2, 10.0 Hz, 1H), 1.02-1.16 (m, 21H).

Step 6: (S)-(1,3-dihydroisobenzofuran-1-yl)methanol

To a solution of (S)-((1,3-dihydroisobenzofuran-1-yl)methoxy)triisopropylsilane (33 mg, 0.11 mmol) in THF (2 mL) was added tetrabutylammonium fluoride (14 mg, 0.06 mmol). The resulted mixture was stirred at room temperature for 5 h, and then directly purified by prep-TLC (petroleum ether:ethyl acetate=3:1) to afford (S)-(1,3-dihydroisobenzofuran-1-yl) methanol (5 mg, yield: 30%, ee %: 97.2%) as colorless oil.

$^1$H NMR (400 MHz, CDCl$_3$): δ 7.23-7.35 (m, 4H), 5.35-5.36 (m, 1H), 5.13-5.22 (m, 2H), 3.97 (dd, J=3.2, 12.0 Hz, 1H), 3.82 (dd, J=5.6, 11.6 Hz, 1H).

$[α]_D^{25}$=22.11 (C=0.502, MeOH)

Example 14: (R)-(1,3-dihydroisobenzofuran-1-yl)methanol

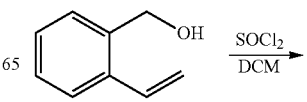

-continued

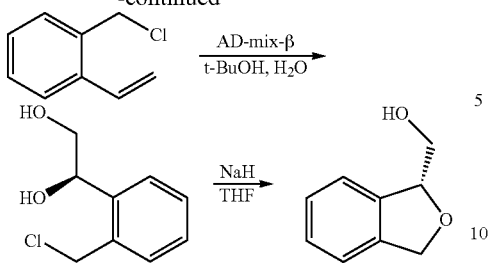

Step 1: 1-(chloromethyl)-2-vinylbenzene

A solution of (2-vinylphenyl)methanol (3.10 g, 23.1 mmol) in DCM (30 mL) was cooled down to 0° C., and then added MsCl (2.01 mL, 27.7 mmol) dropwise. The resulted mixture was stirred at room temperature for overnight. After the mixture was diluted with DCM (50 mL), the organic layer was washed with $H_2O$ (30 mL×2), saturated $NaHCO_3$ aqueous solution and brine successively, then dried over sodium sulfate, filtered and concentrated to afford 1-(chloromethyl)-2-vinylbenzene (2.92 g, yield: 83%) as colorless oil, which can directly used for next step.

Step 2: (R)-1-(2-(chloromethyl)phenyl)ethane-1,2-diol

A solution of AD-mix-β (34.6 g) in a mixed solvent of tert-butanol (t-BuOH) and $H_2O$ (260 mL, 1:1) was cooled down to 0° C., and then added 1-(chloromethyl)-2-vinylbenzene (4.0 g, 26.2 mmol, in 5 mL t-BuOH). The resulted mixture was stirred at 0° C. for 2 h. The mixture was quenched by addition of $Na_2SO_3$ (39 g), and then extracted with ethyl acetate (100 mL×2). the combined organic layer was washed with $H_2O$ and brine, then dried over sodium sulfate, filtered and concentrated to afford (R)-1-(2-(chloromethyl)phenyl)ethane-1,2-diol (3.5 g, yield: 72%) as a light yellow solid.

$^1$H NMR (400 MHz, $CDCl_3$): δ 7.58 (d, J=7.6 Hz, 1H), 7.28-7.43 (m, 3H), 5.21 (dd, J=3.2, 8.4 Hz, 1H), 4.72 (s, 2H), 3.86 (dd, J=3.2, 11.2 Hz, 1H), 3.76 (dd, J=8.8, 11.2 Hz, 1H), 2.70 (brs, 1H), 2.23 (brs, 1H).

Step 3: (R)-(1,3-dihydroisobenzofuran-1-yl)methanol

A solution of (R)-1-(2-(chloromethyl)phenyl)ethane-1,2-diol (34.6 g, 18.8 mmol) in THF (35 mL) was cooled down to 0° C., and then added NaH (1.65 g, 60%, 41.3 mmol) in small portions. The resulted mixture was stirred at room temperature for 2 h. The mixture was quenched by addition of ice water, and then extracted with ethyl acetate (50 mL×2). The combined organic layer was washed with $H_2O$ and brine, then dried over sodium sulfate, filtered and concentrated. to afford (R)-(1,3-dihydroisobenzofuran-1-yl)methanol (1.8 g, yield: 64%, ee %: 97%) as light yellow oil.

$^1$H NMR (400 MHz, $CDCl_3$): δ 7.24-7.36 (m, 4H), 5.35-5.36 (m, 1H), 5.14-5.23 (m, 2H), 3.95 (dd, J=3.2, 12 Hz, 1H), 3.82 (dd, J=5.6, 11.6 Hz, 1H).

$[α]_D^{25}$=−24.14 (C=0.505, MeOH)

Example 15: (S)-(5-methyl-1,3-dihydroisobenzofuran-1-yl)methanol

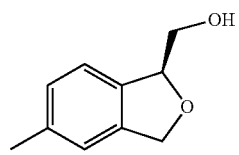

(S)-(5-methyl-1,3-dihydroisobenzofuran-1-yl)methanol was prepared according to the synthetic method of compound of Example 14, by using AD-mix-α as chiral material.

$^1$H NMR (400 MHz, $CDCl_3$): δ 7.13 (s, 1H), 7.08 (s, 2H), 5.52 (s, 1H), 5.09-5.18 (m, 2H), 3.95 (dd, J=3.2, 12.0 Hz, 1H), 3.79 (dd, J=5.6, 12.0 Hz, 1H), 2.39 (s, 3H), 1.78 (s, 1H).

Example 16: (S)-(5-fluoro-1,3-dihydroisobenzofuran-1-yl)methanol

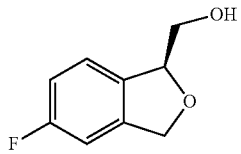 [SMILES: OC[C@H]1OCc2cc(F)ccc21]

(S)-(5-fluoro-1,3-dihydroisobenzofuran-1-yl)methanol was prepared according to the synthetic method of compound of Example 14, by using AD-mix-α as chiral material.

$^1$H NMR (400 MHz, $CDCl_3$): δ 7.19 (dd, J=4.8, 8.4 Hz, 1H), 6.95-7.03 (m, 2H), 5.30 (s, 1H), 5.09-5.19 (m, 2H), 3.94 (dd, J=3.2, 12.0 Hz, 1H), 3.79 (dd, J=6.0, 12.0 Hz, 1H), 1.92 (s, 1H).

Example 17: Synthesis of 2-allyl-5-fluorophenol and 2-allyl-3-fluorophenol

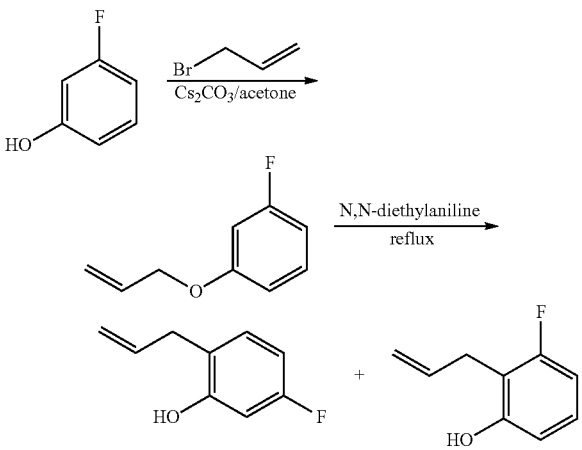

Step 1: 1-(allyloxy)-3-fluorobenzene

To a solution of 3-fluorophenol (20 g, 178 mmol) in acetone (200 mL) was added solid $Cs_2CO_3$ (87 g, 268 mmol). The resulted mixture was cooled down under ice-bath and added 3-bromoprop-1-ene (19 mL, 214 mmol)

dropwise, and then stirred at room temperature for 4 h. The solid was filtered; the filtrate was diluted with ethyl acetate (200 mL). The organic layer was washed with H₂O and brine successively, dried over sodium sulfate, filtered and concentrated to afford 1-(allyloxy)-3-fluorobenzene (25 g, yield: 92%) as brown liquid.

Step 2: 2-allyl-5-fluorophenol and 2-allyl-3-fluorophenol

A mixture of 1-(allyloxy)-3-fluorobenzene (obtained from step 1) (10 g, 66 mmol) and N,N-diethylaniline (15 mL) was stirred at 225° C. for 2 h, and then cooled down to room temperature. The mixture was diluted with ethyl acetate; the organic layer was washed with hydrochloric acid (6 M, 100 mL) and brine, dried over sodium sulfate, filtered and concentrated. The residue was purified by column chromatography on silica gel (petroleum ether/ethyl acetate=100: 1-20:1) to afford 2-allyl-5-fluorophenol (4.0 g, yield: 40%) and 2-allyl-3-fluorophenol (2.2 g, yield: 22%) as light yellow oil.

2-allyl-5-fluorophenol

¹H NMR (400 MHz, CDCl₃): δ 7.06 (dd, J=6.8, 8.0 Hz, 1H), 6.58-6.65 (m, 2H), 5.97-6.05 (m, 1H), 5.32 (br s, 1H), 5.16-5.21 (m, 1H), 3.39 (d, J=6.0 Hz, 2H).

2-allyl-3-fluorophenol

¹H NMR (400 MHz, CDCl₃): δ 7.07-7.12 (m, 1H), 6.64-6.71 (m, 2H), 5.96-6.06 (m, 1H), 5.16-5.21 (m, 2H), 5.14 (t, J=2.0 Hz, 1H), 3.48 (dd, J=1.2, 5.6 Hz, 2H).

Example 18: Synthesis of 2-((4-(5-bromo-2-chlorobenzyl)phenoxy)methyl)-7-fluoro-2,3-dihydrobenzofuran

Step 1: 1-(allyloxy)-2-fluorobenzene

To a solution of 2-fluorophenol (21 g, 187 mmol) in acetone (210 mL) was added solid Cs₂CO₃ (91.5 g, 281 mmol). The resulted mixture was cooled down in ice-bath and added 3-bromoprop-1-ene (27.1 g, 225 mmol) dropwise, and then stirred at room temperature for overnight. The solid was filtered, the filter cake was washed with ethyl acetate (400 mL), the filtrate was washed with 10% NaOH aqueous solution, H₂O and brine successively, dried over sodium sulfate, filtered and concentrated to afford 1-(allyloxy)-2-fluorobenzene (25 g, yield: 88%) as yellow oil.

Step 2: 2-allyl-6-fluorophenol

A mixture of 1-(allyloxy)-2-fluorobenzene (obtained from step 1) (5.0 g, 32 mmol) and 1-methyl-2-pyrrolidinone (50 mL) was stirred at 225° C. for 3 h, and then cooled down to room temperature. The mixture was diluted with ethyl acetate (200 mL), the organic layer was washed with H₂O and brine, dried over sodium sulfate, filtered and concentrated to afford 2-allyl-6-fluorophenol (5.0 g, yield: 100%) as yellow oil, which can be directly used for next step.

Step 3: (7-fluoro-2,3-dihydrobenzofuran-2-yl)methanol

To a solution of 2-allyl-6-fluorophenol (obtained from step 3) (5.0 g, 32.9 mmol) in chloroform was added m-CPBA (7.6 g, 32.9 mmol, 75%). The reaction mixture was stirred at reflux for 3 h, and then cooled down to room temperature, the mixture was washed with saturated NaHCO₃ aqueous solution, H₂O and brine, dried over sodium sulfate and concentrated under vacuum. The residue was purified by column chromatography on silica gel (petroleum ether:ethyl acetate=10:1) to afford (7-fluoro-2,3-dihydrobenzofuran-2-yl) methanol (2.1 g, yield: 38%) as light yellow oil.

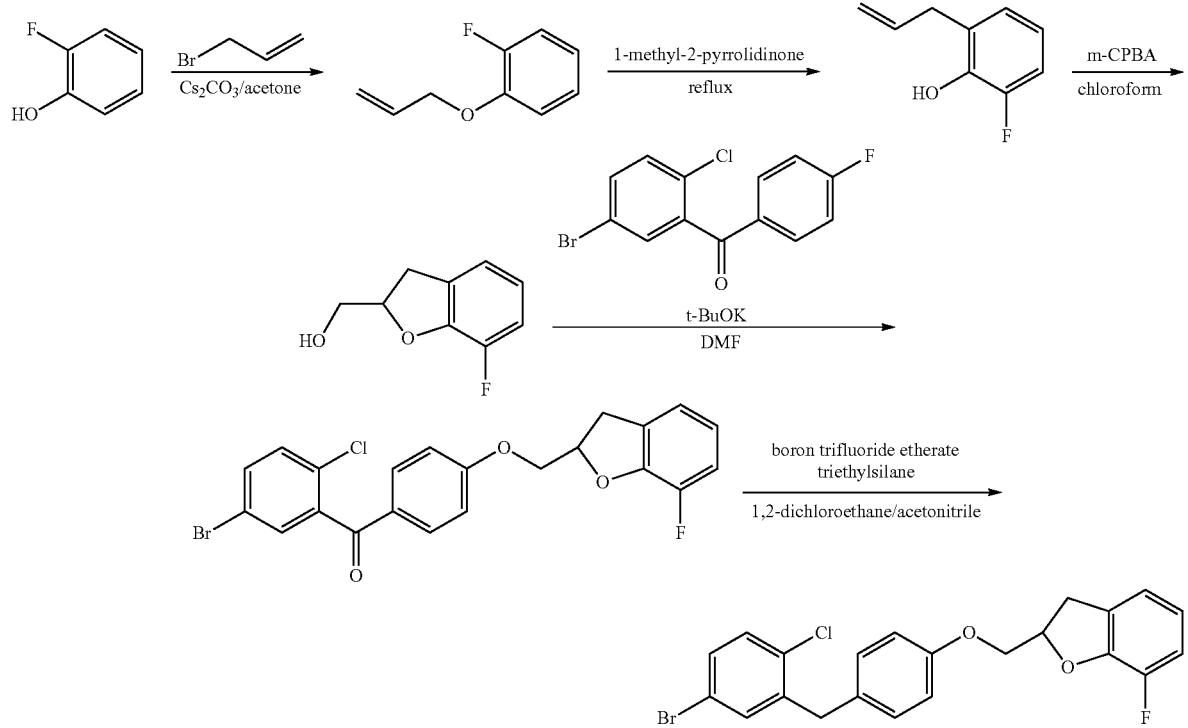

$^1$H NMR (400 MHz, CDCl$_3$): δ 6.90-6.97 (m, 2H), 6.78-6.83 (m, 1H), 5.00-5.06 (m, 1H), 3.93 (dd, J=3.2, 12.4 Hz, 1H), 3.79 (dd, J=6.0, 12.0 Hz, 1H), 3.31 (dd, J=9.2, 15.6 Hz, 1H), 3.14 (dd, J=7.6, 16.0 Hz, 1H).

Step 4: (5-bromo-2-chlorophenyl)(4-((7-fluoro-2,3-dihydrobenzofuran-2-yl)methoxy) phenyl)methanone To an ice-cooling solution of (7-fluoro-2,3-dihydrobenzofuran-2-yl)methanol (obtained from step 3) and (5-bromo-2-chlorophenyl)(4-fluorophenyl)methanone (1.10 g, 3.51 mmol) in DMF (10 mL) was added t-BuOK (413 mg, 3.68 mmol). The resulted mixture was turned to dark brown, and then warm up to room temperature and stirred for overnight. The reaction was quenched by addition of H$_2$O (50 mL), and extracted with ethyl acetate (30 mL×3). The combined organic layer was washed with H$_2$O and brine, dried over sodium sulfate and concentrated under vacuum. The residue was purified by prep-TLC (petroleum ether:ethyl acetate=3:1) to afford (5-bromo-2-chlorophenyl)(4-((7-fluoro-2,3-dihydrobenzofuran-2-yl) methoxy)phenyl)methanone (700 mg, yield: 48%) as colorless oil.

m/z: [M+H]$^+$ 461.0

Step 5: 2-((4-(5-bromo-2-chlorobenzyl)phenoxy) methyl)-7-fluoro-2,3-dihydrobenzofuran To an ice-cooling solution of (5-bromo-2-chlorophenyl)(4-((7-fluoro-2,3-dihydro benzofuran-2-yl)methoxy)phenyl) methanone (770 mg, 1.67 mmol) and triethylsilane (1.07 mL, 6.67 mmol) in a mixed solvent of 1,2-dichloroethane (3 mL) and acetonitrile (3 mL) was added boron trifluoride etherate (0.62 mL, 5 mmol). The resulted mixture was slowly warmed up to room temperature and stirred for overnight, and then added H$_2$O (30 mL) and ethyl acetate (50 mL), the aqueous layer was extracted with ethyl acetate (30 mL). The combined organic layer was washed with saturated NaHCO$_3$ aqueous solution (20 mL×2) and brine, dried over sodium sulfate and concentrated under vacuum. The residue was purified by prep-TLC (petroleum ether: ethyl acetate=5:1) to afford 2-((4-(5-bromo-2-chlorobenzyl) phenoxy)methyl)-7-fluoro-2,3-dihydrobenzofuran (400 mg, yield: 54%) as a white solid.

$^1$H NMR (400 MHz, CDCl$_3$): δ 7.23-7.31 (m, 3H), 7.10 (d, J=11.2 Hz, 2H), 6.88-7.00 (m, 4H), 6.79-6.84 (m, 1H), 5.23-5.29 (m, 1H), 4.24 (dd, J=5.6, 10.0 Hz, 1H), 4.14 (dd, J=5.2, 10.0 Hz, 1H), 4.01 (s, 2H), 3.44 (dd, J=9.2, 15.6 Hz, 1H), 3.27 (dd, J=7.2, 15.6 Hz, 1H).

Compounds of Examples 19-41 were Prepared According to the Synthetic Method of Example 18

Example 19: 2-((4-(5-bromo-2-chlorobenzyl)phenoxy)methyl)-2,3-dihydrobenzofuran

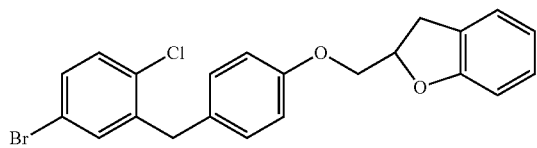 [SMILES: Clc1ccc(Br)cc1Cc1ccc(OCC2Cc3ccccc3O2)cc1]

$^1$H NMR (400 MHz, CDCl$_3$): δ 7.21-7.31 (m, 4H), 7.10-7.17 (m, 3H), 6.84-6.92 (m, 4H), 5.14-5.20 (m, 1H), 4.22 (dd, J=6.8, 10 Hz, 1H), 4.10 (dd, J=4.4, 10 Hz, 1H), 4.01 (s, 2H), 3.40 (dd, J=9.6, 16 Hz, 1H), 3.16 (dd, J=7.2, 15.6 Hz, 1H).

Example 20: 2-((4-(5-bromo-2-chlorobenzyl)phenoxy)methyl)-4-fluoro-2,3-dihydro benzofuran

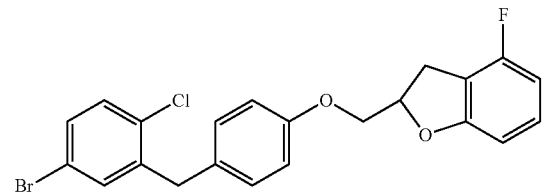 [SMILES: Fc1cccc2c1CC(COc1ccc(Cc3cc(Br)ccc3Cl)cc1)O2]

m/z: [M+H]$^+$ 447.1

Example 21: 2-((4-(5-bromo-2-chlorobenzyl)phenoxy)methyl)-5-fluoro-2,3-dihydrobenzofuran

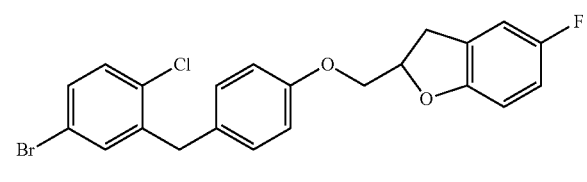 [SMILES: Fc1ccc2c(c1)CC(COc1ccc(Cc3cc(Br)ccc3Cl)cc1)O2]

m/z: [M+H]$^+$ 447.1

Example 22: 2-((4-(5-bromo-2-chlorobenzyl)phenoxy)methyl)-6-fluoro-2,3-dihydrobenzofuran

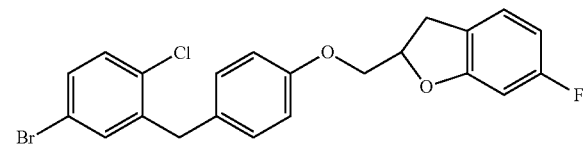 [SMILES: Fc1ccc2c(c1)OC(COc1ccc(Cc3cc(Br)ccc3Cl)cc1)C2]

m/z: [M+H]$^+$ 447.1

Example 23: 4-bromo-2-(4-((2,3-dihydrobenzofuran-2-yl)methoxy)benzyl)benzonitrile

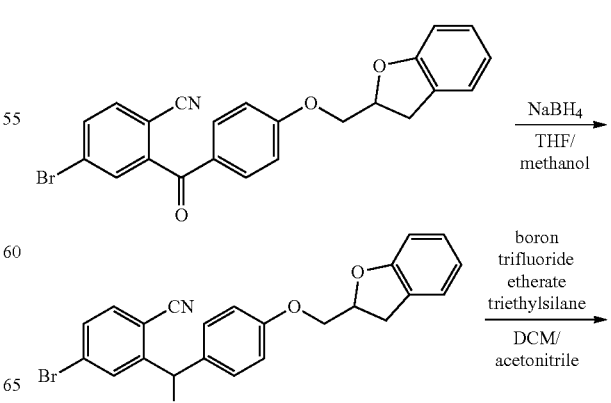

-continued

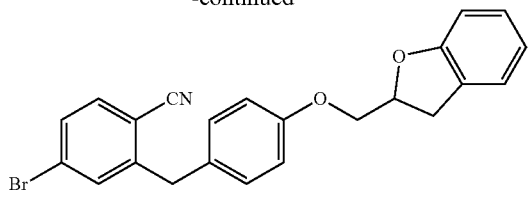

Step 1: 4-bromo-2-((4-((2,3-dihydrobenzofuran-2-yl)methoxy)phenyl)(hydroxy)methyl)benzonitrile A solution of 4-bromo-2-(4-((2,3-dihydrobenzofuran-2-yl)methoxy)benzoyl) benzonitrile (620 mg, 1.43 mmol) in a mixed solvent of THF (6 mL) and methanol (6 mL) was cooled down to 0° C., and then NaBH$_4$ (81 mg, 2.14 mmol) was added slowly. The resulted mixture was stirred at 0° C. for 30 min and then poured into water (20 mL), after ethyl acetate (30 mL) was added and the aqueous layer was removed. The organic layer was dried over sodium sulfate, filtered and concentrated to afford 4-bromo-2-((4-((2,3-dihydrobenzofuran-2-yl)methoxy) phenyl)(hydroxy)methyl) benzonitrile (600 mg, yield: 96%).

Step 2: 4-bromo-2-(4-((2,3-dihydrobenzofuran-2-yl)methoxy)benzyl)benzonitrile

A solution of 4-bromo-2-((4-((2,3-dihydrobenzofuran-2-yl)methoxy)phenyl)(hydroxy) methyl)benzonitrile (600 mg, 1.38 mmol) and triethylsilane (479 mg, 4.13 mmol) in a mixed solvent of acetonitrile (3.5 mL) and DCM (3.5 mL) was cooled down to 0° C., and then boron trifluoride etherate (390 mg, 2.75 mmol) was added dropwise under nitrogen. The resulted mixture was stirred at 0° C. for 2 h and then poured into water (20 mL), the aqueous layer was extracted with ethyl acetate (20 mL×3). The combined organic layer was dried over sodium sulfate, filtered and concentrated. The residue was purified by prep-TLC to afford 4-bromo-2-(4-((2,3-dihydrobenzofuran-2-yl)methoxy)benzyl)benzonitrile (275 mg, yield: 48%).

$^1$H NMR (400 MHz, CDCl$_3$): δ 7.70 (d, J=8.0 Hz, 1H), 7.37 (dd, J=2.0, 7.6 Hz, 1H), 7.32 (d, J=2.0 Hz, 1H), 7.22 (d, J=7.6 Hz, 1H), 7.15 (t, J=7.6 Hz, 1H), 7.10 (d, J=8.4 Hz, 2H), 6.83-6.93 (m, 4H), 5.14-5.21 (m, 1H), 4.23 (dd, J=6.4, 10.0 Hz, 1H), 4.12 (dd, J=4.8, 9.6 Hz, 1H), 4.06 (s, 2H), 3.41 (dd, J=9.6, 15.6 Hz, 1H), 3.16 (dd, J=7.2, 15.6 Hz, 1H).

Example 24: 2-((4-(5-bromo-2-methoxybenzyl)phenoxy)methyl)-2,3-dihydrobenzofuran

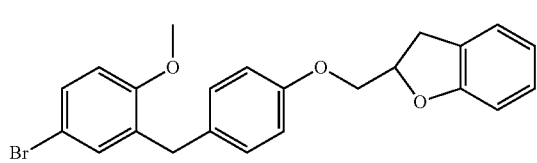 [SMILES: COc1ccc(Br)cc1Cc1ccc(OCC2Cc3ccccc3O2)cc1]

m/z: [M+H]$^+$ 425.2

Example 25: 2-((4-(3-bromobenzyl)phenoxy)methyl)-2,3-dihydrobenzofuran

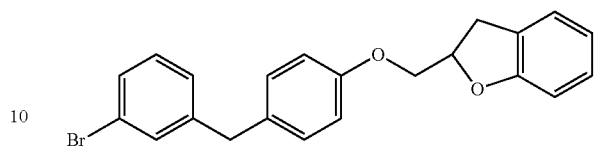

$^1$H NMR (400 MHz, CDCl$_3$): δ 7.10-7.35 (m, 8H), 6.84-6.91 (m, 4H), 5.13-5.20 (m, 1H), 4.21 (dd, J=6.4, 10 Hz, 1H), 4.10 (dd, J=4.4, 10 Hz, 1H), 3.91 (s, 2H), 3.40 (dd, J=9.6, 16 Hz, 1H), 3.15 (m, J=6.8, 16 Hz, 1H).

Example 26: 2-((4-(5-bromo-2-methoxybenzyl)phenoxy)methyl)benzofuran

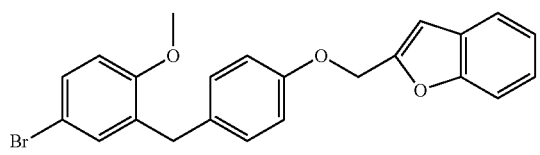 [SMILES: COc1ccc(Br)cc1Cc1ccc(OCc2cc3ccccc3o2)cc1]

m/z: [M+H]$^+$ 422.9

Example 27: 3-((4-(5-bromo-2-chlorobenzyl)phenoxy)methyl)-1,1-dimethyl-1,3-dihydroisobenzofuran

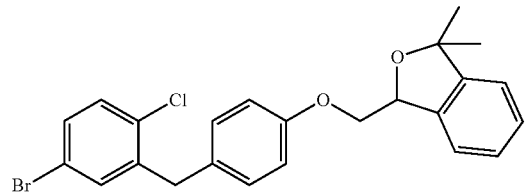 [SMILES: CC1(C)OC(COc2ccc(Cc3cc(Br)ccc3Cl)cc2)c2ccccc21]

m/z: [M+H]$^+$ 456.8

Example 28: 1-((4-(5-bromo-2-chlorobenzyl)phenoxy)methyl)-1,3-dihydroisobenzofuran

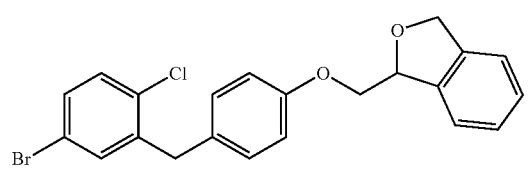

$^1$H NMR (400 MHz, CDCl$_3$): δ 7.23-7.37 (m, 7H), 7.09-7.12 (m, 2H), 6.88-6.94 (m, 2H), 5.61 (t, J=5.2 Hz, 1H), 5.17-5.27 (m, 2H), 4.20 (d, J=5.6 Hz, 2H), 4.01 (s, 2H).

Example 29: 1-((4-(5-bromo-2-methylbenzyl)phenoxy)methyl)-1,3-dihydroisobenzofuran

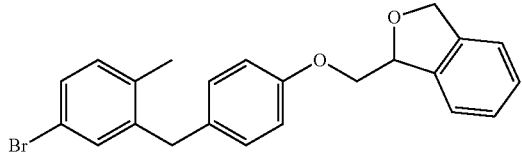 [SMILES: Cc1ccc(Br)cc1Cc1ccc(OCC2OCc3ccccc32)cc1]

¹H NMR (400 MHz, CDCl₃): δ 7.22-7.38 (m, 6H), 7.03 (d, J=8.8 Hz, 3H), 6.87-6.91 (m, 2H), 5.61 (t, J=5.2 Hz, 1H), 5.17-5.27 (m, 2H), 4.19 (d, J=5.2 Hz, 2H), 3.89 (s, 2H), 2.20 (s, 3H).

Example 30: (S)-1-((4-(5-bromo-2-chlorobenzyl)phenoxy)methyl)-1,3-dihydroisobenzofuran

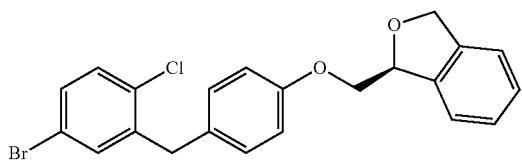 [SMILES: Clc1ccc(Br)cc1Cc1ccc(OC[C@H]2OCc3ccccc32)cc1]

m/z: [M+H]⁺ 429.4

Example 31: 2-((4-(5-bromo-2-chlorobenzyl)phenoxy)methyl)-5-methyl-2,3-dihydrobenzofuran

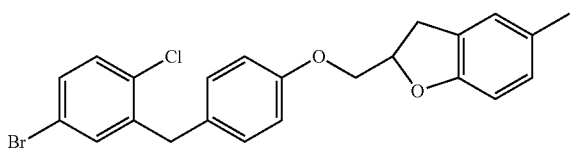 [SMILES: Cc1ccc2c(c1)CC(COc1ccc(Cc3cc(Br)ccc3Cl)cc1)O2]

¹H NMR (400 MHz, CDCl₃): δ 7.24-7.32 (m, 3H), 7.03-7.14 (m, 3H), 6.89-6.96 (m, 3H), 6.42 (d, J=8.0 Hz, 1H), 5.12-5.18 (m, 1H), 4.21 (dd, J=6.8, 10.0 Hz, 1H), 4.09 (dd, J=5.6, 6.0 Hz, 1H), 4.02 (s, 2H), 3.36 (dd, J=9.2, 16.0 Hz, 1H), 3.12 (dd, 7.2, 16.0 Hz, 1H), 2.31 (s, 3H).

Example 32: 2-((4-(5-bromo-2-methylbenzyl)phenoxy)methyl)-2,3-dihydrobenzofuran

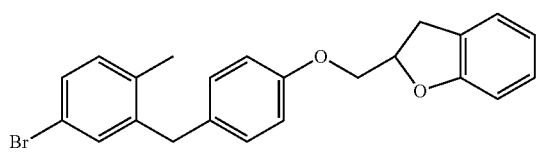 [SMILES: Cc1ccc(Br)cc1Cc1ccc(OCC2Cc3ccccc3O2)cc1]

¹H NMR (400 MHz, CDCl₃): δ 7.26-7.28 (m, 1H), 7.20-7.22 (m, 2H), 7.14 (t, J=8.0 Hz, 1H), 7.02-7.04 (m, 3H), 6.83-6.90 (m, 4H), 5.13-5.20 (m, 1H), 4.20 (dd, J=6.0, 10.0 Hz, 1H), 4.10 (dd, J=4.8, 10 Hz, 1H), 3.88 (s, 2H), 3.40 (dd, J=9.2, 15.6 Hz, 1H), 3.15 (dd, J=6.8, 15.6 Hz, 1H), 2.19 (s, 3H).

Example 33: (S)-1-((4-(5-bromo-2-chlorobenzyl)phenoxy)methyl)-5-methyl-1,3-dihydroisobenzofuran

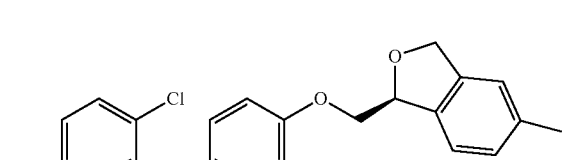

m/z: [M+H]⁺ 443.2

Example 34: (S)-1-((4-(5-bromo-2-chlorobenzyl)phenoxy)methyl)-5-fluoro-1,3-dihydroisobenzofuran

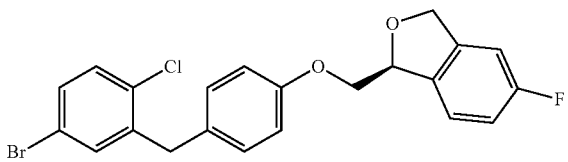 [SMILES: Fc1ccc2c(c1)CO[C@@H]2COc1ccc(Cc2cc(Br)ccc2Cl)cc1]

m/z: [M+H]⁺ 447.2

Example 35: (S)-2-((4-(5-bromo-2-chlorobenzyl)phenoxy)methyl)-2,3-dihydrobenzofuran

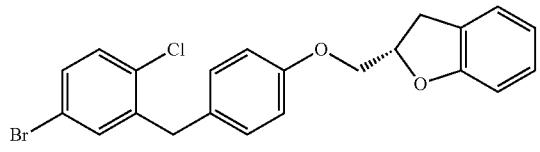 [SMILES: Clc1ccc(Br)cc1Cc1ccc(OC[C@@H]2Cc3ccccc3O2)cc1]

m/z: [M+H]⁺ 429.2

Example 36: (R)-1-((4-(5-bromo-2-chlorobenzyl)phenoxy)methyl)-1,3-dihydroisobenzofuran

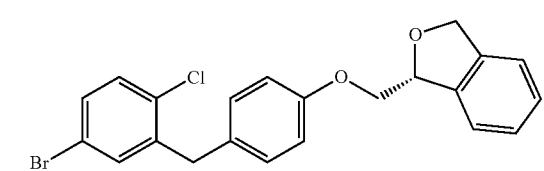 [SMILES: Clc1ccc(Br)cc1Cc1ccc(OC[C@@H]2OCc3ccccc32)cc1]

¹H NMR (400 MHz, CDCl₃): δ 7.23-7.38 (m, 7H), 7.10-7.12 (m, 2H), 6.89-6.93 (m, 2H), 5.61 (t, J=5.2 Hz, 1H), 5.17-5.27 (m, 2H), 4.20 (d, J=6.0 Hz, 2H), 4.01 (s, 2H).

Example 37: (S)-2-((4-(5-bromo-2-methylbenzyl)phenoxy)methyl)-2,3-dihydrobenzofuran

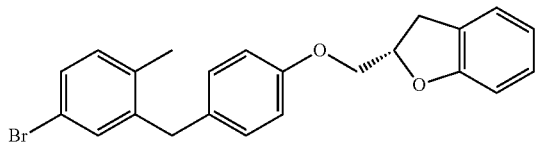 [SMILES: Cc1ccc(Br)cc1Cc1ccc(OC[C@@H]2Cc3ccccc3O2)cc1]

m/z: [M+H]⁺ 409.3

Example 38: 2-((4-(5-bromo-2-chlorobenzyl)phenoxy)methyl)-2-methyl-2,3-dihydrobenzofuran

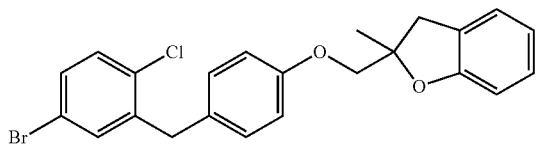 [SMILES: CC1(COc2ccc(Cc3cc(Br)ccc3Cl)cc2)Cc2ccccc2O1]

Compound of Example 38 was prepared according to the synthetic method of Example 18 by replacing 3-bromoprop-1-ene to 3-bromo-2-methylpropene in step 1.

¹H NMR (400 MHz, CDCl₃): δ 7.69 (m, 2H), 7.47 (m, 1H), 7.41 (m, 1H), 7.25 (m, 1H), 7.08 (m, 2H), 6.88 (m, 2H), 6.80 (m, 1H), 6.71 (m, 1H), 4.02 (m, 4H), 3.28 (d, J=16 Hz, 1H), 2.99 (d, J=16 Hz, 1H), 1.56 (s, 3H).

Example 39: 2-((4-(5-bromo-2-methylbenzyl)phenoxy)methyl)-2-methyl-2,3-dihydrobenzofuran

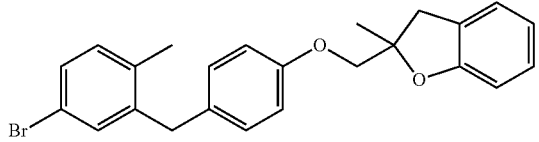 [SMILES: Cc1ccc(Br)cc1Cc1ccc(OCC2(C)Cc3ccccc3O2)cc1]

Compound of Example 39 was prepared according to the synthetic method of Example 18 by replacing 3-bromoprop-1-ene to 3-bromo-2-methylpropene in step 1.

¹H NMR (400 MHz, CDCl₃): δ 7.26 (m, 1H), 7.12-7.21 (m, 3H), 7.01-7.04 (m, 3H), 6.83-6.89 (m, 3H), 6.80 (m, 1H), 3.97-4.02 (m, 2H), 3.88 (s, 2H), 3.37 (d, J=16 Hz, 1H), 3.04 (d, J=16 Hz, 1H), 2.19 (s, 3H), 1.63 (s, 3H).

Example 40: 1-((4-(5-bromo-2-chlorobenzyl)phenoxy)methyl)-1-methyl-1,3-dihydroisobenzofuran

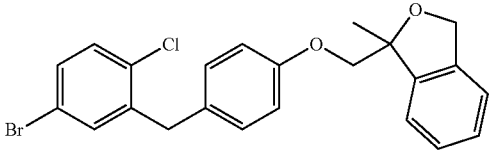 [SMILES: CC1(COc2ccc(Cc3cc(Br)ccc3Cl)cc2)OCc2ccccc21]

¹H NMR (400 MHz, CDCl₃): δ 7.07-7.35 (m, 7H), 7.08-7.10 (m, 2H), 6.85-6.89 (m, 2H), 5.19 (s, 2H), 4.01-4.16 (m, 2H), 3.99 (s, 2H), 1.68 (s, 3H).

Example 41: 1-((4-(5-bromo-2-methylbenzyl)phenoxy)methyl)-1-methyl-1,3-dihydroisobenzofuran

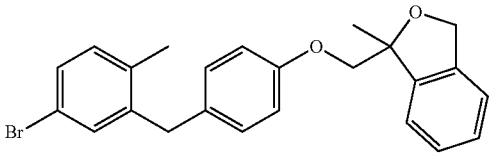 [SMILES: Cc1ccc(Br)cc1Cc1ccc(OCC2(C)OCc3ccccc32)cc1]

¹H NMR (400 MHz, CDCl₃): δ 7.32-7.34 (m, 3H), 7.23-7.30 (m, 2H), 7.22 (d, J=2.0 Hz, 1H), 7.01-7.05 (m, 3H), 6.84-6.86 (m, 2H), 5.20 (s, 2H), 4.06 (dd, J=9.2, 17.6 Hz, 2H), 3.88 (s, 2H), 2.21 (s, 3H), 1.69 (s, 3H).

Example 42: Synthesis of (2S,3R,4R,5S,6R)-2-(4-chloro-3-(4-((7-fluoro-2,3-dihydrobenzofuran-2-yl)methoxy)benzyl)phenyl)-6-(hydroxymethyl)tetrahydro-2H-pyran-3,4,5-triol (I-34)

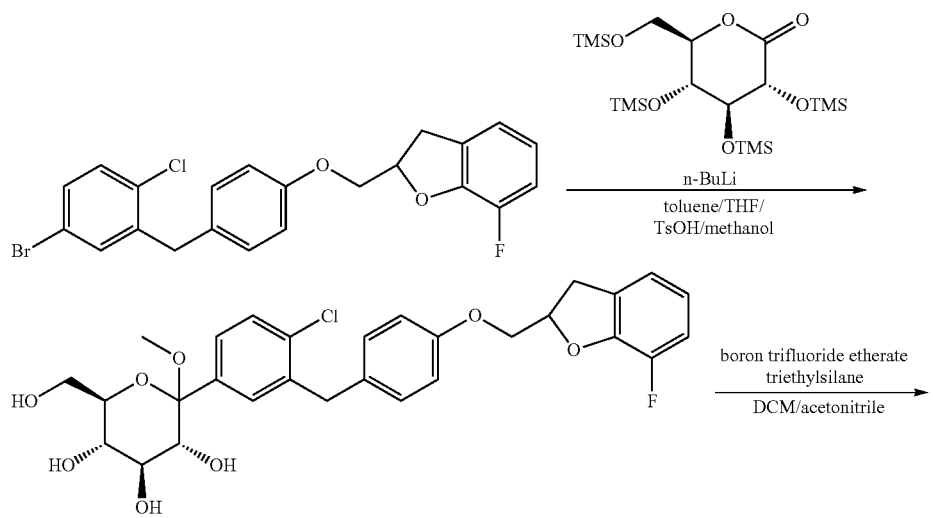

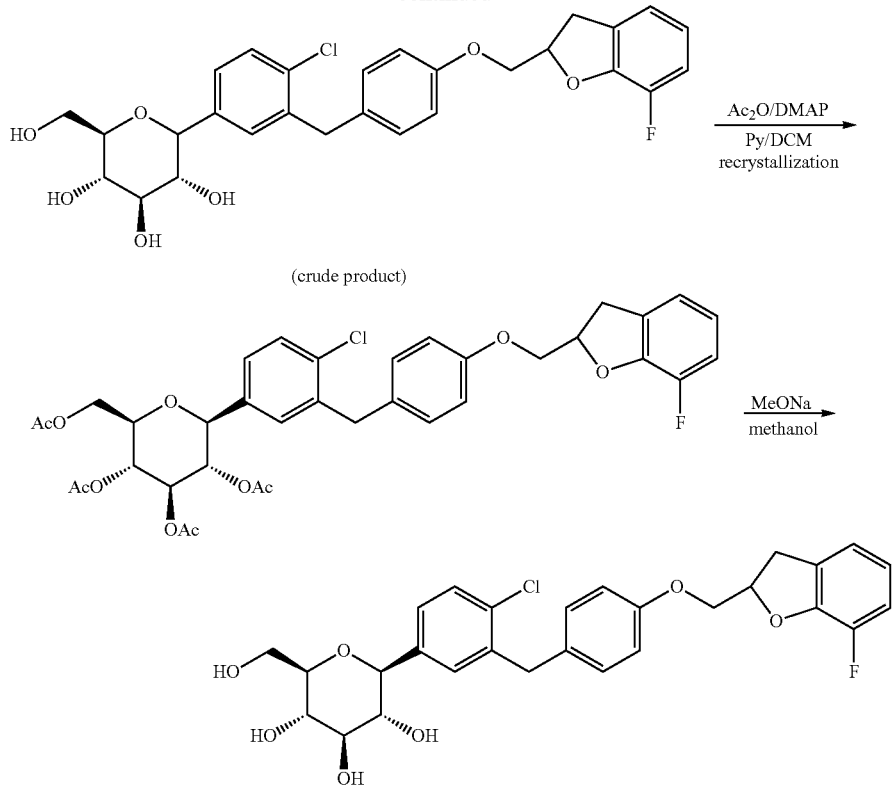

(crude product)

Step 1: (3R,4S,5S,6R)-2-(4-chloro-3-(4-((7-fluoro-2,3-dihydrobenzofuran-2-yl)methoxy)benzyl)phenyl)-6-(hydroxymethyl)-2-methoxytetrahydro-2H-pyran-3,4,5-triol At −78° C., To a solution of 2-((4-(5-bromo-2-chlorobenzyl)phenoxy)methyl)-7-fluoro-2,3-dihydrobenzofuran (400 mg, 0.89 mmol) in dry THF (2 mL) and toluene (4 mL) was added n-BuLi (2.5 M solution in THF, 0.35 mL, 0.89 mmol) dropwise under nitrogen, the inner temperature was below −60° C. during the addition. The resulted mixture was stirred at −70° C. for 30 min, and then added (3R,4S,5R,6R)-3,4,5-tris((trimethylsilyl)oxy)-6-(((trimethylsilyl)oxy) methyl)tetrahydro-2H-pyran-2-one (in toluene, 3 mL). The mixture was stirred at −70° C. for 1 h, and then added methanesulfonic acid (TsOH) (in methanol, 103 mg/5 mL). The mixture was slowly warmed to room temperature and stirred for overnight. The reaction was quenched by addition of saturated NaHCO₃ aqueous solution (20 mL), extracted with ethyl acetate (30 mL×3). The combined organic layer was washed with brine, dried over sodium sulfate, filtered and concentrated. The residue was purified by column chromatography on silica gel (methanol/DCM=1:20) to afford (3R,4S,5S,6R)-2-(4-chloro-3-(4-((7-fluoro-2,3-dihydrobenzofuran-2-yl) methoxy)benzyl)phenyl)-6-(hydroxymethyl)-2-methoxytetrahydro-2H-pyran-3,4,5-triol (330 mg, yield: 66%) as a white foam.

m/z: [M−H]⁻ 558.9

Step 2: (3R,4R,5S,6R)-2-(4-chloro-3-(4-((7-fluoro-2,3-dihydrobenzofuran-2-yl)methoxy)benzyl)phenyl)-6-(hydroxymethyl)tetrahydro-2H-pyran-3,4,5-triol At −15° C., To a solution of (3R,4S,5S,6R)-2-(4-chloro-3-(4-((7-fluoro-2,3-dihydrobenzofuran-2-yl)methoxy)benzyl)phenyl)-6-(hydroxymethyl)-2-methoxytetrahydro-2H-pyran-3,4,5-triol (300 mg, 0.59 mmol) and triethylsilane (0.17 mL, 1.18 mmol) in a mixed solvent of acetonitrile (2 mL) and DCM (2 mL) was added boron trifluoride etherate (0.11 mL, 0.88 mmol) was added dropwise. The resulted mixture was slowly warmed up to 0° C. stirred for 2 h, and then the reaction was quenched by addition of saturated NaHCO₃ aqueous solution (20 mL), the aqueous layer was extracted with ethyl acetate (20 mL×3). The combined organic layer was washed with brine and dried over sodium sulfate, filtered and concentrated to afford (3R,4R,5S,6R)-2-(4-chloro-3-(4-((7-fluoro-2,3-dihydrobenzofuran-2-yl) methoxy)benzyl)phenyl)-6-(hydroxymethyl)tetrahydro-2H-pyran-3,4,5-triol (300 mg, yield: 94%) as a light yellow foam.

m/z: [M+NH₄]⁺ 547.9

Step 3: (2R,3R,4R,5S,6S)-2-(acetoxy methyl)-6-(4-chloro-3-(4-((7-fluoro-2,3-dihydrobenzofuran-2-yl) methoxy)benzyl)phenyl)tetrahydro-2H-pyran-3,4,5-triyl triacetate To a solution of (3R,4R,5S,6R)-2-(4-chloro-3-(4-((7-fluoro-2,3-dihydrobenzofuran-2-yl) methoxy)benzyl)phenyl)-6-(hydroxymethyl)tetrahydro-2H-pyran-3,4,5-triol (obtained from step 2) (330 g, 0.62 mmol) in DCM (3 mL) was added Ac₂O (380 mg, 3.37 mmol), pyridine (491 mg, 6.22 mmol) and catalytic amount of DMAP. The resulted mixture was stirred at room temperature for 2 h, and then diluted with ethyl acetate (50 mL). The organic layer was washed with hydrochloric acid (2 M, 10 mL), H₂O (10 mL), saturated NaHCO3 aqueous solution (10 mL) and brine successively, dried over sodium sulfate, filtered and concentrated. The residue was purified by recrystallization using ethanol to afford (2R,3R,4R,5S,6S)-2-(acetoxymethyl)-6-(4-chloro-3-(4-((7-fluoro-2,3-dihydrobenzofuran-2-yl)methoxy)benzyl)phenyl)tetrahydro-2H-pyran-3,4,5-triyl triacetate (210 mg, yield: 48%) as a white solid.

m/z: [M+H₂O]⁺ 716.2

Step 4: (2S,3R,4R,5S,6S)-2-(4-chloro-3-(4-((7-fluoro-2,3-dihydrobenzofuran-2-yl)methoxy)benzyl)phenyl)-6-(hydroxymethyl)tetrahydro-2H-pyran-3,4,5-triol To a solution of (2R,3R,4R,5S,6S)-2-(acetoxymethyl)-6-(4-chloro-3-(4-((7-fluoro-2,3-dihydrobenzofuran-2-yl)methoxy)benzyl)phenyl)tetrahydro-2H-pyran-3,4,5-triyl triacetate (obtained from step 3) (210 g, 0.30 mmol) in methanol (2 mL) was added sodium methanolate (16 mg, 0.30 mmol). The resulted mixture was stirred at room temperature for 2 h, and then neutralized with acetic acid. The solvent was evaporated under vacuum. The residue was purified by prep-TLC (DCM:methanol=10:1) to afford (2S,3R,4R,5S,6S)-2-(4-chloro-3-(4-((7-fluoro-2,3-dihydrobenzofuran-2-yl)methoxy)benzyl)phenyl)-6-(hydroxymethyl)tetrahydro-2H-pyran-3,4,5-triol (120 mg, yield: 75%) as a white solid.

m/z: [M+H₂O]⁺ 548.2

¹H NMR (400 MHz, CD₃OD): δ 7.28-7.37 (m, 3H), 7.13 (d, J=8.8 Hz, 2H), 7.01 (d, J=7.6 Hz, 1H), 6.79-6.94 (m, 4H), 5.18-5.24 (m, 1H), 4.17-4.19 (m, 2H), 4.00-4.11 (m, 3H), 3.87-3.90 (d, J=11.6 Hz, 1H), 3.68-3.72 (m, 1H), 3.36-3.46 (m, 4H), 3.20-3.29 (m, 2H).

Compounds of Example 43-56 were Prepared According to the Synthetic Method of Example 42 by Using Corresponding Bromide Example 43: (2S,3R,4R,5S,6R)-2-(4-chloro-3-(4-((4-fluoro-2,3-dihydrobenzofuran-2-yl)methoxy)benzyl)phenyl)-6-(hydroxymethyl)tetrahydro-2H-pyran-3,4,5-triol (I-31)

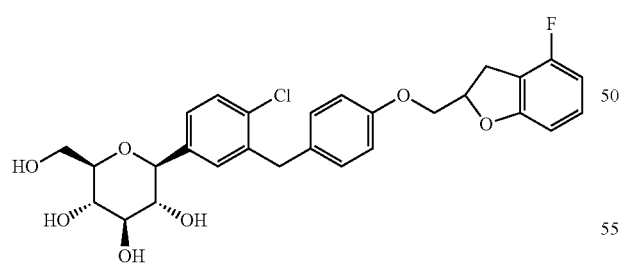

m/z: [M+NH₄]⁺547.9

¹H NMR (400 MHz, CD₃OD): δ 7.28-7.37 (m, 3H), 7.09-7.14 (m, 3H), 6.84-6.88 (m, 2H), 6.57-6.61 (m, 2H), 5.16-5.21 (m, 1H), 4.10-4.20 (m, 5H), 3.87-3.90 (m, 1H), 3.68-3.73 (m, 1H), 3.28-3.49 (m, 5H), 3.18 (dd, J=7.2, 16.0 Hz, 1H).

Example 44: (2S,3R,4R,5S,6R)-2-(4-chloro-3-(4-((5-fluoro-2,3-dihydrobenzofuran-2-yl)methoxy)benzyl)phenyl)-6-(hydroxymethyl)tetrahydro-2H-pyran-3,4,5-triol (I-32)

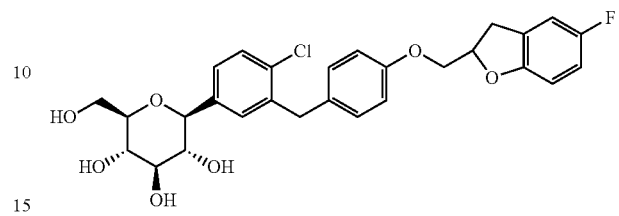

m/z: [M+NH₄]⁺547.9

¹H NMR (400 MHz, CD₃OD): δ 7.28-7.37 (m, 3H), 7.12 (d, J=8.8 Hz, 2H), 6.85-6.88 (m, 1H), 6.79-6.87 (m, 3H), 6.66-6.70 (m, 1H), 5.09-5.16 (m, 1H), 4.00-4.14 (m, 5H), 3.87-3.90 (m, 1H), 3.68-3.73 (m, 1H), 3.28-3.49 (m, 5H), 3.16 (dd, J=7.2, 16.0 Hz, 1H).

Example 45: (2S,3R,4R,5S,6R)-2-(4-chloro-3-(4-((6-fluoro-2,3-dihydrobenzofuran-2-yl)methoxy)benzyl)phenyl)-6-(hydroxymethyl)tetrahydro-2H-pyran-3,4,5-triol (I-33)

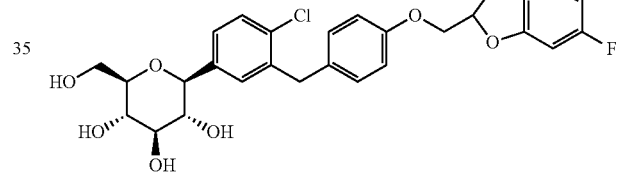

m/z: [M+NH₄]⁺547.9

¹H NMR (400 MHz, CD₃OD): δ 7.28-7.37 (m, 3H), 7.12-7.17 (m, 3H), 6.84-6.87 (m, 2H), 6.49-6.59 (m, 2H), 5.14-5.19 (m, 1H), 4.00-4.18 (m, 5H), 3.87-3.91 (m, 1H), 3.68-3.73 (m, 1H), 3.28-3.49 (m, 5H), 3.11 (dd, J=7.2, 16.0 Hz, 1H).

Example 46: 2-(4-((2,3-dihydrobenzofuran-2-yl)methoxy)benzyl)-4-((2S,3R,4R,5S,6R)-3,4,5-trihydroxy-6-(hydroxymethyl)tetrahydro-2H-pyran-2-yl)benzonitrile (I-28)

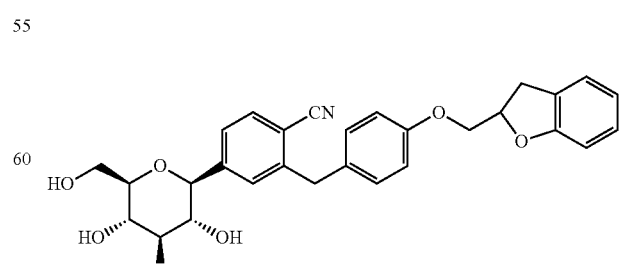

m/z: [M+NH₄]⁺ 520.9

Example 47: (2S,3R,4R,5S,6R)-2-(3-(4-((2,3-dihydrobenzofuran-2-yl)methoxy)benzyl)-4-methoxyphenyl)-6-(hydroxymethyl)tetrahydro-2H-pyran-3,4,5-triol (I-29)

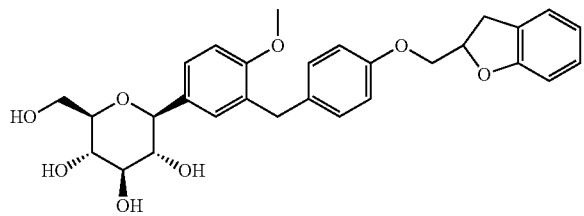 [SMILES: COc1ccc([C@@H]2O[C@H](CO)[C@@H](O)[C@H](O)[C@H]2O)cc1Cc1ccc(OCC2Cc3ccccc3O2)cc1]

m/z: [M+NH$_4$]$^+$ 526.0

Example 48: (2S,3R,4R,5S,6R)-2-(3-(4-((2,3-dihydrobenzofuran-2-yl)methoxy)benzyl)phenyl)-6-(hydroxymethyl)tetrahydro-2H-pyran-3,4,5-triol (I-30)

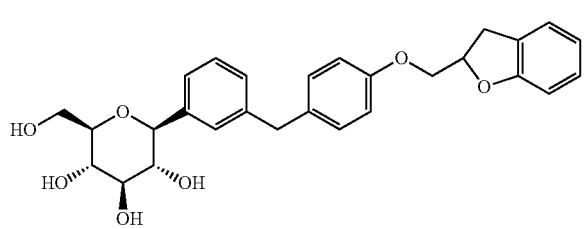 [SMILES: OC[C@H]1O[C@@H](c2cccc(Cc3ccc(OCC4Cc5ccccc5O4)cc3)c2)[C@H](O)[C@@H](O)[C@@H]1O]

m/z: [M+Na]$^+$ 501.1

Example 49: (2S,3R,4R,5S,6R)-2-(3-(4-(benzofuran-2-ylmethoxy)benzyl)-4-methoxyphenyl)-6-(hydroxymethyl)tetrahydro-2H-pyran-3,4,5-triol (I-5)

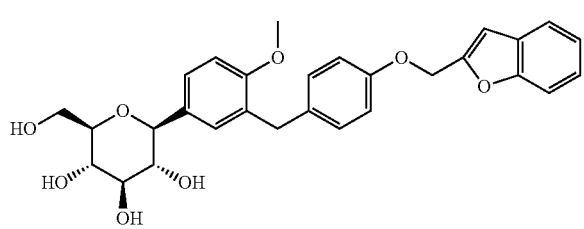 [SMILES: COc1ccc([C@@H]2O[C@H](CO)[C@@H](O)[C@H](O)[C@H]2O)cc1Cc1ccc(OCc2cc3ccccc3o2)cc1]

m/z: [M+NH$_4$]$^+$523.9

Example 50: (2S,3R,4R,5S,6R)-2-(4-chloro-3-(4-((3,3-dimethyl-1,3-dihydroisobenzofuran-1-yl)methoxy)benzyl)phenyl)-6-(hydroxymethyl)tetrahydro-2H-pyran-3,4,5-triol (I-63)

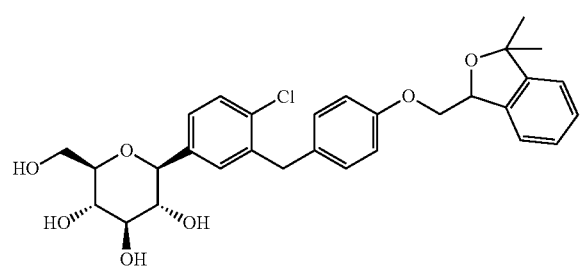 [SMILES: CC1(C)OC(COc2ccc(Cc3cc([C@@H]4O[C@H](CO)[C@@H](O)[C@H](O)[C@H]4O)ccc3Cl)cc2)c2ccccc21]

m/z: [M+H]$^+$540.9

Example 51: (2S,3R,4R,5S,6R)-2-(4-chloro-3-(4-((5-methyl-2,3-dihydrobenzofuran-2-yl)methoxy)benzyl)phenyl)-6-(hydroxymethyl)tetrahydro-2H-pyran-3,4,5-triol (I-85)

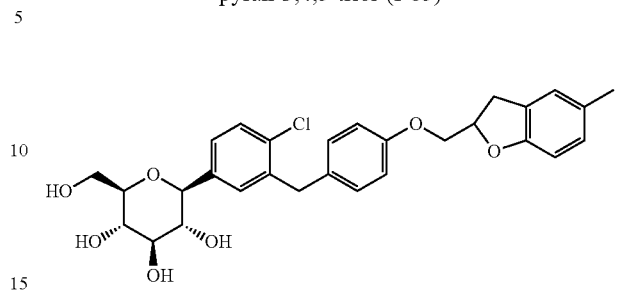

m/z: [M+Na]$^+$ 549.1

Example 52: (2S,3R,4R,5S,6R)-2-(4-chloro-3-(4-(((S)-1,3-dihydroisobenzofuran-1-yl)methoxy)benzyl)phenyl)-6-(hydroxymethyl)tetrahydro-2H-pyran-3,4,5-triol (I-37)

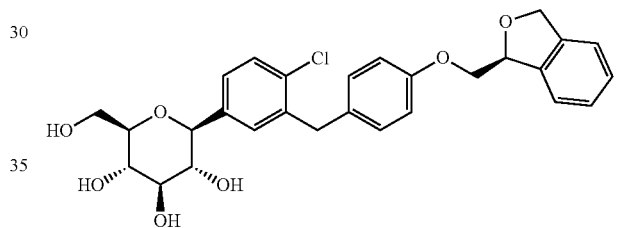

m/z: [M+H]$^+$513.2

Compound I-37 was detected by chiral analysis method C with the 5.00 min retention time (ee %: 100%).

Example 53: (2S,3R,4R,5S,6R)-2-(4-chloro-3-(4-(((S)-5-methyl-1,3-dihydroisobenzofuran-1-yl)methoxy)benzyl)phenyl)-6-(hydroxymethyl)tetrahydro-2H-pyran-3,4,5-triol (I-101)

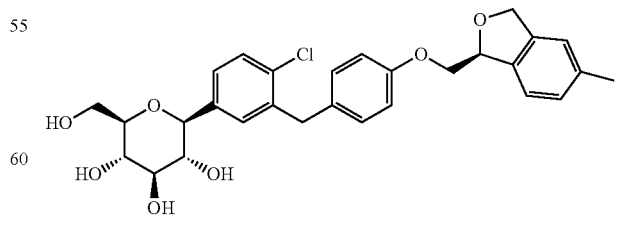

m/z: [M+H]$^+$527.2

Example 54: (2S,3R,4R,5S,6R)-2-(4-chloro-3-(4-(((S)-5-fluoro-1,3-dihydroisobenzofuran-1-yl)methoxy)benzyl)phenyl)-6-(hydroxymethyl)tetrahydro-2H-pyran-3,4,5-triol (I-103)

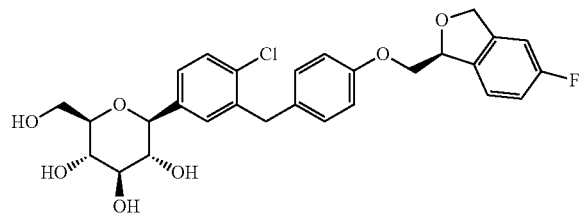 [SMILES: OC[C@H]1O[C@@H](c2ccc(Cl)c(Cc3ccc(OC[C@H]4OCc5cc(F)ccc54)cc3)c2)[C@H](O)[C@@H](O)[C@@H]1O]

m/z: [M+H]⁺ 531.1

Example 55: (2S,3R,4R,5S,6R)-2-(4-chloro-3-(4-(((R)-1,3-dihydroisobenzofuran-1-yl)methoxy)benzyl)phenyl)-6-(hydroxymethyl)tetrahydro-2H-pyran-3,4,5-triol (I-38)

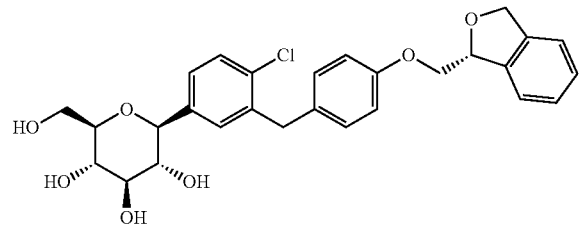 [SMILES: OC[C@H]1O[C@@H](c2ccc(Cl)c(Cc3ccc(OC[C@@H]4OCc5ccccc54)cc3)c2)[C@H](O)[C@@H](O)[C@@H]1O]

m/z: [M+H]⁺ 513.2

Compound I-38 was detected by chiral analysis method C with the 3.23 min retention time (ee %: 100%).

Example 56: (2S,3R,4R,5S,6R)-2-(3-(4-(((S)-2,3-dihydrobenzofuran-2-yl)methoxy)benzyl)-4-methylphenyl)-6-(hydroxymethyl)tetrahydro-2H-pyran-3,4,5-triol (I-26)

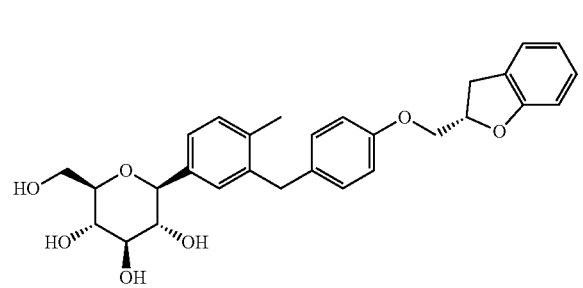 [SMILES: Cc1ccc([C@@H]2O[C@H](CO)[C@@H](O)[C@H](O)[C@H]2O)cc1Cc1ccc(OC[C@@H]2Cc3ccccc3O2)cc1]

m/z: [M+Na]⁺ 515.2

$[\alpha]_D^{25}$ = +44.1° (C=0.204%, MeOH)

Compound I-26 was detected by chiral analysis method B₁ with the 9.05 min retention time (ee %: 100%).

Example 57: Synthesis of Compounds I-22, I-23 and I-24

(2S,3R,4R,5S,6R)-2-(4-chloro-3-(4-((2,3-dihydrobenzofuran-2-yl)methoxy)benzyl)phenyl)-6-(hydroxymethyl)tetrahydro-2H-pyran-3,4,5-triol (I-22)

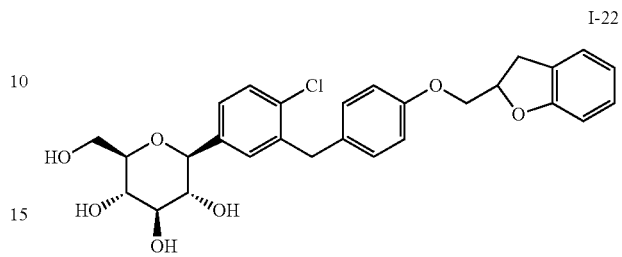

I-22

Compound I-22 was prepared according to the synthetic method of Example 42. Compound I-22 (800 mg) was separated by chiral resolution method A to afford compound I-23 (300 mg) (chiral analysis method A, RT=4.18 min, ee %: 99.0%) and compound I-24 (170 mg) (chiral analysis method A, RT=4.91 min, ee %: 98.9%). Compound I-23 obtained from Example 57 was mixed with Compound I-23 obtained from Example 102 in the proportion of 1:1, the mixture was detected by chiral analysis method A with the 4.27 min retention time (ee %: 100%). Compound I-24 obtained from Example 57 was mixed with compound I-24 obtained from Example 103 in the proportion of 1:1, the mixture was detected by chiral analysis method A with the 4.78 min retention time (ee %: 98%).

I-22 m/z: [M+Na]⁺ 535.2

¹H NMR (400 MHz, CD₃OD): δ 7.28-7.37 (m, 3H), 7.20 (dd, J=0.4, 7.6 Hz, 1H), 7.07-7.13 (m, 3H), 6.82-6.87 (m, 3H), 6.74 (d, J=8.0 Hz, 1H), 5.06-5.13 (m, 1H), 3.99-4.13 (m, 5H), 3.87-3.90 (m, 1H), 3.68-3.72 (m, 1H), 3.27-3.49 (m, 5H), 3.14 (dd, J=7.2, 16.0 Hz, 1H).

I-23 $[\alpha]_D^{25}$ = +54.3° (C=0.053%, MeOH)
I-24 $[\alpha]D^{25}$ = –20.0° (C=0.051%, MeOH)

Example 58: Synthesis of Compounds I-25, I-26 and I-27

(2S,3R,4R,5S,6R)-2-(3-(4-((2,3-dihydrobenzofuran-2-yl)methoxy)benzyl)-4-methylphenyl)-6-(hydroxymethyl)tetrahydro-2H-pyran-3,4,5-triol (I-25)

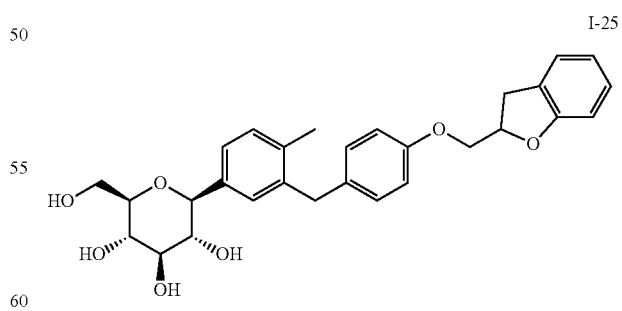

I-25

Compound I-25 was prepared according to the synthetic method of Example 42. Compound I-25 (1.0 g) was separated by chiral resolution method B to afford compound I-26 (240 mg) (chiral analysis method B₁, RT=9.28 min, ee %: 100%) and compound I-27 (205 mg) (chiral analysis method B₁, RT=13.37 min, ee %: 98.7%). Compound I-26 obtained from Example 58 was mixed with Compound I-26 obtained from Example 56 in the proportion of 1:1, the mixture was detected by chiral analysis method $B_1$ with the 9.68 min retention time (ee %: 100%).

I-25 m/z: [M+Na]$^+$515.2

$^1$H NMR (400 MHz, CD$_3$OD): δ 7.04-7.22 (m, 7H), 6.82-6.85 (m, 3H), 6.74 (d, J=7.6 Hz, 1H), 5.06-5.12 (s, 1H), 4.08-4.12 (m, 3H), 3.88-3.94 (m, 3H), 3.68-3.72 (m, 1H), 3.35-3.50 (m, 5H), 3.11-3.16 (m, 1H), 2.20 (s, 3H).

I-26 $[α]_D^{25}$=+44.3° (C=0.212%, MeOH)
I-27 $[α]_D^{25}$=−20.9° (C=0.210%, MeOH)

Example 59: Synthesis of Compounds I-105, I-106 and I-107

(2S,3R,4R,5S,6R)-2-(4-chloro-3-(4-((2-methyl-2,3-dihydrobenzofuran-2-yl)methoxy)benzyl)phenyl)-6-(hydroxymethyl)tetrahydro-2H-pyran-3,4,5-triol (I-105)

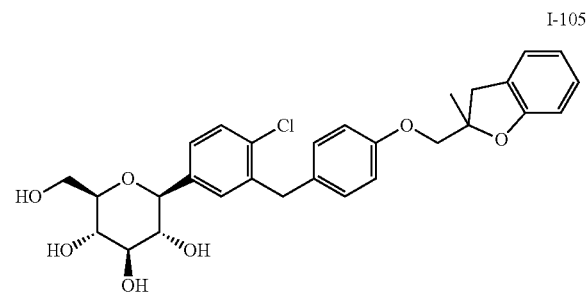 [SMILES: CC1(COc2ccc(Cc3cc([C@@H]4O[C@H](CO)[C@@H](O)[C@H](O)[C@H]4O)ccc3Cl)cc2)Cc2ccccc2O1]

I-105

Compound I-105 was prepared according to the synthetic method of Example 42. Compound I-105 (72 mg) was separated by chiral resolution method D to afford compound I-106 (10 mg) (chiral analysis method D, RT=10.21 min, ee %: 100%) and compound I-107 (23 mg) (chiral analysis method D, RT=6.27 min, ee %: 100%).

I-105 m/z: [M+NH$_4$]$^+$544.2

$^1$H NMR (400 MHz, CDCl$_3$): δ 7.32 (m, 1H), 7.04-7.17 (m, 6H), 6.75-6.87 (m, 4H), 4.07 (m, 1H), 4.00 (m, 2H), 3.93 (s, 1H), 3.80 (m, 3H), 3.59-3.65 (m, 2H), 3.40 (m, 2H), 3.30 (d, J=16 Hz, 1H), 3.00 (d, J=16 Hz, 1H), 1.58 (s, 3H).

Example 60: Synthesis of Compounds I-109, I-110 and I-111

(2S,3R,4R,5S,6R)-2-(3-(4-((2-methyl-2,3-dihydrobenzofuran-2-yl)methoxy)benzyl)-4-methylphenyl)-6-(hydroxymethyl)tetrahydro-2H-pyran-3,4,5-triol (I-109)

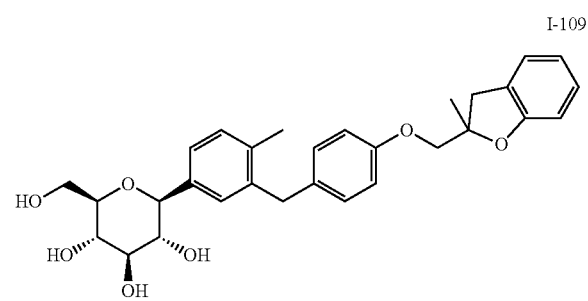 [SMILES: Cc1ccc([C@@H]2O[C@H](CO)[C@@H](O)[C@H](O)[C@H]2O)cc1Cc1ccc(OCC2(C)Cc3ccccc3O2)cc1]

I-109

Compound I-109 was prepared according to the synthetic method of Example 42. Compound I-109 (115 mg) was separated by chiral resolution method D to afford compound I-110 (44 mg) (chiral analysis method D, RT=13.63 min, ee %: 100%) and compound I-111 (70 mg) (chiral analysis method D, RT=7.97 min, ee %: 100%)

I-109 m/z: [M+NH$_4$]$^+$524.2

$^1$H NMR (400 MHz, CDCl$_3$): δ 7.10-7.17 (m, 5H), 6.99 (m, 2H), 6.86 (m, 1H), 6.81 (m, 3H), 4.12 (d, J=9.2 Hz, 1H), 3.96 (m, 2H), 3.90 (s, 2H), 3.82 (m, 1H), 3.68 (m, 2H), 3.47 (m, 3H), 3.34 (d, J=16 Hz, 1H), 3.01 (d, J=16 Hz, 1H), 2.2 (s, 3H), 1.60 (s, 3H).

I-110 $[α]_D^{25}$=+4.52° (C=0.051%, MeOH)
I-111 $[α]_D^{25}$=−27.1° (C=0.050%, MeOH)

Example 61: Synthesis of Compounds I-36, I-37 and I-38

(2S,3R,4R,5S,6R)-2-(4-chloro-3-(4-((1,3-dihydroisobenzofuran-1-yl)methoxy)benzyl)phenyl)-6-(hydroxymethyl)tetrahydro-2H-pyran-3,4,5-triol (I-36)

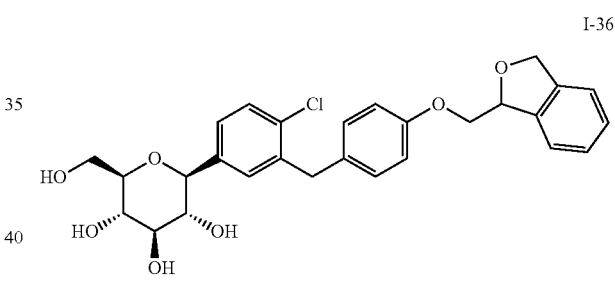

I-36

Compound I-36 was prepared according to the synthetic method of Example 42. Compound I-36 (1.0 g) was separated by chiral resolution method A to afford compound I-38 (190 mg) (chiral analysis method C, RT=3.28 min, ee %: 100%) and compound I-37 (100 mg) (chiral analysis method C, RT=4.89 min, ee %: 100%). Compound I-37 obtained from Example 61 was mixed with Compound I-37 obtained from Example 55 in the proportion of 1:1, the mixture was detected by chiral analysis method C with the 3.31 min retention time (ee %: 100%).

I-36 m/z: [M+H]$^+$513.2

$^1$H NMR (400 MHz, CD$_3$OD): δ 7.28-7.39 (m, 7H), 7.11-7.13 (m, 2H), 6.84-6.87 (m, 2H), 5.54 (s, 1H), 5.10-5.22 (m, 2H), 4.23 (dd, J=4.0, 10.0 Hz, 1H), 4.00-4.16 (m, 4H), 3.87-3.90 (m, 1H), 3.68-3.72 (m, 1H), 3.28-3.49 (m, 4H).

Example 62: Synthesis of Compounds I-43, I-75 and I-76

(2S,3R,4R,5S,6R)-2-(3-(4-((1,3-dihydroisobenzo-furan-1-yl)methoxy)benzyl)-4-methylphenyl)-6-(hydroxymethyl)tetrahydro-2H-pyran-3,4,5-triol (I-43)

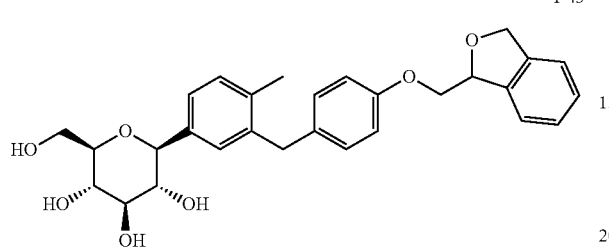

I-43

Compound I-43 was prepared according to the synthetic method of Example 42. Compound I-43 (30 mg) was separated by chiral resolution method D to afford compound I-76 (10 mg) (chiral analysis method C, RT=3.32 min, ee %: 100%) and compound I-75 (6 mg) (chiral analysis method C, RT=5.92 min, ee %: 100%).

I-43 m/z: [M+NH$_4$]$^+$510.3

$^1$HNMR (400 MHz, CD$_3$OD): δ 7.29-7.39 (m, 4H), 7.12-7.22 (m, 3H), 7.04 (d, J=8.4 Hz, 2H), 6.84 (m, J=8.4 Hz, 2H), 5.53 (s, 1H), 5.10-5.21 (m, 2H), 4.08-4.24 (m, 3H), 3.88-3.94 (m, 3H), 3.68-3.72 (m, 1H), 3.37-3.50 (m, 4H), 2.20 (s, 3H).

Example 63: Synthesis of Compounds I-108, I-115 and I-116

(2S,3R,4R,5S,6R)-2-(4-chloro-3-(4-((1-methyl-1,3-dihydroisobenzofuran-1-yl)methoxy)benzyl)phenyl)-6-(hydroxymethyl)tetrahydro-2H-pyran-3,4,5-triol (I-108)

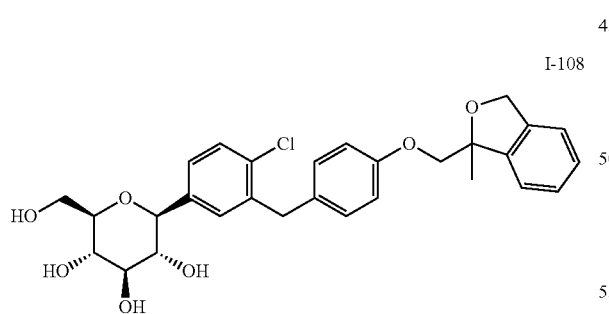

I-108

Compound I-108 was prepared according to the synthetic method of Example 42. Compound I-108 (900 mg) was separated by chiral resolution method E to afford compound I-115 (313 mg) (chiral analysis method B$_2$, RT=7.99 min, ee %: 99.3%) and compound I-116 (369 mg) (chiral analysis method B$_2$, RT=6.23 min, ee %: 99.2%).

I-108 m/z: [M+NH$_4$]$^+$544.2

$^1$H NMR (400 MHz, CD$_3$OD): δ 7.12-7.30 (m, 7H), 6.99-7.01 (m, 2H), 6.71-6.73 (m, 2H), 5.06 (d, J=4.0, 10.8 Hz, 2H), 3.85-4.00 (m, 5H), 3.68-3.75 (m, 2H), 3.49-3.60 (m, 2H), 3.25-3.38 (m, 2H), 1.57 (s, 3H).

Example 64: Synthesis of Compounds I-112, I-113 and I-114

(2S,3R,4R,5S,6R)-2-(3-(4-((1-methyl-1,3-dihydroisobenzofuran-1-yl)methoxy)benzyl)-4-methylphenyl)-6-(hydroxymethyl)tetrahydro-2H-pyran-3,4,5-triol (I-112)

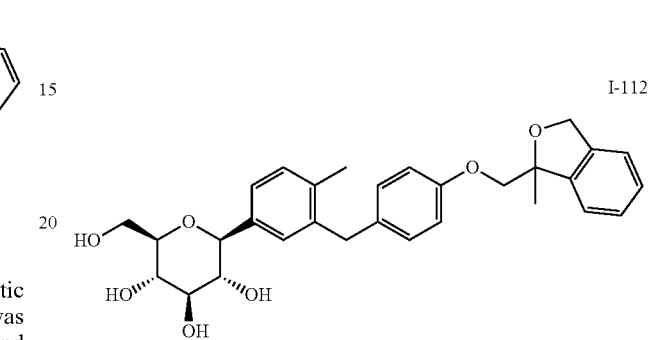

I-112

Compound I-112 was prepared according to the synthetic method of Example 42. Compound I-112 (1.2 g) was separated by chiral resolution method E to afford compound I-113 (342 mg) (chiral analysis method B$_2$, RT=12.00 min, ee %: 98.1%) and compound I-114 (414 mg) (chiral analysis method B$_2$, RT=8.78 min, ee %: 99.4%).

I-112 m/z: [M+NH$_4$]$^+$524.4

$^1$H NMR (400 MHz, CD$_3$OD): δ 7.22-7.33 (m, 4H), 7.09-7.18 (m, 3H), 6.97 (d, J=8.8 Hz, 2H), 6.78 (d, J=8.4 Hz, 2H), 5.14 (d, J=4.0 Hz, 2H), 4.09-4.16 (m, 1H), 3.96-4.02 (m, 2H), 3.77-3.88 (m, 4H), 3.62-3.70 (m, 2H), 3.42-3.52 (m, 2H), 2.19 (s, 3H), 1.63 (s, 3H).

Method 2

Example 65: Synthesis of 4-bromo-1-chloro-2-(4-ethoxybenzyl)benzene

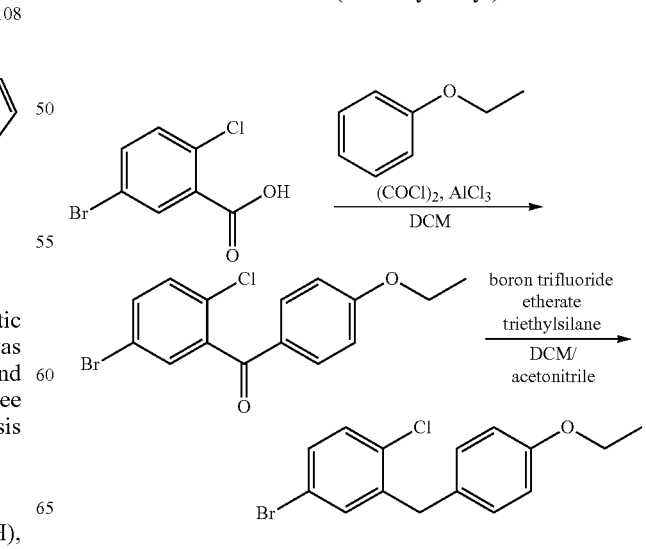

Step 1: (5-bromo-2-chlorophenyl)(4-ethoxyphenyl)methanone

To a mixture of 5-bromo-2-chlorobenzoic acid (15 g, 63.7 mmol) in DCM (50 mL) was added oxalyl chloride (8.1 mL, 95.6 mmol) and DMF (0.5 mL). The resulted mixture was stirred at room temperature for overnight and then the solvent was evaporated under vacuum. The residue was dissolved in DCM (30 mL), and added AlCl$_3$ (10.2 g, 95.6 mmol) in small portions under ice-bath. The mixture was stirred under ice-bath for 1 h, and then poured into ice water (100 g) to quench the reaction. The mixture was extracted with ethyl acetate (100×2), the organic layer was washed with NaOH aqueous solution (1 M, 100×2), H$_2$O and brine, dried over sodium sulfate, filtered and concentrated. The residue was purified by recrystallization using ethanol to afford (5-bromo-2-chlorophenyl)(4-ethoxyphenyl)methanone (20 g, yield: 92%) as a white solid.

Step 2: 4-bromo-1-chloro-2-(4-ethoxybenzyl)benzene

To an ice-cooling solution of (5-bromo-2-chlorophenyl)(4-ethoxyphenyl)methanone (20 g, 58.9 mmol) in a mixed solvent of acetonitrile (20 mL) and DCM (40 mL) was added triethylsilane (21 g, 177 mmol) and boron trifluoride etherate (15 g, 106 mmol). The resulted mixture was slowly warmed up to room temperature stirred for overnight, and then the reaction was quenched by addition of KOH aqueous solution (7 M, 50 mL), the aqueous layer was extracted with DCM (200 mL×2). The combined organic layer was washed with saturated NaHCO3 aqueous solution (100 mL×2), H$_2$O and brine, dried over sodium sulfate, filtered and concentrated. The residue was purified by recrystallization using ethanol to afford 4-bromo-1-chloro-2-(4-ethoxybenzyl)benzene (12 g, yield: 60%) as a white solid.

$^1$H NMR (400 MHz, CDCl$_3$): δ 7.24-7.31 (m, 3H), 7.11 (d, J=8.8 Hz, 2H), 6.86 (d, J=8.8 Hz, 2H), 4.04 (q, J=6.8 Hz, 2H), 4.01 (s, 2H), 1.43 (t, J=6.8 Hz, 3H).

Compounds of Example 66-70 were Prepared According to the Synthetic Method of Example 65

Example 66: 4-bromo-2-(4-ethoxybenzyl)-1-methylbenzene

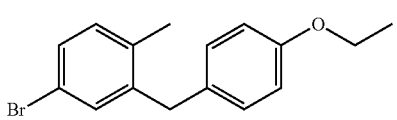 [SMILES: CCOc1ccc(Cc2cc(Br)ccc2C)cc1]

Example 67: 4-bromo-2-(4-ethoxybenzyl)-1-fluorobenzene

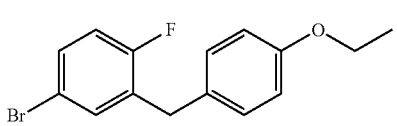

$^1$H NMR (400 MHz, CDCl$_3$): δ 7.24-7.32 (m, 2H), 7.12 (d, J=8.2 Hz, 2H), 6.84-6.96 (m, 3H), 4.03 (q, J=6.8 Hz, 2H), 3.91 (s, 2H), 1.42 (t, J=6.8 Hz, 3H).

Example 68: 4-bromo-1-chloro-2-(3-fluoro-4-methoxybenzyl)benzene m/z: [M+H]$^+$ 331.1

Example 69: 1-bromo-3-(4-ethoxybenzyl)benzene $^1$H NMR (400 MHz, CDCl$_3$): δ 7.08-7.35 (m, 6H), 6.84-6.88 (m, 2H), 4.04 (q, J=6.8 Hz, 2H), 3.90 (s, 2H), 1.43 (t, J=6.8 Hz, 3H).

Example 70: 4-bromo-2-(4-ethoxybenzyl)benzonitrile m/z: [M+NH$_4$]$^+$ 332.8

Example 71: Synthesis of (2R,3R,4R,5S,6S)-2-(acetoxymethyl)-6-(4-chloro-3-(4-hydroxybenzyl)phenyl)tetrahydro-2H-pyran-3,4,5-triyl triacetate

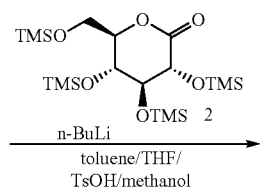

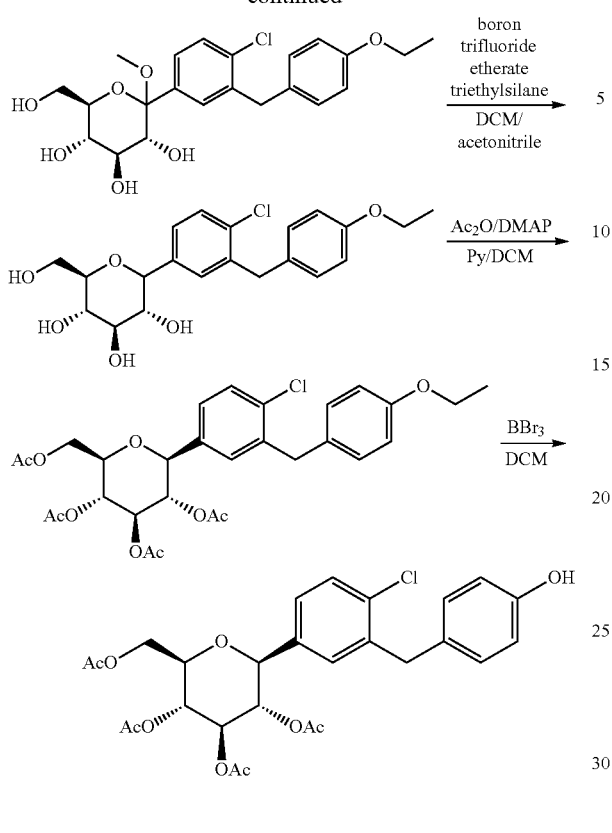

Step 1: (2R,3R,4R,5S,6S)-2-(acetoxymethyl)-6-(4-chloro-3-(4-ethoxybenzyl)phenyl)tetrahydro-2H-pyran-3,4,5-triyl triacetate (2R,3R,4R,5S,6S)-2-(acetoxymethyl)-6-(4-chloro-3-(4-ethoxybenzyl)phenyl)tetrahydro-2H-pyran-3,4,5-triyl triacetate was prepared according to the synthetic method of Example 42 or *J. Med. Chem.* 2008, 51, 1145-1149

Step 2: (2R,3R,4R,5S,6S)-2-(acetoxymethyl)-6-(4-chloro-3-(4-hydroxybenzyl)phenyl)tetrahydro-2H-pyran-3,4,5-triyl triacetate At −70° C., to a solution of (2R,3R,4R,5S,6S)-2-(acetoxymethyl)-6-(4-chloro-3-(4-ethoxybenzyl)phenyl)tetrahydro-2H-pyran-3,4,5-triyl triacetate (obtained from step 1) in dry DCM (15 mL) was added boron tribromide (0.94 mL, 9.71 mmol). The resulted mixture was warmed up to −15° C. and stirred for 1 h, and then diluted with diethyl ether (10 mL) and stirred for further 30 min. The mixture was diluted with H$_2$O (50 mL), and extracted with DCM (100×2). The combined organic layer was washed dried over sodium sulfate, filtered and concentrated to afford (2R,3R,4R,5S,6S)-2-(acetoxymethyl)-6-(4-chloro-3-(4-hydroxybenzyl)phenyl)tetrahydro-2H-pyran-3,4,5-triyl triacetate (650 mg, yield: 98%) as a white foam.

m/z: [M+NH$_4$]$^+$ 565.9

Compounds of Example 72-76 were Prepared According to the Synthetic Method of Example 71

Example 72: (2R,3R,4R,5S,6S)-2-(acetoxymethyl)-6-(3-(4-hydroxybenzyl)-4-methylphenyl)tetrahydro-2H-pyran-3,4,5-triyl triacetate

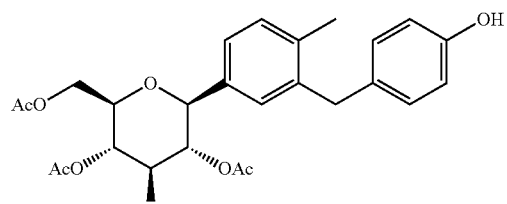

m/z: [M+NH$_4$]$^+$ 545.9

Example 73: (2R,3R,4R,5S,6S)-2-(acetoxymethyl)-6-(4-fluoro-3-(4-hydroxybenzyl)phenyl)tetrahydro-2H-pyran-3,4,5-triyl triacetate

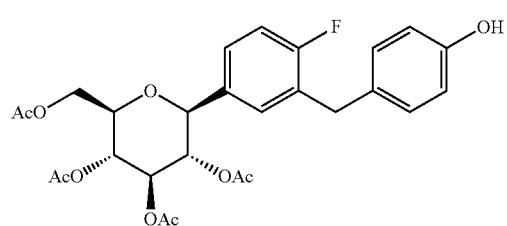 [SMILES: CC(=O)OC[C@H]1O[C@@H](c2ccc(F)c(Cc3ccc(O)cc3)c2)[C@H](OC(C)=O)[C@@H](OC(C)=O)[C@@H]1OC(C)=O]

m/z: [M+Na]$^+$ 555.2

Example 74: (2R,3R,4R,5S,6S)-2-(acetoxymethyl)-6-(4-chloro-3-(3-fluoro-4-hydroxybenzyl)phenyl)tetrahydro-2H-pyran-3,4,5-triyl triacetate

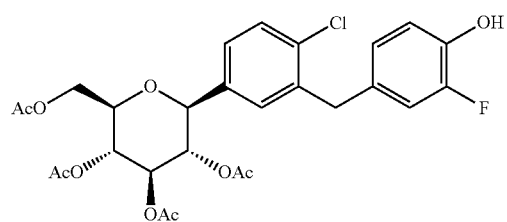 [SMILES: CC(=O)OC[C@H]1O[C@@H](c2ccc(Cl)c(Cc3ccc(O)c(F)c3)c2)[C@H](OC(C)=O)[C@@H](OC(C)=O)[C@@H]1OC(C)=O]

m/z: [M+Na]$^+$ 589.2

Example 75: (2R,3R,4R,5S,6S)-2-(acetoxymethyl)-6-(3-(4-hydroxybenzyl)phenyl)tetrahydro-2H-pyran-3,4,5-triyl triacetate

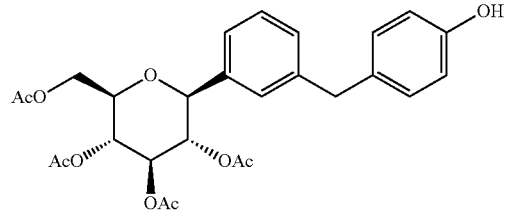 [SMILES: CC(=O)OC[C@H]1O[C@@H](c2cccc(Cc3ccc(O)cc3)c2)[C@H](OC(C)=O)[C@@H](OC(C)=O)[C@@H]1OC(C)=O]

m/z: [M+NH$_4$]$^+$ 531.9

Example 76: (2R,3R,4R,5S,6S)-2-(acetoxymethyl)-6-(4-cyano-3-(4-hydroxybenzyl)phenyl)tetrahydro-2H-pyran-3,4,5-triyl triacetate

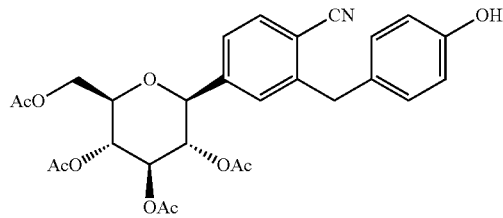 [SMILES: CC(=O)OC[C@H]1O[C@@H](c2ccc(C#N)c(Cc3ccc(O)cc3)c2)[C@H](OC(C)=O)[C@@H](OC(C)=O)[C@@H]1OC(C)=O]

m/z: [M+NH$_4$]$^+$556.9

Example 77: Synthesis of (2S,3R,4R,5S,6R)-2-(3-(4-((2,3-dihydrobenzofuran-2-yl) methoxy)benzyl)-4-methylphenyl)-6-(hydroxymethyl)tetrahydro-2H-pyran-3,4,5-triol

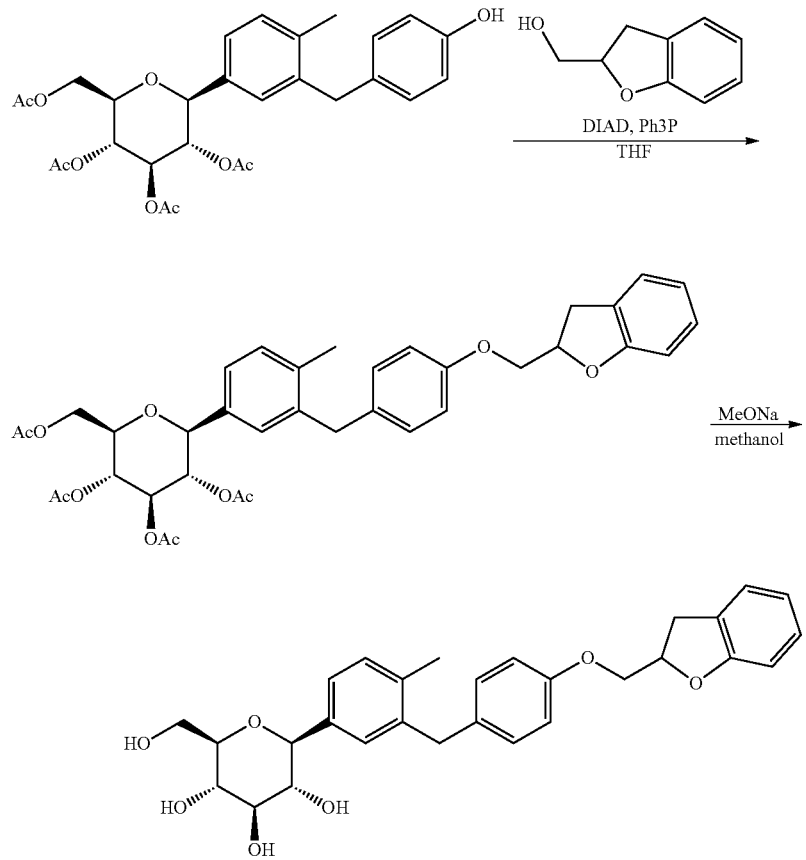

Step 1: (2R,3R,4R,5S,6S)-2-(acetoxymethyl)-6-(3-(4-((2,3-dihydrobenzofuran-2-yl)methoxy)benzyl)-4-methylphenyl)tetrahydro-2H-pyran-3,4,5-triyl triacetate To an ice-cooling solution of (2R,3R,4R,5S,6S)-2-(acetoxymethyl)-6-(3-(4-hydroxy benzyl)-4-methylphenyl)tetrahydro-2H-pyran-3,4,5-triyl triacetate (obtained from Example 72) (350 mg, 0.66 mmol), (2,3-dihydrobenzofuran-2-yl)methanol (298 mg, 1.99 mmol) and triphenylphosphine (521 mg, 1.99 mmol) in THF (10 mL) was added DIAD (0.39 mL, 1.99 mmol) dropwise. The resulted mixture was stirred at room temperature for overnight, and then diluted with ethyl acetate (50 mL). The organic layer was washed with H$_2$O and brine, dried over sodium sulfate, filtered and concentrated. The residue was purified by prep-TLC (petroleum ether/ethyl acetate=2/1) to afford ((2R,3R,4R,5S,6S)-2-(acetoxymethyl)-6-(3-(4-((2,3-dihydrobenzofuran-2-yl)methoxy)benzyl)-4-methylphenyl)tetrahydro-2H-pyran-3,4,5-triyl triacetate (60 mg, yield: 14%) as a white solid.

Step 2: (2S,3R,4R,5S,6R)-2-(3-(4-((2,3-dihydrobenzofuran-2-yl)methoxy)benzyl)-4-methylphenyl)-6-(hydroxymethyl)tetrahydro-2H-pyran-3,4,5-triol To a solution of (2R,3R,4R,5S,6S)-2-(acetoxymethyl)-6-(3-(4-((2,3-dihydrobenzofuran-2-yl)methoxy)benzyl)-4-methylphenyl)tetrahydro-2H-pyran-3,4,5-triyl triacetate (obtained from step 1) (60 mg, 0.09 mmol) in methanol (2 mL) was added sodium methanolate (6 mg, 0.10 mmol). The resulted mixture was stirred at room temperature for 2 h, and then neutralized with acetic acid. The solvent was evaporated under vacuum. The residue was purified by prep-TLC (DCM:methanol=10:1) to afford (2S,3R,4R,5S,6R)-2-(3-(4-((2,3-dihydrobenzofuran-2-yl)methoxy)benzyl)-4-methylphenyl)-6-(hydroxymethyl)tetrahydro-2H-pyran-3, 4,5-triol (34 mg, yield: 76%) as a white solid.

m/z: [M+Na]$^+$515.2

Compounds of Example 78-79 were Prepared According to the Synthetic Method of Example 77 by Using Corresponding Alcohol Example 78: (2S,3R,4R,5S,6R)-2-(3-(4-((2,3-dihydrobenzofuran-2-yl)methoxy)benzyl)-4-fluorophenyl)-6-(hydroxymethyl)tetrahydro-2H-pyran-3,4,5-triol (I-21)

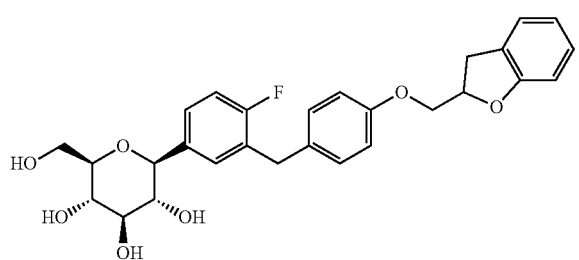

m/z: [M+Na]$^+$ 519.2

$^1$H NMR (400 MHz, CD$_3$OD): δ 7.29-7.31 (m, 2H), 7.21 (d, J=7.2 Hz, 1H), 7.14 (d, J=8.8 Hz, 2H), 7.01-7.11 (m, 2H), 6.82-6.87 (m, 3H), 6.73 (d, J=8.8 Hz, 1H), 5.06-5.14 (m, 1H), 4.08-4.13 (m, 3H), 3.8-3.94 (m, 3H), 3.67-3.72 (m, 1H), 3.29-3.48 (m, 5H), 3.11-3.16 (m, 1H).

Example 79: (2S,3R,4R,5S,6R)-2-(4-chloro-3-(4-((2,3-dihydrobenzofuran-2-yl)methoxy)-3-fluorobenzyl)phenyl)-6-(hydroxymethyl)tetrahydro-2H-pyran-3,4,5- triol (I-12)

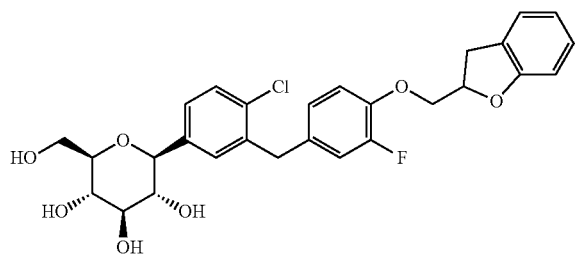 [SMILES: OC[C@H]1O[C@@H](c2ccc(Cl)c(Cc3ccc(OCC4Cc5ccccc5O4)c(F)c3)c2)[C@H](O)[C@@H](O)[C@@H]1O]

m/z: [M+Na]$^+$ 553.0

Method 3

Example 80: Synthesis of 5-fluoro-2-hydroxybenzaldehyde

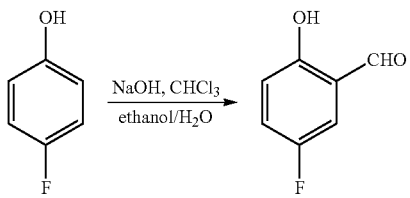 [SMILES: Oc1ccc(F)cc1 ; O=Cc1cc(F)ccc1O]

To a solution of 4-fluorophenol (25 mg, 223 mmol) in a mixed solvent of ethanol (100 mL) and H$_2$O (75 mL) was added NaOH aqueous solution (39 g, 970 mmol, in 200 mL H$_2$O). The resulted mixture was warmed up to 70° C. and added chloroform (55 mL, 691 mmol) dropwise during 2 h, and then the mixture was stirred at 70° C. for overnight. The reaction was cooled down to room temperature and quenched by addition of hydrochloric acid (6 M, 100 mL), and then the mixture was extracted with DCM (250 mL×2). The combined organic layer was washed with H$_2$O and brine, dried over sodium sulfate and concentrated under vacuum. The residue was purified by column chromatography on silica gel (petroleum ether:ethyl acetate=25:1) to afford 5-fluoro-2-hydroxybenzaldehyde (6.5 g, yield: 21%) as a light yellow solid.

$^1$H NMR (400 MHz, CDCl$_3$): δ 10.01 (s, 1H), 9.88 (s, 1H), 7.26-7.32 (m, 2H), 7.00 (dd, J=4.0, 8.8 Hz, 1H).

Example 81: Synthesis of 4-fluoro-2-hydroxybenzaldehyde

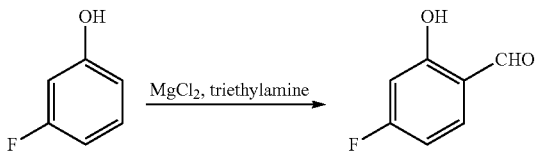 [SMILES: Oc1cccc(F)c1 ; O=Cc1ccc(F)cc1O]

To a mixture of 3-fluorophenol (5 mL, 55.3 mmol), MgCl$_2$ (14.2 g, 149 mmol) in dry acetonitrile (250 mL) was added dry trimethylamine (27 mL) and paraformaldehyde (11 g). The resulted mixture was stirred at reflux for 5 h, and then cooled down to room temperature. The reaction was quenched by addition of hydrochloric acid (5%, 250 mL), extracted with ethyl acetate (100×3). The combined organic layer was washed with hydrochloric acid (5%), H$_2$O and brine, dried over sodium sulfate and concentrated under vacuum. The residue was purified by column chromatography on silica gel (petroleum ether:ethyl acetate=50:1-20:1) to afford 4-fluoro-2-hydroxybenzaldehyde (5 g, yield: 65%) as a light yellow solid.

$^1$H NMR (400 MHz, CDCl$_3$): δ 11.37 (d, J=1.6 Hz, 1H), 9.83 (s, 1H), 7.55-7.59 (m, 1H), 6.65-6.75 (m, 2H).

Example 82: Synthesis of 2-fluoro-6-hydroxybenzaldehyde

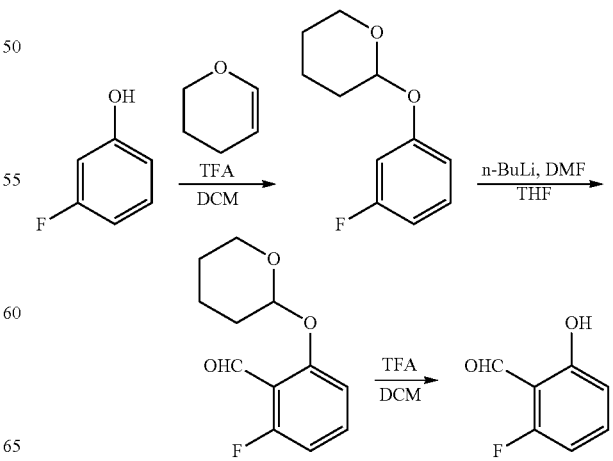

Step 1: 2-(3-fluorophenoxy)tetrahydro-2H-pyran

A solution of 3-fluorophenol (5 g, 44.6 mmol), 3,4-dihydro-2H-pyran (11.2 mL, 134 mmol) and TFA (0.3 mL, 4.0 mmol) in DCM (60 mL) was stirred at room temperature for overnight, and then the mixture was washed with saturated NaHCO₃ aqueous solution and brine, dried over sodium sulfate and concentrated under vacuum. The residue was purified by column chromatography on silica gel (petroleum ether:ethyl acetate=100:1-50:1) to afford 2-(3-fluorophenoxy)tetrahydro-2H-pyran (7.5 g, yield: 86%) as light yellow liquid.

$^1$H NMR (400 MHz, CD$_3$OD): δ 7.20-7.26 (m, 1H), 6.80-6.86 (m, 2H), 6.68-6.73 (m, 1H), 5.42 (t, J=3.2 Hz, 1H), 3.88-3.94 (m, 1H), 3.62-3.66 (m, 1H), 1.99-2.02 (m, 1H), 1.86-1.90 (m, 2H), 1.57-1.74 (m, 3H).

Step 2: 2-fluoro-6-((tetrahydro-2H-pyran-2-yl)oxy)benzaldehyde

At −78° C., to a solution of 2-(3-fluorophenoxy)tetrahydro-2H-pyran (obtained from step 1) (6 g, 30.6 mmol) in THF (60 mL) was added n-BuLi (2.5 M solution in THF, 14 mL, 36.7 mmol) dropwise under nitrogen. The resulted mixture was stirred at −78° C. for 1.5 h, and then added DMF (6.7 g, 91.3 mmol). The mixture was slowly warmed to room temperature and stirred for overnight. The reaction was quenched by addition of saturated NH₄Cl aqueous solution (50 mL), extracted with ethyl acetate (100 mL×2). The combined organic layer was dried over sodium sulfate, filtered and concentrated to afford 2-fluoro-6-((tetrahydro-2H-pyran-2-yl)oxy)benzaldehyde (6.5 g, yield: 95%) as light yellow oil.

Step 3: 2-fluoro-6-hydroxybenzaldehyde

A solution of 2-fluoro-6-((tetrahydro-2H-pyran-2-yl)oxy)benzaldehyde (obtained from step 2) (6.5 g, 29.0 mmol) and TsOH (2 g, 11.6 mmol) in DCM (30 mL) was stirred at room temperature for 5 h, and then the mixture was diluted with DCM (100 mL). The organic layer was washed with saturated NaHCO3 aqueous solution and brine, dried over sodium sulfate and concentrated under vacuum. The residue was purified by column chromatography on silica gel (petroleum ether:ethyl acetate=100:1-20:1) to afford 2-fluoro-6-hydroxybenzaldehyde (3.0 g, yield: 74%) as a light yellow solid.

$^1$H NMR (400 MHz, CDCl₃): δ 11.49 (s, 1H), 10.29 (s, 1H), 7.46-7.52 (m, 1H), 6.79 (d, J=8.8 Hz, 1H), 6.63-6.68 (m, 1H).

Example 83: Synthesis of 2-(chloromethyl)-5-fluorobenzofuran

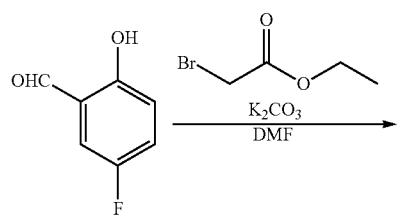

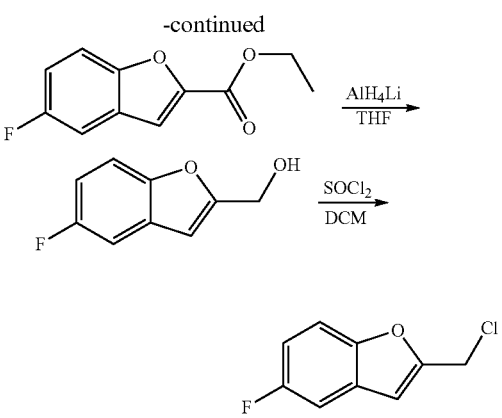

Step 1: ethyl 5-fluorobenzofuran-2-carboxylate

A mixture of 5-fluoro-2-hydroxybenzaldehyde (obtained from Example 80) (0.85 g, 6.07 mmol) and K₂CO₃ (1.68 g, 12.1 mmol) was warmed up to 60° C., and then added ethyl 2-bromoacetate (1.27 g, 7.58 mmol). The mixture was stirred at 60° C. for 1 h, and then warmed up to 60° C. and stirred for 10 h. The reaction was diluted with ethyl acetate (50 mL), and then washed with saturated NH₄Cl aqueous solution and brine, dried over sodium sulfate and concentrated under vacuum. The residue was purified by prep-TLC (petroleum ether:ethyl acetate=10:1) to afford ethyl 5-fluorobenzofuran-2-carboxylate (450 mg, yield: 36%) as a light yellow solid.

$^1$H NMR (400 MHz, CDCl₃): δ 7.56 (dd, J=4.0, 8.8 Hz, 1H), 7.51 (s, 1H), 7.34-7.36 (m, 1H), 7.17-7.23 (m, 1H), 4.47 (q, J=7.2 Hz, 2H), 1.45 (t, J=7.2 Hz, 3H).

Step 2: (5-fluorobenzofuran-2-yl)methanol

To an ice-cooling solution of ethyl 5-fluorobenzofuran-2-carboxylate (450 mg, 2.16 mmol) in THF (10 mL) was added AlH₄Li (82 mg, 2.16 mmol). The resulted mixture was stirred at 0° C. for 0.5 h, and then the reaction was quenched by addition of NaSO₄.10H₂O. After filtration, the filter cake was washed with ethyl acetate, the filtrate was evaporated under vacuum. The residue was purified by prep-TLC (petroleum ether:ethyl acetate=5:1) to afford (5-fluorobenzofuran-2-yl)methanol (300 mg, yield: 84%) as colorless oil.

$^1$H NMR (400 MHz, CDCl₃): δ 7.39 (dd, J=4.0, 8.8 Hz, 1H), 7.20-7.23 (m, 1H), 6.99-7.04 (m, 1H), 6.64 (s, 1H), 4.78 (s, 1H), 2.24 (s, 1H).

Step 3: 2-(chloromethyl)-5-fluorobenzofuran

To an ice-cooling solution of (5-fluorobenzofuran-2-yl)methanol (150 mg, 0.90 mmol) in DCM (5 mL) was added SOCl₂ (0.13 mL, 1.81 mmol). The resulted mixture was warmed up to room temperature and stirred for 1 h, and then the solvent was evaporated under vacuum to afford 2-(chloromethyl)-5-fluorobenzofuran (165 mg, yield: 100%), which can be used directly for next step without further purification.

Compounds of Example 84-87 were Prepared According to the Synthetic Method of Example 83

Example 84: 2-(chloromethyl)-7-fluorobenzofuran

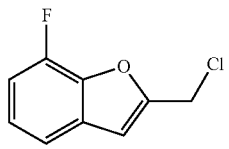 [SMILES: Fc1cccc2cc(CCl)oc12]

Example 85: 2-(chloromethyl)-6-fluorobenzofuran

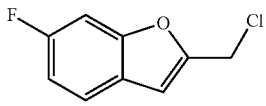

Example 86: 2-(chloromethyl)-4-fluorobenzofuran

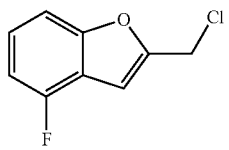 [SMILES: Fc1cccc2oc(CCl)cc12]

Example 87: 2-(chloromethyl)benzofuran

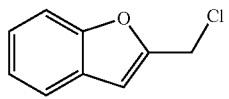 [SMILES: ClCc1cc2ccccc2o1]

Example 88: Synthesis of 2-(2-bromoethyl)-2,3-dihydrobenzofuran

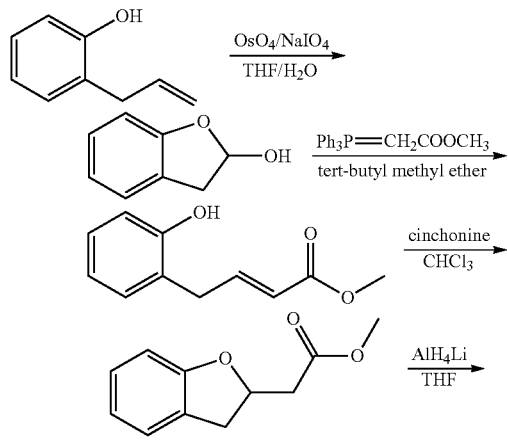

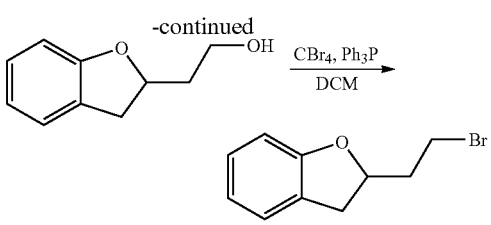

Step 1: 2,3-dihydrobenzofuran-2-ol

To an ice-cooling solution of 2-allylphenol (5 g, 37.3 mmol) in a mixed solvent of THF (25 mL) and H$_2$O (25 mL) was added NaIO$_4$ (23.9 g, 112 mmol) and OsO$_4$ (95 mg, 0.37 mmol). The resulted mixture was stirred at room temperature for overnight, and then the reaction was quenched by addition of H$_2$O (100 mL). The mixture was extracted with ethyl acetate (100×2). The combined organic layer was dried over sodium sulfate and concentrated under vacuum. The residue was purified by column chromatography on silica gel (petroleum ether:ethyl acetate=20:1-5:1) to afford 2,3-dihydrobenzofuran-2-ol (3.0 g, yield: 60%) as light yellow oil.

$^1$H NMR (400 MHz, CDCl$_3$): δ 7.16-7.28 (m, 2H), 6.86-6.95 (m, 2H), 6.07 (d, J=5.6, 1H), 3.85 (s, 1H), 3.36-3.42 (m, 1H), 3.03-3.07 (m, 1H).

Step 2: methyl 4-(2-hydroxyphenyl)but-2-enoate

A mixture of 2,3-dihydrobenzofuran-2-ol (obtained from step 1) (1.4 g, 10.3 mmol) and methyl (triphenylphosphoranylidene)acetate (3.4 g, 10.3 mmol) in tert-butyl methyl ether (30 mL) was stirred at 35° C. for overnight. Most triphenylphosphine oxide was filtered, the filtrate was evaporated under vacuum. The residue was purified by column chromatography on silica gel (petroleum ether:ethyl acetate=10:1) to afford methyl 4-(2-hydroxyphenyl)but-2-enoate (1.8 g, yield: 91%) as light yellow oil.

m/z: [M+H]$^+$ 193.1

Step 3: methyl 2-(2,3-dihydrobenzofuran-2-yl)acetate

A mixture of methyl 4-(2-hydroxyphenyl)but-2-enoate (obtained from step 2) (1.8 g, 9.36 mmol) and cinchonine (0.83 g, 2.81 mmol) in chloroform (60 mL) was stirred at 35° C. for 4 d, and then the solvent was evaporated under vacuum. The residue was purified by column chromatography on silica gel (petroleum ether:ethyl acetate=20:1-10:1) to afford methyl 2-(2,3-dihydrobenzofuran-2-yl)acetate (1.5 g, yield: 83%) as colorless oil.

$^1$H NMR (400 MHz, CDCl$_3$): δ 7.12-7.20 (m, 2H), 6.80-6.89 (m, 2H), 5.16-5.24 (m, 1H), 3.76 (s, 3H), 3.44 (dd, J=9.2, 15.6 Hz, 1H), 2.88-2.99 (m, 2H), 2.71 (dd, J=6.4, 16.0 Hz, 1H).

Step 4: 2-(2,3-dihydrobenzofuran-2-yl)ethanol

To an ice-cooling solution of methyl 2-(2,3-dihydrobenzofuran-2-yl)acetate (1.5 g, 7.80 mmol) in THF (15 mL) was added AlH$_4$Li (0.37 g, 9.75 mmol) in small portions. The resulted mixture was stirred at 0° C. for 0.5 h, and then the reaction was quenched by addition of NaSO$_4$.10H$_2$O. The mixture was filtered through celite, the filtrate was evaporated under vacuum to afford 2-(2,3-dihydrobenzofuran-2-yl)ethanol (1.15 g, yield: 90%) as colorless oil.

m/z: [M+H]⁺ 165.1

Step 5: 2-(2-bromoethyl)-2,3-dihydrobenzofuran

To an ice-cooling solution of 2-(2,3-dihydrobenzofuran-2-yl)ethanol (obtained from step 4) (0.35 g, 2.13 mmol) and triphenylphosphine (0.84 g, 3.2 mmol) in DCM (10 mL) was added CBr₄ (1.1 g, 3.2 mmol) in small portions. The resulted mixture was stirred at room temperature for 1 h. The reaction was quenched by addition of saturated NaHCO₃ aqueous solution (10 mL), the mixture was extracted with DCM (30 mL×2). The combined organic layer was dried over sodium sulfate and concentrated under vacuum. The residue was purified by prep-TLC (petroleum ether:ethyl acetate=10:1) to afford 2-(2-bromoethyl)-2,3-dihydrobenzofuran (450 mg, yield: 93%) as light yellow oil.

Example 89: Synthesis of (S)-2-(bromomethyl)-2,3-dihydrobenzofuran and (S)-(2,3-dihydrobenzofuran-2-yl)methanol

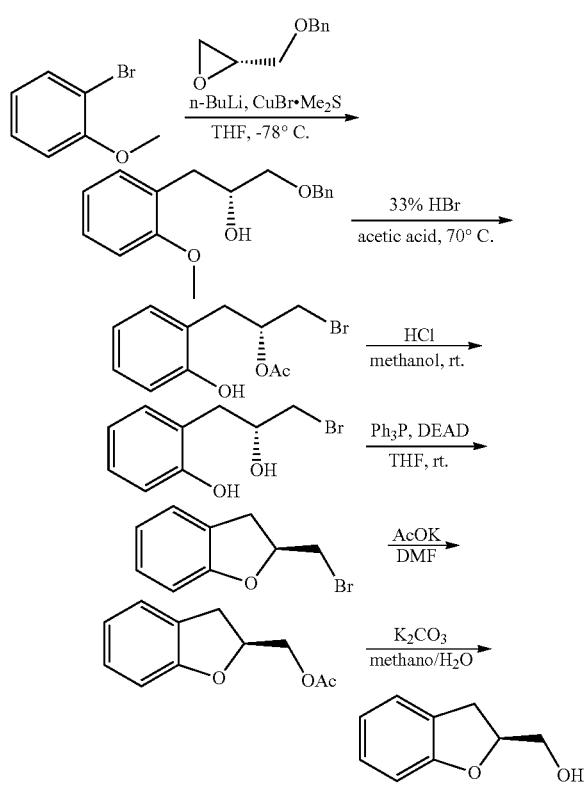

Step 1: (R)-1-(benzyloxy)-3-(2-methoxyphenyl)propan-2-ol

At −78° C., to a solution of 1-bromo-2-methoxybenzene (12 g, 64.2 mmol) in dry THF was added n-BuLi (2.5 M solution in THF, 25.7 mL, 64.2 mmol) dropwise under nitrogen. The resulted mixture was stirred at −78° C. for 1 h, and then added copper(I) bromide-dimethyl sulfide (6.6 g, 32.1 mmol). The mixture was slowly warmed up to −40° C., and then cooled down to −60° C., and then successively added (R)-2-((benzyloxy)methyl)oxirane (2.63 g, 16.1 mmol) and boron trifluoride etherate (109 mg, 0.77 mmol) dropwise. The mixture was warmed up to room temperature and stirred for overnight. The reaction was diluted with petroleum ether. After filtration the insoluble, the filter cake was washed with ethyl acetate. The filtrate was concentrated. The residue was purified by column chromatography on silica gel (petroleum/ethyl acetate=10:1-5:1) to afford (R)-1-(benzyloxy)-3-(2-methoxyphenyl)propan-2-ol (2.9 g, yield: 66%) as colorless oil.

¹H NMR (400 MHz, CDCl₃): δ 7.30-7.40 (m, 5H), 7.17-7.27 (m, 2H), 6.88-6.94 (m, 2H), 4.58 (s, 2H), 4.11-4.16 (m, 1H), 3.84 (s, 3H), 3.54 (dd, J=4.0, 9.6 Hz, 1H), 3.44 (dd, J=6.8, 10 Hz, 1H), 2.83-2.92 (m, 2H), 2.58 (br s, 1H).

Step 2: (R)-1-bromo-3-(2-hydroxyphenyl)propan-2-yl acetate

A solution of (R)-1-(benzyloxy)-3-(2-methoxyphenyl)propan-2-ol (2.9 g, 10.7 mmol) in hydrobromic acid solution (33% in acetic acid, 25 mL) was stirred at 70° C. for overnight, and then the solvent was evaporated under vacuum. The residue was purified by column chromatography on silica gel (petroleum/ethyl acetate=5:1) to afford (R)-1-bromo-3-(2-hydroxyphenyl)propan-2-yl acetate (2.2 g, yield: 75%) as light yellow oil.

¹H NMR (400 MHz, CDCl₃): δ 7.12-7.20 (m, 2H), 6.86-6.89 (m, 2H), 5.09-5.12 (m, 1H), 3.59 (dd, J=3.6, 7.2 Hz, 1H), 3.48 (dd, J=5.6, 10.8 Hz, 1H), 3.08 (dd, J=5.2, 14.0 Hz, 1H), 2.98 (dd, J=6.0, 14.4 Hz, 1H), 2.15 (s, 3H).

Step 3: (R)-2-(3-bromo-2-hydroxypropyl)phenol

To a solution of (R)-1-bromo-3-(2-hydroxyphenyl)propan-2-yl acetate (2.2 g, 8.05 mmol) in methanol (20 mL) was hydrochloric acid solution in diethyl ether (10 mL, 20 mmol, 2.0 M). The resulted mixture was stirred at room temperature for overnight, and then the solvent was evaporated under vacuum. The residue was purified by column chromatography on silica gel (petroleum/ethyl acetate=5:1) to afford (R)-2-(3-bromo-2-hydroxypropyl)phenol (1.7 g, yield: 91%) as light red oil.

¹H NMR (400 MHz, CDCl₃): δ 7.56 (s, 1H), 7.18-7.22 (m, 1H), 7.07-7.09 (m, 1H), 6.93-6.95 (m, 1H), 6.86-6.90 (m, 1H), 4.22 (br s, 1H), 3.54 (dd, J=3.6, 10.4 Hz, 1H), 3.38 (dd, J=8.4, 10.4 Hz, 1H), 3.23 (br s, 1H), 3.05 (dd, J=3.2, 14.4 Hz, 1H), 2.94 (dd, J=7.2, 14.4 Hz, 1H).

Step 4: (S)-2-(bromomethyl)-2,3-dihydrobenzofuran

To a solution of (R)-2-(3-bromo-2-hydroxypropyl)phenol (1.7 g, 7.36 mmol) in THF (20 mL) was added triphenylphosphine (4.82 g, 18.4 mmol) and DEAD (3.2 g, 18.4 mmol) successively. The resulted mixture was stirred at room temperature for overnight and then directly purified by column chromatography on silica gel (petroleum) to afford (S)-2-(bromomethyl)-2,3-dihydrobenzofuran (1.1 g, yield: 70%) as yellow oil.

¹H NMR (400 MHz, CDCl₃): δ 7.13-7.21 (m, 2H), 6.83-6.90 (m, 1H), 6.82 (d, J=8.0 Hz, 1H), 4.99-5.06 (m, 1H), 3.63 (dd, J=5.2, 10.4 Hz, 1H), 3.53 (dd, J=6.8, 10.4 Hz, 1H), 3.42 (dd, J=9.2, 16.0 Hz, 1H), 3.15 (dd, J=6.4, 15.6 Hz, 1H).

[α]_D^25=+19.3° (C=0.558%, MeOH)

Step 5: (S)-(2,3-dihydrobenzofuran-2-yl)methyl acetate

To a round bottom flask was added (S)-2-(bromomethyl)-2,3-dihydrobenzofuran (200 mg, 0.94 mmol), DMF (2 mL)

and potassium acetate (921 mg, 9.39 mmol). The mixture was stirred at 75° C. for overnight, and then the reaction was diluted with ethyl acetate. The mixture was washed with H₂O (×3) and brine, dried over sodium sulfate and concentrated under vacuum. The residue was purified by prep-TLC (petroleum ether:ethyl acetate=5:1) to afford (S)-(2,3-dihydrobenzofuran-2-yl)methyl acetate (108 mg, yield: 54%) as light yellow oil.

¹H NMR (400 MHz, CDCl₃): δ 7.13-7.20 (m, 2H), 6.83-6.90 (m, 2H), 4.99-5.06 (m, 1H), 4.36 (dd, J=3.6, 12 Hz, 1H), 4.23 (dd, J=7.2, 12 Hz, 1H), 3.34 (dd, J=10, 16 Hz, 1H), 3.00 (dd, J=7.6, 16 Hz, 1H), 2.12 (s, 3H).

Step 6: (S)-(2,3-dihydrobenzofuran-2-yl)methanol

To a round bottom flask was added (S)-(2,3-dihydrobenzofuran-2-yl)methyl acetate (100 mg, 0.52 mmol), methanol (2 mL), 2 drops of H₂O, and K₂CO₃ (54 mg, 0.39 mmol). The mixture was stirred at room temperature for 30 min, and then the reaction was diluted with ethyl acetate (10 mL). The mixture was washed with H₂O and brine, dried over sodium sulfate and concentrated under vacuum. The residue was purified by prep-TLC (petroleum ether:ethyl acetate=3:1) to afford (S)-(2,3-dihydrobenzofuran-2-yl)methanol (60 mg, yield: 60%, ee %: 97.3%) as light yellow oil.

¹H NMR (400 MHz, CDCl₃): δ 7.12-7.20 (m, 2H), 6.80-6.89 (m, 2H), 4.90-4.97 (m, 1H), 3.86-3.89 (m, 1H), 3.75-3.78 (m, 1H), 3.27 (dd, J=9.6, 15.6 Hz, 1H), 3.04 (dd, J=7.2, 15.6 Hz, 1H), 1.99 (br s, 1H).

Example 90: Synthesis of (R)-2-(bromomethyl)-2,3-dihydrobenzofuran

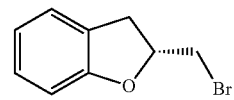 [SMILES: BrC[C@H]1Cc2ccccc2O1]

(R)-2-(bromomethyl)-2,3-dihydrobenzofuran was prepared according to the synthetic method of compound of Example 89, by using (S)-2-((benzyloxy)methyl)oxirane as chiral material.

¹H NMR (400 MHz, CDCl₃): δ 7.13-7.21 (m, 2H), 6.90 (m, 1H), 6.82 (d, J=8.0 Hz, 1H), 4.99-5.06 (m, 1H), 3.63 (dd, J=5.2, 10.4 Hz, 1H), 3.53 (dd, J=6.8, 10.4 Hz, 1H), 3.42 (dd, J=9.2, 16.0 Hz, 1H), 3.15 (dd, J=6.4, 15.6 Hz, 1H).

$[\alpha]_D^{25}$=−33.4° (C=0.515%, MeOH)

Example 91: Synthesis of (2S,3R,4R,5S,6R)-2-(3-(4-(benzofuran-2-ylmethoxy)benzyl)-4-chlorophenyl)-6-(hydroxymethyl)tetrahydro-2H-pyran-3,4,5-triol (I-1)

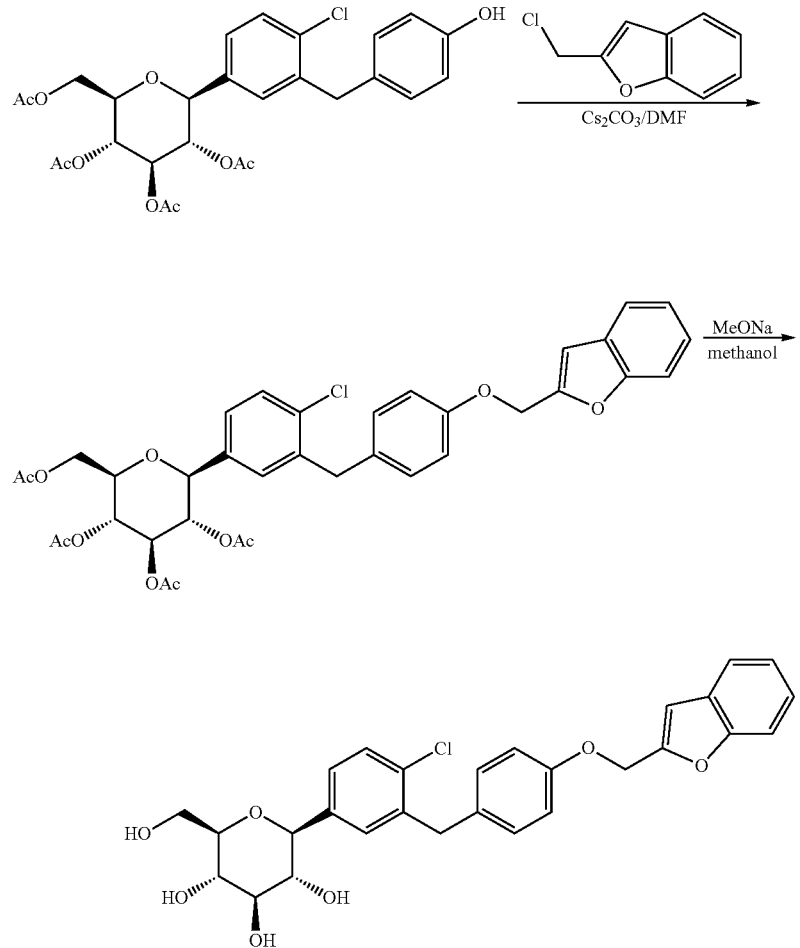

Step 1: (2R,3R,4R,5S,6S)-2-(acetoxymethyl)-6-(3-(4-(benzofuran-2-ylmethoxy)benzyl)-4-chloro phenyl)tetrahydro-2H-pyran-3,4,5-triyl triacetate A mixture of (2R,3R,4R,5S,6S)-2-(acetoxymethyl)-6-(4-chloro-3-(4-hydroxybenzyl) phenyl)tetrahydro-2H-pyran-3,4,5-triyl triacetate (obtained from Example 71) (150 mg, 0.27 mmol), 2-(chloromethyl)benzofuran (obtained from Example 87) (91 mg, 0.55 mmol) and $Cs_2CO_3$ (107 mg, 0.33 mmol) in DMF (2 mL) was stirred at 50° C. for 2 h. The reaction was diluted with ethyl acetate (50 mL). The organic layer was washed with $H_2O$ and brine, dried over sodium sulfate and concentrated under vacuum. The residue was purified by prep-TLC (petroleum ether:ethyl acetate=2:1) to afford (2R,3R,4R,5S,6S)-2-(acetoxymethyl)-6-(3-(4-(benzofuran-2-ylmethoxy)benzyl)-4-chlorophenyl)tetrahydro-2H-pyran-3,4,5-triyl triacetate (75 mg, yield: 40%) as a white solid.

Step 2: (2S,3R,4R,5S,6R)-2-(3-(4-(benzofuran-2-ylmethoxy)benzyl)-4-chlorophenyl)-6-(hydroxymethyl)tetrahydro-2H-pyran-3,4,5-triol To a solution of (2R,3R,4R,5S,6S)-2-(acetoxymethyl)-6-(3-(4-(benzofuran-2-yl)methoxy) benzyl)-4-chlorophenyl)tetrahydro-2H-pyran-3,4,5-triyl triacetate (obtained from step 1) (75 g, 0.11 mmol) in a mixed solvent of methanol (3 mL) and THF (1 mL) was added sodium methanolate (9 mg, 0.17 mmol). The resulted mixture was stirred at room temperature for 2 h, and then neutralized with acetic acid. The solvent was evaporated under vacuum. The residue was purified by prep-TLC (DCM:methanol=10:1) to afford (2S,3R,4R,5S,6R)-2-(3-(4-(benzofuran-2-ylmethoxy)benzyl)-4-chlorophenyl)-6-(hydroxymethyl)tetrahydro-2H-pyran-3,4,5-triol (48 mg, yield: 85%) as a white solid.

m/z: $[M+Na]^+$533.0

Compounds 92-103 were prepared according to the synthetic method of compound of Example 91, by using corresponding bromide and chloride.

Example 92: (2S,3R,4R,5S,6R)-2-(3-(4-(benzofuran-2-ylmethoxy)benzyl)-4-methylphenyl)-6-(hydroxymethyl)tetrahydro-2H-pyran-3,4,5-triol (I-3)

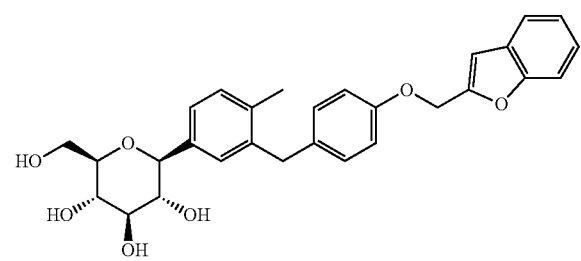 [SMILES: Cc1ccc([C@@H]2O[C@H](CO)[C@@H](O)[C@H](O)[C@H]2O)cc1Cc1ccc(OCc2cc3ccccc3o2)cc1]

m/z: $[M+NH_4]^+$507.9

Example 93: (2S,3R,4R,5S,6R)-2-(3-(4-(benzofuran-2-ylmethoxy)benzyl)-4-fluorophenyl)-6-(hydroxymethyl)tetrahydro-2H-pyran-3,4,5-triol (I-2)

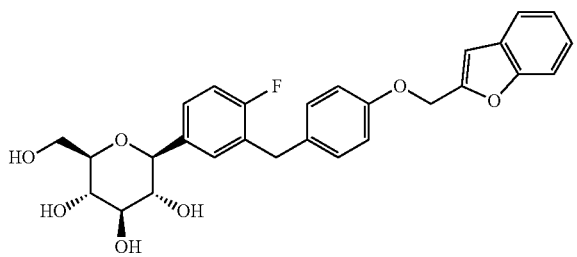 [SMILES: OC[C@H]1O[C@@H](c2ccc(F)c(Cc3ccc(OCc4cc5ccccc5o4)cc3)c2)[C@H](O)[C@@H](O)[C@@H]1O]

m/z: $[M+NH_4]^+$511.9

Example 94: (2S,3R,4R,5S,6R)-2-(3-(4-(benzofuran-2-ylmethoxy)-3-fluorobenzyl)-4-chlorophenyl)-6-(hydroxymethyl)tetrahydro-2H-pyran-3,4,5-triol (I-11)

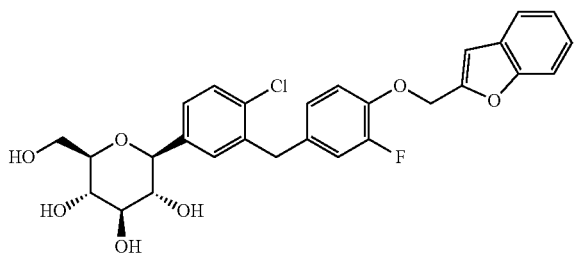 [SMILES: OC[C@H]1O[C@@H](c2ccc(Cl)c(Cc3ccc(OCc4cc5ccccc5o4)c(F)c3)c2)[C@H](O)[C@@H](O)[C@@H]1O]

m/z: $[M+H_2O]^+$546.2

Example 95: (2S,3R,4R,5S,6R)-2-(3-(4-(benzofuran-2-ylmethoxy)benzyl)phenyl)-6-(hydroxymethyl)tetrahydro-2H-pyran-3,4,5-triol (I-6)

m/z: $[M+NH_4]^+$494.0

Example 96: (2S,3R,4R,5S,6R)-2-(4-chloro-3-(4-((7-fluorobenzofuran-2-yl)methoxy)benzyl)phenyl)-6-(hydroxymethyl)tetrahydro-2H-pyran-3,4,5-triol (I-10)

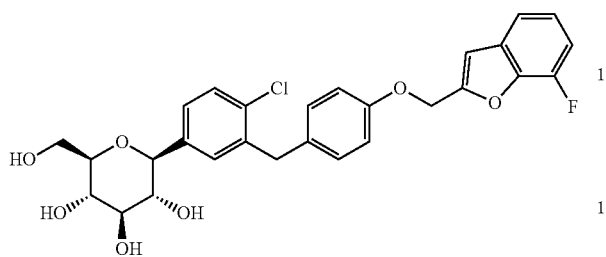

m/z: [M+NH$_4$]$^+$545.8
$^1$H NMR (400 MHz, CDCl$_3$): δ 7.35-7.41 (m, 3H), 7.29-7.31 (m, 1H), 7.16-7.23 (m, 3H), 7.07-7.10 (m, 1H), 6.95-6.99 (m, 3H), 5.20 (s, 2H), 4.02-4.12 (m, 3H), 3.88-3.91 (m, 1H), 3.68-3.73 (m, 1H), 3.28-3.49 (m, 4H).

Example 97: 2-(4-(benzofuran-2-ylmethoxy)benzyl)-4-((2S,3R,4R,5S,6R)-3,4,5-trihydroxy-6-(hydroxymethyl)tetrahydro-2H-pyran-2-yl)benzonitrile (I-4)

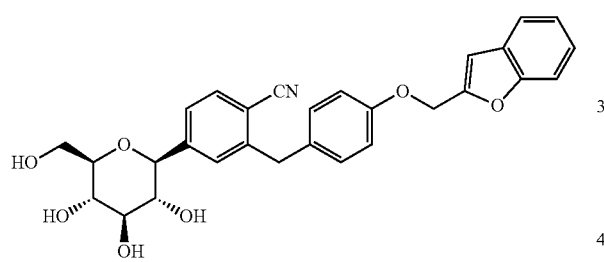

m/z: [M+NH$_4$]$^+$518.9

Example 98: (2S,3R,4R,5S,6R)-2-(4-chloro-3-(4-((6-fluorobenzofuran-2-yl)methoxy)benzyl)phenyl)-6-(hydroxymethyl)tetrahydro-2H-pyran-3,4,5-triol (I-9)

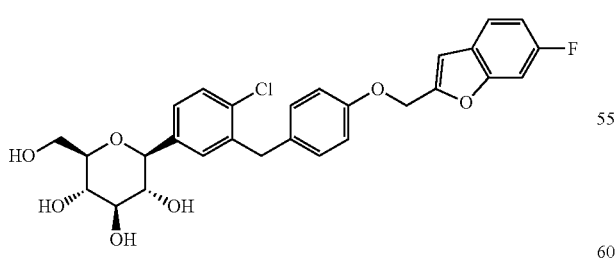

m/z: [M+NH$_4$]$^+$545.9
$^1$H NMR (400 MHz, CDCl$_3$): δ 7.57 (dd, J=5.6, 8.4 Hz, 1H), 7.35-7.38 (m, 2H), 7.28-7.31 (m, 2H), 7.14-7.17 (m, 2H), 7.02-7.07 (m, 1H), 6.94-6.97 (m, 2H), 6.87 (s, 1H), 5.15 (s, 2H), 4.01-4.12 (m, 3H), 3.88-3.91 (m, 1H), 3.69-3.73 (m, 1H), 3.28-3.49 (m, 4H).

Example 99: (2S,3R,4R,5S,6R)-2-(4-chloro-3-(4-((5-fluorobenzofuran-2-yl)methoxy)benzyl)phenyl)-6-(hydroxymethyl)tetrahydro-2H-pyran-3,4,5-triol (I-8)

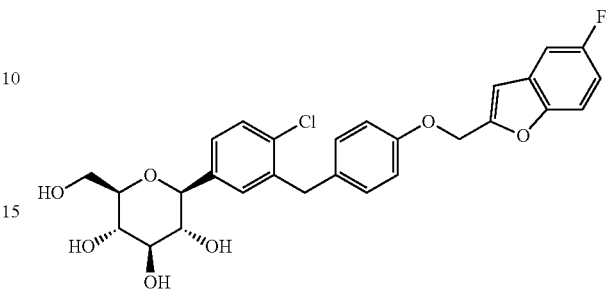

m/z: [M+NH$_4$]$^+$545.9
$^1$H NMR (400 MHz, CDCl$_3$): δ 7.47 (dd, J=4.0, 8.8 Hz, 1H), 7.35-7.37 (m, 2H), 7.27-7.31 (m, 2H), 7.14-7.16 (m, 2H), 7.03-7.08 (m, 1H), 6.93-6.97 (m, 2H), 6.86 (s, 1H), 5.15 (s, 2H), 4.01-4.12 (m, 3H), 3.88-3.91 (m, 1H), 3.69-3.73 (m, 1H), 3.29-3.50 (m, 4H).

Example 100: (2S,3R,4R,5S,6R)-2-(4-chloro-3-(4-((4-fluorobenzofuran-2-yl)methoxy)benzyl)phenyl)-6-(hydroxymethyl)tetrahydro-2H-pyran-3,4,5-triol (I-7)

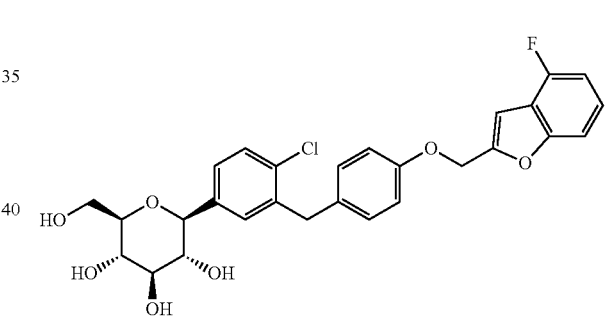

m/z: [M+NH$_4$]$^+$545.9
$^1$H NMR (400 MHz, CDCl$_3$): δ 7.27-7.38 (m, 5H), 7.15-7.17 (m, 2H), 6.95-6.99 (m, 4H), 5.17 (s, 2H), 4.01-4.12 (m, 3H), 3.87-3.91 (m, 1H), 3.69-3.73 (m, 1H), 3.29-3.50 (m, 4H).

Example 101: (2S,3R,4R,5S,6R)-2-(4-chloro-3-(4-(2-(2,3-dihydrobenzofuran-2-yl)ethoxy)benzyl)phenyl)-6-(hydroxymethyl)tetrahydro-2H-pyran-3,4,5-triol (I-60)

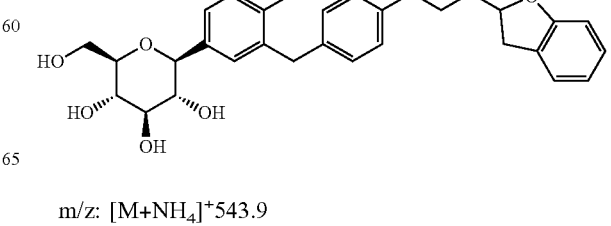

m/z: [M+NH$_4$]$^+$543.9

Example 102: (2S,3R,4R,5S,6R)-2-(4-chloro-3-(4-(((S)-2,3-dihydrobenzofuran-2-yl)methoxy)benzyl)phenyl)-6-(hydroxymethyl)tetrahydro-2H-pyran-3,4,5-triol (I-23)

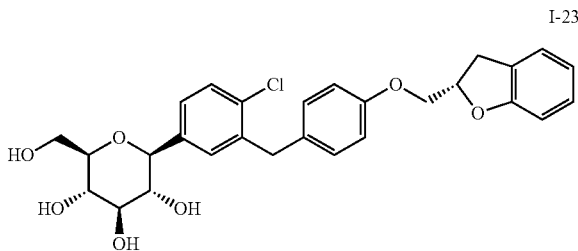 [SMILES: OC[C@H]1O[C@@H](c2ccc(Cl)c(Cc3ccc(OC[C@@H]4Cc5ccccc5O4)cc3)c2)[C@H](O)[C@@H](O)[C@@H]1O]

I-23

Compound I-23 was detected by chiral analysis method A with the 4.09 min retention time (ee %: 100%).

m/z: [M+Na]+ 535.2

$^1$H NMR (400 MHz, CD$_3$OD): δ 7.28-7.37 (m, 3H), 7.20 (dd, J=0.4, 7.6 Hz, 1H), 7.07-7.14 (m, 3H), 6.82-6.88 (m, 3H), 6.74 (d, J=8.0 Hz, 1H), 5.06-5.13 (m, 1H), 4.00-4.14 (m, 5H), 3.87-3.90 (m, 1H), 3.68-3.73 (m, 1H), 3.28-3.49 (m, 5H), 3.14 (dd, J=7.2, 16 Hz, 1H).

$[α]_D^{25}$=+50.0° (C=0.054%, MeOH)

Compound I-23 could be prepared according to the synthetic method of compound of method 2 Example 77.

Example 103: (2S,3R,4R,5S,6R)-2-(4-chloro-3-(4-(((R)-2,3-dihydrobenzofuran-2-yl)methoxy)benzyl)phenyl)-6-(hydroxymethyl)tetrahydro-2H-pyran-3,4,5-triol (I-24)

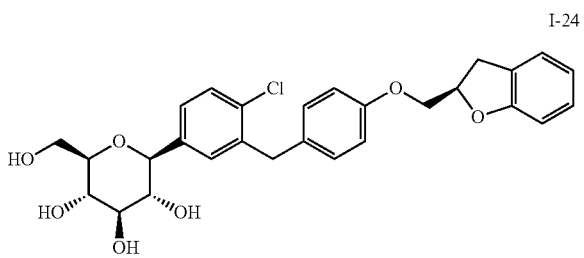 [SMILES: OC[C@H]1O[C@@H](c2ccc(Cl)c(Cc3ccc(OC[C@H]4Cc5ccccc5O4)cc3)c2)[C@H](O)[C@@H](O)[C@@H]1O]

I-24

Compound I-24 was detected by chiral analysis method A with the 4.92 min retention time (ee %: 98.1%).

m/z: [M+Na]$^+$ 535.2

$^1$H NMR (400 MHz, CD$_3$OD): δ 7.28-7.37 (m, 3H), 7.20 (dd, J=0.4, 7.6 Hz, 1H), 7.07-7.13 (m, 3H), 6.82-6.87 (m, 3H), 6.74 (d, J=8.0 Hz, 1H), 5.07-5.11 (m, 1H), 4.00-4.13 (m, 5H), 3.87-3.90 (m, 1H), 3.68-3.73 (m, 1H), 3.28-3.49 (m, 5H), 3.14 (dd, J=7.2, 16 Hz, 1H).

$[α]_D^{25}$=−21.8° (C=0.055%, MeOH)

Compound I-24 could be prepared according to the synthetic method of compound of method 2 Example 77.

Examples of Bioassays

Example 1: [$^{14}$C]-AMG Absorption in Stable SGLT1 and SGLT2 Expressing Flp-in CHO Cells (SGLT-1 and SGLT-2 Activity Screening Assay)

SGLT-1 and SGLT-2 cDNA clones were purchased from OriGene. After sequencing verification, the expression vectors were constructed based on pcDNA5/FRT using conventional molecular biology method. The expression vector was transfected into Flp-in CHO cells using Lipofectamin 2000. The transfected cells were subject hygromycin selection. The single clones of cells were selected by serial dilutions 4-5 weeks after transfection. The expression of SGLT-1 和 SGLT-2 were confirmed by RT-PCR and functional assay and cell line with strong signal was selected for subsequent study.

Culture of stable SGLT-1 and SGLT-2 expressing Flp-in CHO cell line: the culture media contain F12 medium (Invitrogen), 500 μg/ml hygromycin (Calbiochem) and 10% FBS (Invitrogen). Upon 80% confluency, the cells in the T75 flask were washed three times with PBS (Invitrogen), and 5 mL of Trpsin-EDTA solution (Invitrogen) was then added. The flask was gently rotated so that all the cells were submerged in the digestion solution. After the cells detach, 10 mL of culture medium was added and single cell suspension was prepared by pipetting up and down. The cell concentration was adjusted to 3×10$^5$/mL, 100 μL/well was added onto clear bottom 96-well plate (Corning).

The cells were ready for absorption assay once they attached after overnight culture. 12 h after cell plating, the cells were washed once with 150 μL/well absorption solution KRH-NMG (120 mM NMG, 4.7 mM KCl, 1.2 mM MgCl$_2$, 2.2 mM CaCl$_2$, 10 mM HEPES, pH 7.4 1 mM Tris). The solution was then removed from the well. 2.5 μCi/mL $^{14}$C labeled AMG (PerkinElmer) Buffer KRH-Na+ (120 mM NaCl, 4.7 mM KCl, 1.2 mM MgCl$_2$, 2.2 mM CaCl$_2$, 10 mM HEPES, pH 7.4 1 mM Tris) was added at 45 is L/well after washing with Buffer KRH-Na+ and KRH-NMG. The corresponding compound I was immediately added at 5 μL/well, ensuring the concentration of Dimethyl Sulfoxide was 1% (v/v). The plate was subsequently incubated at 37° C. for 1 h, after which 150 μL of ice cold wash buffer (120 mM NaCl, 4.7 mM KCl, 1.2 mM MgCl$_2$, 2.2 mM CaCl$_2$, 10 mM HEPES, 0.5 mM phlorizin, pH 7.4 1 mM Tris) was immediately added to terminate the reaction. Each well was washed three times with wash buffer and finally the solution was removed. Caution was taken to avoid cell detachment during the procedure. 20 μL/well of Lysis Buffer (0.1 mM NaOH) was added, the plate was vortexed at 900 rpm for 5 min. 80 μL/well of scintillation solution Microsint40 was added, and vortexed at 900 rpm for 5 min. The radioactivity was assayed using MicroBeta Trilux (PerkinElmer). The data was analyzed and IC$_{50}$ of the compounds was calculated using XL-fit software. Table 1 shows the compound's IC$_{50}$ against SGLT-1 and SGLT-2.

TABLE 1

| No. | SGLT-2 IC$_{50}$(μM) | SGLT-1 IC$_{50}$(μM) |
| --- | --- | --- |
| A | 0.0066 | 1.900 |
| B | 0.0046 | 0.287 |
| I-1 | 0.0070 | / |
| I-2 | 0.0150 | 2.545 |
| I-3 | 0.0056 | 0.320 |
| I-5 | 0.0180 | 1.505 |
| I-6 | 0.0360 | / |
| I-7 | 0.0140 | 0.444 |
| I-8 | 0.0250 | 1.445 |
| I-9 | 0.0130 | 0.151 |
| I-10 | 0.0120 | 0.444 |
| I-11 | 0.0230 | 2.544 |
| I-12 | 0.0110 | 1.068 |
| I-21 | 0.0130 | 4.300 |
| I-22 | 0.0041 | 2.105 |
| I-23 | 0.0030 | 0.301 |
| I-24 | 0.0043 | 1.190 |

TABLE 1-continued

| No. | SGLT-2 IC$_{50}$(μM) | SGLT-1 IC$_{50}$(μM) |
|---|---|---|
| I-25 | 0.0041 | 0.180 |
| I-26 | 0.0027 | 0.095 |
| I-27 | 0.0043 | 0.396 |
| I-28 | >2 | 41.37 |
| I-29 | 0.0590 | 0.220 |
| I-30 | 0.1249 | 9.370 |
| I-31 | 0.0065 | 0.365 |
| I-32 | 0.0067 | 0.472 |
| I-33 | 0.0062 | 0.599 |
| I-34 | 0.0045 | 0.141 |
| I-36 | 0.0010 | 0.584 |
| I-37 | 0.0020 | 0.615 |
| I-38 | 0.0010 | 0.608 |
| I-43 | 0.0017 | 0.322 |
| I-60 | 0.0380 | / |
| I-63 | 0.0056 | / |
| I-106 | 0.0182 | 0.700 |
| I-107 | >2 | 31.39 |
| I-108 | 0.0102 | 1.805 |
| I-110 | 0.0129 | 0.244 |
| I-111 | >2 | 34.44 |
| I-112 | 0.0080 | 0.179 |
| I-113 | 0.0186 | 0.655 |
| I-114 | 0.0052 | 0.997 |
| I-115 | 0.0127 | 0.725 |
| I-116 | 0.0039 | 1.310 |

Wherein, A: Empagliflozin (CAS No: 864070-44-0) and B: Canagliflozin (CAS No: 842133-18-0) are two known aryl glycoside SGLT-2 inhibitors. The structures are as below:

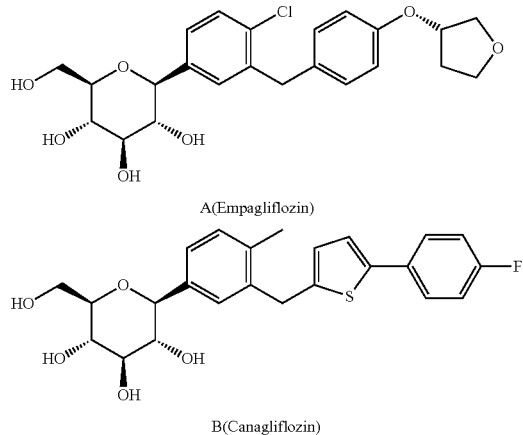

A(Empagliflozin)

B(Canagliflozin)

Example 2: Urinary Glucose Excretion Test in C57/BL6 Mice

Adult male C57/BL6 mice with body weight over 20 g (Shanghai LSK Laboratory Animal Ltd) were orally dosed with test compound I (10 mg/Kg) after which the animals were fed with 5 g/Kg glucose. The animals were housed in metabolic cages to collect total urine in 24 h. The cage was washed with 5 mL of normal saline. Water and food were provided to the mice ad libitum during the 24 h period. The urine samples were immediately frozen after collection, and the glucose levels were then determined. The total amount of excreted urine glucose was calculated based on total amount of urine, and then converted to amount of excreted glucose (mg) per 200 mg body weight in 24 h based on mouse body weight. The result is shown in Table 2 (mean values of 6 mice).

TABLE 2

| No. | Glucose (mg/200 mg body weight/24 h) |
|---|---|
| A | 1536.5 |
| I-1 | 1646.9 |
| I-22 | 3106.6 |
| I-36 | 1723.1 |

A: Empagliflozin (CAS: 864070-44-0) is a known aryl glycoside SGLT-2 inhibitor, and its detailed structure was shown in Example 1.

As shown in Table 2, compounds I-1 and I-22 of this invention are significantly more active than compound A (Empagliflozin).

Taken together, the compounds of this invention are more potent in bioassays described above and therefore represents a significant advancement.

The invention claimed is:

1. A C-aryl glycoside derivative of formula (I), or its isomers, stable isotope derivatives thereof or a pharmaceutically acceptable salt thereof;

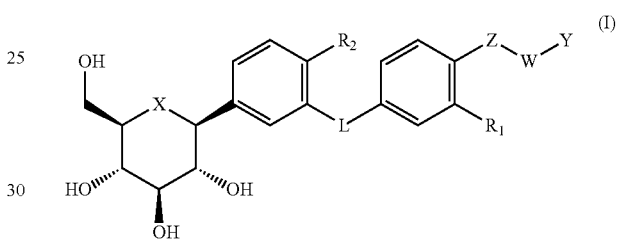

wherein, X is O or S; L is CH$_2$, CD$_2$, C=O or CF$_2$; Z is CH$_2$, S, O or a single bond; W is a single bond or (CH$_2$)$_n$, n=1, 2 or 3;

Y is a bicyclic group; the bicyclic group is substituted or unsubstituted; wherein, the bicyclic group is C$_{5-8}$ cycloalkyl fused C$_6$ aryl, C$_{5-8}$ cycloalkyl fused C$_{3-5}$ heteroaryl, C$_{3-7}$ heterocycloalkyl fused C$_6$ aryl, C$_{3-7}$ heterocycloalkyl fused C$_{3-5}$ heteroaryl, C$_6$ aryl fused C$_6$ aryl, C$_{3-5}$ heteroaryl fused C$_6$ aryl, or C$_{3-5}$ heteroaryl fused C$_{3-5}$ heteroaryl;

when the bicyclic group is substituted, it is substituted by 1 or more substituent(s) at any position independently selected from: alkyl, CN, halogen, CF$_3$, OH, amino, C$_{2-6}$ alkenyl, C$_{2-6}$ alkynyl, alkoxy, haloalkyoxy, cycloalkyl, cycloalkyloxy, cycloalkylalkyl, cycloalkylalkoxy, heterocycloalkyl, heterocycloalkyloxy, heterocycloalkylalkyl, heterocycloalkylalkoxy, alkylamino, carbonyl, COOH, COOR$_7$, COR$_7$, CONR$_7$R$_{7a}$, —NHCOR$_7$, —NHSO$_2$R$_7$, aryl, heteroaryl, alkylsulfonyl, arylsulfonyl, or heteroarylsulfonyl;

the substituent of bicyclic group is unsubstituted or further substituted by one or more substituent(s) selected from: alkyl, halogen, CF$_3$, OH, CN, amino, alkoxy, or haloalkoxy;

R$_1$ is H, halogen, CN, alkyl, alkoxy, haloalkoxy, OCD$_3$, OC$_2$D$_5$, or CF$_3$;

R$_2$ is H, alkyl, halogen, CF$_3$, CN, OH, amino, alkoxy, haloalkoxy, OCD$_3$, OC$_2$D$_5$, C$_{2-6}$ alkenyl, C$_{2-6}$ alkynyl, cycloalkyl, heterocycloalkyl, alkylamino, carbonyl, COOH, COOR$_7$, COR$_7$, CONR$_7$R$_{7a}$, —NHCOR$_7$, —NHSO$_2$R$_7$, aryl, heteroaryl, alkylsulfonyl, arylsulfonyl, or heteroarylsulfonyl; and R$_7$ and R$_{7a}$ are independently selected from alkyl, cycloalkyl, or heterocycloalkyl; or R$_7$ and R$_{7a}$ together with the nitrogen atom to which they are attached, form a 3- to 7-membered heterocycloalkyl ring.

2. The C-aryl glycoside derivative of formula (I), or its isomers, stable isotope derivatives thereof or a pharmaceutically acceptable salt thereof as defined in claim 1, wherein the 3- to 7-membered heterocycloalkyl ring formed by $R_7$ and $R_{7a}$ together with the nitrogen atom to which they are attached, further contains 1 to 3 heteroatoms or groups in the ring: N, O, S, SO, or $SO_2$;

the 3- to 7-membered heterocycloalkyl ring formed by $R_7$ and $R_{7a}$ together with the nitrogen atom to which they are attached, is substituted by alkyl and/or methylsulfonyl;

and/or, in Y, $C_{3-7}$ heterocycloalkyl fused $C_6$ aryl is $C_{4-6}$ heterocycloalkyl fused $C_6$ aryl; and $C_{3-5}$ heteroaryl fused $C_6$ aryl is $C_{3-4}$ heteroaryl fused $C_6$ aryl.

3. The C-aryl glycoside derivative of formula (I), or its isomers, stable isotope derivatives thereof or a pharmaceutically acceptable salt thereof as defined in claim 1, wherein Y is any one of the following Y1 to Y24:

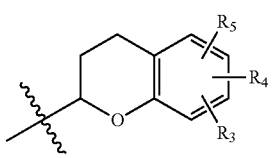
Y1

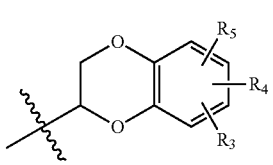
Y2

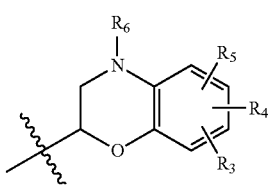
Y3

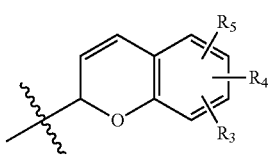
Y4

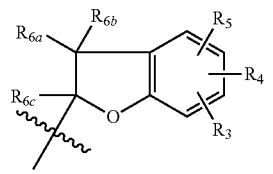
Y5

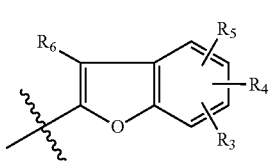
Y6

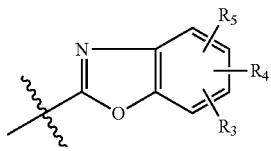
Y7

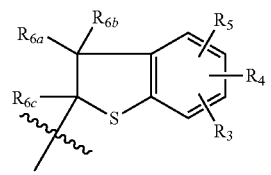
Y8

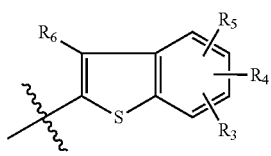
Y9

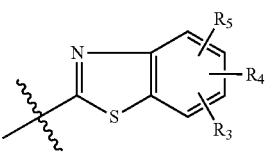
Y10

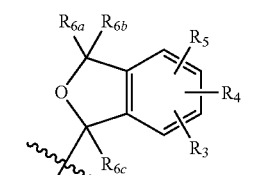
Y11

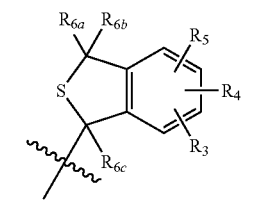
Y12

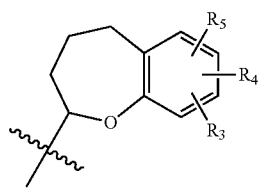
Y13

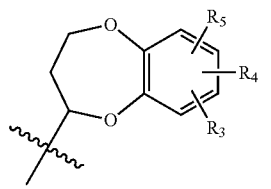
Y14

115
-continued

Y15 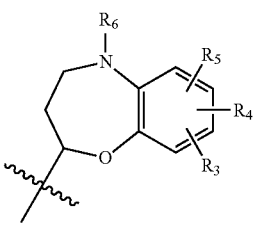

Y16 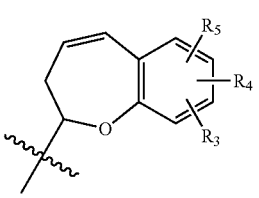

Y17 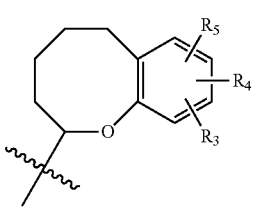

Y18 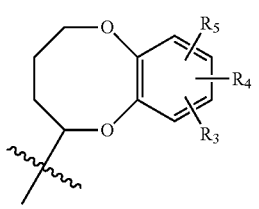

Y19 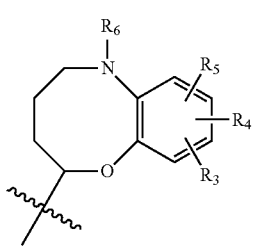

Y20 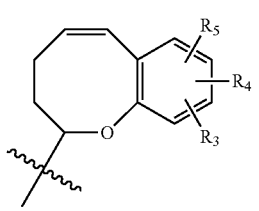

Y21 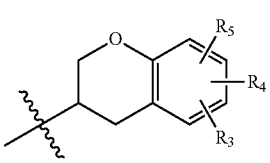

116
-continued

Y22 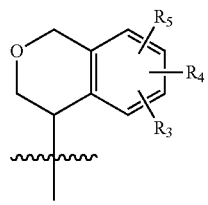

Y23 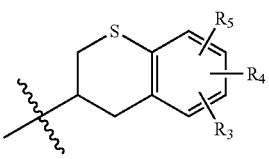

Y24 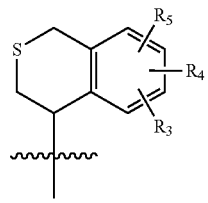

wherein, $R_3$, $R_4$, $R_5$, $R_6$, $R_{6a}$, $R_{6b}$ and $R_{6c}$ are independently H, alkyl, CN, halogen, $CF_3$, OH, amino, $C_{2-6}$ alkenyl, $C_{2-6}$ alkynyl, alkoxy, haloalkoxy, cycloalkyl, cycloalkyloxy, cycloalkylalkyl, cycloalkylalkoxy, heterocycloalkyl, heterocycloalkyloxy, heterocycloalkylalkyl, heterocycloalkylalkoxy, alkylamino, carbonyl, COOH, $COOR_7$, $COR_7$, $CONR_7R_{7a}$, —$NHCOR_7$, —$NHSO_2R_7$, aryl, heteroaryl, alkylsulfonyl, arylsulfonyl, or heteroaryl sulfonyl;

or $R_6$ and $R_{6a}$ together with the atom to which they are attached, form a 3- to 8-membered cycloalkyl ring or 3- to 8-membered heterocycloalkyl ring; wherein said 3- to 8-membered cycloalkyl ring or 3- to 8-membered heterocycloalkyl ring is unsubstituted or substituted by alkyl and/or halogen.

4. The C-aryl glycoside derivative of formula (I), or its isomers, stable isotope derivatives thereof or a pharmaceutically acceptable salt thereof as defined in claim 3, wherein $R_3$, $R_4$, $R_5$, $R_6$, $R_{6a}$, $R_{6b}$ or $R_{6c}$ is further substituted by any one of the following substituents: alkyl, halogen, $CF_3$, OH, CN, amino, alkoxy, or haloalkoxy when $R_6$ and $R_{6a}$ do not form a cycloalkyl ring or heterocycloalkyl ring together with the atom to which they are attached;

or $R_6$ and $R_{6a}$ together with the atom to which they are attached form a 3- to 8-membered heterocycloalkyl ring containing 1 to 3 heteroatoms or groups in the ring: N, O, S, SO, or $SO_2$.

5. The C-aryl glycoside derivative of formula (I), or its isomers, stable isotope derivatives thereof or a pharmaceutically acceptable salt thereof as defined in claim 1, wherein Y is

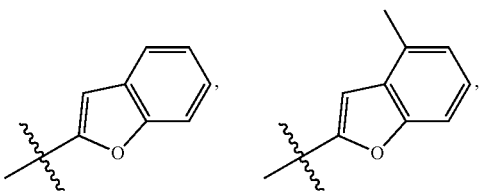

-continued
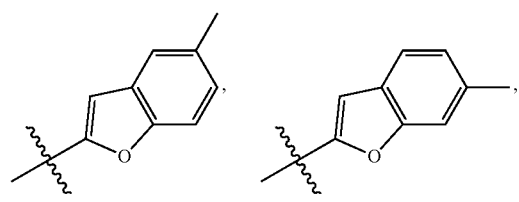
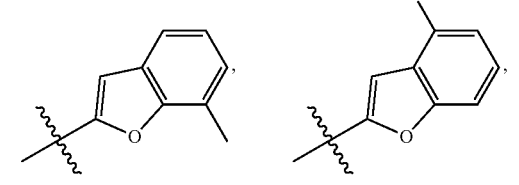
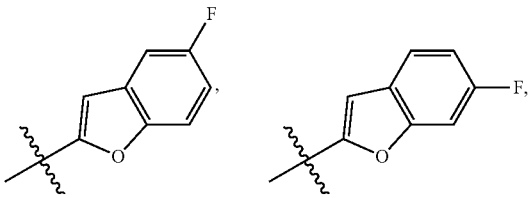
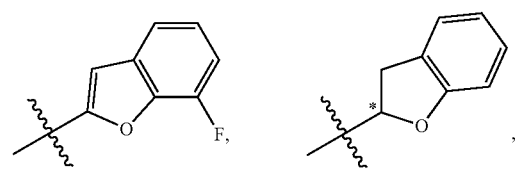
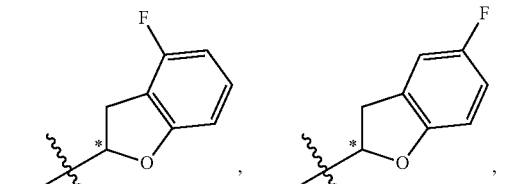
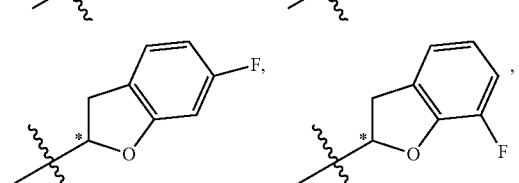
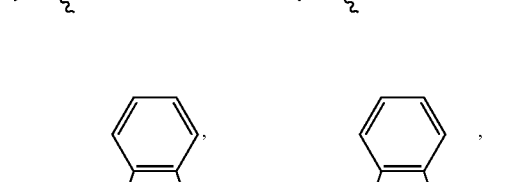
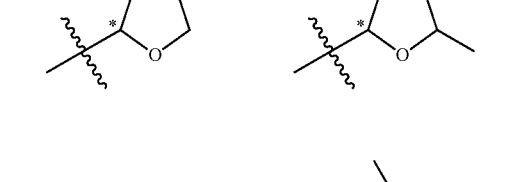
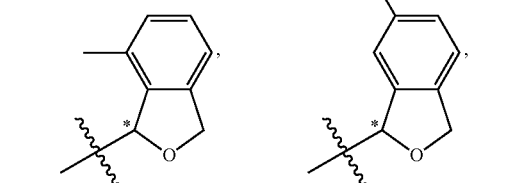
-continued
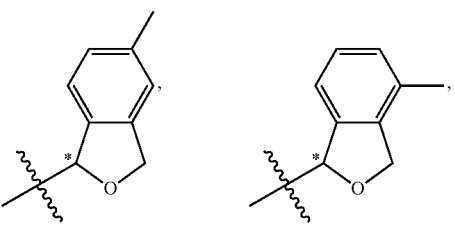
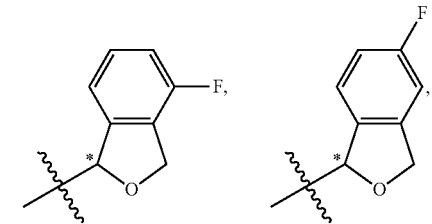
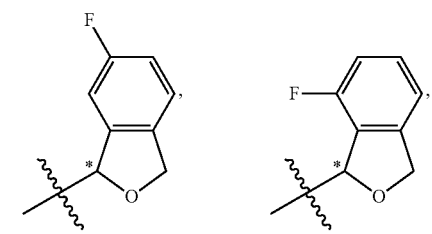
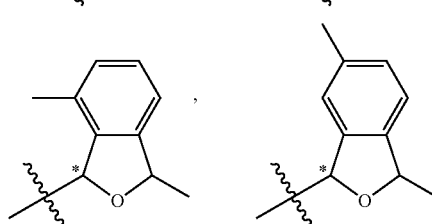
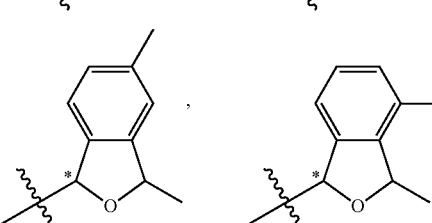
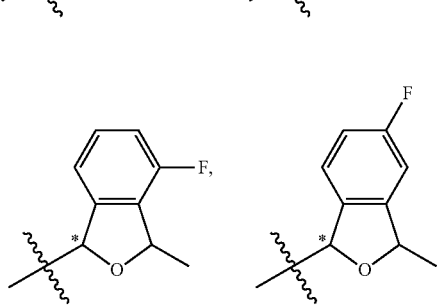
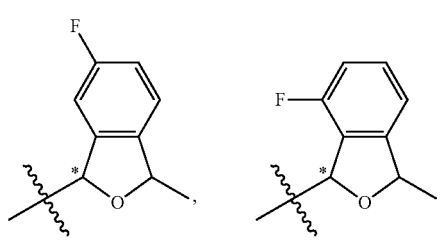

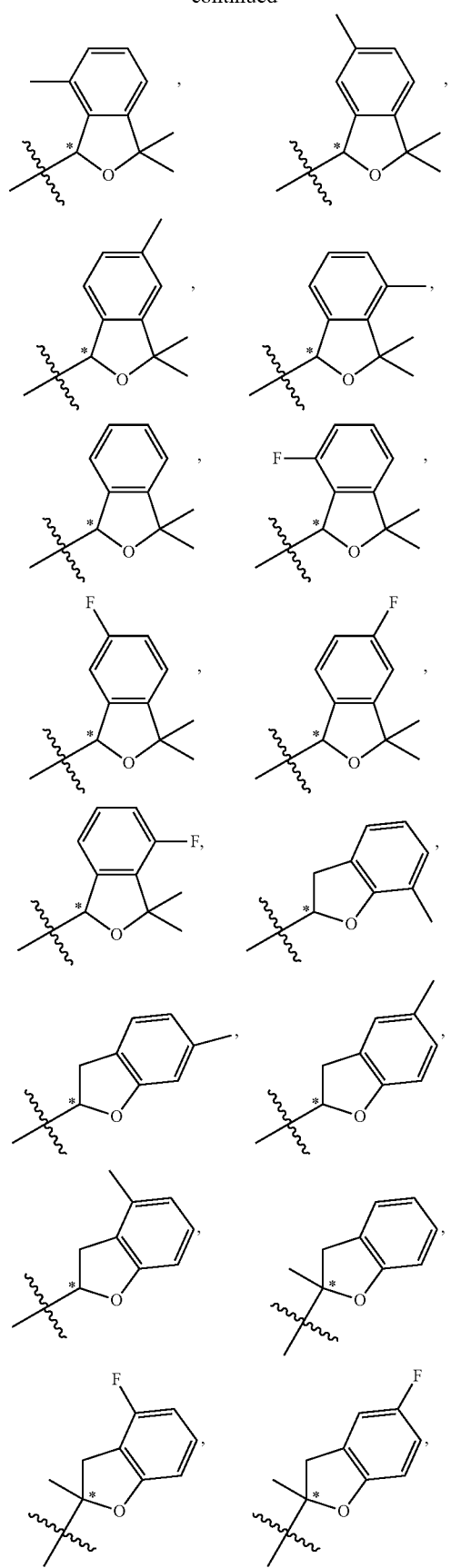
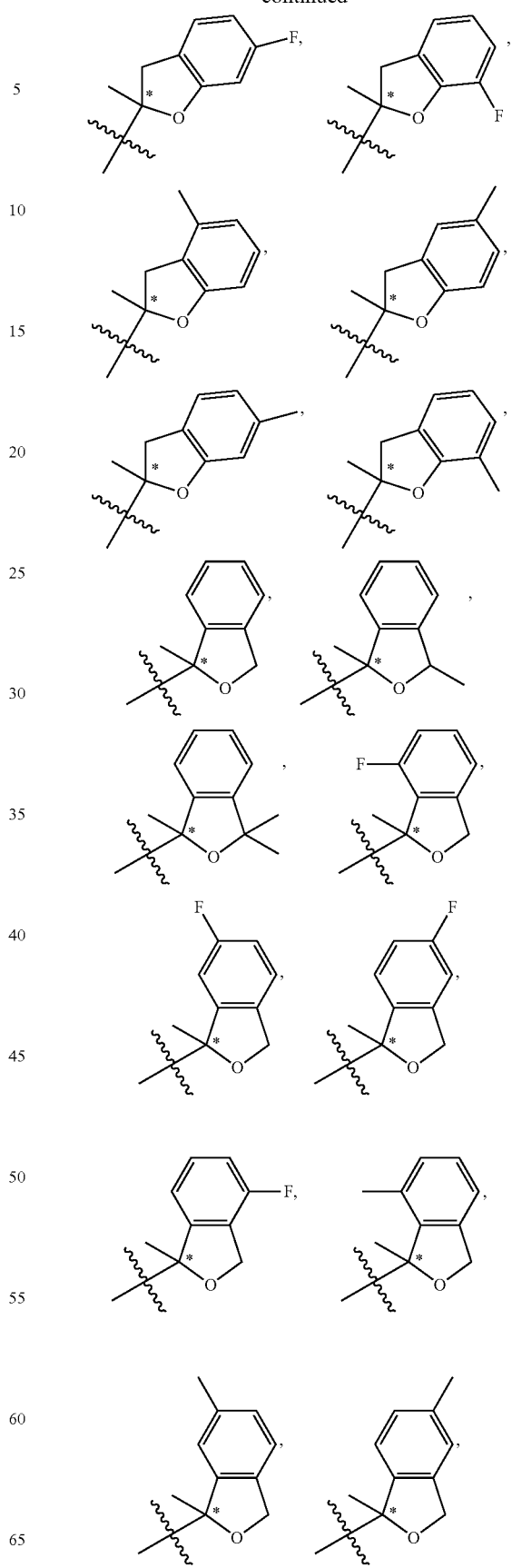

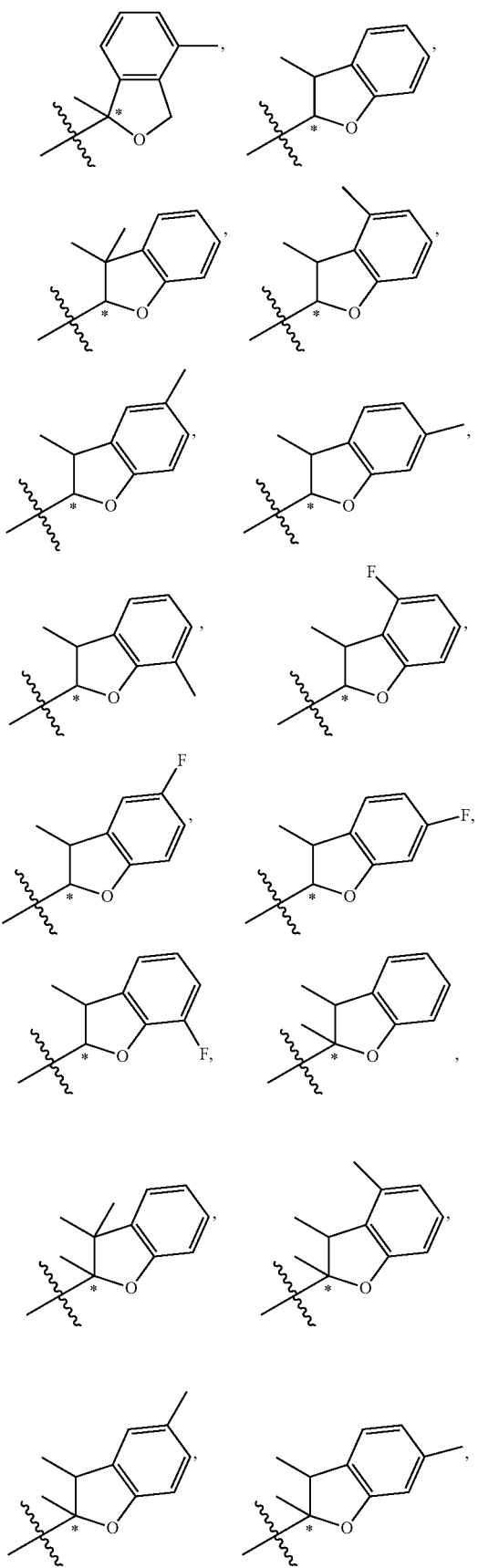

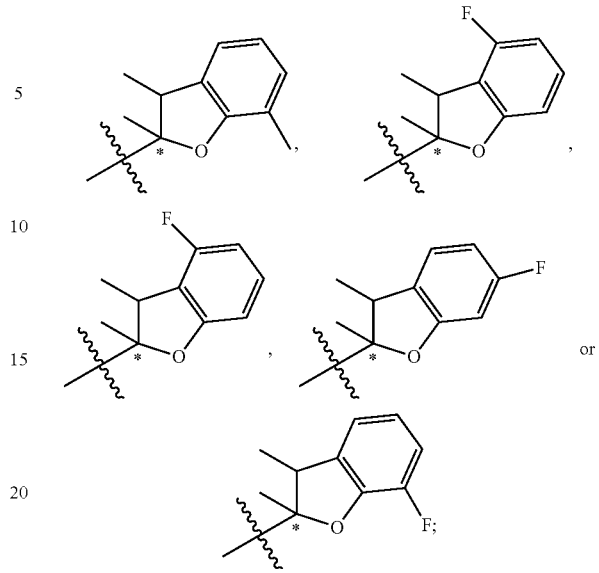

wherein * denotes chiral carbon, including racemates, the absolute configuration of S or R.

6. The C-aryl glycoside derivative of formula (I), or its isomers, stable isotope derivatives thereof or a pharmaceutically acceptable salt thereof as defined in claim 1, wherein the C-aryl glycoside derivative of formula (I) is formulae (IA), (IB) or (IC),

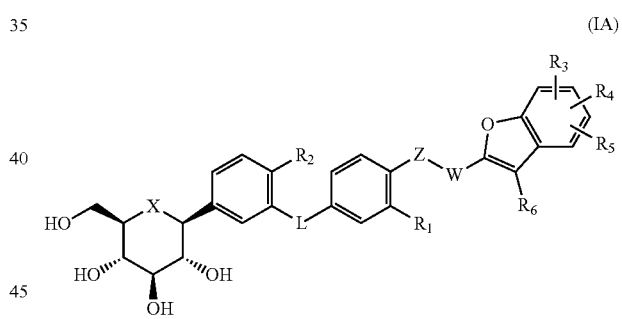
(IA)

In IA, X is O; L is CH$_2$; Z is O; W is (CH$_2$)$_n$, n is 1 or 2;

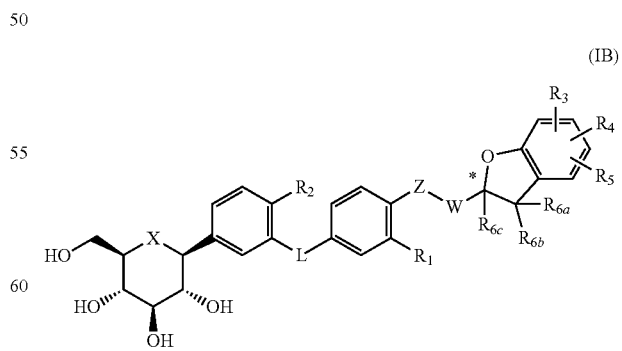
(IB)

In IB, X is O; L is CH$_2$; Z is O; W is (CH$_2$)$_n$, n is 1 or 2; * denotes chiral carbon, including racemates, the absolute configuration of S or R;

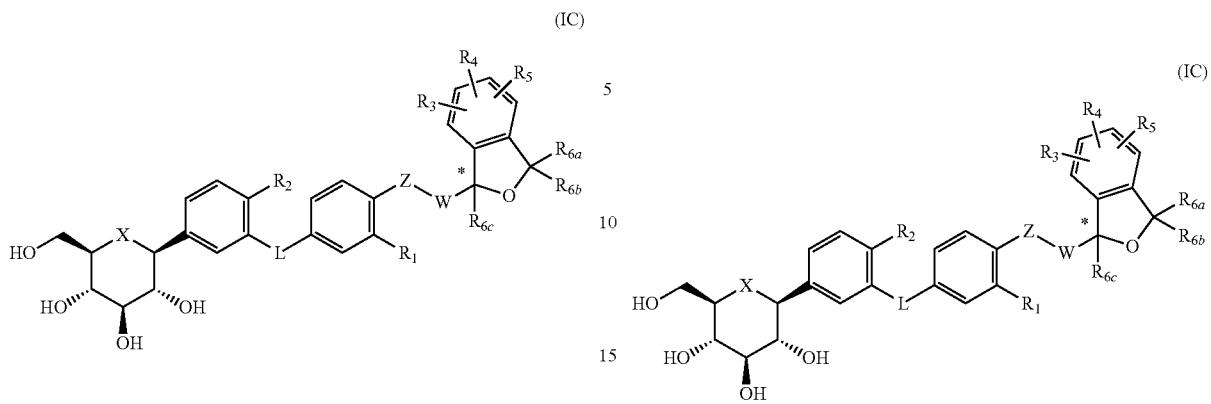

In IC, X is O; L is CH$_2$; Z is O; W is (CH$_2$)$_n$, n is 1 or 2; * denotes chiral carbon, including racemates, the absolute configuration of S or R.

7. The C-aryl glycoside derivative of formula (I), or its isomers, stable isotope derivatives thereof or a pharmaceutically acceptable salt thereof as defined in claim 6, wherein the C-aryl glycoside derivative of formula (IA) is:

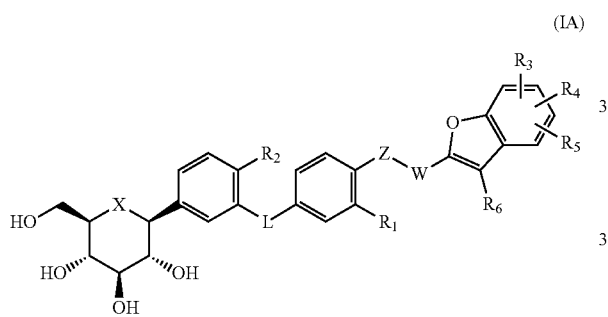

wherein, X is O; L is CH$_2$; Z is O; W is (CH$_2$)$_n$, n is 1 or 2; R$_1$ is H or F; R$_2$ is H, F, Cl, CN, CH$_3$ or OCH$_3$; R$_3$, R$_4$ and R$_5$ are independently H, methyl or F; R$_6$ is H;

the C-aryl glycoside derivative of formula (IB) is:

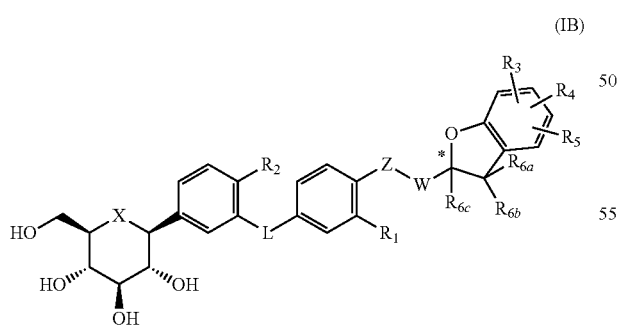

wherein, X is O; L is CH$_2$; Z is O; W is (CH$_2$)$_n$, n is 1 or 2; R$_1$ is H or F; R$_2$ is H, F, Cl, CN, CH$_3$ or OCH$_3$; R$_3$, R$_4$ and R$_5$ are independently H, methyl or F; R$_{6a}$, R$_{6d}$ and R$_{6c}$ are independently H or methyl; wherein * denotes chiral carbon, including racemates, the absolute configuration of S or R;

the C-aryl glycoside derivative of formula (IC) is:

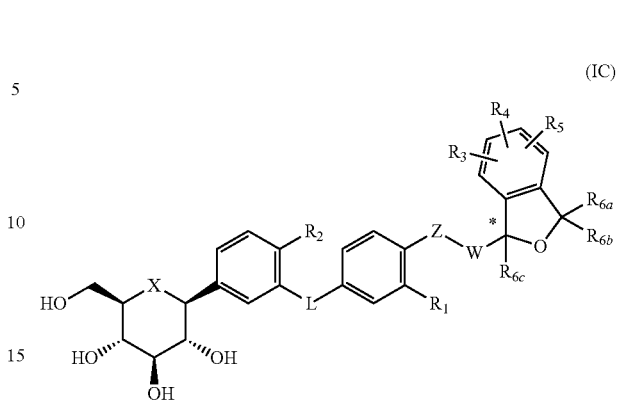

wherein, in IC, X is O; L is CH$_2$; Z is O; W is (CH$_2$)$_n$, n is 1 or 2; R$_1$ is H or F; R$_2$ is H, F, Cl, CN, CH$_3$ or OCH$_3$; R$_3$, R$_4$ and R$_5$ are independently H, methyl or F; R$_{6a}$, R$_{6b}$ and R$_{6c}$ are independently H or CH$_3$; wherein * denotes chiral carbon, including racemates, the absolute configuration of S or R.

8. The C-aryl glycoside derivative of formula (I), or its isomers, stable isotope derivatives thereof or a pharmaceutically acceptable salt thereof as defined in claim 1, wherein the C-aryl glycoside derivative of formula (I) is any one of the compounds of following I-1 to I-148:

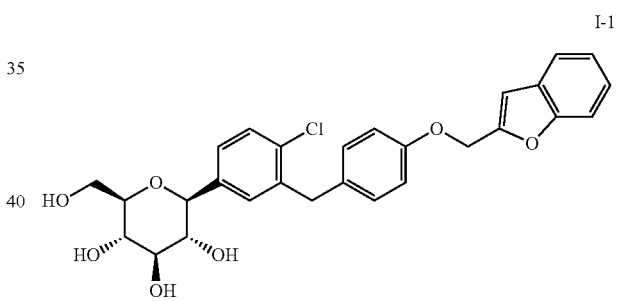

I-1

I-2

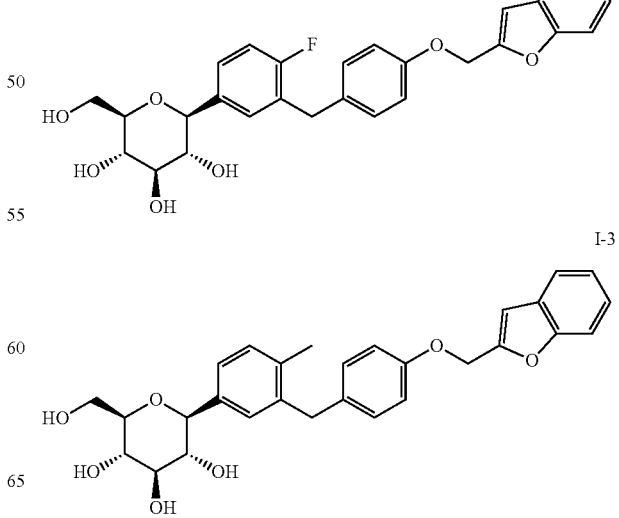

I-3

I-4
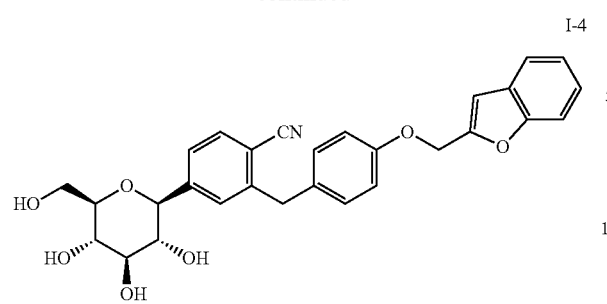
I-5
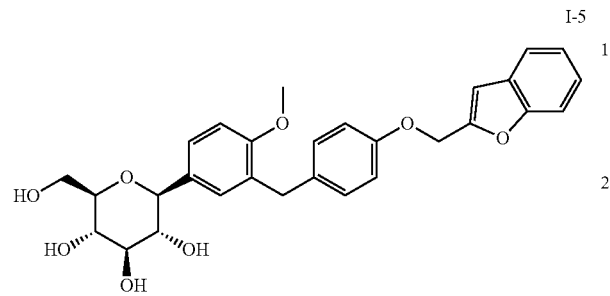
I-6
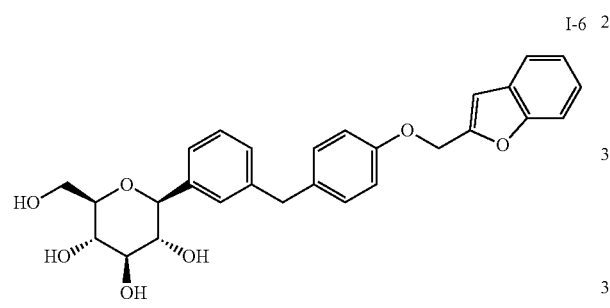
I-7
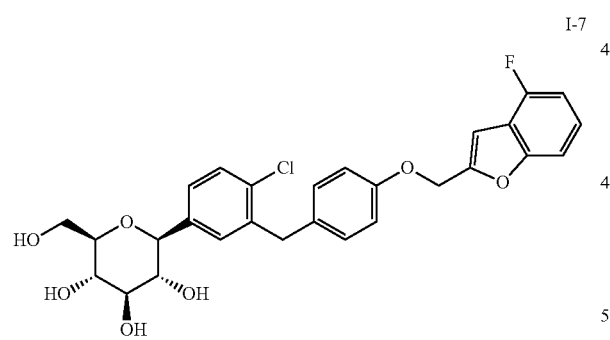
I-8
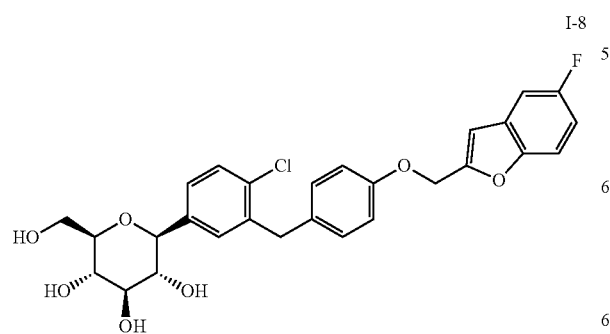
I-9
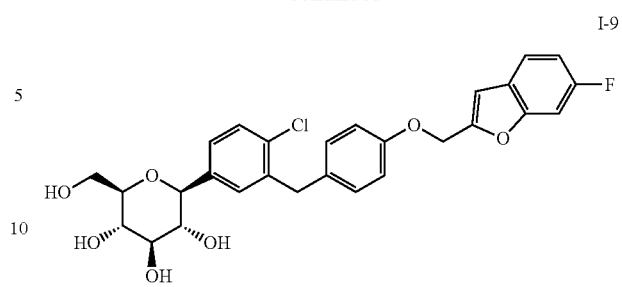
I-10
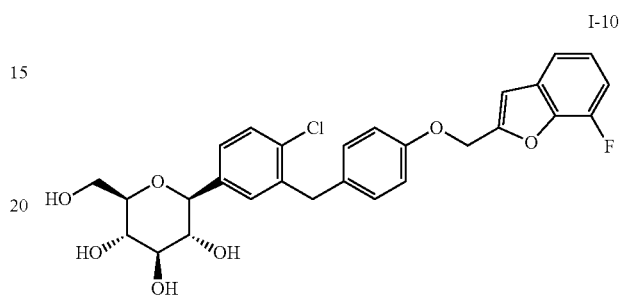
I-11
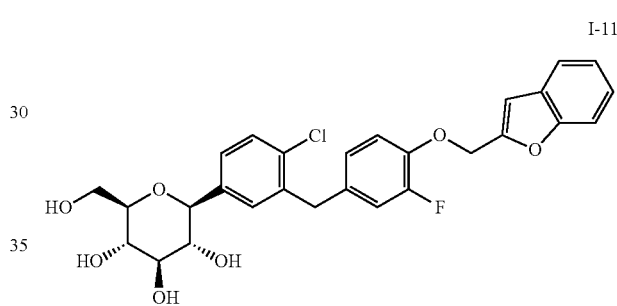
I-12
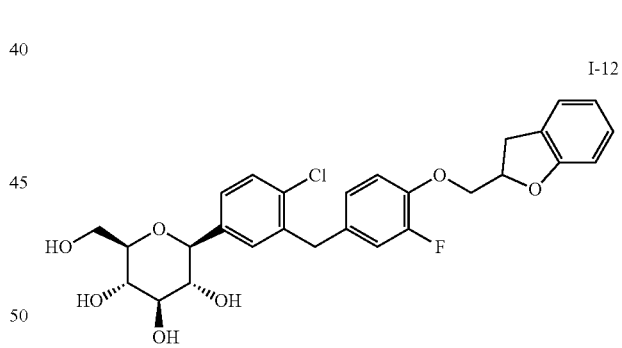
I-13
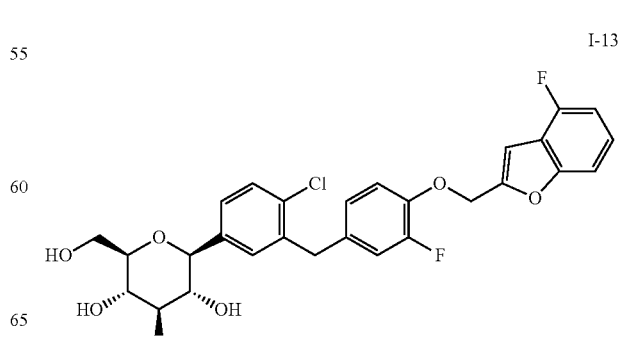

-continued
I-14
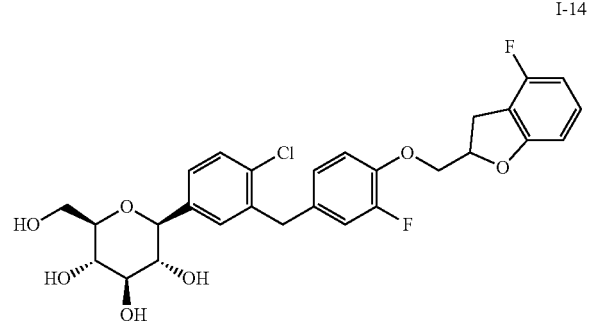
I-15
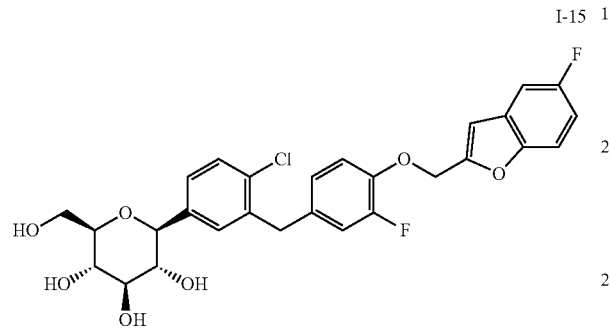
I-16
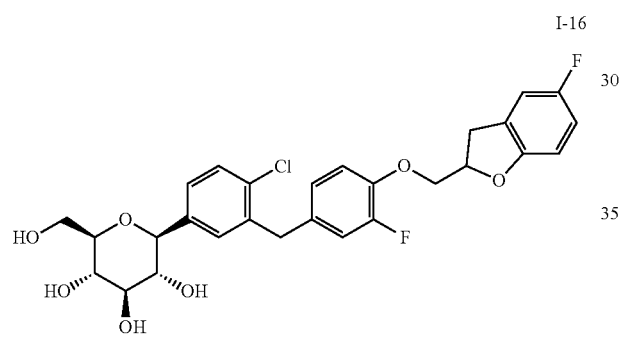
I-17
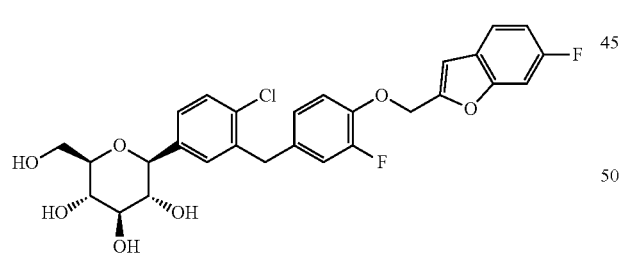
I-18
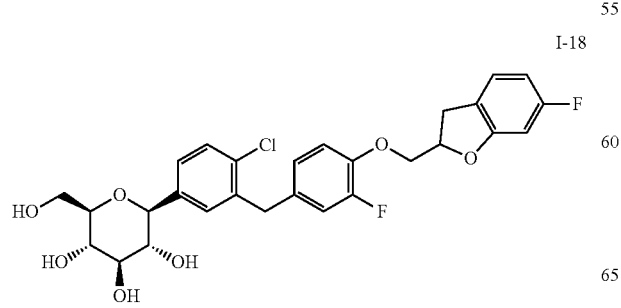
-continued
I-19
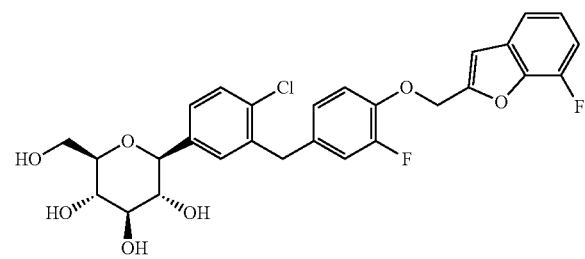
I-20
I-21
I-22
I-23

-continued

I-34
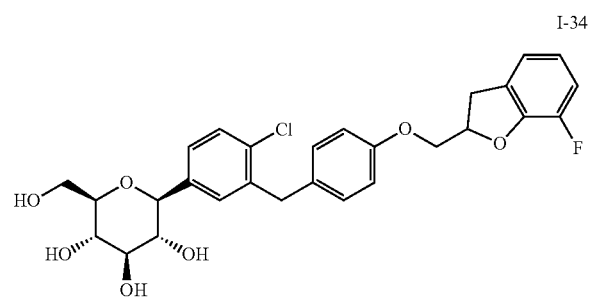
I-35
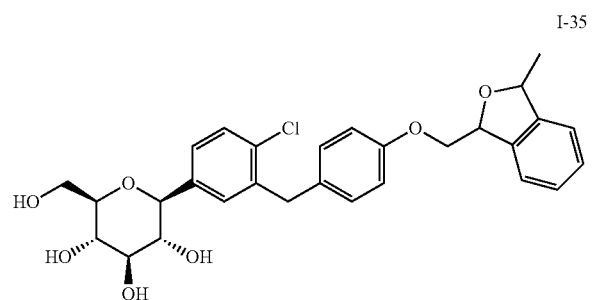
I-36
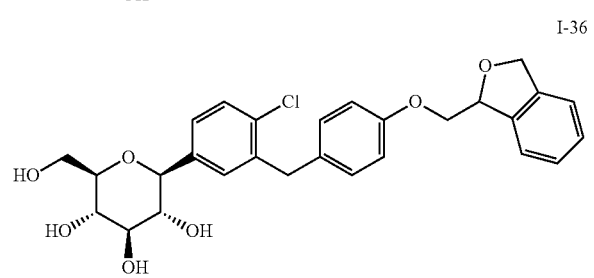
I-37
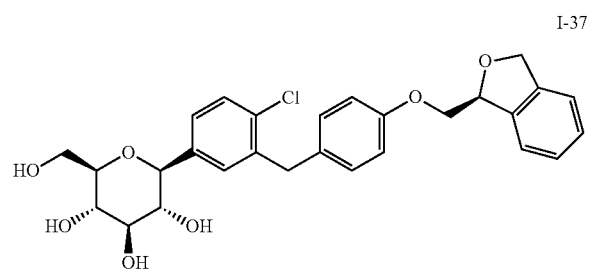
I-38
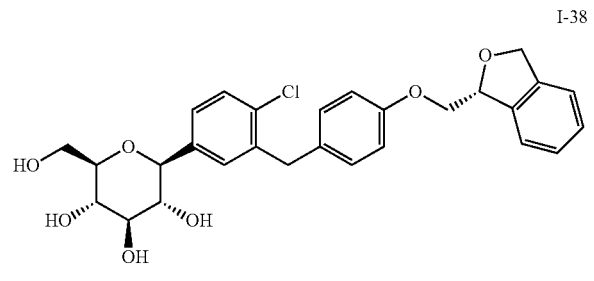
I-39
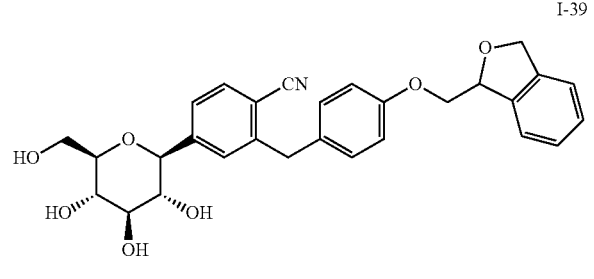
I-40
I-41
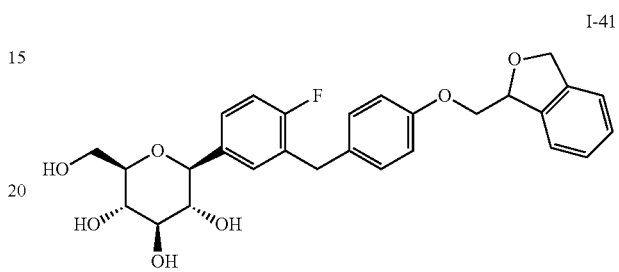
I-42
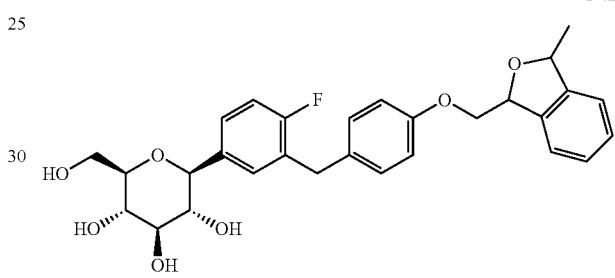
I-43
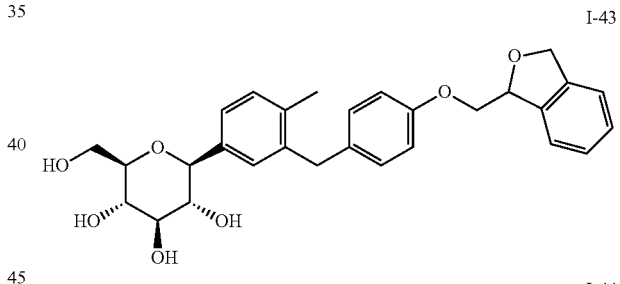
I-44
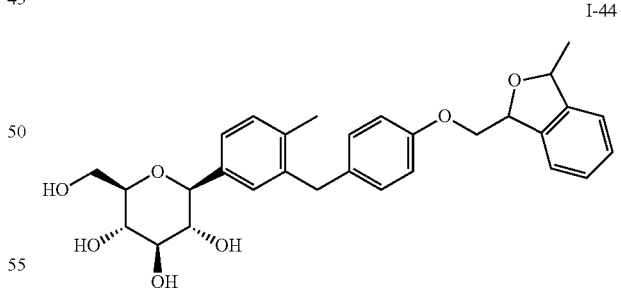
I-45
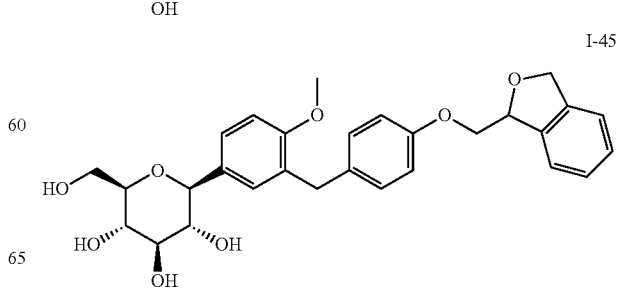

I-46
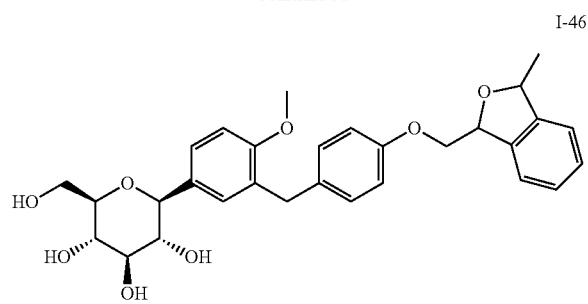
I-47
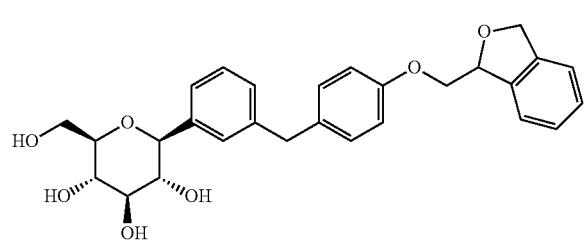
I-48
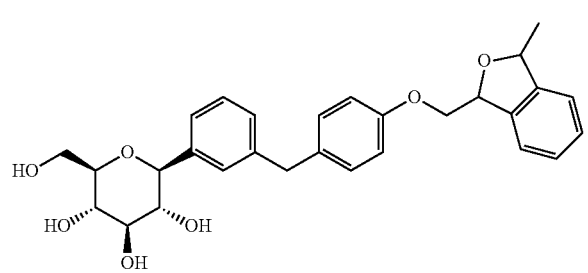
I-49
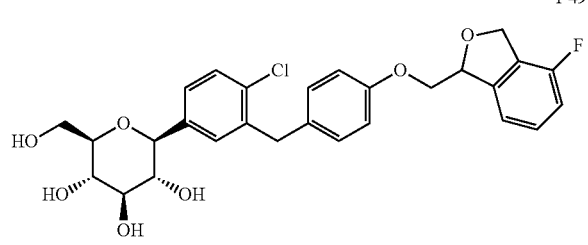
I-50
I-51
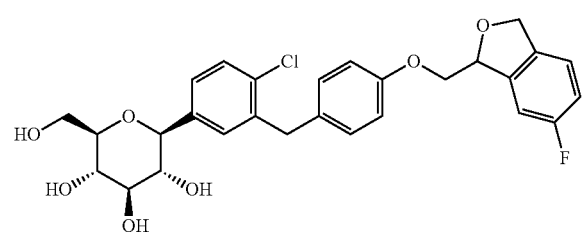
I-52
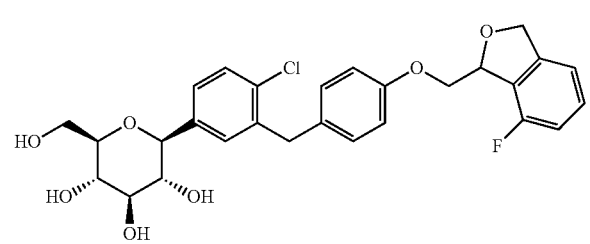
I-53
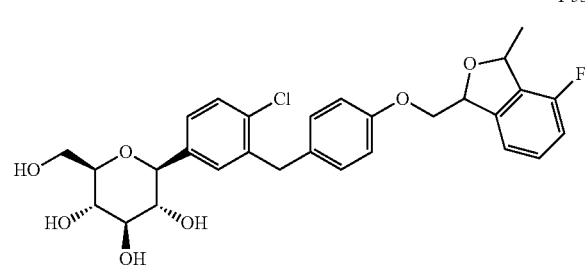
I-54
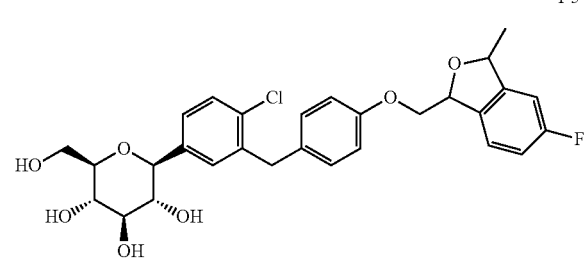
I-55
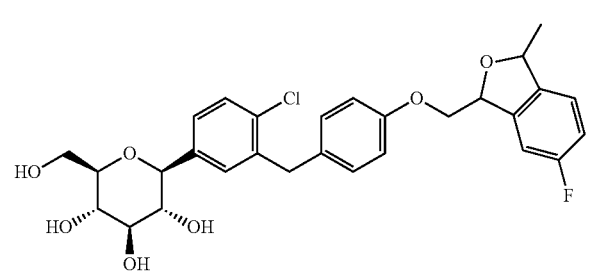
I-56
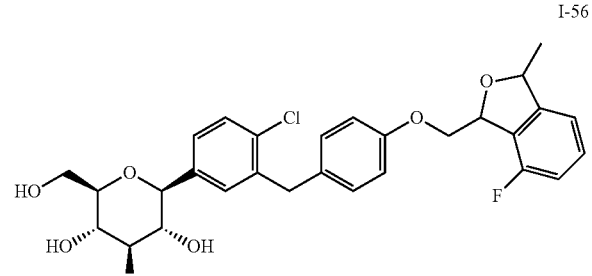
I-57
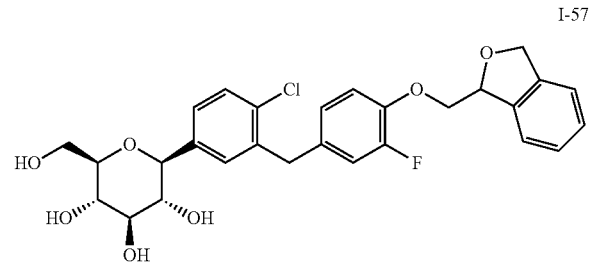

I-58
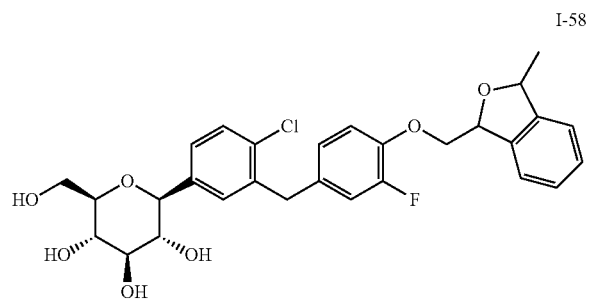
I-59
I-60
I-61
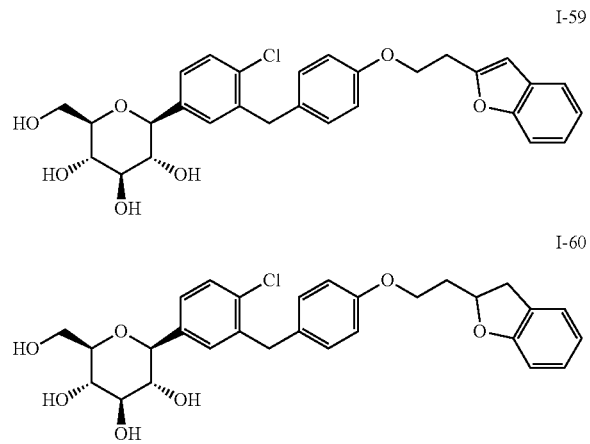
I-62
I-63
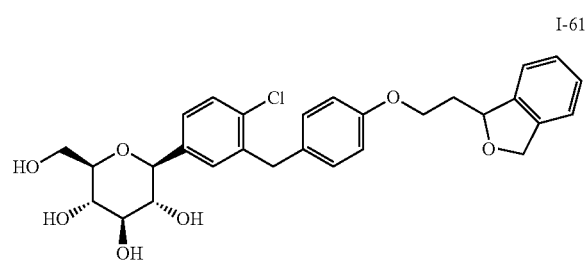
I-64
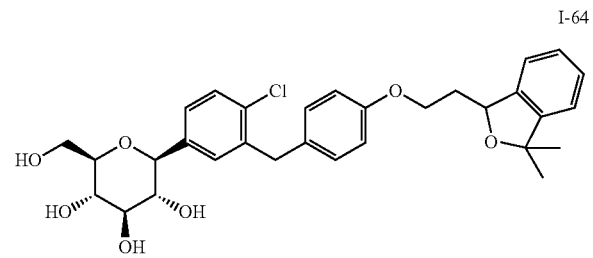
I-65
I-66
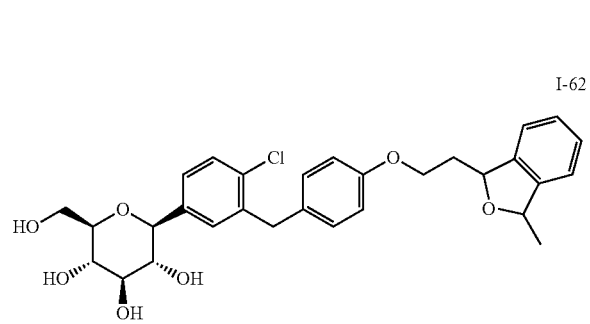
I-67
I-68
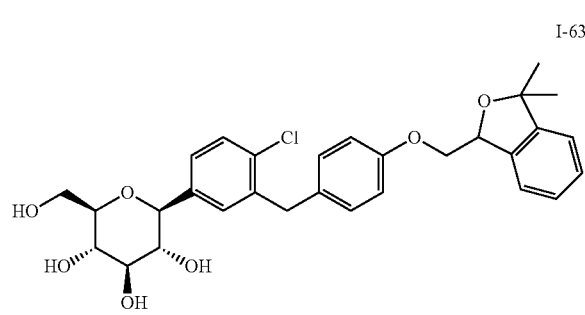
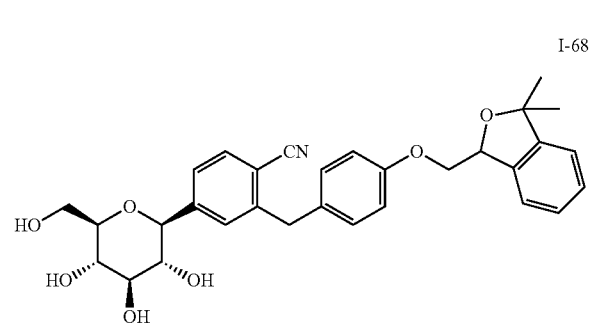

I-69
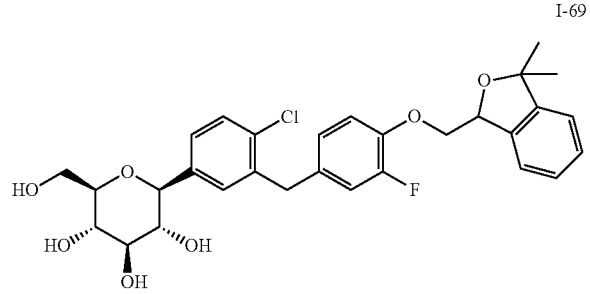
I-70
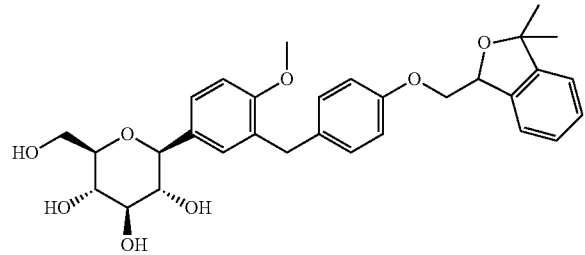
I-71
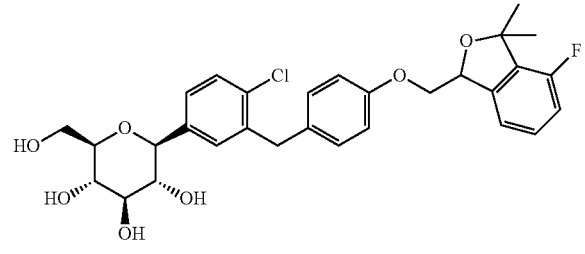
I-72
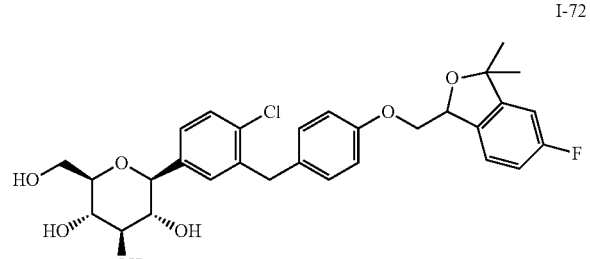
I-73
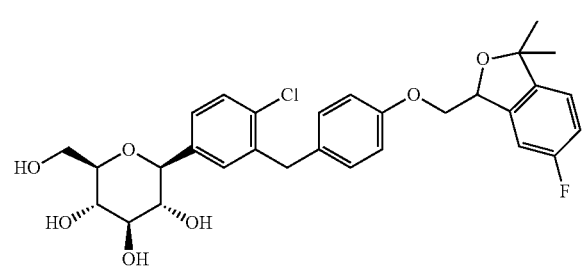
I-74
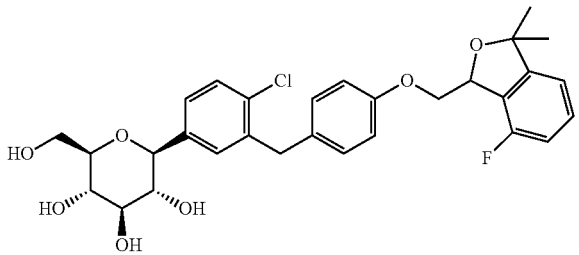
I-75
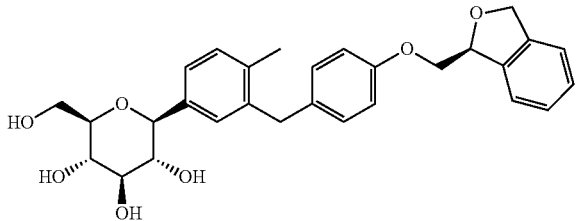
I-76
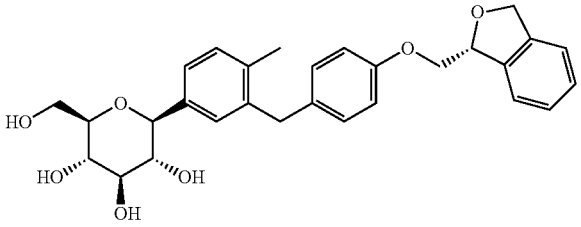
I-77
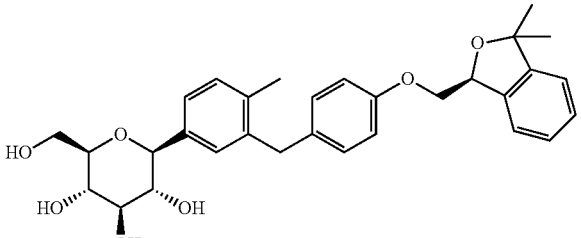
I-78
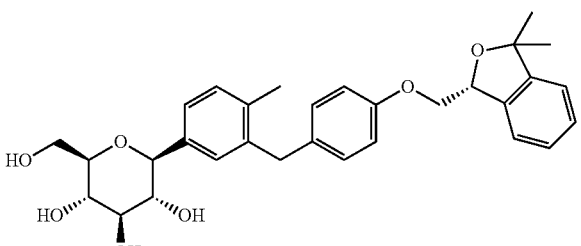
I-79
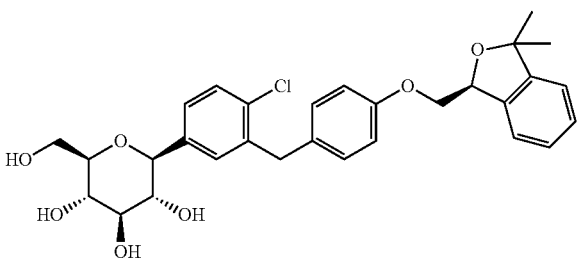

I-80
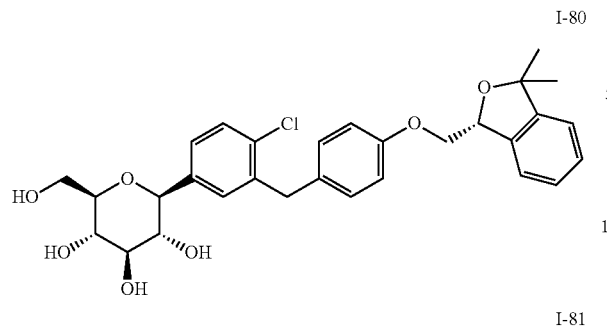
I-81
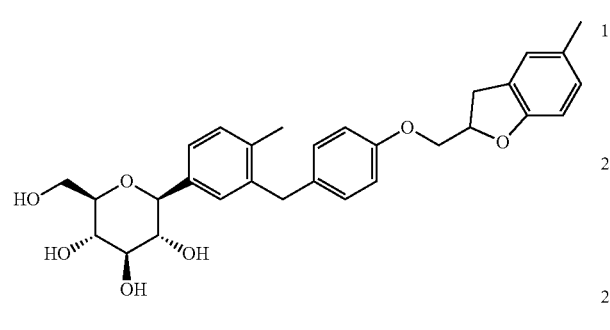
I-82
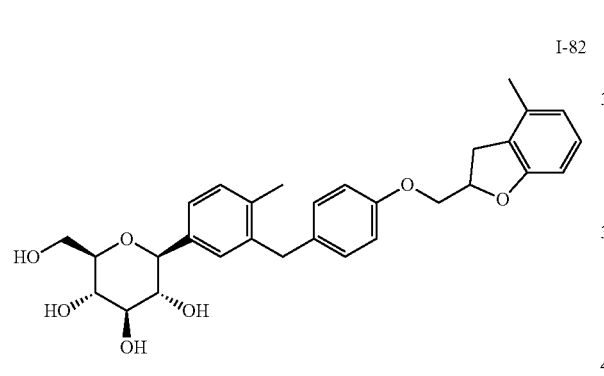
I-83
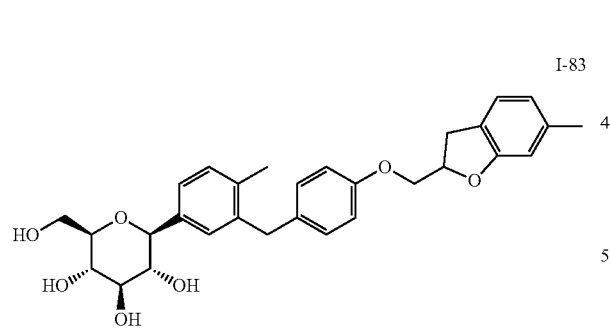
I-84
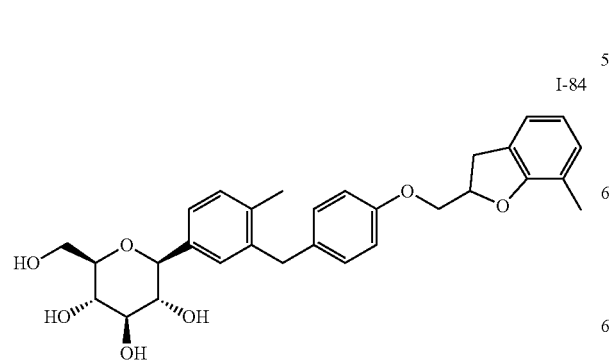
-continued
I-85
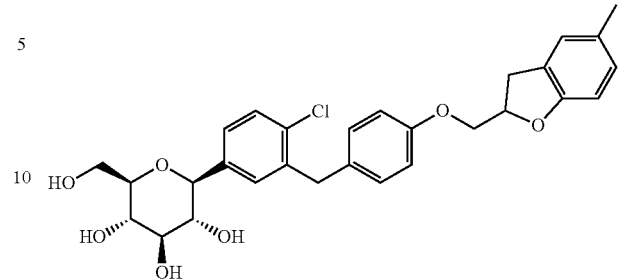
I-86
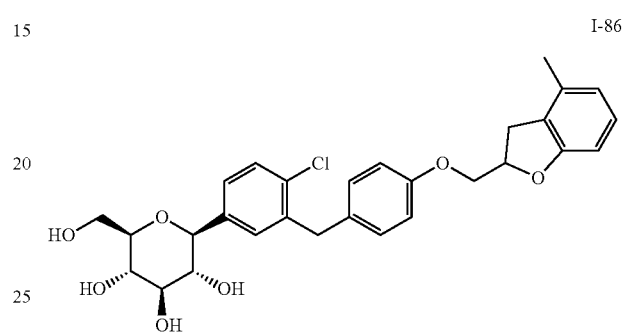
I-87
I-88
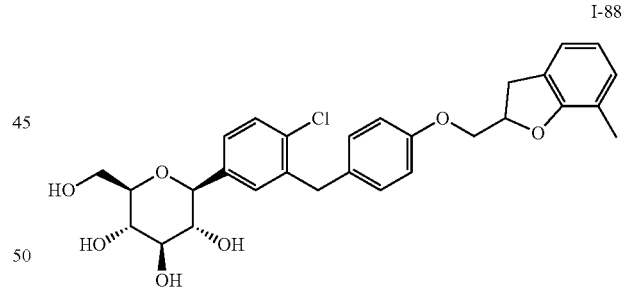
I-89
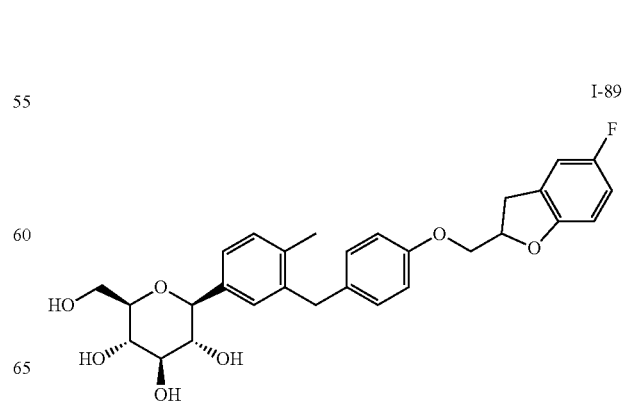

I-90
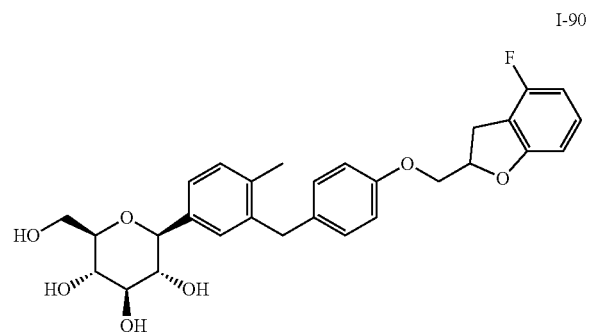
I-91
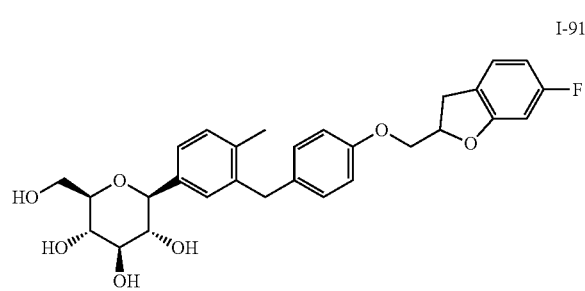
I-92
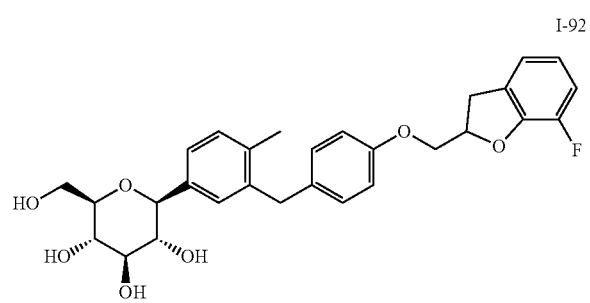
I-93
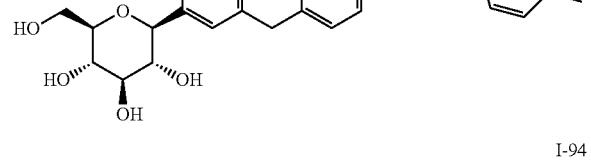
I-94
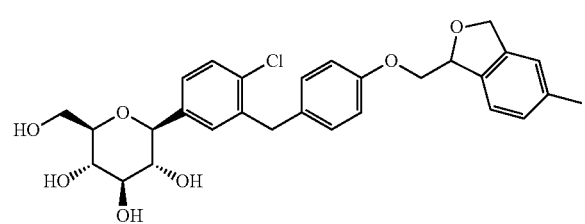
I-95
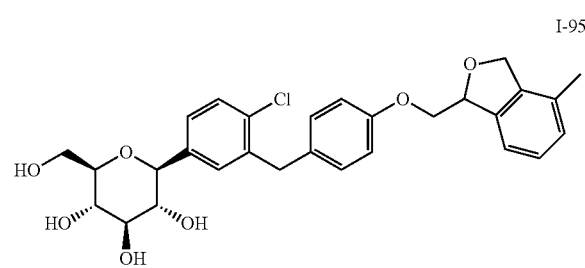
I-96
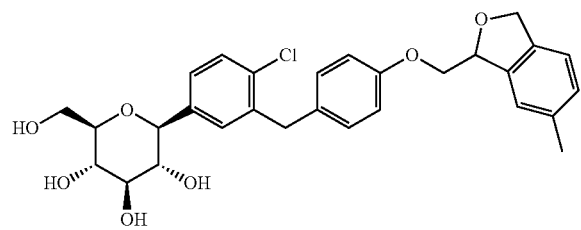
I-97
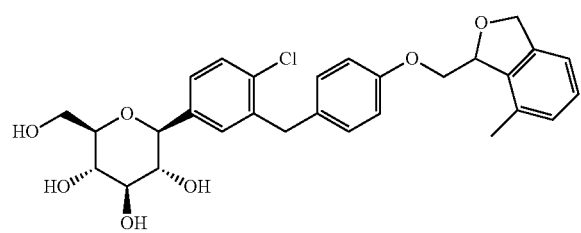
I-98
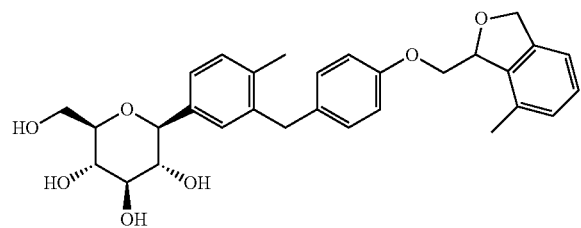
I-99
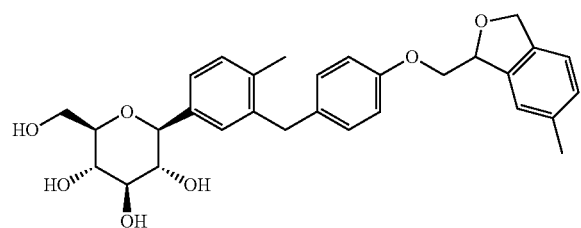
I-100
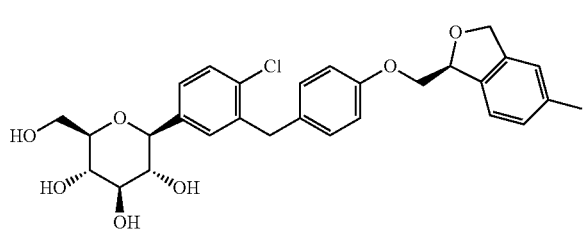
I-101

I-102
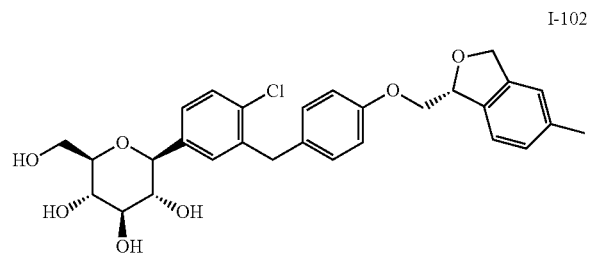
I-103
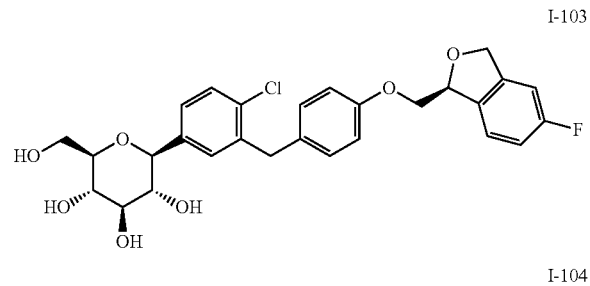
I-104
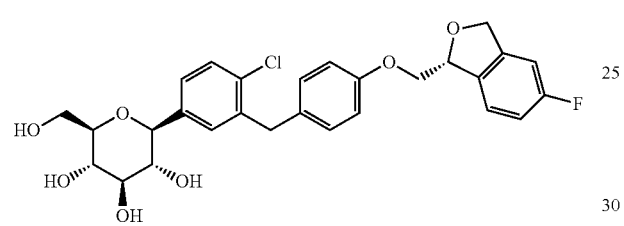
I-105
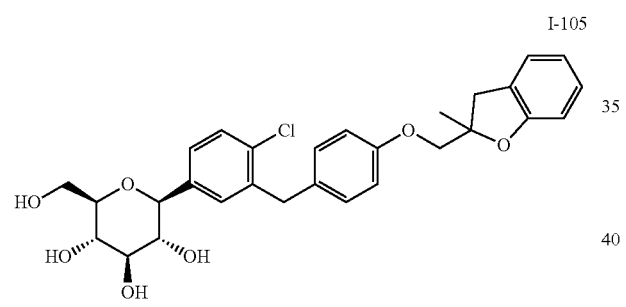
I-106
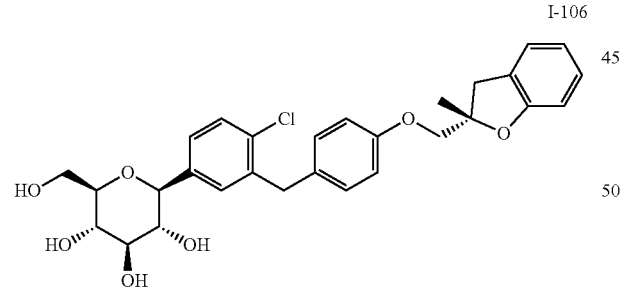
I-107
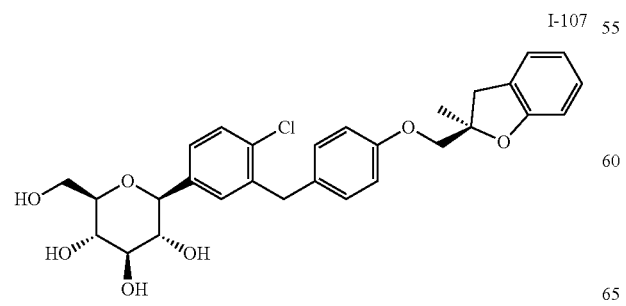
I-108
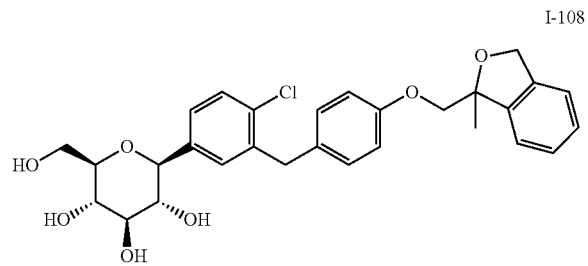
I-109
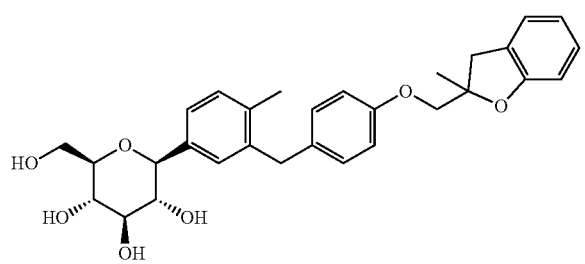
I-110
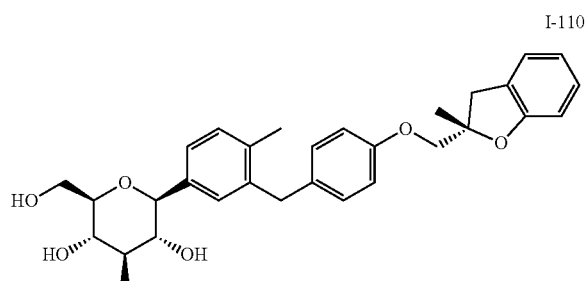
I-111
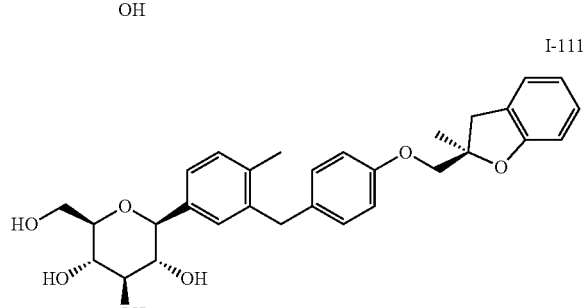
I-112
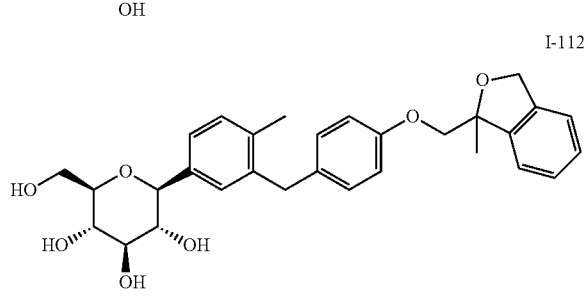
I-113
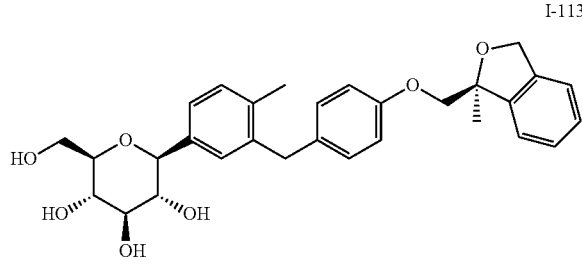

I-114
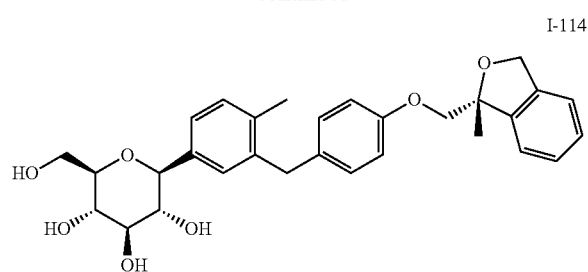
I-115
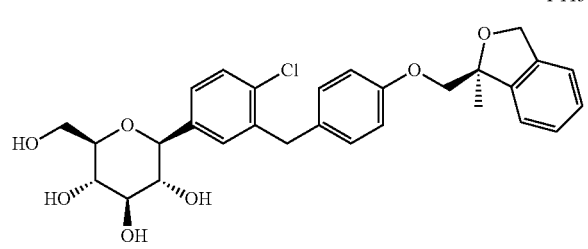
I-116
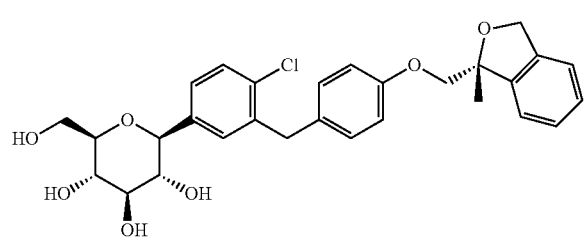
I-117
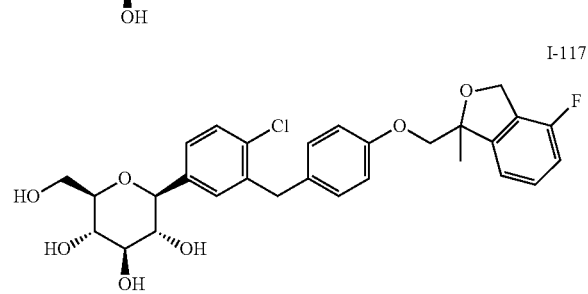
I-118
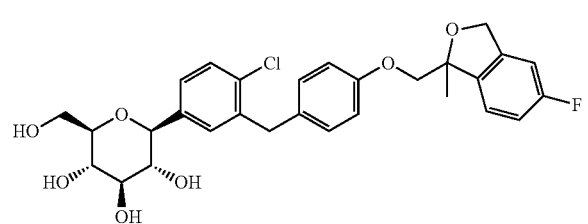
I-119
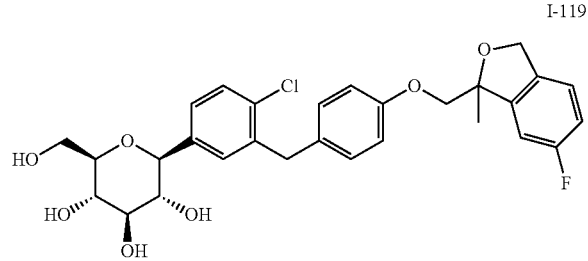
I-120
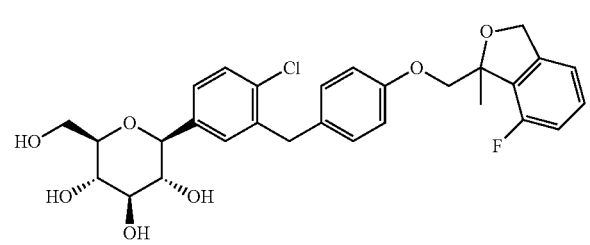
I-121
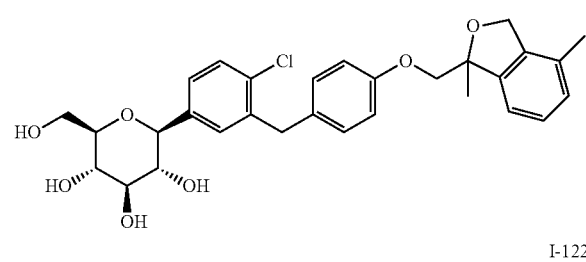
I-122
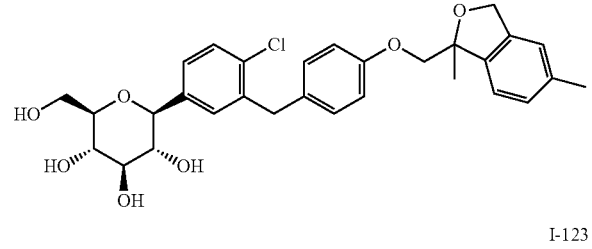
I-123
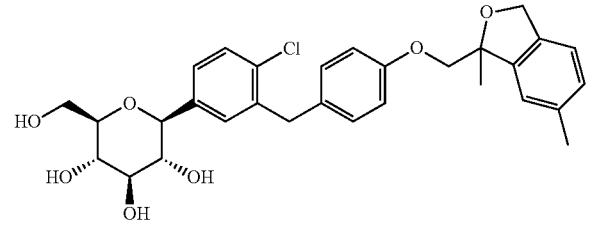
I-124
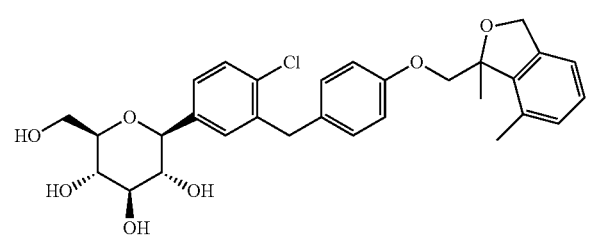
I-125
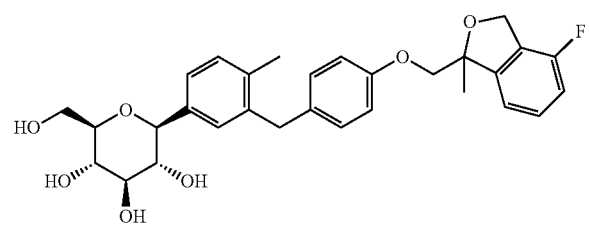

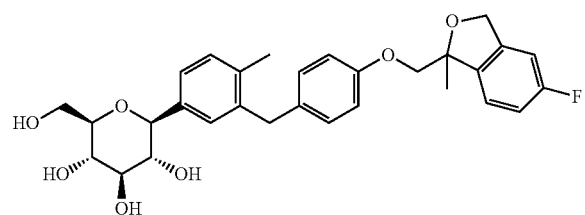
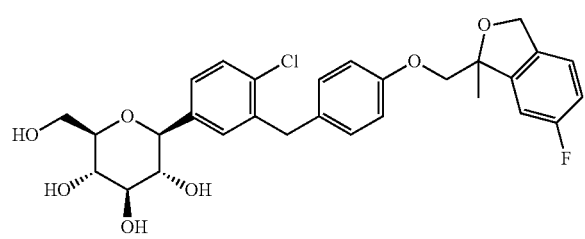
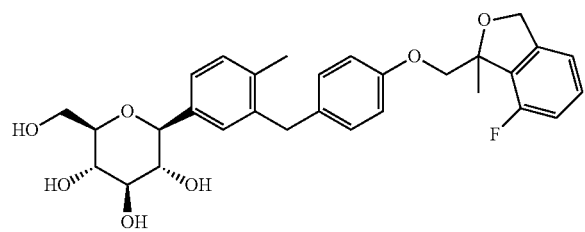
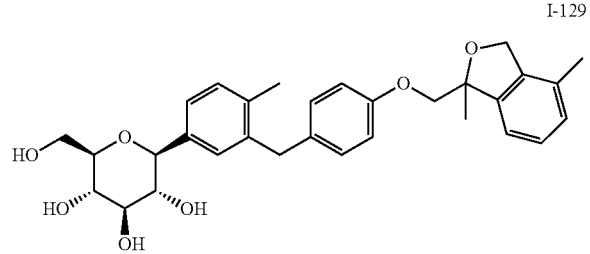
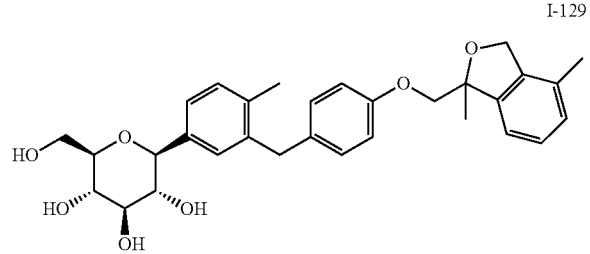

I-137
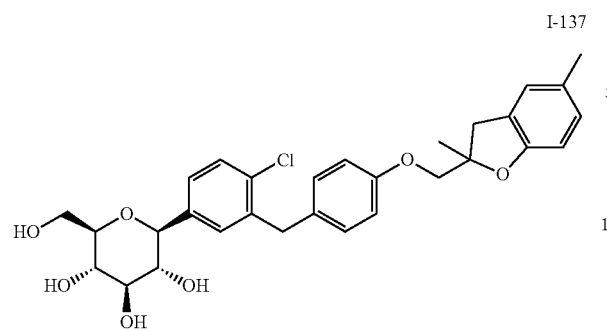
I-138
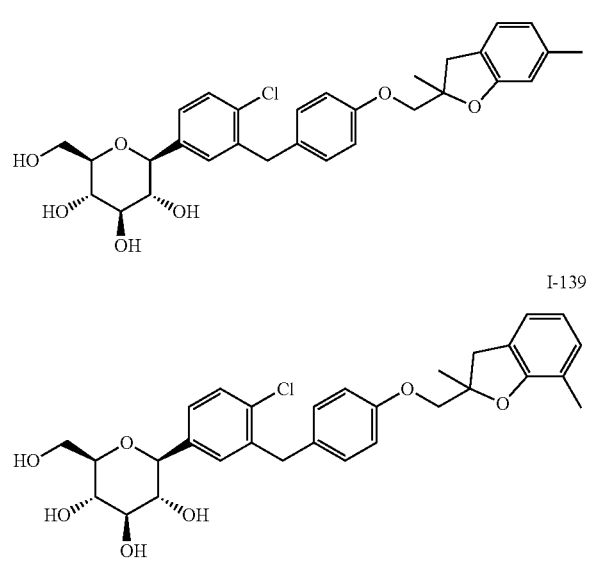
I-139
I-140
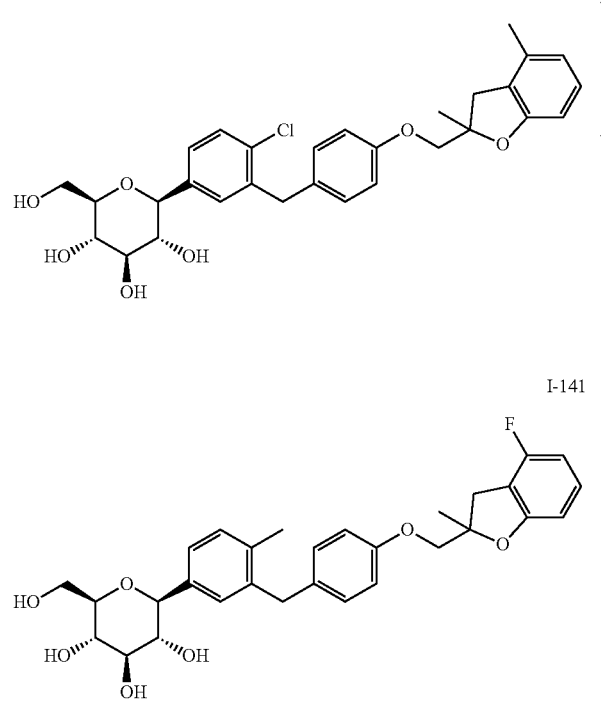
I-141
I-142
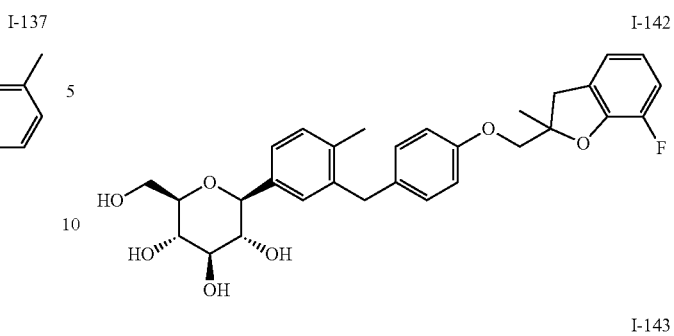
I-143
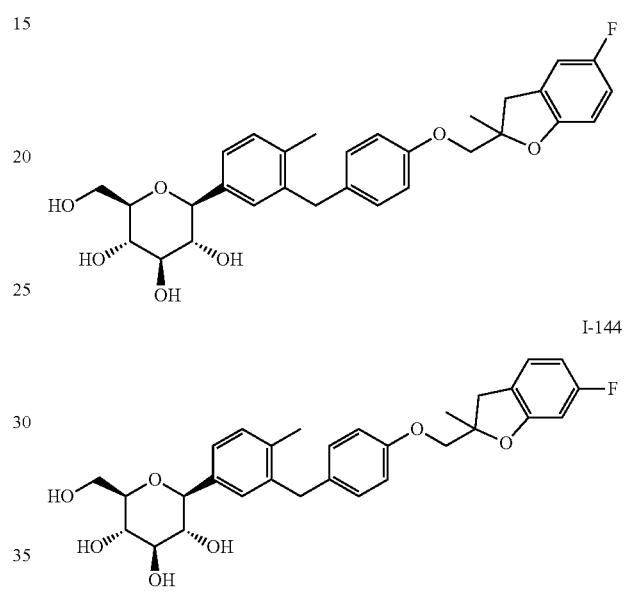
I-144
I-145
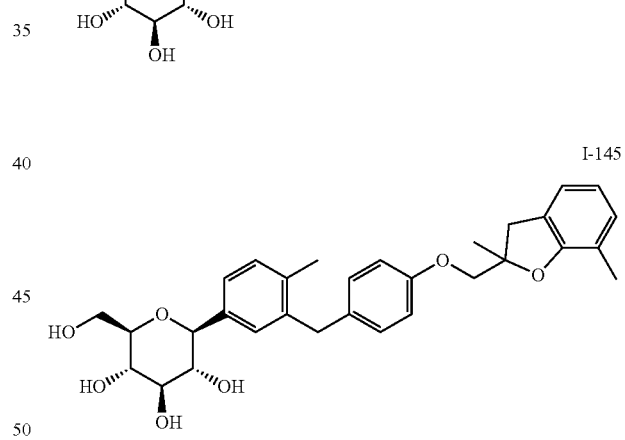
I-146
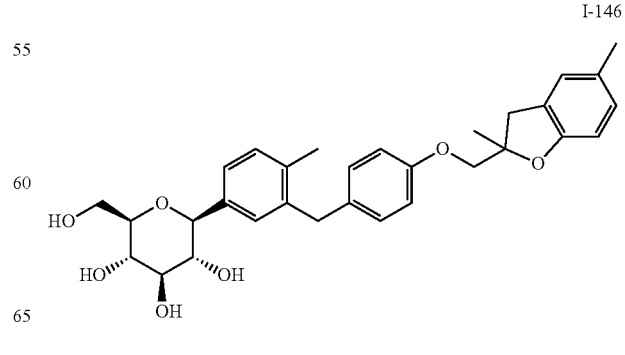

-continued

I-147

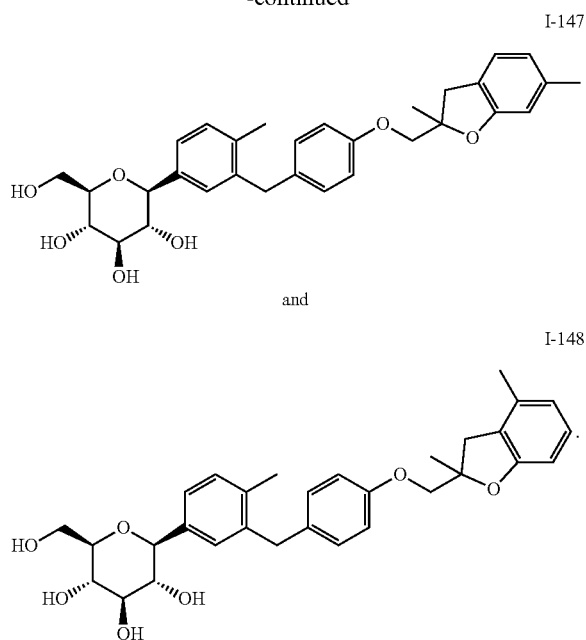

and

I-148

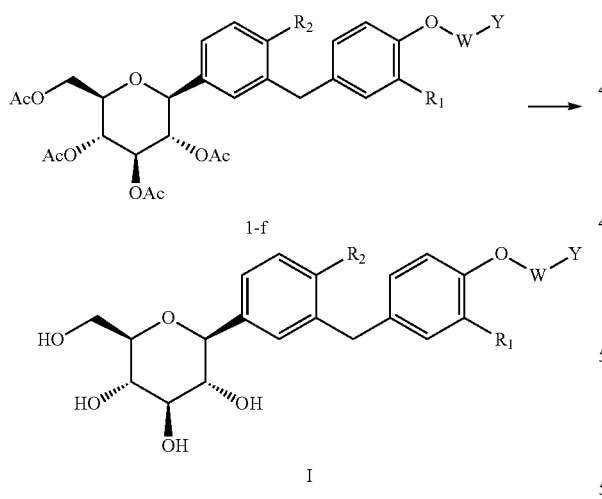

9. A preparation method for preparing a C-aryl glycoside derivative of formula (I), or its stereoisomers, stable isotope derivatives thereof or a pharmaceutically acceptable salt thereof according to claim 1, wherein said preparation method is any one of the following methods:

method 1: wherein said method comprises the following steps: in a solvent, deprotecting the acetyl protecting groups of compound 1-f in the presence of a base;

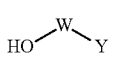

method 2: wherein said method comprises the following steps: 1) in a solvent, compound 2-g reacts with

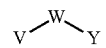

via Mitsunobu reaction in the presence of a condensation agent; 2) in a solvent, deprotecting the acetyl protecting groups of compound 2-f in the presence of a base;

or method 3: wherein said method comprises the following steps: 1) in a solvent, compound 2-g reacts with

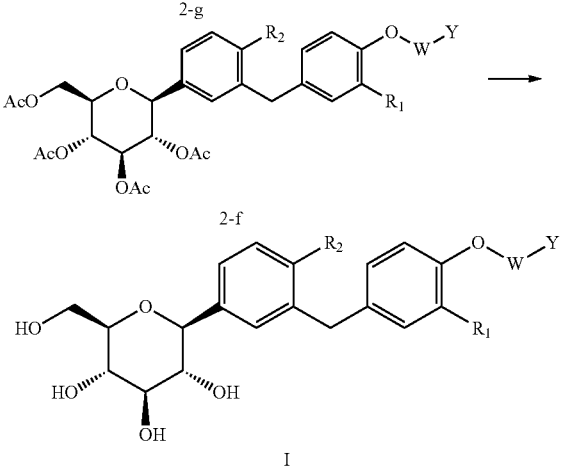

via nucleophilic substitution reaction in the presence of a base; 2) in a solvent, deprotecting the acetyl protecting groups of compound 3-f in the presence of a base;

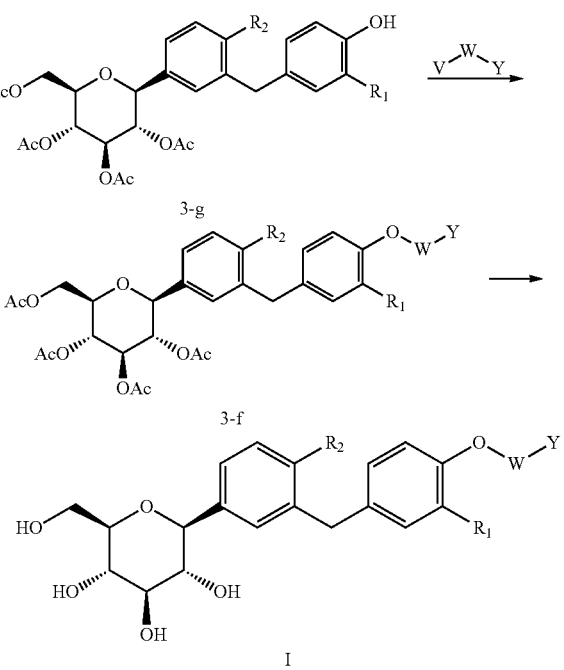

wherein, V is Cl, Br or I.

10. The preparation method of claim 9, wherein in method 1, the deacetylation reaction uses sodium methanolate and methanol system, or lithium hydroxide, methanol, tetrahydrofuran and water system; wherein said solvent is methanol, or a mixed solvent of methanol, tetrahydrofuran and water; when using a mixed solvent, the volume ratio of methanol, tetrahydrofuran to water is 4:1:0.5~0.5:1:0.5, the base is sodium methanolate or lithium hydroxide; the mole ratio of a base to compound 1-f is 0.1:1-2:1; and the reaction temperature is in the range from 0 to 30° C.

11. The preparation method of claim 9, wherein in method 1, the deacetylation reaction comprises the following steps: in a solvent, a hydroxyl acetylation reaction is carried out with compound 1-e, and then recrystallization to afford compound 1-f;

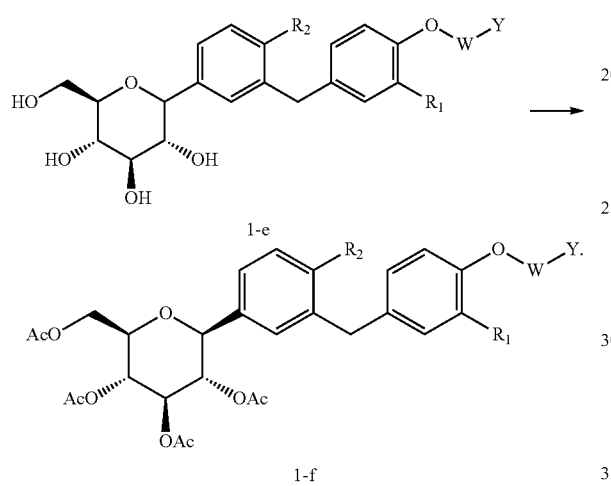

12. The preparation method of claim 11, wherein in method 1, the deacetylation reaction comprises the following steps: in a solvent, a reduction reaction is carried out with compound 1-d, boron trifluoride etherate and triethylsilane to afford compound 1-e;

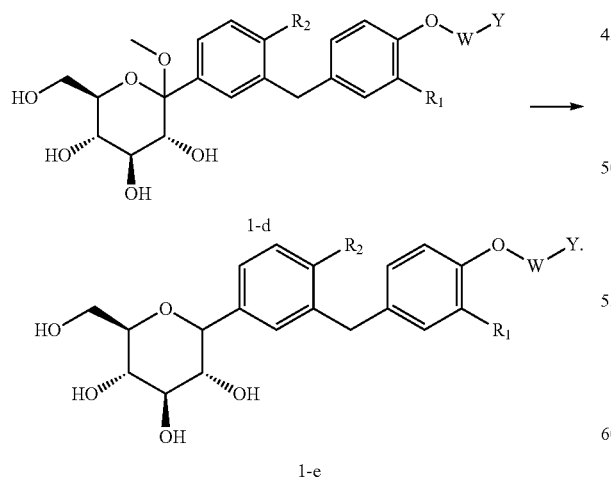

13. The preparation method of claim 12, wherein in method 1, the deacetylation reaction comprises the following steps: in a solvent, at −78--60° C., treating compound 1-c with alkali lithium reagent for 0.5-1 h, followed by treating with 2,3,4,6-tetrakis-O-(trimethylsilyl)-D-gluconolactone, and then at 10-30° C., treating with methanesulfonic acid methanol solution to afford compound 1-d;

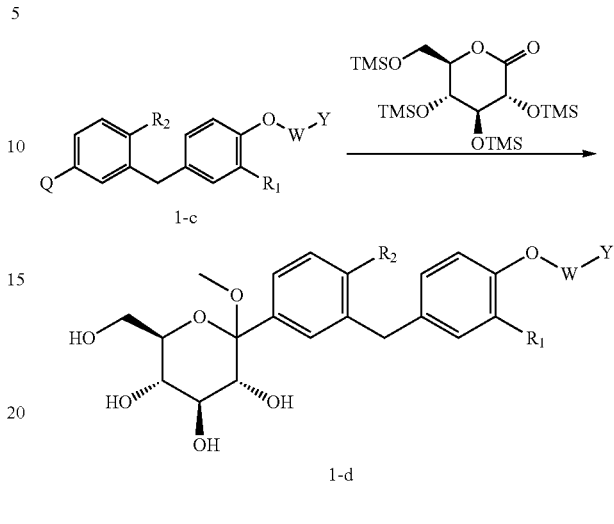

wherein, Q is Br or I.

14. Any one of the following compounds:

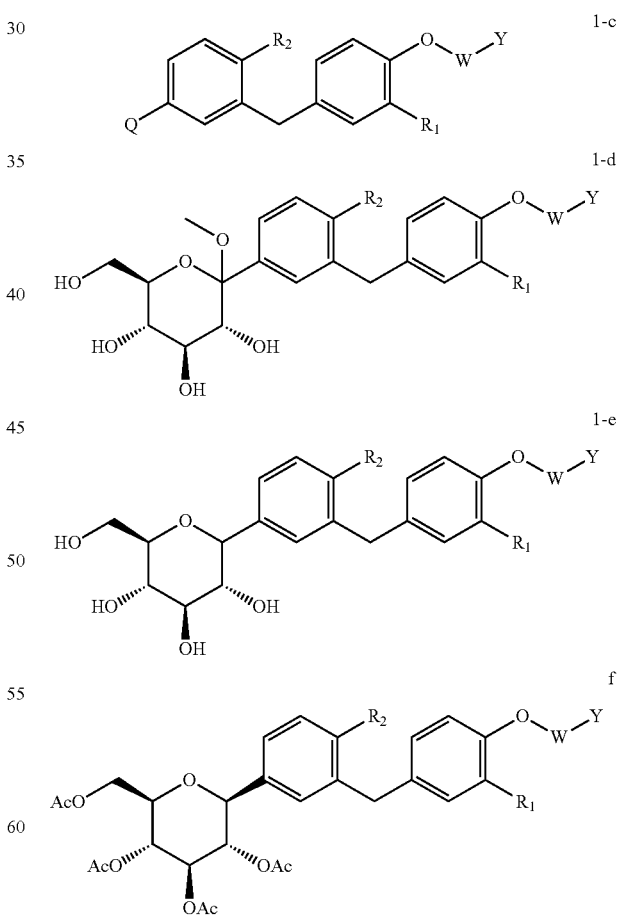

wherein, Q is Br or I; $R_1$, $R_2$, W and Y are the same as defined in claim 1.

15. A pharmaceutical composition comprising a C-aryl glycoside derivative of formula (I) of claim 1 or its pharmaceutically acceptable salt, and a pharmaceutically acceptable excipient.

16. The pharmaceutical composition of claim 15, wherein the pharmaceutical composition further comprises other kind of drug for treatment of diabetes or other kind of pharmaceutical agent; where said pharmaceutically acceptable excipient is pharmaceutically acceptable carrier, diluent, and/or vehicle.

17. The pharmaceutical composition of claim 16, wherein said drug for treatment of diabetes or pharmaceutical agent is one or more therapeutic agent(s) for treatment of diabetes, diabetic complications, hyperlipidemia, obesity, and hypertension.

* * * * *